US008871219B2

(12) United States Patent
Heeney et al.

(10) Patent No.: US 8,871,219 B2
(45) Date of Patent: Oct. 28, 2014

(54) RECOMBINANT VECTORS BASED ON THE MODIFIED VACCINIA ANKARA VIRUS (MVA) AS PREVENTIVE AND THERAPEUTIC VACCINES AGAINST AIDS

(75) Inventors: Jonathan Heeney, Rijswijk (NL); Petra Mooij, Rijswijk (NL); Carmen Elena Gomez Rodriguez, Madrid (ES); Jose Luis Najera Garcia, Madrid (ES); Victoria Jimenez Tentor, Madrid (ES); Mariano Esteban Rodriguez, Madrid (ES)

(73) Assignee: Consejo Superior de Investigaciones Cientificas, Madrid (ES)

( * ) Notice: Subject to any disclaimer, the term of this patent is extended or adjusted under 35 U.S.C. 154(b) by 1775 days.

(21) Appl. No.: 11/989,425

(22) PCT Filed: Jul. 25, 2006

(86) PCT No.: PCT/ES2006/070114
§ 371 (c)(1),
(2), (4) Date: May 26, 2009

(87) PCT Pub. No.: WO2007/012691
PCT Pub. Date: Feb. 1, 2007

(65) Prior Publication Data
US 2010/0047276 A1 Feb. 25, 2010

(30) Foreign Application Priority Data

Jul. 27, 2005 (ES) .................................. 200501841
Mar. 24, 2006 (ES) .................................. 200600762

(51) Int. Cl.
*C12N 15/863* (2006.01)
*A61K 39/21* (2006.01)
*A61K 31/7088* (2006.01)
*C12N 15/63* (2006.01)

(52) U.S. Cl.
USPC .................. 424/199.1; 424/208.1; 424/188.1; 435/320.1

(58) Field of Classification Search
None
See application file for complete search history.

(56) References Cited

PUBLICATIONS

Didierlaurent et al. Attenuated poxviruses expressing a synthetic HIV protein stimulate HLA-A2-restricted cytotoxic T-cell responses. Vaccine 2004, vol. 22, pp. 3395-3403.*
Van der Groen et al. Genetic variation of HIV Type 1: relevance of interclade variation to vaccine development. AIDS Research and Human Retroviruses 1998, vol. 14, Supplement 3, pp. S211-S221.*
Su et al. Characteization of a virtually full-length Human Immunodeficiency Virus Type 1 genome of a prevalent intersubtype (C/B') recombinant strain in China. Journal of Virology 2000, vol. 74, No. 23, p. 11367-11376.*
Vinner et al. Immunogenicity in Mamu-A*01 rhesus macaques of a CCR5-tropic human immunodeficiency virus type 1 envelope from the primary isolate (Bx08) after synthetic DNA prime and recombinant adenovirus 5 boost. Journal of General Virology 2003, vol. 84, p. 203-213.*
Altman et al. HIV escape: there and back again. Nature Medicine Mar. 2004 vol. 10, No. 3, p. 229-230.*
Derosiers. Prospects for an AIDS vaccine. Nature Medicine Mar. 2004, vol. 10, No. 3, p. 221-223.*
Feinberg et al. AIDS vaccine models: Challenging challenge viruses. Nature Medicine, Mar. 2002, vol. 8, No. 3, pp. 207-210.*
Haigwood, Predictive Value of Primate Models for AIDS. AIDS Reviews 2004, vol. 6, p. 187-198.*
Klein et al. Examination of the contributions of size and avidity to the neutralization mechanisms of the anti-HIV antibodies b12 and 4E10. Proceedings of the National Academy of Sciences of the United States of America Apr. 16, 2009, electronic publication Early Edition.*
Letvin. Progress toward an HIV vaccine. Annual Review of Medicine 2005, vol. 56, p. 213-223.*
Phogat et al. Inhibition of HIV-1 entry by antibodies: potential viral and cellular targets. Journal of Internal Medicine 2007. vol. 262, p. 26-43.*
Santra et al. Recombinant poxvirus boosting of DNA-primed rhesus monkeys augments peak but not memory T lymphocyte responses. Proceedings from the National Academy of Sciences USA . 2004, vol. 101, p. 11088-11093.*
Sekaly, R. The failed HIV Merck vaccine study: a step back or a launching point for future vaccine development? Journal of Experimental Medicine, Jan. 21, 2008, vol. 205, No. 1, p. 7-12.*
Tonini et al. Current approaches to developing a preventative HIV vaccine. Current Opinion in Investigational Drugs 2005, vol. 6, No. 2, p. 155-162.*
Whitney et al. Live attenuated HIV vaccines: pitfalls and prospects. Current Opinions in Infectious Disease 2004, vol. 17, p. 17-26.*
Yee et al. Prospects for gene therapy using HIV-based vectors. Somatic Cell and Molecular Genetics, Nov. 2001, vol. 26, No. 1/6, pp. 159-174.*

* cited by examiner

*Primary Examiner* — Louise Humphrey
(74) *Attorney, Agent, or Firm* — Wenderoth, Lind & Ponack, LLP.

(57) ABSTRACT

Recombinant vectors which are based on the Modified Ankara Virus (MVA) as preventive and therapeutic vaccines against AIDS. The recombinant viruses contain sequences which are inserted at an MVA insertion site and enable simultaneous expression of antigens, a HIV-1 Env protein consisting of a gp120 protein lacking sequences corresponding to protein gp 41 and a chimeric fusion protein of Gag, Pol and Nef. These viruses are stable and can trigger immune responses against a large variety of antigens. Viruses having a chimeric protein from HIV-1 are suitable for the preparation of vaccines against AIDS.

35 Claims, 60 Drawing Sheets

FIGURE 3
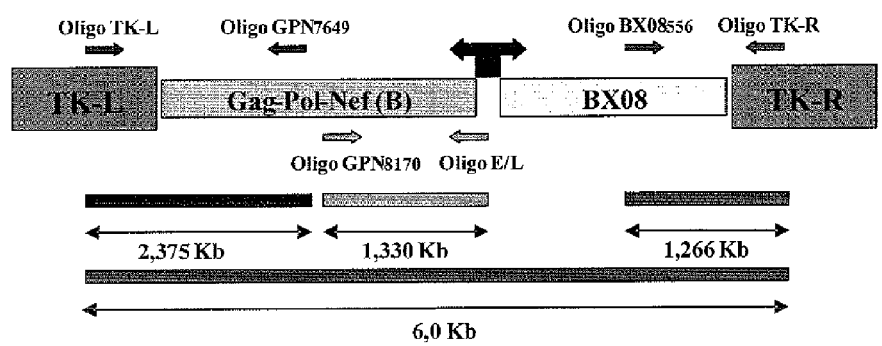
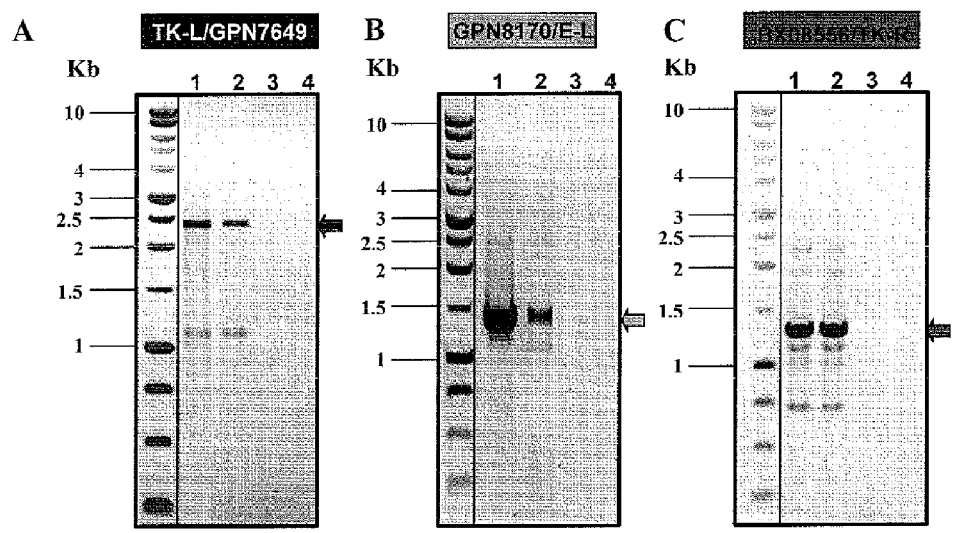

FIGURE 6
A
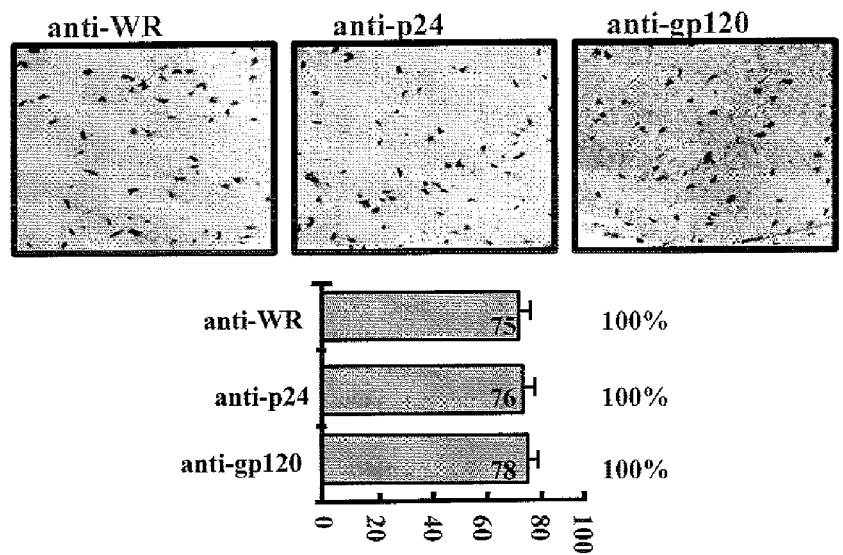
B
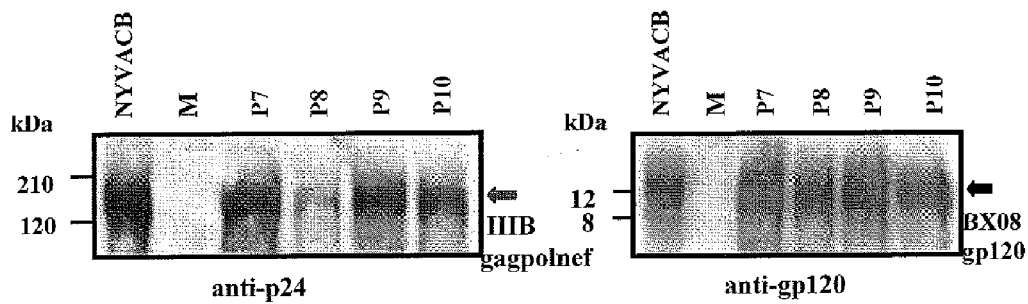

FIGURE 26
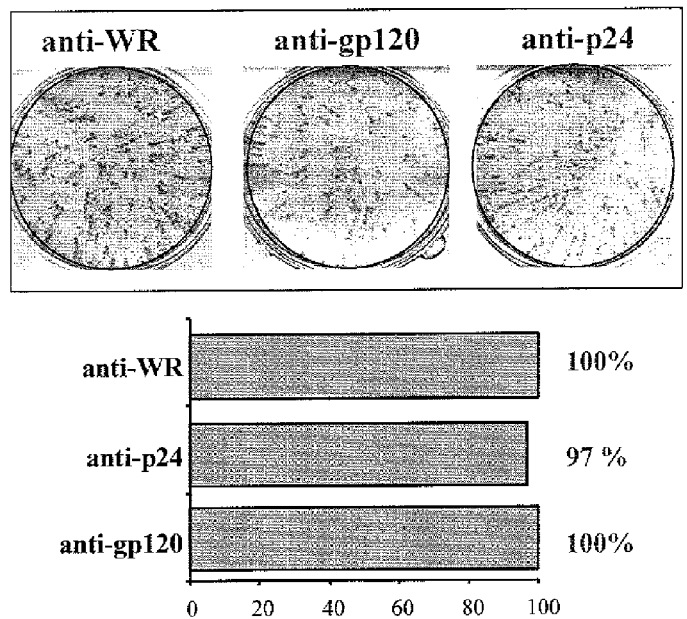
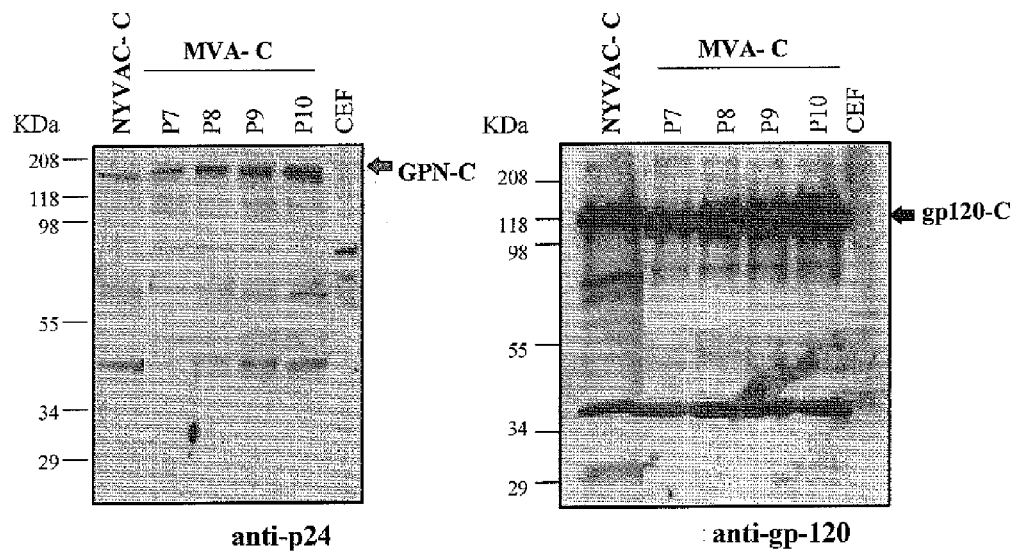

FIGURE 27
MVA-C
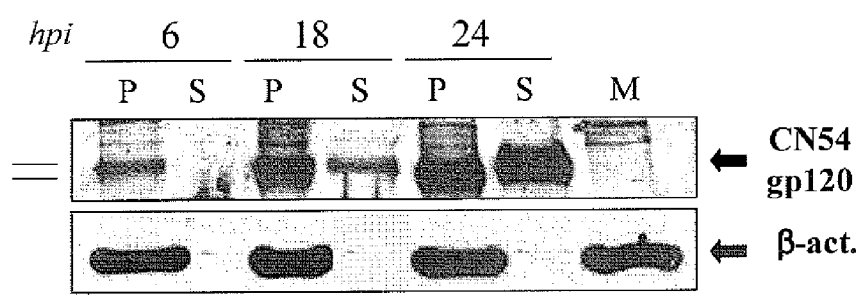
NYVAC-C
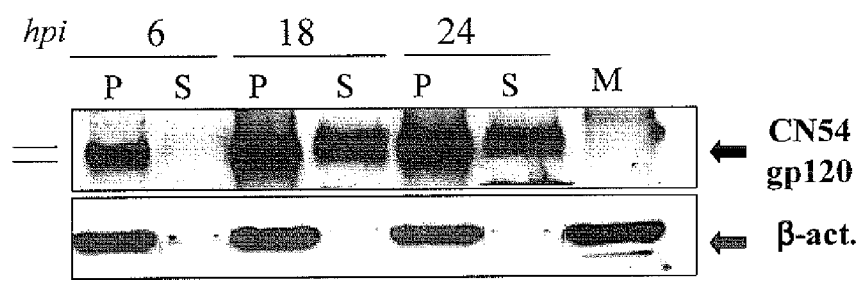

FIGURE 29
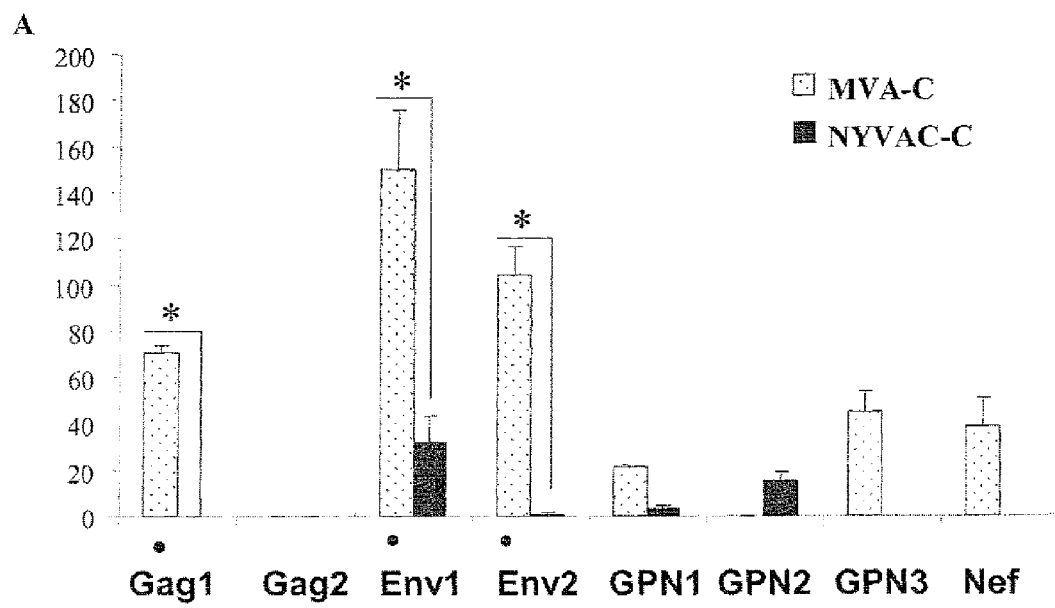
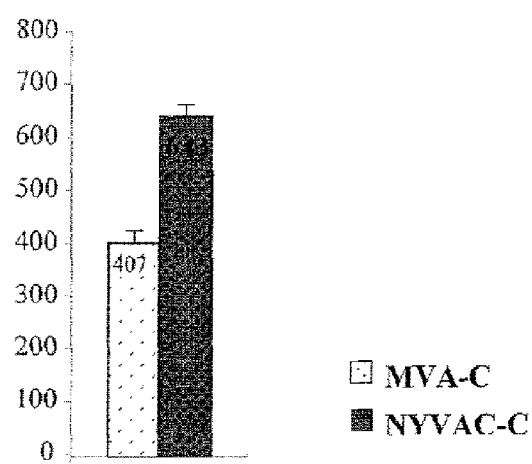

FIGURE 38B
MVA
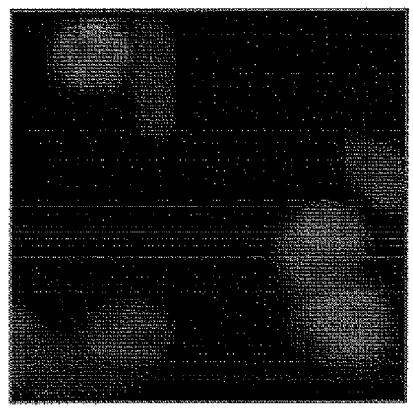
NYVAC
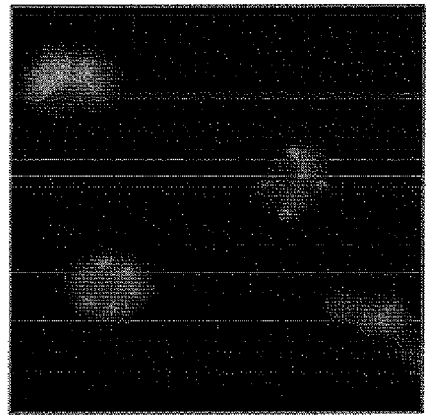

FIGURE 40
ENV
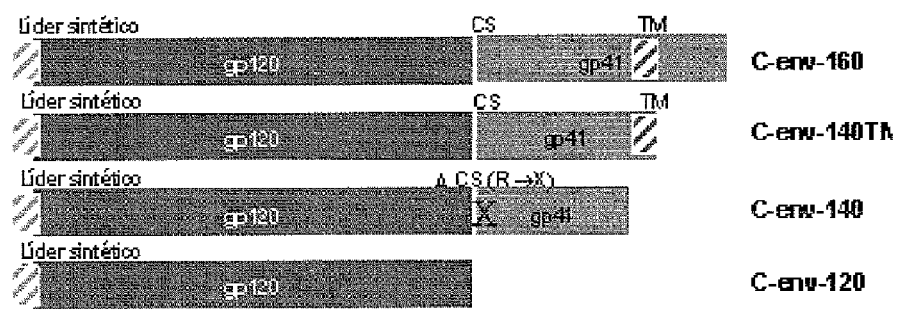
GagPolNef (gpn)

FIGURE 42
A
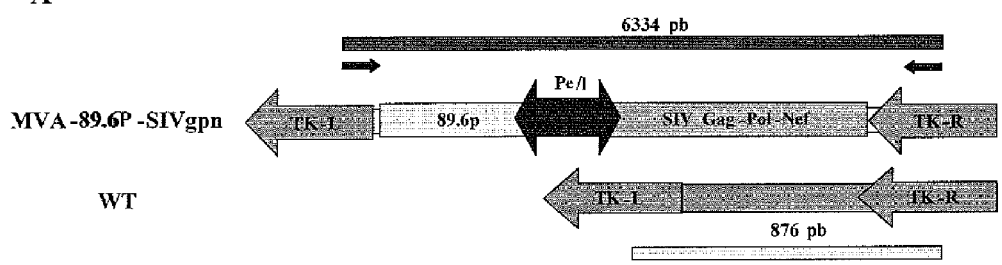
B
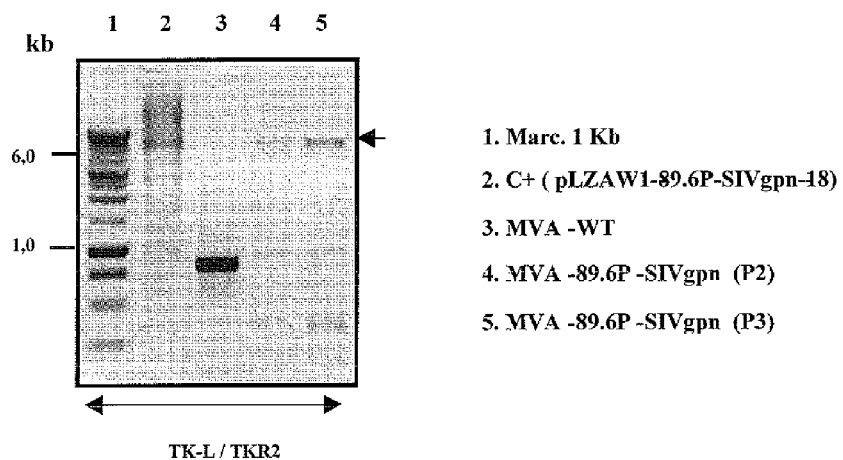
1. Marc. 1 Kb
2. C+ ( pLZAW1-89.6P-SIVgpn-18)
3. MVA -WT
4. MVA -89.6P -SIVgpn (P2)
5. MVA -89.6P -SIVgpn (P3)
TK-L / TKR2

FIGURE 43
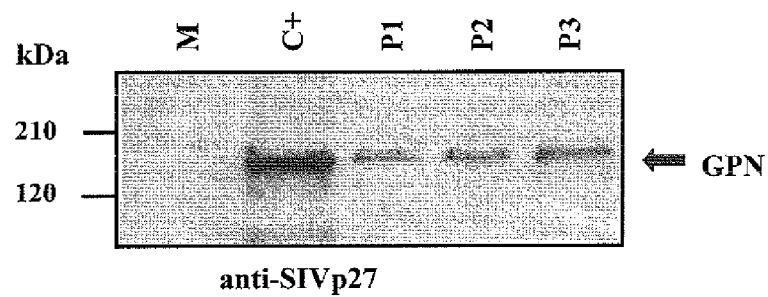

FIGURE 44
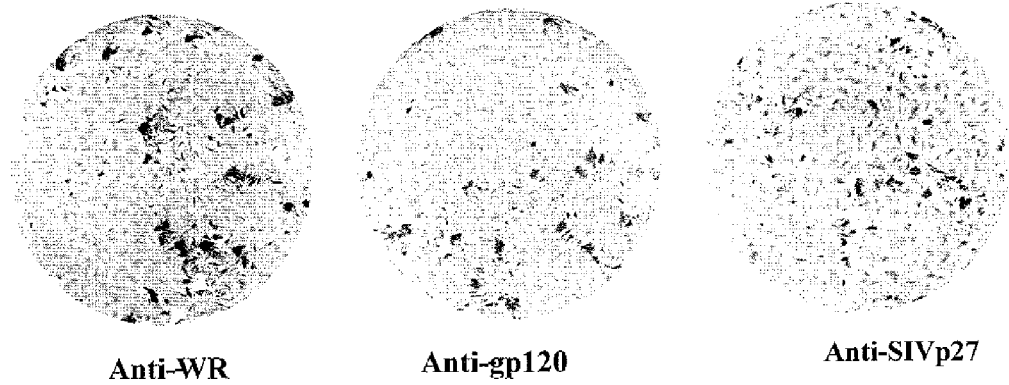
Anti-WR     Anti-gp120     Anti-SIVp27
MVA-89.6P-SIVgpn
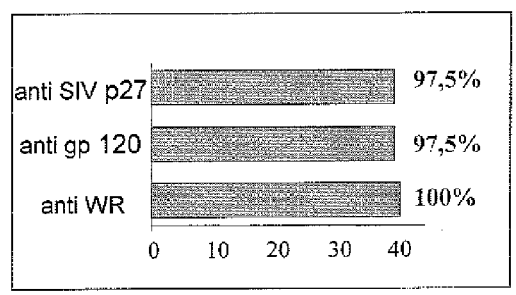

FIGURE 45
A
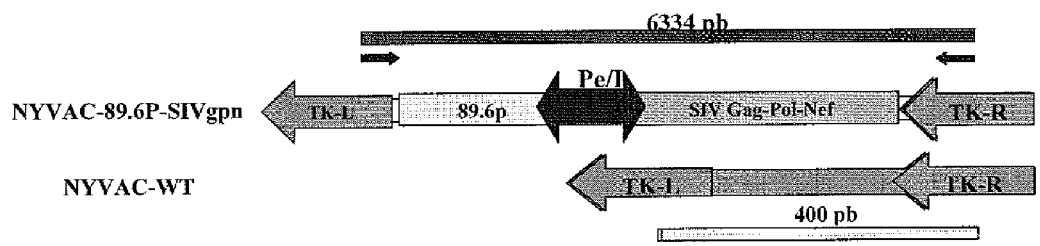
B
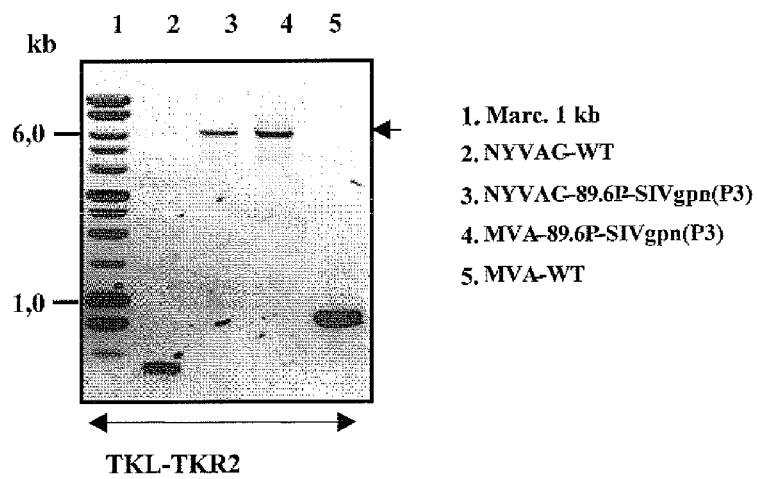
1. Marc. 1 kb
2. NYVAC-WT
3. NYVAC-89.6P-SIVgpn(P3)
4. MVA-89.6P-SIVgpn(P3)
5. MVA-WT FIGURE 46
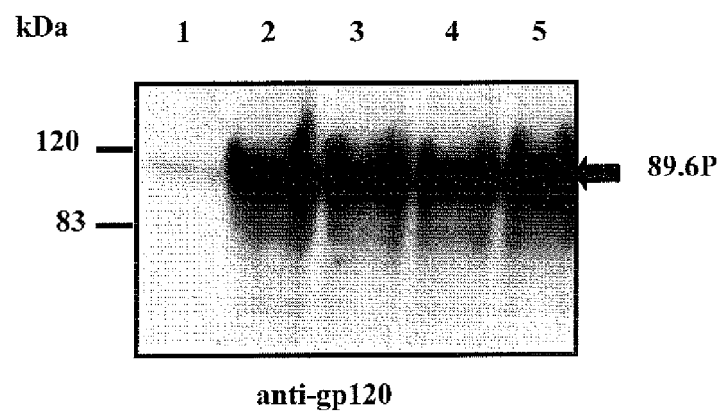
anti-gp120
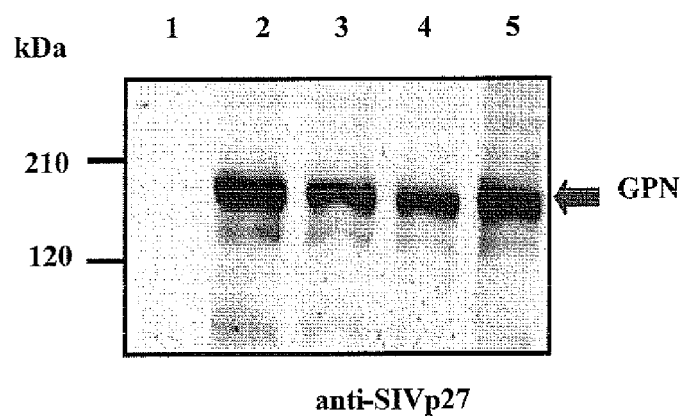
anti-SIVp27

FIGURE 47
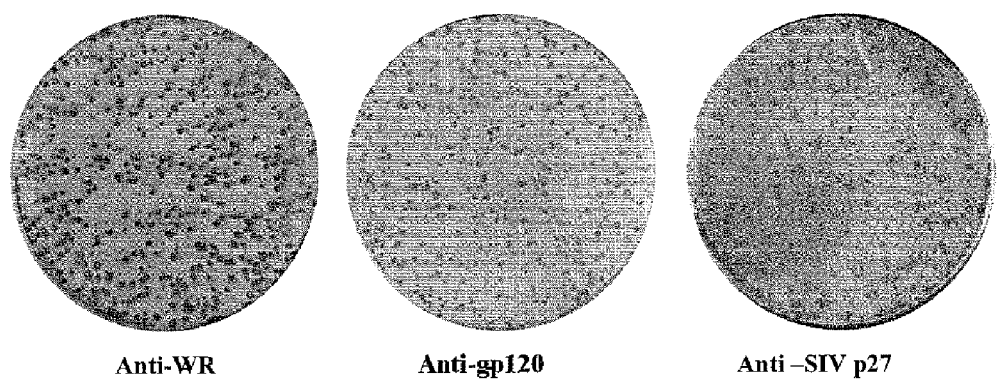
Anti-WR     Anti-gp120     Anti –SIV p27
NYVAC-89.6P-SIVgpn
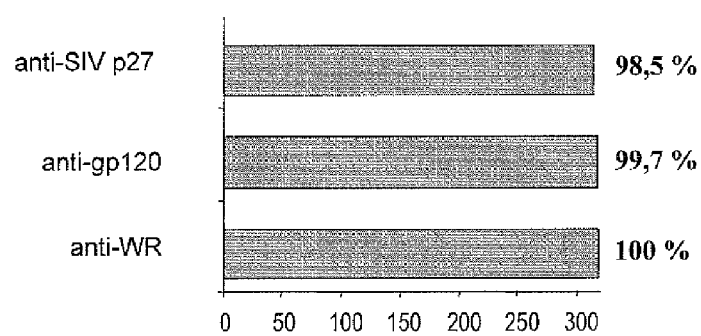

RECOMBINANT VECTORS BASED ON THE MODIFIED VACCINIA ANKARA VIRUS (MVA) AS PREVENTIVE AND THERAPEUTIC VACCINES AGAINST AIDS

The present application claims priority of Spanish patent applications ES200501841 (published as ES2281252-A1 and granted on 28 Jan. 2009) as well as ES200600762 (published as ES2282041-A1 and granted on 23 Feb. 2009).

FIELD OF THE INVENTION

The present invention refers to recombinant viruses that express human immunodeficiency virus antigens (HIV-1), designed to be used as preventative and therapeutic vaccines against AIDS. More specifically, the invention refers to recombinant viruses based on the Modified Vaccinia Ankara virus (MVA) that simultaneously express the gp120 envelope protein and a chimeric protein that results from the fusion of Gag, Pol and Nef. The invention also refers to recombinant viruses based on the Modified Vaccinia Ankara virus (MVA) that express antigens of the chimeric simian and human immunodeficiency virus (SHIV) that are valid to immunize apes and thus be able to verify the degree of protection the apes acquire after being infected with the SHIV virus, a hybrid of the SIV and HIV viruses. In this manner the efficacy of said vectors derived from the MVA as vaccines is confirmed in creatures that are evolutionary very close to humans, and thus susceptible to be infected in a natural manner by a virus similar to the human immunodeficiency virus, which is indicative of the potential of the aforementioned homologous vectors, the MVA-derived viruses that express HIV-1 antigens, to be efficient vaccines to protect humans against the human immunodeficiency virus.

STATE OF THE ART

Data from the WHO indicates that in the year 2004 the AIDS disease had caused more than 23 million deaths, with more than 40 million people infected and with a forecast that there will be more than 60 million people infected by the year 2012. The geographical and economic differences of this disease are evident, since more than 95% of the cases and 95% of the deaths caused by AIDS take place in the third world, most of them in Sub-Saharan Africa and in Southeast Asia, particularly amongst young adults and with a progressive increase amongst women. Amongst the developed countries Spain, with 150,000 cases, continues to be the country with a greater number of infected persons in Europe. Although it is true that an improvement in the health care services of many regions would contribute to reduce the speed of transmission of the virus, there is a consensus in the international community of the urgent need to develop prophylactic and therapeutic vaccines against AIDS that can help solve the problem.

The development of AIDS represents the last stages of the infection caused by the retrovirus known as the human immunodeficiency virus (HIV). The HIV virus is a retrovirus that belongs to the Lentivirus genus and has a genome size of 9.8 kb. The virion contains two copies of single band RNA and has positive polarity. During the first stages of the infection the genomic RNA is converted to linear double band DNA by the action of reverse transcriptase (RT) that arrives to the cell associated to the viral RNA. This DNA is transported to the nucleus, where it integrates in the host cell as a provirus from which the structural genes gag, pol and env, the regulator genes tat, rev, nef, and the accessory genes vif, vpr and vpu are transcribed. The gene translation products are as follows:

The translation product obtained from the Gag gene is the gag-p55 precursor polyprotein that is processed to create the p17 matrix protein, the p24 capsid protein and the p6 and p7 nucleocapsid proteins.

Processing the Pol precursor results in the three viral enzymes: protease (p11), reverse transcriptase (p6S/S1) (RT) and integrase (p32), of which RT has DNA polymerase activity (that is both RNA and DNA dependent) and endonuclease activity (RNasa H), both required during DNA synthesis, while integrase is involved in the provirus integration process, acting as endonuclease.

The product of the Env gene is an 88 kDa strongly glycosylated protein (gp160). This protein is processed by cellular proteases giving rise to proteins gp120 and gp41 that remain joined by non covalent bonds on the virion's surface. The binding sites for cellular receptors—the CD4 receptor and the CXCR4 (known as X4) and the CCR5 (known as C5) coreceptors—are located on the gp120 glycoprotein. This is the protein that is mostly responsible for the genetic variability of the HIV virus and for its capacity to escape both the humoral and cellular immune response mechanisms, because is the protein more exposed on the virus surface. On the other hand, the gp41 glycoprotein or transmembrane glycoprotein, acts as anchor to the lipid membrane. It has a highly preserved hydrophobic area on its terminal amine end that is required for fusion to the viral membrane and to the cell membrane during the process in which the virus enters the host cell.

The regulator and auxiliary genes are codified by six overlapping open reading frame fragments. The Tat and Rev genes are necessary for viral replication in all infected cells. The Tat gene codifies a 14 kDa protein that increases the expression of HIV genes. The rev gene codifies a 19 kDa protein that facilitates transportation of mRNA to the cytoplasm. The Nef protein, having 210 aminoacids, is associated to membrane structures and induces the internalization and degradation of CD4 molecules in lysosomes. The Vif gene codifies a protein necessary for virus propagation in peripheral blood lymphocytes, primary macrophages and in some established cellular lines. The Vpr gene codifies a 15 kDa protein that is associated to the p6 nucleocapsid. The Vpu protein is a phosphoprotein that facilitates dissociation inside the gp160 and CD4 infected cell by degradation of the CD4 molecule in the endoplasmic reticule.

The LTR (long terminal repeats) sequences are found on the 5' and 3' ends of viral DNA, on which there are important regulating regions that play a primordial role during the retrotranscription process.

Two virus classes have been identified: HIV-1 and HIV-2, of which the second, the HIV-2 virus, appears to be less pathogenic than the first and it is mainly localized on the Western part of Africa. HIV-1 is the form of the virus that generates the disease faster, is more extended on the planet and has diversified more. There are three HIV-1 subtypes known as M, N and O, although more than 95% of all HIV isolates, at the global population level, belong to the M subtype. According to the differences found in the nucleotide sequences, particularly in the part corresponding to the envelope proteins (Env), this subtype is further subdivided in eight main lineages that are generally known as clades and are named after the following letters: A, B, C, D, F, G, H and J. Clades B and C represent approximately 80% of the infections worldwide, while in Europe and North America the most representative is the B clade, while C clade is prevalent in Africa and Asia. There are also abundant areas where both types are present in the population (China, India, Sub-Saharan Africa), and this is why it is thought that vaccines containing antigens for clades B and C would be much more efficacious in those areas.

A design possibility for said vaccines consists in generating recombinant DNA molecules containing sequences capable to express HIV proteins or fragments or fusion forms thereof in such a manner that when they are administered to a subject, said proteins, fragments or fusion forms are synthesized and an immune response is generated against them. Said recombinant DNA molecules may be generated from the genomes of viruses in which the regions which expression is necessary for virus replication in the target cells have been eliminated or inactivated and/or in which regions that codify for proteins that are not essential for the virus to develop the intended part of its life cycle in the target cell have been substituted. In these cases the recombinant DNA may be administered as complete viral particles that facilitate transfection of recombinant DNA to the target cell. Amongst the viruses that are used as vectors, the modified forms of the Vaccinia virus are amongst the most tentative viral vectors to be applied as recombinant vaccine. Some of said forms, such as the NYVAC virus, (which genome is represented in the lower part of FIG. 1) have been generated by directed mutagenesis and resulted in the elimination of 18 genes of the Vaccinia virus (Copenhagen lineage), or approximately 10 kb. Other, such as the modified Vaccinia Ankara virus (MVA), have been generated in a less controlled form; more specifically, the MVA has been generated by passing the virus through more than 570 serial passages in primary cultures of chicken embryo fibroblasts (CEF), achieving a loss of 15% of the parental viral genome (1, 2) which entails deletions in genes some of which are intact in the genome of the NYVAC virus (the names of these genes are underlined in FIG. 1) and others have been deleted in both vectors (the names of these genes appear in bold type in FIG. 1), while there are also genes that remain intact in the genome of the MVA virus and present deletions in the genome of the NYVAC virus (the names of these genes appear in italics in FIG. 1). In the MVA virus, the structural genes of the virus have remained unaltered, while the genes involved in evading the immune system (3), and the genes related to the host range (2, 4, 5), have been deleted or fragmented. The MVA virus develops its complete infectious cycle in CEF cycles and in Hamster kidney cells (BHK), while in human cell lineages, including the HeLa cells, it has an abortive cycle (6, 7). Although viral replication depends on the cellular type, the morphogenesis program block in non-permissive cells occurs in the steps that follow the formation of immature viral forms (IV), without alterations of the expression of early and late viral genes (8, 9). In cultured cells, the MVA recombinant vectors produce similar or greater levels of heterologous protein than the vectors derived from the wild strain of the Vaccinia WR virus (Western Reserve) (9-11), which makes it interesting as an expression system. In mammals, Recombinant MVA vectors have been shown to induce protective immunity before a wide spectrum of pathogens (6, 12-16), exhibiting the following advantages as expression vector for heterologous antigens:

High level of safety, as evidenced when it was used in more than 120,000 subjects during the smallpox eradication campaign that took place in Germany.

Avirulent in a wide number of animals in immunosuppressor conditions.

Little or no systemic or local reaction after inoculation in humans, including high risk subjects.

Highly plastic and stable genome, which enables the introduction of large quantities of exogenous genic material.

Potent inducer of efficacious immune responses against a large variety of antigens.

Given its safety and capacity to generate protection, it may be very useful in generating live vaccines against infectious diseases and in cancer therapy applications. As any other vaccine intended for humans, in order to carry out clinical trials to test the possible efficacy of MVA-derived vectors as vaccines, it is first necessary to obtain prior information about its immunogenic behavior and its capacity to confer protection in animal models. In the case of AIDS, however, it is not easy to find a suitable animal model. The usual animal species that are used for experimentation with other diseases, such as mice, are not suitable for infection models, since neither the human immunodeficiency virus (HIV) nor the simian equivalent, the simian immunodeficiency virus (SIV) replicate in them. What it is possible is to obtain prior information from mice about the immunologic behavior of the vectors under study that will enable a prior evaluation of its possible efficacy and help to either rule out or continue with the essays if they prove to be of interest. Also, the transgenic mouse model that expresses the human histocompatibility antigen MHC class I (HLA-A2) allows demonstrating whether vaccination confers an antigenic presentation similar to that of humans by the HLA-A2 antigen, which is the prevalent in the population, something that is not possible to do at the moment in primates because there are no transgenic primates having said human antigen. Studies on the protection conferred by vaccines require, however, models other than the mice model.

In this sense, the non-human primate models have become important to evaluate the candidate AIDS vaccine in clinical trials. Infecting chimpanzees with the HIV-1 virus has shown to have important limitations, such as its high cost, little availability and the absence of clinical symptoms. It has been found that the simian immunodeficiency virus (or SIV) is a much more useful model. It is a lentivirus that infects several types of primates naturally. Five subgroups of this virus have been described. The isolated Macacus rhesus (*Macaca mulatta*) form, known as SIVmac, belongs to the first type.

In the same manner that occurs with the HIV virus, its genome is characterized in that it has two LTR sequences in the 3' and 5' ends in which the promoter and the regulator or transcriptional factor binding sequences are found. They have three open reading frames for structural proteins: gag, pol and env; open reading frames for regulator genes: nef, tat and rev; and for the so called accessory genes: vif, vpr and vpx. The members of the SIVmac subgroup share a high degree of genetic homology with the HIV-2 class virus.

The SIV and HIV viruses share some characteristics, such as cellular tropism, genomic organization, ultra-structural characteristics, mode of transmission, the host response to infection and clinical symptoms of the disease except in the case of asymptomatic infections. These characteristics have made the SIV based models attractive to evaluate the efficacy of vaccine candidates and design new vaccines to be tested in humans.

The SIV infection is characterized by a maximum viremia during the first two weeks followed by a decrease of viral levels until it reaches a point that is variable and on which the progression of the disease will hinge. The period of viral incubation is shorter than that provoked by HIV infection. The variability of the progression of the disease depends on the genetic heterogeneity of the Macacus monkeys used in the experiments, as well as that of the virus used in the challenge and the pathway of exposure (intravenous, mucous, or perinatal). The response of the host to the SIV infection is similar to that generated against HIV infection, but it differs in the specificity of the neutralizing antibodies against the envelope antigens.

The SIV virus has several disadvantages as experimentation model. First, it is a virus different from the HIV virus, and therefore the envelope proteins, which are the essential target of the neutralizing antibodies, are very divergent in both models. Another disadvantage is that the SIV virus only uses the CCR5 coreceptor to enter the cell, while the HIV virus uses additionally other coreceptors such as the CXCR4, the CCR2 or the CCR3. For these and other reasons, the quality and efficacy of a candidate tested in this model is not considered necessarily as extrapolable to humans.

To overcome these disadvantages, a hybrid virus from SIV and HIV was first obtained in 1991. This virus was named the Simian-Human Immunodeficiency Virus or SHIV (25). This hybrid contained the env and tat genes from HIV and the remaining genetic material was that of SIV. SHIV was able to infect Macacus rhesus monkeys, although it was not capable of reproducing the characteristic symptoms of AIDS in the animals inoculated with it.

This first hybrid virus made possible to have a useful infectious model for Macacus monkeys for protection against infection studies, although this model still did not allow concluding whether the vaccine candidates were capable to confer protection against the disease. A few years later through successive passages through Macacus monkeys and in culture, lead to the isolation of several aggressive SHIV variants capable not only to infect Macacus monkeys, but to produce a syndrome similar to that of AIDS. These strains, adapted to multiply in the animals thus inoculated provoked the depletion of $CD4^+$ lymphocytes and caused the death of the Macacus monkeys less than 1 year after inoculation. One of the most used SHIV variants amongst those, is the SHIV89.6P variant obtained by means of serial passages in Macacus rhesus monkeys of the SHIV89.6 parental virus that contains the gag, pol, vif, vpx, vpr and nef genes of the SIVmac239 simian virus, while the auxiliary genes tat, rev and vpu and the envelope protein env gene come from a cytopathic isolate of the HIV-1 subtype, the HIV89.6 virus (26, 27). The SHIV89.6P virus and similar have provided a model to evaluate the protection against disease and death conferred by the possible vaccines being developed.

This model has made possible to carry out studies in Macacus monkeys that have demonstrated the relevance of recombinant MVA vectors as a potential vaccine against HIV, especially when used in combined immunization systems in which two or more vaccination doses separate in time are administered, providing, at least in the first dose a vector that is different from the following doses, although the antigens expressed from each of the vectors may be the same. These vaccination protocols—in which a first dose that triggers the immune response is supplied with a vector that gives rise to the expression of an antigen and one or more subsequent boosting doses to reinforce the immune response generated with the first dose contain a different vector, although it generally triggers the expression of the same antigen—are often known in Spanish by their English name prime/boost protocols. These protocols are considered especially suitable for the prevention or treatment of infections caused by the HIV virus, since on the one hand they avoid having to administer attenuated live forms of the virus, resorting only to the use of some of its components, and on the other hand, the use of expression vectors capable to enter the cells rather than having to resort to the direct administration of the proteins that express it, makes possible that the proteins that must act as antigens are present in the cytoplasm of the host cell to processes them by means of the MHC class I antigen presentation pathway, a process required to trigger the immune response of the T cells, particularly the cytotoxic immune responses associated to the $CD8^+$ T lymphocytes. Lastly, using different vectors in each dose decreases the possibility that the vaccination factor as such is quickly eliminated by the host's immune system, thus avoiding boosting the immune response directed against the parts of the vector that do not come from the specific microorganism against which protection is sought.

In the studies with Macacus monkeys (12), the MVA-derived recombinant vectors have shown to be particularly useful to be used in combined prime/boost protocols of the immune response with different vectors, especially when the MVA-derived recombinant vector is administered in the second and/or in some of the subsequent doses and expresses—like the vector used in the first dose—multiple HIV and SIV (Simian Immunodeficiency Virus) antigens. The response of the cytotoxic T cells and the memory cells that is generated by this approach shows the potential of MVA-derived recombinant vectors as vaccines against the HIV virus (17).

For these reasons, different recombinant vectors based on the MVA virus have been designed that are capable to express several HIV antigens. Trying to find more efficacious forms to generate a protective response, vectors capable of expressing more than one protein of said virus have been constructed, on occasion forming fusion proteins. Some examples are found, for instance, in patent applications WO 02/072754 and WO 2004/087201, in which MVA-derived vectors are described that express the Env, Gag and Pol (rMVA) proteins, considering as an additional option that the immunizing antigen includes also vif, vpr, tat, rev, vpu or nef, sequences, although not discussing that the expression of some of theses sequences may be very important in terms of the possible protection response generated, or without using this option in the embodiments of the invention. Although in these international patent applications it is mentioned that the vif, vpr, tat, rev, vpu or nef sequences, as well as those corresponding to env, gag and pol, may generally codify only fragments of the corresponding protein and/or present mutations, a defining characteristic of the invention that said international applications try to protect is that the env gene lacks part or all of the nucleotides that codify the cytoplasmic domain of the gp41 protein. The state of the art does not describe specifically the possibility that the part that codifies for the gp41 protein is completely eliminated, nor the possible consequences this may have. This not withstanding, both patent applications mention in their respective example section that said envelope proteins, because of the truncation of the gp41 protein, can accumulate more easily in the membrane of the cells that express it, a fact that is treated as an intended positive effect. Also treated as a desired positive effect is the formation of particles similar to the HIV virus in which the Gag and Env proteins are present and can be detected, amongst other locations, outside the cells that the corresponding proteins have expressed. In terms of the insertion site of the expressed sequences, there is no mention of this fact having a particular significance except to manifest as positive the fact that choosing the deletion III site as one of the sites in which sequences are inserted allows the MVA-derived recombinant vector to continue to be $TK^+$. This implies that the MVA-derived recombinant vector described in said state of the art section expresses thymidine kinase, and therefore maintains certain virulence. Also not discussed is the fact that using more than one insertion site to include in the vector the sequences that codify the antigens whose expression is desired has any relevance, and evidence to show the stability of said vectors is not provided.

Patent application WO 2004/035006 also describes MVA-derived vectors that contain codifying sequences of several HIV proteins expressed as fusion proteins, specifically a Gag-Pol fusion and a nef-tat fusion. However, the approach is different from the international patents previously mentioned: the goal in this patent application is to avoid packaging in viral proteins. The solution proposed is that at least one of the HIV protein codifying sequences is bound to a heterologous leader sequence, selecting the tPA sequence for the embodiments corresponding to the MVA-derived vectors, and thus promoting the secretion of the synthesized proteins. In what regards sequence insertion, also, preference is shown for the deletion III site, using again the same vector a second insertion site for the additional sequences—deletion II—for a tPA-nef-tat fusion protein, without considering that this course of action may have consequences for the stability of the vector or carrying out experiments to verify that it is indeed stable. Also, the only form considered for the env sequence, delta V2 env, has deletions in the part corresponding to the gp120 protein, again not considering the possibility of eliminating the gp41 protein or the possible consequences this may have.

The present invention provides different recombinant vectors derived from the MVA virus that are capable to express various HIV antigens and respond to an approach different from the ones described in previous patent applications. These MVA-derived recombinant vectors have sequences that enable the simultaneous expression of the gp120 protein and of the Gag-Pol-Nef fusion protein. Both the sequence expressing the gp120 protein as the Gag-Pol-Nef fusion protein sequence are inserted in the same site, the site that corresponds to the thymidine kinase gene. This fact increases the stability of the vectors, because there is only one single site of insertion as compared to other MVA-derived vectors that contain several HIV protein codifying sequences. And since these vectors carry each sequence in a different site of the MVA virus, they easily lose the inserts present in them. Also, using the thymidine kinase locus specifically as insertion site causes the vectors object of the invention to be MVA-derived recombinant viruses, which are safer as vaccines because they lack one gene, the thymidine kinase gene that is involved in the virulence aspect. Contrary to what is described in patent applications such the WO 02/072754 and WO 2004/087201 applications, the expression of the gp120 protein the absence of gp41 protein related sequences, enables their release to the extracellular media a few hours after they have been synthesized in the cytoplasm of the infected cell, which facilitates both the induction of the humoral and the cellular responses against this protein, the one protein which sequence has a greater variability from amongst the different clades.

The recombinant viruses of the present invention express, at least, four antigens: Env, Gag, Pot and Nef, because it is considered that a vector that expresses said four antigens is much more efficacious than recombinant vectors capable to express only some of said antigens or even other antigens, because of the capability of the selected antigens to induce specific cellular responses, and because of the lesser genetic diverse that exists amongst HIV isolates in terms of the Gag, Pol and Nef sequences. Also, the presence of sequences that correspond to the regulator gene nef, together with those corresponding to the structural gag, pol and env genes is considered a particularly interesting characteristic of the present invention, because it is expressed in early stages of the HIV cycle and the generation of a cellular response to its products is regarded as necessary to increase the repertoire of the immunological defense against HIV and thus attain an adequate protective response that permits the immunological control of the HIV-1 infection. The association of the codifying sequences for gag, pol and nef has been done in the vectors object of the invention in a manner that would generate the fusion proteins necessary to maintain all the epitopes capable of generating a cellular response, and thus enabling a greater antigenic representation than other vectors that express fusions corresponding only to the Gag and Pot proteins, but generating a fusion protein that does not proteolyze by the action of the viral protease, does not give rise to the formation of viral particles, and contrary to what happened to the proteins expressed by other vectors of the prior art, accumulates in the cytoplasm as a stable polyprotein. Using an identical synthetic promoter to direct the expression of both the gp120 protein and the fusion of Gag-Pol-Nef—a promoter chosen to enable the expression of the corresponding proteins in early and later stages of the MVA replication—enables the simultaneous expression of the gp120 protein sequence and of the Gag-Pol-Nef chimeric protein, its accumulation throughout the MVA infection cycle and their antigenic processing during early and later stages.

A group of vectors object of the invention have been specifically designed for human vaccination purposes. In these vectors, both the sequence of the gp120 protein as the sequence of the Gag-Pol-Nef fusion protein has been generated from sequences of the human immunodeficiency HIV-1 virus. Using sequences obtained specifically from natural isolates that belong preferably to the HIV-1 clades more represented in nature (the B and C clades) in the generation of recombinant vectors also makes possible a worldwide vaccine more representative of the infected or of the at risk population. Based on all of the above, using these vectors for vaccination purposes, in an isolated manner or as part of immunization protocols during which antigen codifying vectors are administered in several dosages spaced in time, has been considered as being particularly useful to help contain the expansion of the HIV virus. In addition, these MVA-derived vectors represent both an alternative to similar constructions derived from the NYVAC virus as a useful complement to use each of said recombinant vectors in different phases of immunization protocols during which one or two doses are administered to trigger the immune response and one or more successive doses are administered to boost it, since the tests done so far by the group of inventors show that, in addition to differ in their genome and in the immune response that generate in mice against the HIV antigens gp120 and Gag-Pol-Nef, both vectors exhibit a different behavior in cellular cultures than in animal experimentation models (induction of different patterns of human gene expression in HeLa cells, less induction of apoptosis by MVA than by the NYVAC vector, the latter inducing greater cellular destruction and humoral response against itself (28)). This differential behavior allows us to predict that their behavior will also be different after they have been administered to humans as recombinant vectors vaccines generated from each of said vectors.

As it is described later in Example section of the present report, the trials done with mice show the immunological capacity of these vectors object of the invention designed for purposes of human vaccination and, in particular, of the two embodiments of the inventive vectors that were used in the trials, the MVA-B and the MVA-C vectors. This not withstanding, in order to evaluate their capacity to confer protection to control the HIV infection, it is necessary to resort to a non-human primate model, such as the Macacus rhesus monkeys mentioned before, so these animals are subjected to a triggering/boosting protocol of the immune response and in which later the capacity to control the infection of the immune response generated in this manner is evaluated to see if it is capable to confer after challenging it by inoculating a virus capable to infect the Macacus monkeys and to cause in them symptoms similar to those of AIDS. For this type of challenge, one of the pathogenic variants of the SHIV virus mentioned previously would be suitable. These type of trials, however, cannot be carried out with the inventive vectors that have been designed for purposes of human vaccination, vectors which inserts codify proteins exogenous to the MVA virus, all derived from sequences of HIV-1 proteins. They require the generation of special vectors that fulfill the following conditions:

a) Contain retroviral codifying sequences having the same origin as those contained in the virus that is going to be used during the challenge. This virus may very well be the SHIV virus, so the sequence corresponding to the env gene will come from the HIV-1 virus, while the possible sequences corresponding to other genes such as gag, pol or nef, will come from the SIV virus.
b) Present the same genic organization structure, insertion site and promoters than the vectors designed for human use and to which they are being compared.

Satisfying these conditions will make the study viable and will also make possible that from the results obtained the expected behavior in humans may be extrapolated when using in humans the vectors to which the are being compared. The present invention also provides vectors that allow assessing the protective capacity that could be generated in humans vaccinated with the recombinant viruses object of the present invention, derived from the MVA virus and having exogenous sequences that are all derived from HIV-1 protein sequences. Additionally, analogous recombinant vectors built from another derivate of the poxvirus, the NYVAC virus, are provided in order to be able to compare the effect of both of them.

DESCRIPTION OF THE INVENTION

The invention provides new recombinant vectors derived from the MVA virus that are capable of simultaneously express a form of the HIV-1 Env protein that lacks the part corresponding to the gp41 protein and a fusion protein corresponding to the Gag, Pol and Nef HIV-1 virus that does not proteolyze through the action of the HIV protease, the Env protein and Gag-Pol-Nef fusion protein sequences being under the control of identical promoters inserted at the same insertion site of the vector. These vectors object of the invention, in which the codifying sequences of MVA exogenous antigens are all derived from sequences belonging to the human immunodeficiency virus 1 (HIV-1), have been designed in order to manufacture with them drugs that can be used as preventative or therapeutic vaccines against AIDS in human beings. To do this, and to differentiate the vectors of the present invention that will be described from here on and that comprise the sequences derived from the SIVmac virus and have been designed to be administered to Macacus monkeys, in the present report, on occasion, the first such vectors object of the invention are referred to as "the vectors object of the invention designed for human vaccination purposes", "the MVA-derived vectors designed for human vaccination purposes" or similar expressions. For clarity purposes when using these expressions, said vectors are on occasion also referred to as "the vectors in which the codifying sequences of MVA exogenous antigens are all derived from HIV-1 characteristic sequences".

Therefore, the invention also refers to both the composition of said recombinant vectors as to the use of said vectors in the manufacture of a drug intended as a vaccine to help prevent or treat the infection caused by the HIV virus.

The expression of the Env protein synthesized from the vectors of the present invention originates gp120 proteins that are not associate to gp41 proteins or to fragments of said protein, which facilitates the exit of the cell and their release to the media, which in turn makes activation of B cells and the production of HIV neutralizing antigens more probable. In the preferred embodiments of the vectors of the present invention, the nucleotide sequence corresponding to the Env protein part of the vectors object of the invention codifies a complete gp120 protein, having deleted all the env gene sequence, that in the natural sequence of said gene appears after the last triplet corresponding to the gp120 protein, and thus eliminating the complete codifying sequence corresponding to the gp41 protein.

The Gag, Pol and Nef fusion protein is designed in such a manner that it does not originate the formation of particles that are similar to viral particles. The form used to construct the embodiments of the invention, that are described in detail in the present report, accumulate in the cytoplasm of the cells infected with the recombinant vectors object of the invention in polyprotein form, without experiencing the characteristic processing of the HIV virus caused by viral protease that would cause its splicing into smaller proteins, although later it will experience the cellular process that allows the presentation of antigenic peptides of fusion protein and the generation of an immune response against them.

It is especially preferred that the site of the vector in which the sequences of the Env protein and the Gag-Pol-Nef fusion protein are inserted be the thymidine kinase gene, a gene that is then deactivated by the presence of the sequences inserted in it, which increases the safety of the vectors object of the invention to be administered to subjects with the purpose of generating in them an immune response to HIV. In the preferred embodiments of said vectors of the present invention, designed to vaccinate humans, the codifying sequence of the Gag-Pol-Nef fusion protein is generated from the Gag, Pol and Nef proteins sequences for which a cDNA sequence is deducted using reading codons frequent in mammals to increase the levels of expression of the fusion protein. In addition, in the codifying sequence of the fusion protein modifications of the natural sequences are provoked to increase their immunogenecity and their safety. The preferred modifications include inactivation by mutagenesis of the protease active site and the elimination by deletion of the integrase active site, deletions in the nef gene and its insertion in the codifying region of the RT, translocation of the RT active site to the C-terminal end of the fusion protein and the fusion of the gag gene sequence in reading phase with pol-nef, creating a deviation of a reading phase and introducing a glycine to alanine change to prevent the formation of virus-like particles. Amongst them and specifically preferred are the modifications done to generate the sequence corresponding to the fusion protein as described by Didierlaurent A. et al. (18). An outline of the elements that configure the Gag-Pol-Nef fusion protein that meet all these characteristics is shown in the lower part of FIG. 40 marked as GagPolNef (gpn).

In the preferred embodiments of the vectors of the present invention which design is intended to serve as vaccination for humans, the promoter is selected in a manner conducive to the expression of the Env protein and of the fusion protein Gag-Pol-Env both in early and late stages of the infective cycle of the MVA virus. The early/late synthetic promoter of the pE/L poxvirus (19) has been selected for the more preferred embodiments of the invention, although any other poxvirus promoter could be used in the same manner to build the vectors object of the invention.

In a particularly preferred embodiment of the vectors object of the invention designed for purposes of human vaccination, in which the codifying sequences of MVA-exogenous antigens are all derived from HIV-1 characteristic sequences, both the sequence corresponding to the Env protein as the sequences used to generate the sequence that originates the Gag-Pol-Nef fusion protein come from natural B and/or C clade isolates. In even more preferred embodiments of the present invention, the sequence corresponding to the Env protein and the sequences used to generate the sequence that originates the Gag-Pol-Nef fusion protein come from natural isolates belonging to the same clade, preferably the B clade or the clade, but those embodiments in which the sequence corresponding to the Env protein comes from an isolate from one clade and the sequences used to generate the sequence that originate the Gag-Pol-Nef fusion protein come from an isolate from a different clade are also considered embodiments of the present invention.

Also included within the scope of the present invention are those embodiments in which at least one of the sequences used to generate the sequence corresponding to the fusion protein, that is, the gag sequence, the pol sequence or the nef sequence, come from a different isolate, and in which said three isolates from which each of the corresponding codifying sequences is obtained may be a different one and, even not belong to the same clade. The compositions of the present invention that contain the recombinant vectors object of the invention, intended for vaccination purposes against the HIV virus, may contain recombinant vectors generated solely from isolates from a specific clade, preferably the B or C clades, mixes of recombinant vectors from different clades in which each of the vectors has been constructed with sequences from isolates of one single clade, vectors that are identical to each other that have been constructed from sequences of isolates from different clades or mixes of any of the vectors included within the scope of the invention. The preferred compositions are those that contain the inventive vectors that have been generated from one single clade, preferably the B or C clades, or mixes of vectors generated from isolates of the B clade and vectors generated from isolates of the C clade. The compositions containing vectors that have been both generated from isolates of the B clade and from isolates of the C clade must be of special usefulness in the prevention and/or treatment of the HIV infection in those areas in which both clades are represented in a significant manner.

In the embodiments of the invention which construction is described in examples of the present report, the sequence corresponding to the Env protein is inserted in the opposite direction to the direction of the transcription of the Gag-Pol-Nef fusion protein. The promoters of each of the sequences corresponding to HIV proteins are inserted in opposite directions and in the most internal area of the insert. Each of the vectors of the present invention designed for purposes of human vaccination which construction is described were generated from natural isolates corresponding to different clades. The first vector, the MVA-B vector, allows the expression of a form of the env gene obtained from isolating HIV BX08, originary from Europe, and a Gag-Pol-Nef fusion protein resulting from the translation of a polynucleotide sequence generated from sequences corresponding to the gag, pol and nef genes obtained from the IIIB isolate that is part, as the BX08 isolate, of the B clade. The second vector, the MVA-C vector, allows the expression of a form of the env gene obtained from the HIV CN54 isolate, which originated in China, and a Gag-Pol-Nef fusion protein that results from the translation of a polynucleotide sequence generated from sequences corresponding to the gag, pol and nef genes of the same CN54 isolate, belonging to the C clade. The amino acid sequences expressed from each of the env genes contained in the MVA-derived vectors reproduces the complete sequence of the gp120 proteins from the BX08 isolate viruses, in the case of the MVA-B, and from the CN54 isolate viruses in the case of the MVA-C. The vector construction and the evaluation of their immunogenic capacity in mice are described later in this document with the aid of FIGS. 1 to 38 and Examples 1 to 32 in later sections of this document. However, and as was noted above, mice are not an adequate model to evaluate the capacity of the vectors to control HIV infection in humans immunized with said vectors. To do that, it is more appropriate to resort to animals that are evolutionary closer to human beings, such as non-human primates like Macacus rhesus, that can be inoculated with a virus capable to infect them and cause in them a syndrome similar to AIDS. Some pathogenic variants of the SHIV virus such as SHIV89.6P meet the above conditions. Challenge the immunological response thus caused by one or more vaccination vectors with a variant of the SHIV entails that immunization cannot be done with the inventive vectors described above, that are designed to express proteins derived from sequences characteristic of the virus against which infection protection is sought—the HIV-1 virus—since the assay would not reproduce the conditions as would occur in a human infection process. Thus, in order to be able to evaluate the capacity to control the infection of the vectors of the present invention, designed to vaccinate humans, special vectors must be generated. Those special vectors fulfill several conditions:

a) Contain retroviral codifying sequences having the same origin as those contained in the virus used for the challenge—a virus that may be the SHIV virus—in such a manner that the sequence corresponding to the env gene will come from the HIV-1 virus, while the possible sequences corresponding to other genes such as the gag, pol or nef genes will come from the SIV virus;

b) Present the same genic structural organization, insertion site and promoters than the vectors designed for humans with which they are going to be compared.

The invention also provides vectors that fulfill these characteristics, which are also objects of the present invention. Hence, the invention also refers to new recombinant vectors derived from the MVA virus capable to express simultaneously a form of the Env protein from HIV-1 that lacks the part corresponding to the gp41 protein and a fusion protein that contains sequences from the Gag, Pol and Nef proteins of the Simian Immunodeficiency Virus (SIV), and in which the sequence corresponding to the Env protein and the sequence corresponding to the Gag-Pol-Nef protein fusion are under the control of identical promoters and both inserted at the same insertion site of the vector. In both of these vectors, the fusion protein corresponding to the Gag, Pol and Nef proteins is not synthesized from sequences coming from HIV-1, but from sequences of the SIVmac (simian immunodeficiency virus isolated from Macacus monkeys). This a difference with the vectors designed for vaccinating humans. This difference allows that the vectors with SIVmac sequences may be used in immunization protocols involving Macacus monkeys and later in the immunity challenge created with a pathogen SHIV virus in which the sequence of the env gene is derived from the corresponding sequence of an HIV-1 isolate, while the sequences corresponding to genes gag, pol and nef corresponds to the simian virus that infects the Macacus monkeys.

In this manner, the retroviral coding sequences contained in the vectors designed to carry out clinical trials in Macacus monkeys, as well as the sequences present in the retrovirus that is going to be used for the challenge, have as origin the same type of virus. Thus, the immunity generated against the proteins synthesized from said vectors will serve to control the infection triggered by the retrovirus inoculated in the challenge.

In order for the parallelism established between the results observed in Macacus monkeys and those that could be expected in humans to make sense, the vectors object of the invention designed to carry out experiments in Macacus monkey fulfill the condition of having the same genic organization structure, insertion site and promoters than the vectors object of the invention designed for purposes of human vaccination with which they are going to be compared. According to this, in an analogous manner to the vectors in which the codifying sequences of MVA exogenous antigens are all derived from sequences characteristic of HIV-1, the expression of the Env protein synthesized from the vectors object of the invention designed to be used in Macacus monkeys results in gp120 proteins that are not associated to gp41 proteins or to fragments of said protein, which facilitates their exiting the cell and their release into the media, which in turn increases the probability of activating the B cells and the production of HIV neutralizing antibodies. In the preferred embodiments of the present invention, the sequence of nucleotides corresponding to the Env protein belonging to the vectors object of the invention codifies a complete gp120 protein, the entire sequence of the env gene that naturally appears after the gp120 protein having been deleted, and thus eliminating the complete coding sequence corresponding to the gp41 protein. An outline of the Env protein sequence belonging to the vectors object of the invention is shown in the upper part of FIG. 40. The last graph correspond to the gp120 protein sequence expressed from the from the vectors object of the present invention, and shows that the entire codifying sequence of the gp41 protein has been eliminated, while the prior graphs represent envelope proteins with sequences corresponding to the gp41 protein.

As for the Gag, Pol and Nef fusion protein, is designed—also in an analogous form to the homologous protein synthesized from the vectors in which the corresponding codifying sequence is derived from sequences characteristic of HIV-1—in a manner that does not give rise to the formation of particles that are similar to viral particles. The form used to build the embodiments of the vectors object of the present invention, that are described in a detailed manner in this report, accumulates in the cytoplasm of the cells infected with the recombinant vectors object of the present invention as a polyprotein, without experiencing the processing characteristic of the HIV virus caused by the viral protease that would splice it into smaller proteins, although later it will experience the cellular processing that allows the presentation of antigenic peptides from the fusion protein and the generation of an immune response against them.

As it has been noted previously, the main utility of the vectors object of the present invention comprising sequences derived from the SIVmac virus is to be used in immunization protocols to extract data on their possible usefulness as vaccines from vectors designed to be administered to human beings, that must have the same gene structure, the same promoters and the same insertion site. That is the reason that the embodiments equivalent to the preferred embodiments of the vectors object of the present invention designed for human vaccination purposes (excepting those that refer to HIV-1 isolates as the preferred origin of the codifying sequences of the Env and Gag-Pol-Nef proteins) are also preferred embodiments for the vectors designed to carry out clinical trials in Macacus monkeys. Therefore, it is especially preferred that thymidine kinase be the vector site at which the Env protein sequences and the Gag-Pol-Nef fusion protein are inserted, since this is a virulence-related gene that would then be rendered inactive by the presence of the sequences inserted in it, which also increases the safety of the vectors.

In the preferred embodiments, the codifying sequence of the Gag-Pol-Nef fusion proteins is generated from the sequences of the Gag, Pol and Nef proteins in which a cDNA sequence is deducted using reading codons frequently encountered in mammals, the intention behind it being to increase the levels of expression of the fusion protein. Also, modifications from the natural sequence have been provoked in the codifying sequence of the fusion protein to increase its immunogenecity and its safety. The more preferred modifications include deactivation by mutagenesis of the protease active site and the elimination by deletion of the integrase active site, deletions in the nef gene and inserting it in the RT codifying region, translocation of the RT active site to the C-terminal end of the fusion protein, and the fusion of the sequence of the gag gene in reading phase with pol-nef, thus creating a deviation from a reading phase and introducing a glycine to alanine change to prevent the formation of virus-like particles. Amongst these modifications, the preferred are specifically those modifications that have been done to generate the sequence corresponding to the fusion protein described by Didierlaurent A., et al. (18). As is was the case for the Gag-Pol-Nef proteins derived from sequences characteristic of HIV-1, the Gag-Pol-Nef proteins that fulfill all these characteristics, although in this case they have been derived from sequences characteristic of the SIVmac virus, are represented by the outline shown on the lower part of FIG. 40 and labeled as GagPolNef (gpn).

In the preferred embodiments of the invention, the promoter is selected in a manner conducive to the expression of the Env protein and of the Gag-Pol-Env fusion protein both during early and late stages of the infective cycle of the MVA virus. The option chosen for the more preferred options of the present invention is the early/late synthetic promoter of the pE/L poxvirus (19), although any other poxvirus promoter could be similarly used to construct the vectors object of the present invention.

Examples 1 and 19 describe, respectively, the construction of the vectors known as MVA-B and MVA-C vectors, that are each embodiments of the vectors object of the present invention, designed for purposes of human vaccination, that fulfill all the characteristics preferred for these inventive vectors. In them, the sequence corresponding to the Env protein is inserted in the direction opposite to that of the transcription of the Gag-Pol-Nef fusion protein, and the promoters corresponding to each of the sequences corresponding to HIV proteins are inserted in opposite directions and in the most internal part of the insert.

In order to extract data regarding the possible protection that these vectors may confer to the humans vaccinated with them, this report contains the construction process of a vector also obtained from the MVA virus that has similarly inserted in the thymidine kinase locus an insert that comprises the codifying sequence of a Gag-Pol-Nef fusion protein generated from sequences of the SIVmac virus in which all the modifications previously listed have been implemented as detailed by Didierlaurent et al. (18), and under the control of an early/late synthetic pE/L promoter, as well as the codifying sequence of a gp120 protein, that originated in a HIV-1 virus, that lacks completely the codifying part corresponding to the gp41 protein, and is similarly under the control of an early/late synthetic pE/L promoter, the promoters corresponding to each of the sequences corresponding to HIV proteins being inserted in opposite directions and in the most internal area of the insert. The vectors that satisfy these characteristics have been named, in a general manner, MVA-SHIV vectors.

The chimeric simian and human SHIV89.6P virus has been selected for the challenge subsequent to the administration of the MVA-SHIV vector. The construction process of said vector is described later in this report. Therefore to be able to carry out the experiments to assess the protection conferred by immunization with the vector in optimum conditions, an MVA-SHIV vector has been constructed which genome contains an insert configured by both the codifying sequence of the 89.6P-gp120 protein, that is, a sequence corresponding to the Env protein of the SHIV89.6P virus (which originally came from the 89.6 isolate of the HIV-1 virus), modified to completely lack the part corresponding to the gp41 protein, as codifying sequences for the Gag, Pol and Nef antigens of the aforementioned SHIV89.6P virus (which originally came from the simian immunodeficiency virus, Macacus isolate, SIVmac239), from which the sequence corresponding to the SIVgpn fusion protein has been generated carrying out in them the preferred modifications of the present invention. That is the reason the vector built in this manner is specifically named MVA-89.6P-SIVgpn vector, or in a more detailed manner the MVA-gp120-HIV89.6p-SIVmac239-gag-pol-nef vector.

It has been considered appropriate, both in the Examples that describe the immunogenecity studies done with the MVA-B and MVA-C vectors, as the Examples intended to assess the immunogenic capacity of the vectors object of the invention designed to carry out trials in Macacus monkeys, and additionally their capacity to confer protection against SHIV caused infections, to a have a positive control to compare against the results obtained with the MVA-derived vectors against. To that end the vectors used have been recombinant NYVAC-derived vectors having the same genic organization structure, same site of insertion in the viral genome (the thymidine kinase locus (TK)) and the early/late synthetic promoters located in the same arrangement as that of the MVA-derived vector that they are going to be compared to: the NYVAC-B vectors (used in the studies done with MVA-B), the NYVAC-C vectors (used in the studies done with MVA-C) and an additional vector that is included for comparative studies with the vectors known as MVA-SHIV vectors, that have been specifically designed to carry out the studies to evaluate the protective capacity described in this report, and which abbreviated name is NYVAC-SHIV. Taking into account the provenance of the sequences contained in its insert, identical to that of the sequences present in the vector known as MVA-89.6P-SIVgpn or to that of the comparison vector MVA-gp120-HIV89.6p-SIVmac239-gag-pol-nef, the specific NYVAC-SHIV vector which construction is described in this report has been named NYVAC-89.6P-SIVgpn or, in a more detailed manner NYVAC-gp120-HIV89.6-SIVmac239-gag-pol-nef. Given its usefulness as positive control in the studies that are the main application of the MVA-SHIV vectors of the present invention, the type NYVAV-SHIV vectors are also comprised within the scope of the present invention. The present invention also refers to compositions containing the recombinant vectors object of the invention that comprise a codifying sequence of a form of the HIV-1 Env protein—that lacks entirely the part that correspond to the gp41 protein- and a codifying sequence of the Gag-Pol-Nef fusion protein derived from sequences of the SIVmac virus, as well as referring to its use in assessing the immunologic response and the protective capacity against the HIV infection triggered by vectors having the same gene organization structure, promoters and insertion site intended to use for human vaccination purposes. The preferred embodiment of this manner of use of the inventive vectors consists in administering them to apes, preferably Macacus rhesus (*Macaca mulatta*) to evaluate the immune response produced and the capacity of protection generated after said administration, and later subjecting them to a challenge with a pathogenic SHIV virus. In this manner information relevant to the assessment of the results can be obtained and evaluate whether the results point towards continuing with the next battery of clinical trials in humans using the homologous vectors intended for human vaccination purposes, as well as obtaining information on the adequate procedure to carry out said trials.

Preferably, the protocol used to administer the vectors object of the invention to Macacus monkeys will correspond to the approach intended for human vaccination protocols, or to a scheme which degree of suitability is to be evaluated.

The immunogenicity studies done with the MVA-B and MVA-C, vectors—described later on in the Example section of the preset report—as well as the assays with Macacus monkeys to test the degree of protection the vectors offer against infection by SHIV89.6P using the MVA-89.6P-SIVgpn vector, are both indicative of the usefulness as vaccines for humans of the vectors of the invention and of the validity of the immunization protocols used. Based on all of the above, also objects of the present invention are the vaccination methods used to prevent or treat HIV caused infections that entail administering at least one recombinant vector object of the invention derived from the MVA virus and capable of simultaneously express a form of the HIV-1 Env protein that entirely lacks the part corresponding to the gp41 protein and the fusion protein that contains sequences of the Gag, Pot and Nef proteins of the HIV-1, that is, one of the vectors object of the present invention designed to manufacture drugs useful as preventative or therapeutic vaccines against AIDS.

The vaccination methods included within the scope of the invention may comprise one or more vaccination doses, provided that in one of them at least one of the vectors of the invention is administered. The preferred methods are those in which more than one vaccination doses are administer to trigger or boost the immune response. Specially preferred amongst said methods are the combined protocols in which different vectors are used in the first dose to trigger the immune response and in the subsequent doses used to reinforce the triggered response (booster dose). Since the MVA-derived vectors appear to be more useful in terms of obtaining a protective response against HIV infection when they are supplied in the second or subsequent doses intended as boosters of the previously triggered immune response, the first preference is that at least one of the MVA-derived recombinant vectors of the invention is present in the second or subsequent doses, while it may or may not be present in the first vaccine dose. For those cases in which at least one MVA-derived vector is present in the second dose and/or in a subsequent vaccination dose it is preferred that at least one of the vectors administered in the first vaccine dose has the capability to express the same HIV-derived proteins than the inventive vector present in a different dose. Amongst said vectors, the vectors derived from the NYVAC, NYVAC-B and NYVAC-C viruses and their combinations thereof are a suitable option to be used in the first vaccine dose as part of a vaccination method object of the invention when the inventive vector administered in the second and/or a subsequent vaccination dose is, respectively, the vector object of the invention that will be later referred to as MVA-B vector, or the vector that will be later known as MVA-C vector, or a composition that comprises both the MVA-B and the MVA-C vectors. Also preferred embodiments of the invention are those vaccination methods in which the first vaccine dose contains the naked DNA vector DNA-B when in the second and/or subsequent vaccination doses the MVA-B vector object of the invention is present, as well as in those in which the first vaccine dose contains the naked DNA vector DNA-C when in the second and/or subsequent vaccination doses the MVA-C vector object of the invention is present.

The vector construction process and the assays in which both their immunogenic capacity and their protective capacity are evaluated are described in more detail later in this report with the aid of the Figures and Examples discussed in their corresponding sections.

BRIEF DESCRIPTION OF THE FIGURES

FIG. 3 shows the fragments generated during PCR analysis of the TK locus in the MVA-B virus. The sample on the upper part of the figure shows an outline representing the positions of the oligonucleotides used as primers, the estimated sizes of the fragments generated during the course of the PCR with the different oligonucleotide combinations, as well as their placement in relation to the inserts and the insert flanking sequences. The sample on the lower part shows photographs of the gels obtained by subjecting to electrophoresis the products of different PCR analysis in which different primer pairs have been used to. A: PCR primed with TK-L and GPN7649 olegonucleotides; B: PCR primed with GPN8170 and E/L oligonucleotides; C: PCR primed with BX08556/TK-R oligonucleotides. The samples corresponding to each lane are: 1: pLZAW1gp120B/gagpolnef-B-1; 2: MVA-B; 3: MVA-WT; 4: NYVAC-WT.

FIG. 6 shows the results of the stability tests of the MVA-B vector. Part A shows the results of the immunostains of CEF cells infected with the MVA-B vector and treated with the anti-WR antibodies (photo on the left), anti-p24 (central photo) and anti-gp120 (photo on the right), together with a graph representing the total cells stained by each antibody. Part B shows the detection of the expression of the gagpolnef-IIIB (photo on the left) and gp120-BX08 proteins (photo on the right side) obtained by Western blot transfer and antibody-based detection with antibodies directed against said proteins in cells infected with the NYVAC-B recombinant virus (NYVACB), cells in which the infection had been simulated (M) and virus stocks corresponding to passages 7 to 10 (P7, P8, P9 and P10).

Figure 9:
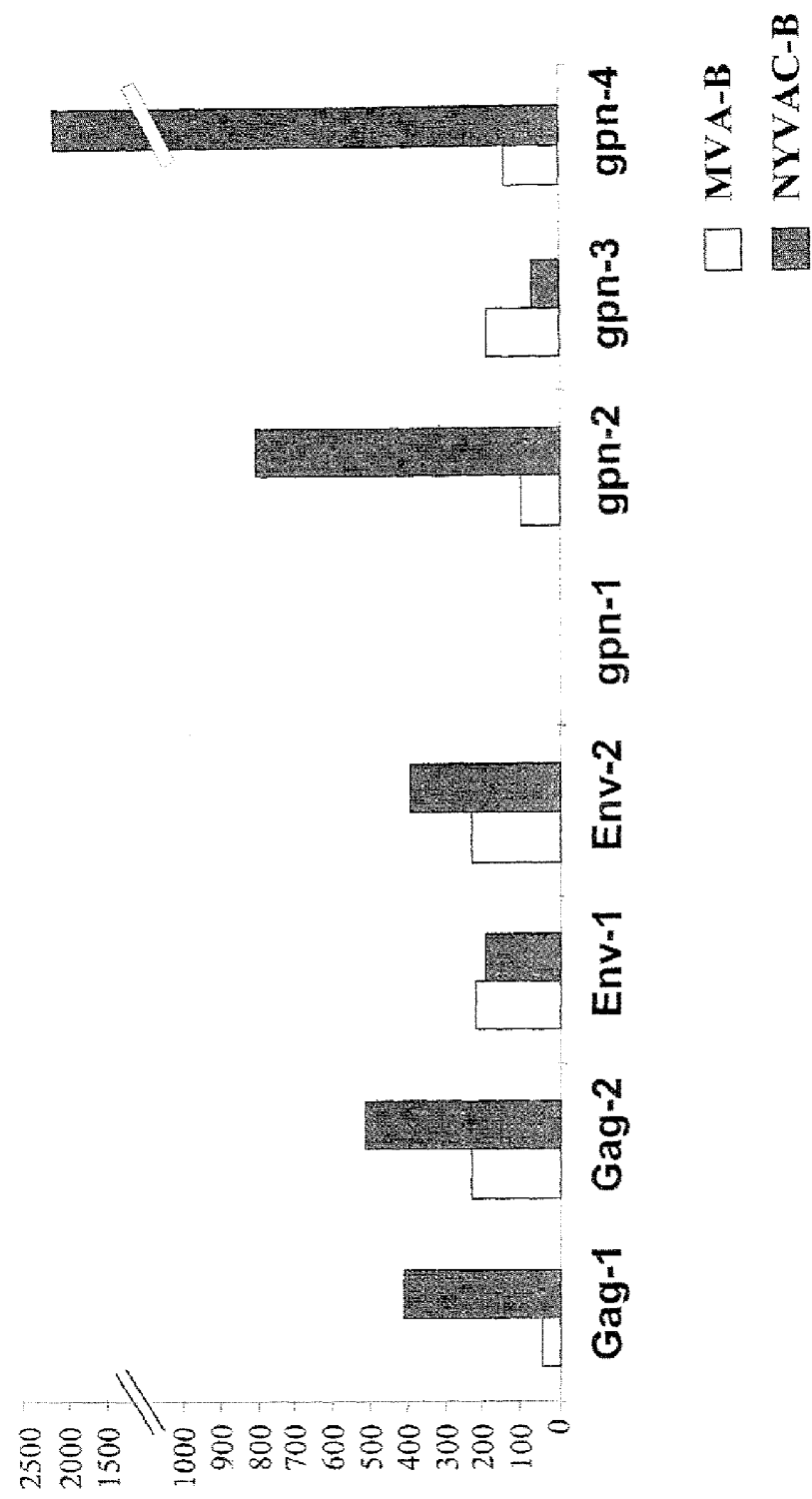

The graph shown in FIG. 9 represents the detection by ELISPOT of IFN-γ secreting T cells generated by immunizing BAB/c mice with recombinant viruses from which the gp120-BX08 and the gagpolnef-IIIB proteins can be expressed. On the Y axis are the number of IFN-γ secreting T cells detected by each $10^6$ splenocytes specific for each of the peptide groups of the B clade indicated on the X axis. For each of those peptide groups, the first bar correspond to the value detected in animals immunized with MVA-B and the second bar correspond to animals immunized with NYVAC-B.

Figure 10:
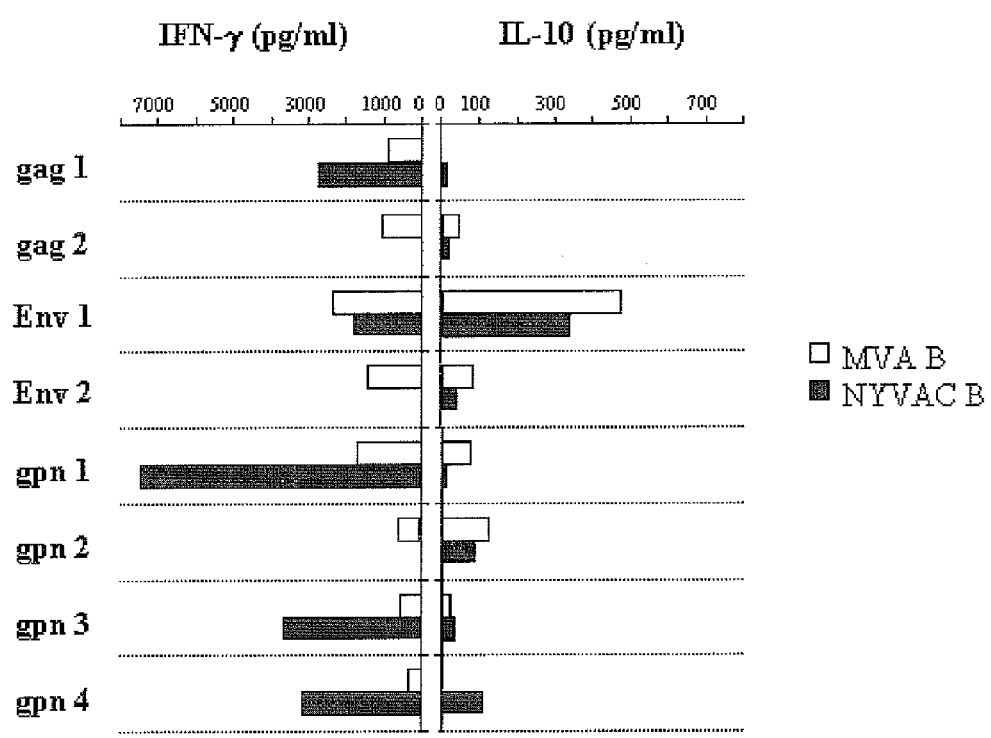

FIG. 10 shows cytokine production detected in BALB/c immunized mice with recombinant viruses from which the gp120-BX08 and the gagpolnef-IIIB proteins can be expressed. The left part correspond to the IFN-γ levels and the right part to the IL-10 levels—both expressed in pg/ml—detected in the splenocyte supernatants of animals inoculated with MVA-B (first bar of each peptide group) or NYVAC-B (second bar of each peptide group) versus specific peptide groups representative of the B clade.

Figure 11:
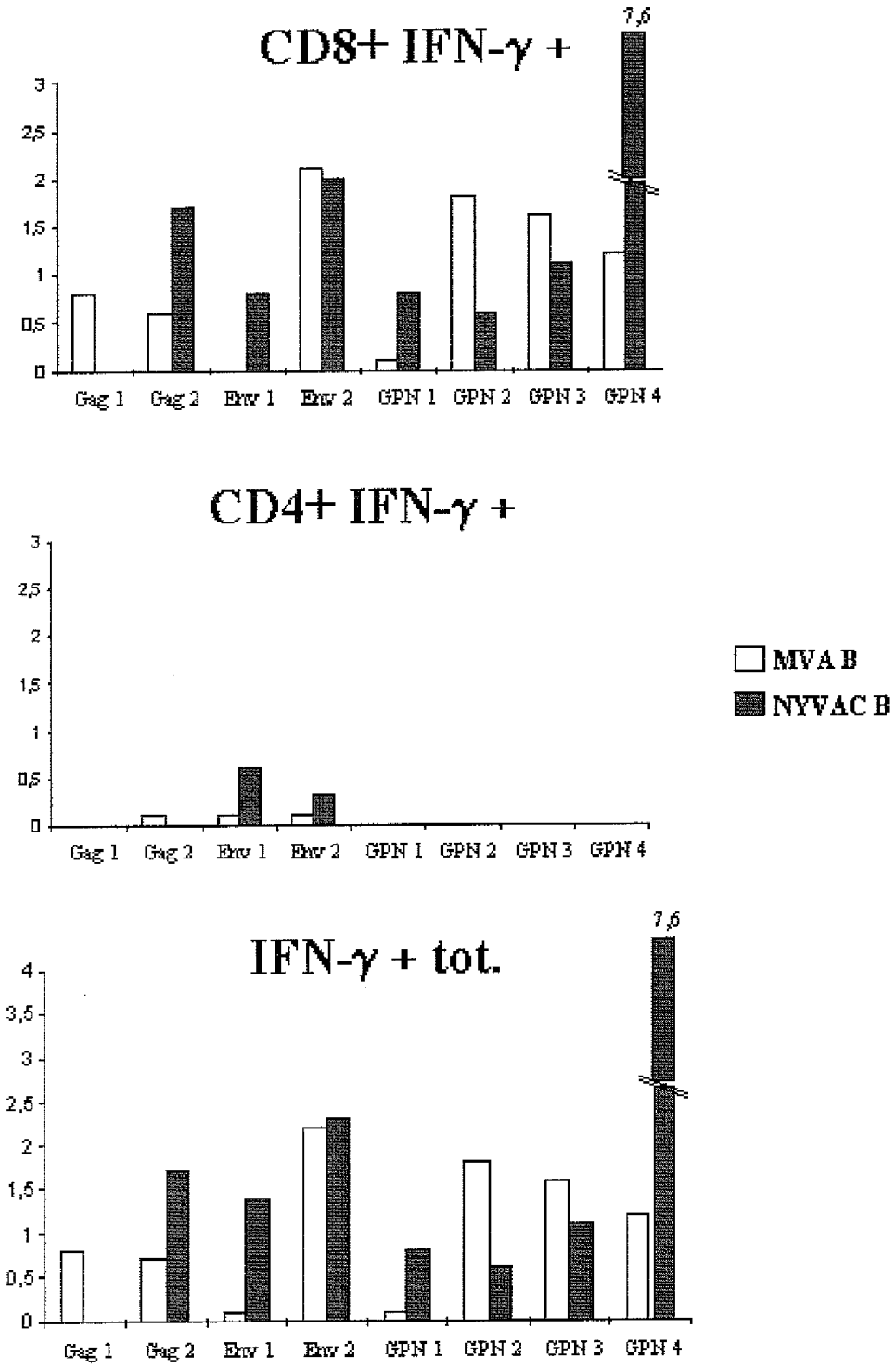

FIG. 11 shows graphs corresponding to the levels of different types of IFN-γ secreting T cells and present in the splenocytes of BALB/c mice inoculated with MVA-B (first bar of each peptide group) or NYVAC-B (second bar of each peptide group) reestimulated by the peptide groups that are representative of the B clade as indicated on the X axis. The upper graphs shows the percentage of IFN-γ secreting TCD8$^+$ cells, the intermediate graph shows the percentage of IFN-γ secreting TCD4$^+$ cells, and the lower graph shows the total percentage of IFN-γ secreting TCD8$^+$ and T CD4$^+$ cells, all of them detected by each $3\times10^5$ splenocytes.

Figure 12:
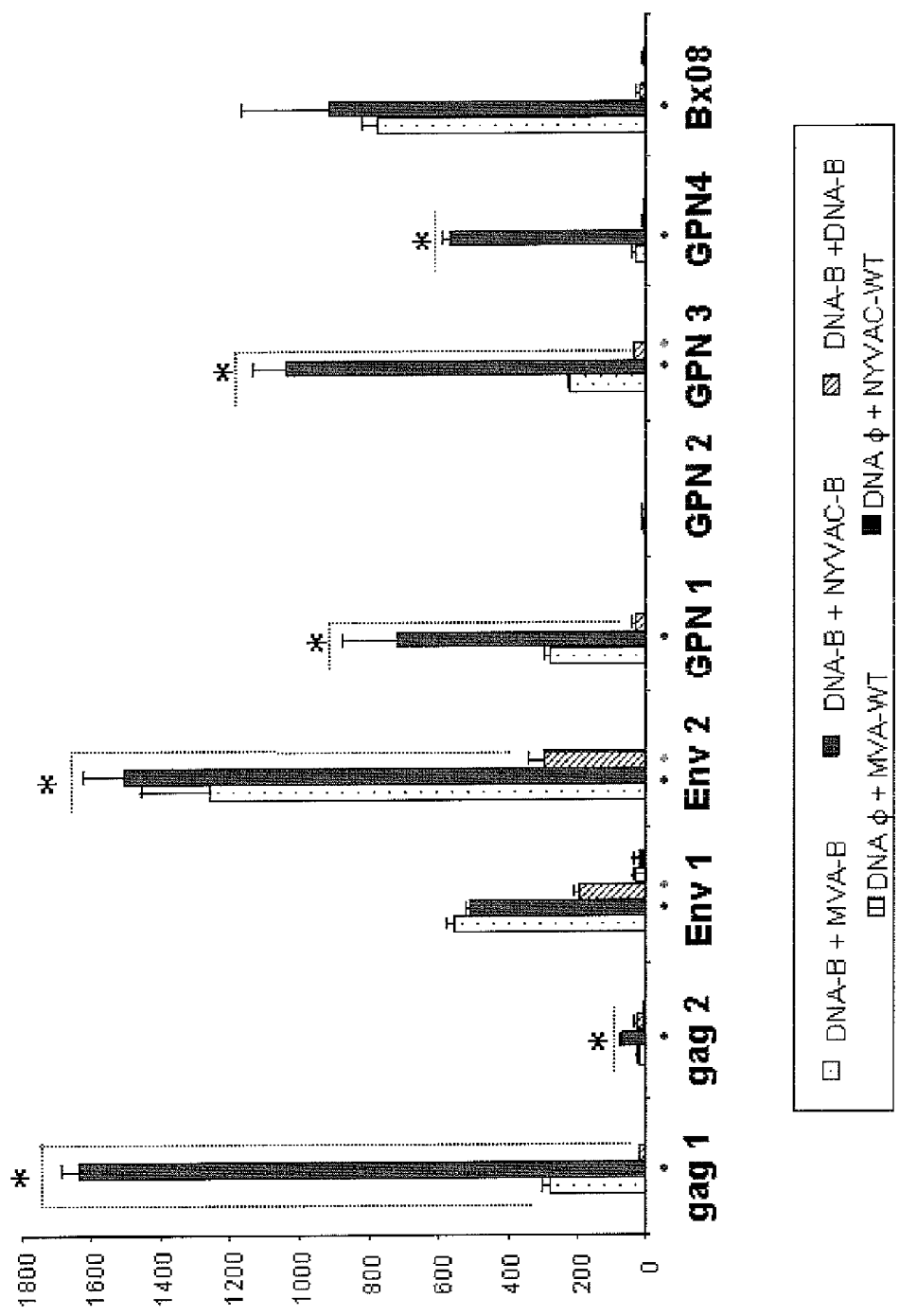

FIG. 12 shows a graph corresponding to the detection by ELISPOT of IFN-γ secreting T cells generated by immunizing BALB/c mice with different vector combinations from which the gp120-BX08 and the gagpolnef-IIIB proteins can be expressed, as well as the results corresponding to the controls, the vectors having been administered, in all cases, according to prime/boost protocols. On the Y axis are the number of IFN-γ secreting T cells detected by each of the $10^6$ splenocytes specific for each of the peptide groups of the B clade indicated on the X axis. For each of those peptides, the first bar correspond to the value detected in animals immunized with DNA-B+MVA-B, the second to animals immunized with DNA-B+NYVAC-B, the third bar to animals immunized with DNA-B+DNA-B, the fourth to animals immunized with DNA Ø+MVA-WT and the last bar to animals immunized with DNA0+NYVAC-WT. The circles (•) under the bars indicate the significant differences (p<0.005) exhibited by each peptide group versus the negative control; asterisks (*) indicate significant differences (p<0.05) between the different groups.

Figure 13:
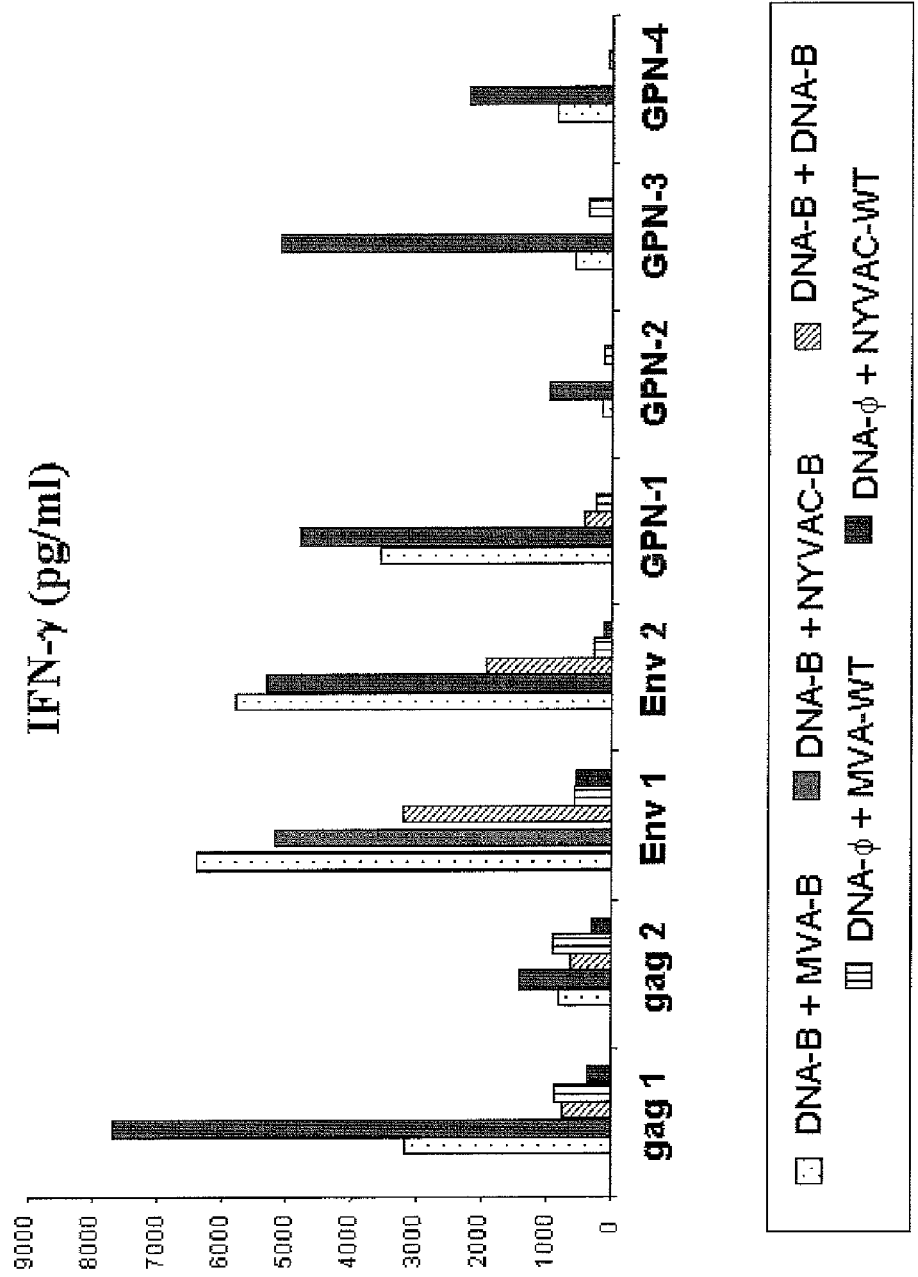

FIG. 13 shows IFN-γ production, expressed in pg/ml, generated after reestimulation, with the peptide groups indicated on the X axis, the splenocytes extracted from immunized BALB/c mice using prime/boost combination protocols in which the DNA-B is included in the first response initiation dose except in the last sample, that is inoculated with insertless DNA (DNA+, inoculating in the second response booster dose the following: MVA-B (first bar of each group), NYVAC-B (second bar), again DNA-B (third bar), MVA-WT (fourth bar) and NYVAC-WT (fifth bar, corresponding to the sample that was first inoculated with DNA-Ø).

Figure 14:
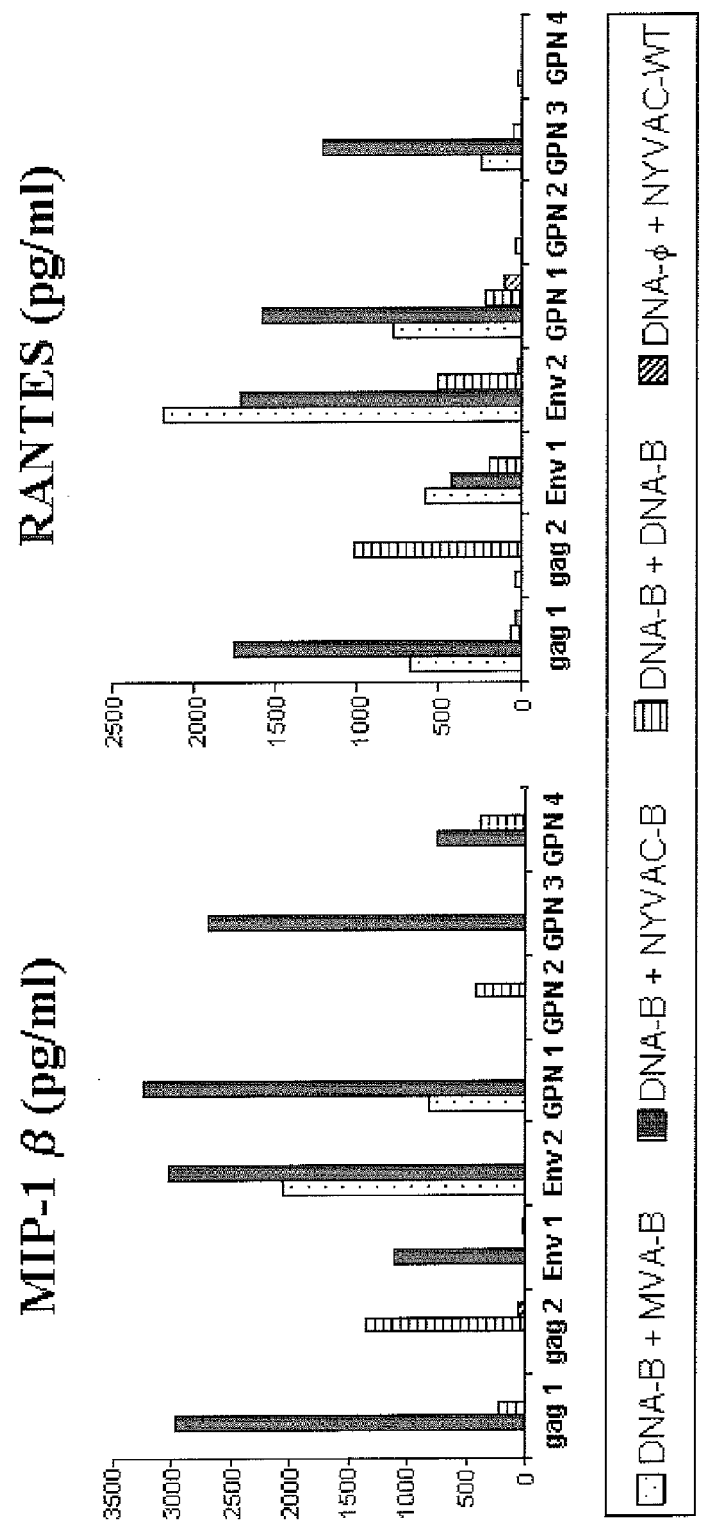

FIG. 14 shows, indicated on the X axis, chemokine production, expressed in pg/ml and generated after reestimulation with the peptide groups of the B clade, of extracted splenocytes from immunized BALB/c mice using prime/boost combination protocols in which the DNA-B is included in the first response initiation dose except in the control, that is inoculated with insertless DNA (DNA-Ø), the second booster dose is inoculated with MVA-B (first bar of each group), NYVAC-B (second bar), again with DNA-B (third bar), and NYVAC-WT (fourth bar, corresponding to the control that was first inoculated with DNA-Ø). The graph on the left sample the MIP-1-β concentration detected and the on the right the detected concentration of RANTES.

Figure 15:
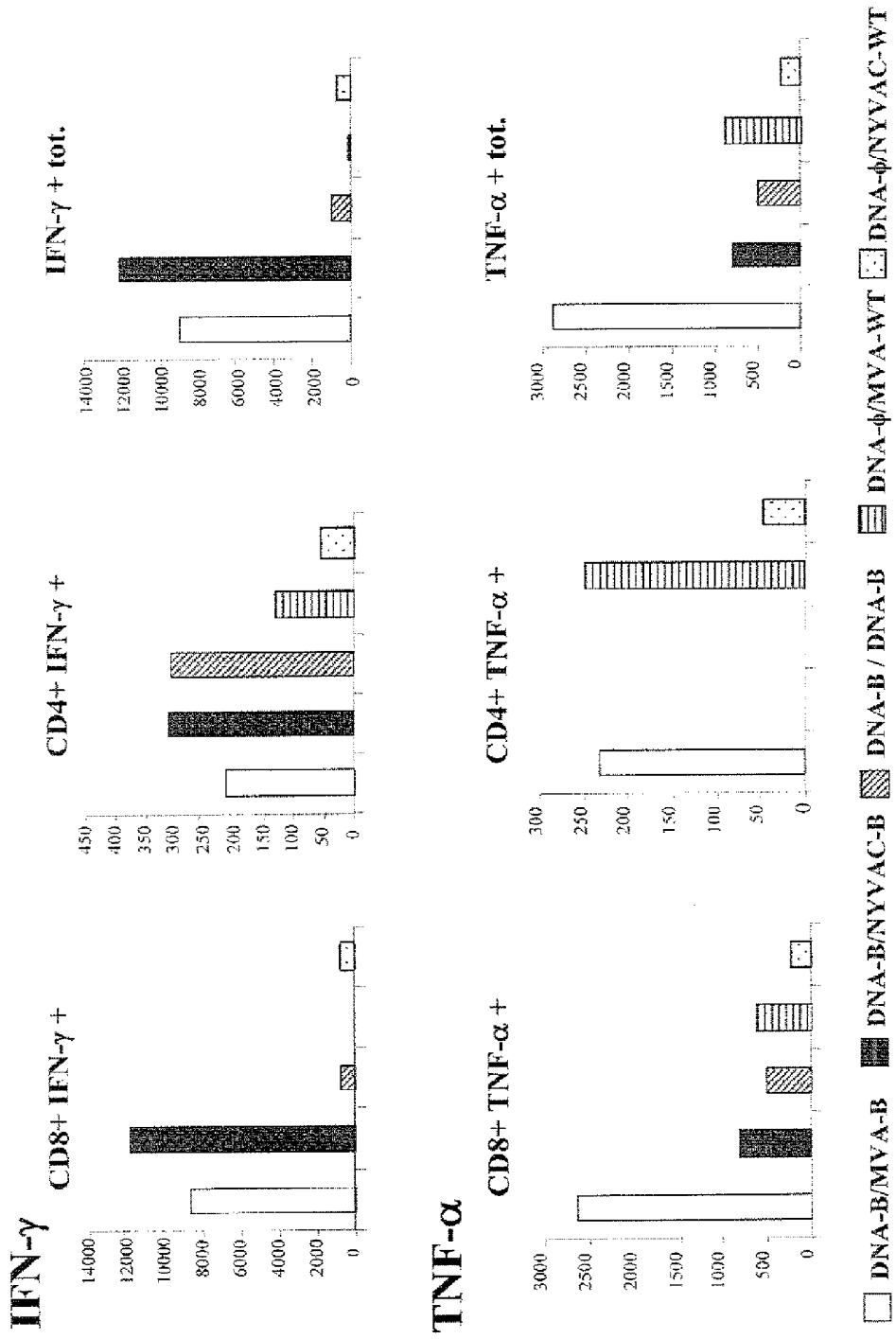

FIG. 15 shows graphs corresponding to the levels of different types of IFN-γ or TNF-α secreting T cells present in reestimulated splenocytes by the peptide groups representative of the B clade indicated on the X axis after having been extracted from immunized BALB/c mice using prime/boost combination protocols in which DNA-B is included in the first response initiation dose—except in the controls, that were inoculated with insertless DNA (DNA-Ø)—the second booster dose is inoculated with MVA-B (first bar of each group), NYVAC-B (second bar), again with DNA-B (third bar), while the controls inoculated with DNA-Ø received MVA-WT (fourth bar) or NYVAC-WT (fifth bar) in the second dose. The sample on the upper part correspond to IFN-γ producing cells and the sample on the lower part to TNFα producing cells. The graphs on the left correspond to CD8$^+$ cells, the intermediate graphs to CD4$^+$ cells and the graphs on the right refer to the total cells involved. In each case, the given value refers to the number of secreting cells of each type (CD8$^+$, CD4$^+$, total) detected by each of the $3\times10^5$ splenocytes.

Figure 16:
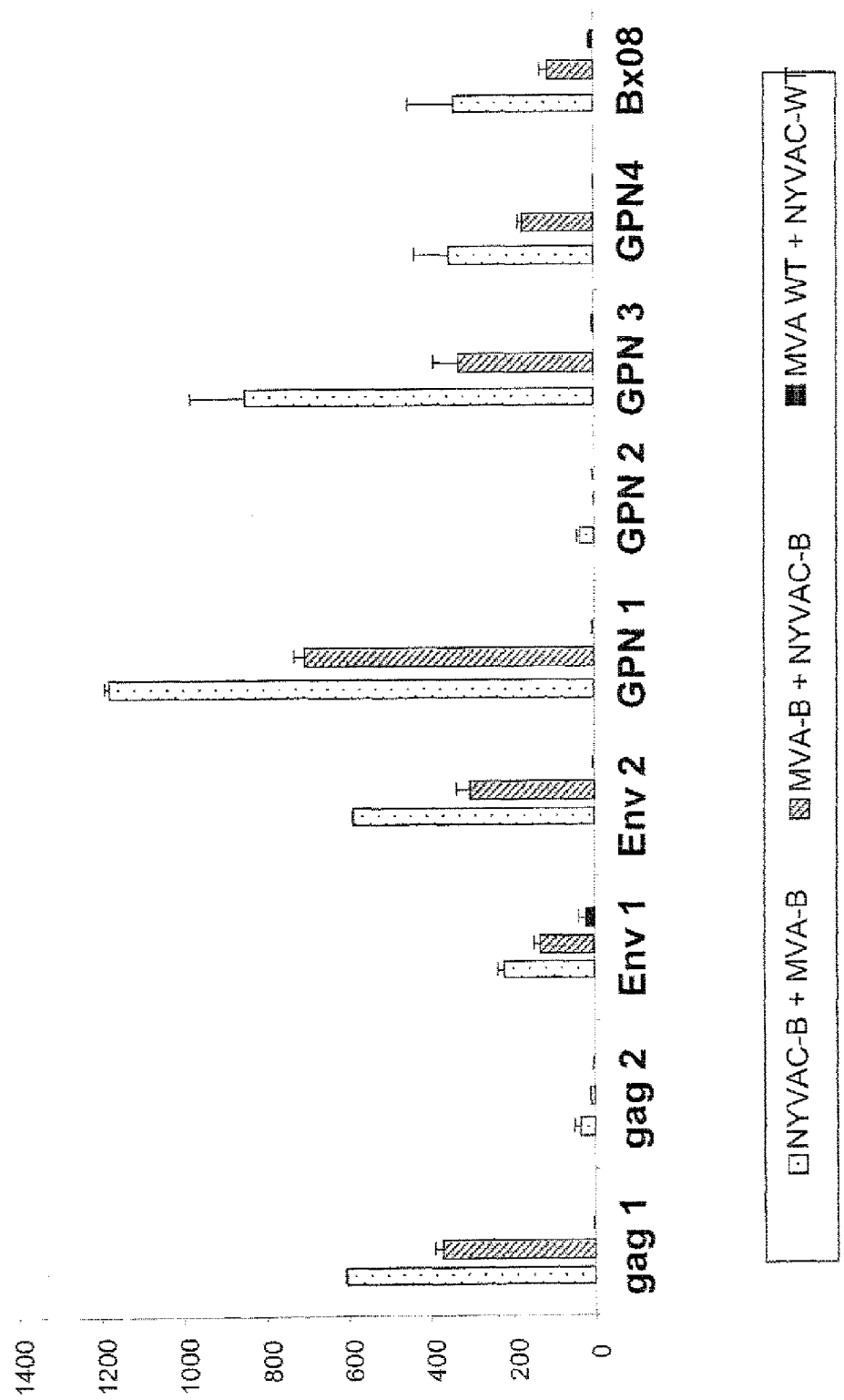

FIG. 16 shows a graph corresponding to the detection by ELISPOT of IFN-γ secreting T cells specific to each peptide group of the B clade indicated on the X axis, generated by immunizing BALB/c mice using prime/boost protocols in which MVA-derived Vaccinia vectors from which the gp120-BX08 and the gagpolnef-IIIB proteins can be expressed are combined. On the Y axis are the number of IFN-γ secreting T cells, specific to each peptide group of the B clade shown on the X axis, as detected by each of the $10^6$ splenocytes. For each of those peptides, the first bar correspond to the value detected in animals immunized with NYVAC-B+MVA-B, the second to animals immunized with MVA-B+NYVAC-B and the third to animals immunized with MVA-WT+NYVAC-WT.

Figure 17:
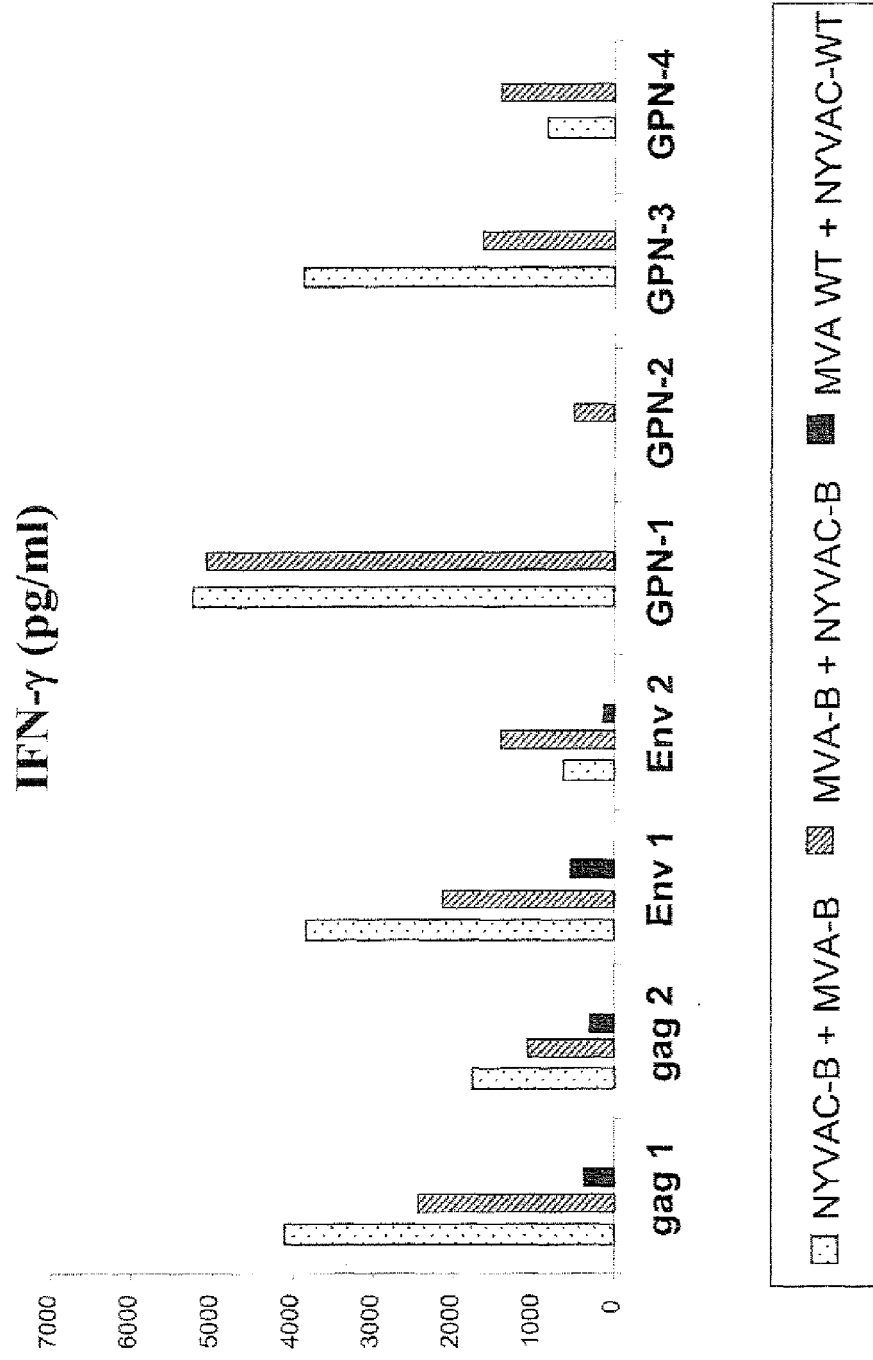

FIG. 17 shows IFN-γ production, expressed in pg/ml, generated after reestimulation with the peptide groups of the B clade indicated on the X axis, of extracted splenocytes from immunized BALB/c mice using prime/boost combination protocols in which MVA-derived Vaccinia vectors from which the gp120-BX08 and the gagpolnef-IIIB proteins can be expressed are combined: NYVAC-B+MVA-B (first bar), MVA-B+NYVAC-B (second bar) and MVA-WT+NYVAC-WT (third bar).

Figure 18:
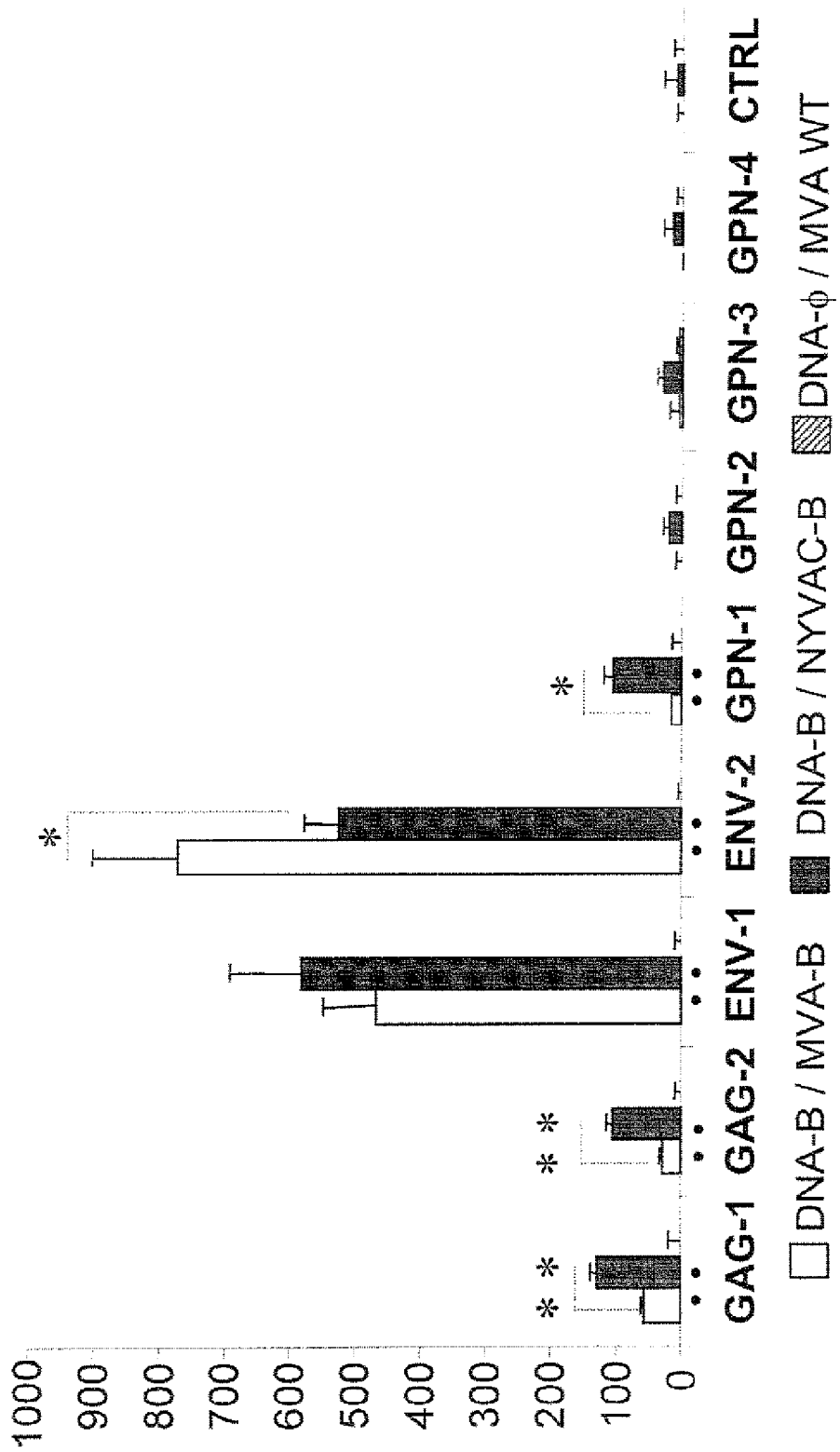
Figure 19:
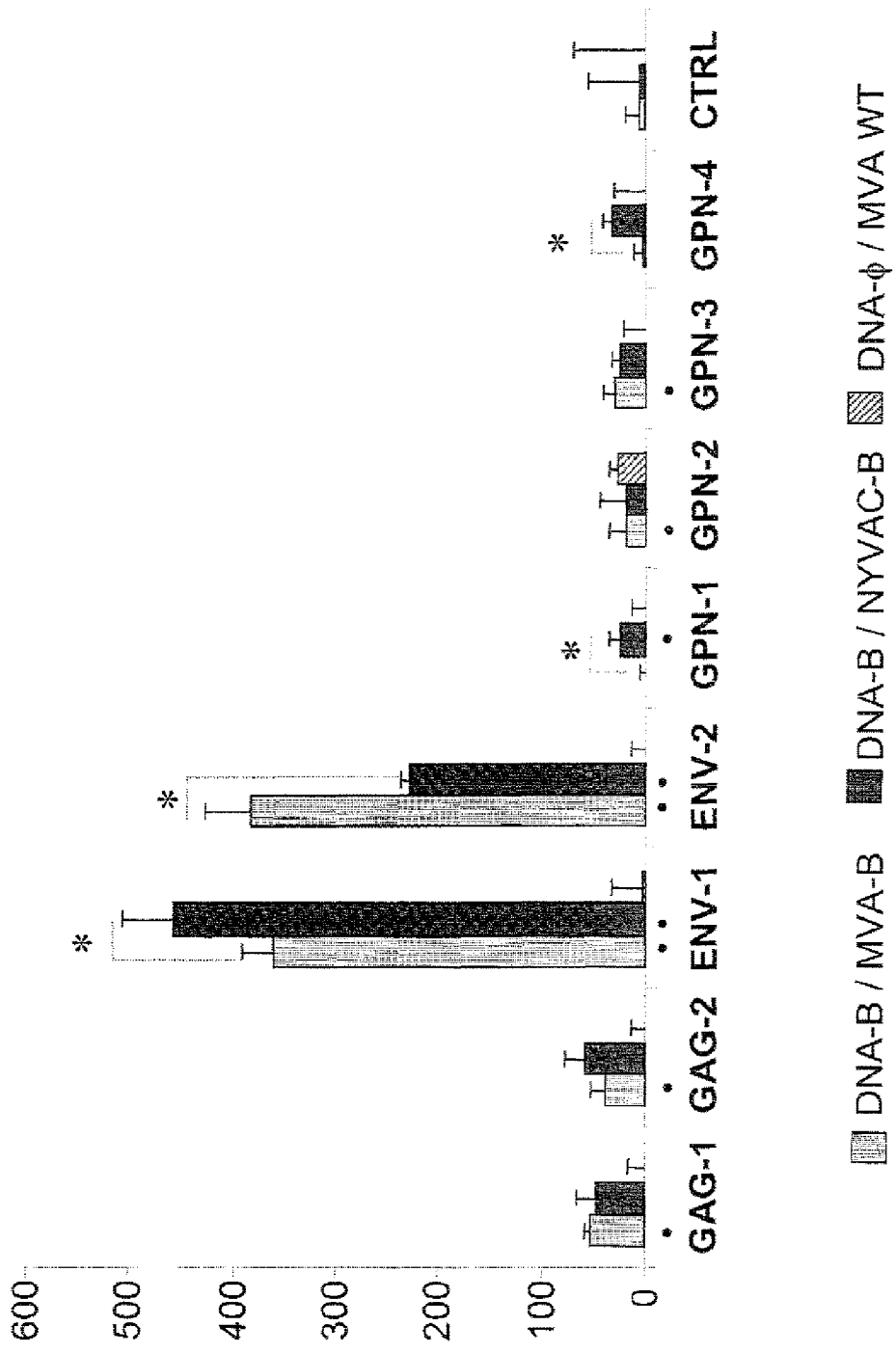

FIG. 18 shows a graph corresponding to detection by ELISPOT of IFN-γ secreting T cells specific to each peptide group of the B clade indicated on the X axis, generated by immunizing HHDII humanized mice and using prime/boost protocols in which DNA-B is included in the first response inducing dose, inoculating in the second booster dose MVA-B (first bar of each group) or NYVAC-B (second bar). The third bar corresponds to the inoculation control of an insertless DNA (DNA Ø) in the first doses and MVA-WT in the second. The circles (•) under the bars indicate the significant differences (p<0.005) found between each peptide group versus the negative control; asterisks (*) indicate significant differences (p<0.05) between the different groups FIG. 19 shows a graph corresponding to the detection by ELISPOT of the IL-2 secreting T cells specific to each peptide group of the B clade indicated on the X axis, generated by immunizing HHDII mice using prime/boost protocols in which DNA-B is included in the first response inducing dose, and MVA-B (first bar of each group) or NYVAC-B (second bar) are inoculated in the second booster dose. The third bar corresponds to the inoculation control of an insertless DNA (DNA Ø) in the first dose and MVA-WT in the second. The circles (●) under the bars indicate significant differences (p<0.005) found in each peptide group versus the negative control; asterisks (*) indicate significant differences (p<0.05) between the different groups.

Figure 20:
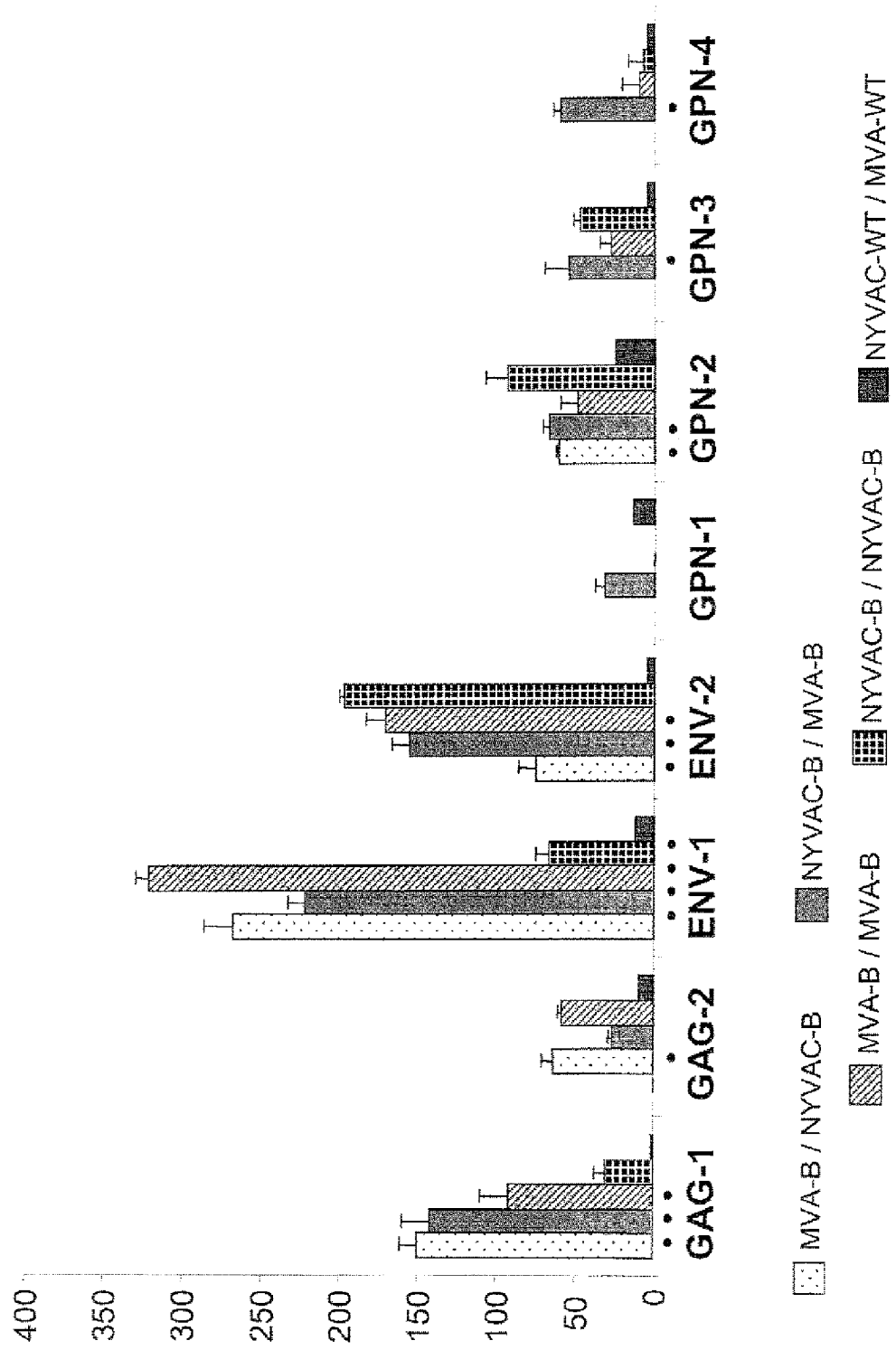

FIG. 20 shows a graph corresponding to the detection, by ELISPOT of IFN-γ secreting T cells specific to each of the peptide groups of the B clade indicated on the X axis, generated by immunizing HHDII humanized mice using prime/boost protocols in which MVA-derived Vaccinia vectors from which the gp120-BX08 and the gagpolnef-IIIB proteins can be expressed are combined. Shown in the Y axis are the number of INF- and secreting T cells specific to each of the peptide groups, detected by each $10^6$ splenocytes. For each of those peptide groups, the first bar correspond to the value detected in animals immunized with MVA+NYVAC-B, the second to animals immunized with NYVAC-B+MVA-B, the third to animals immunized with MVA-B+MVA-B, the fourth to animals immunized with NYVAC-B+NYVAC-B and the fifth to animals immunized with NYVAC-WT+MVA-WT. The circles (•) under the bars indicate the significant differences (p<0.005) found between each peptide group versus the negative control.

Figure 21:
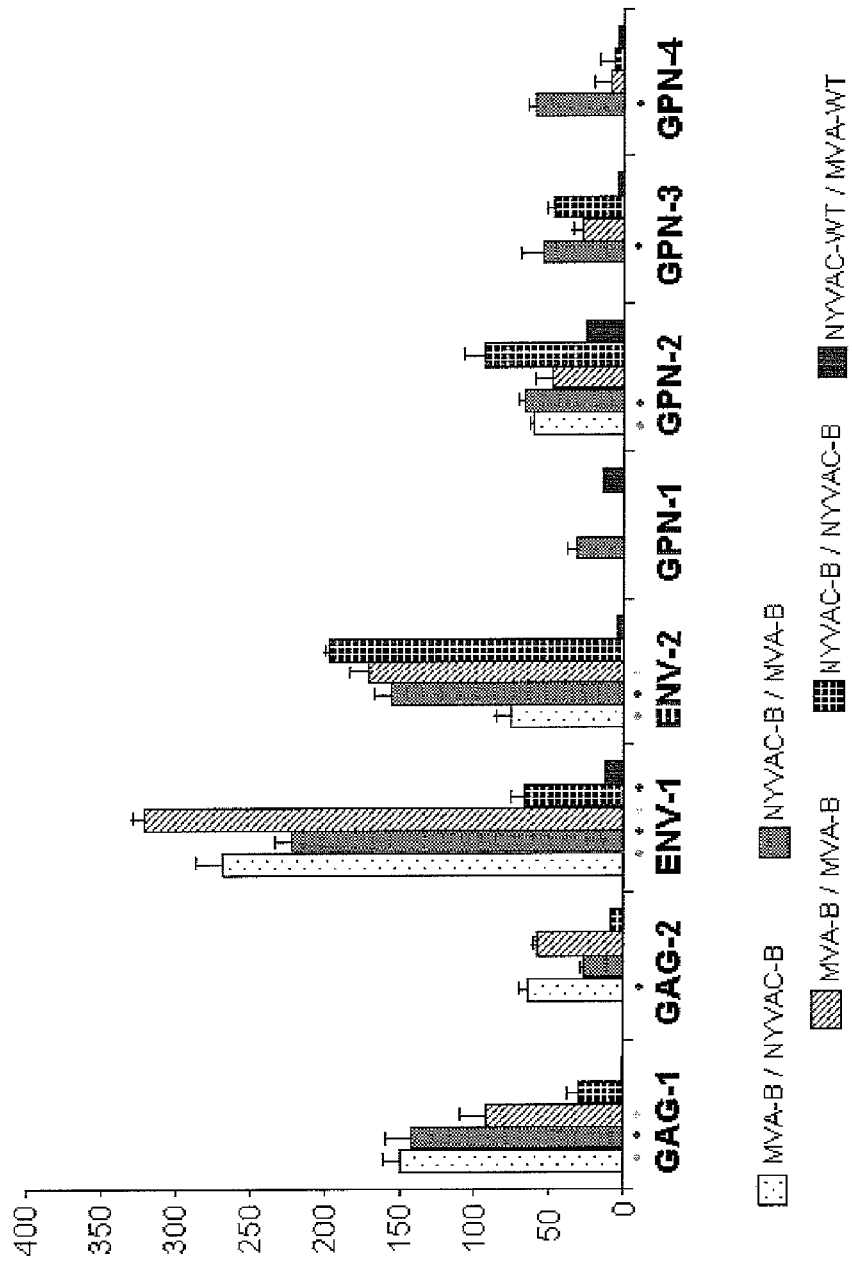

FIG. 21 shows a graph corresponding to the detection by ELISPOT of the IL-2 secreting T cells specific to each peptide group of the B clade indicated on the X axis, present per each of the 10⁶ splenocytes of HHDII immunized mice using prime/boost protocols in which MVA-derived Vaccinia vectors from which the gp120-BX08 and the gagpolnef-IIIB proteins can be expressed are combined. For each of those peptide groups, the first bar correspond to the value detected in animals immunized with MVA+NYVAC-B, the second to animals immunized with NYVAC-B+MVA-B, the third to animals immunized with MVA-B+MVA-B, the fourth to animals immunized with NYVAC-B+NYVAC-B and the fifth to animals immunized with NYVAC-WT+MVA-WT. The circles (•) under the bars indicate the significant differences ($p<0.005$) found between each peptide group versus the negative control.

Figure 22:
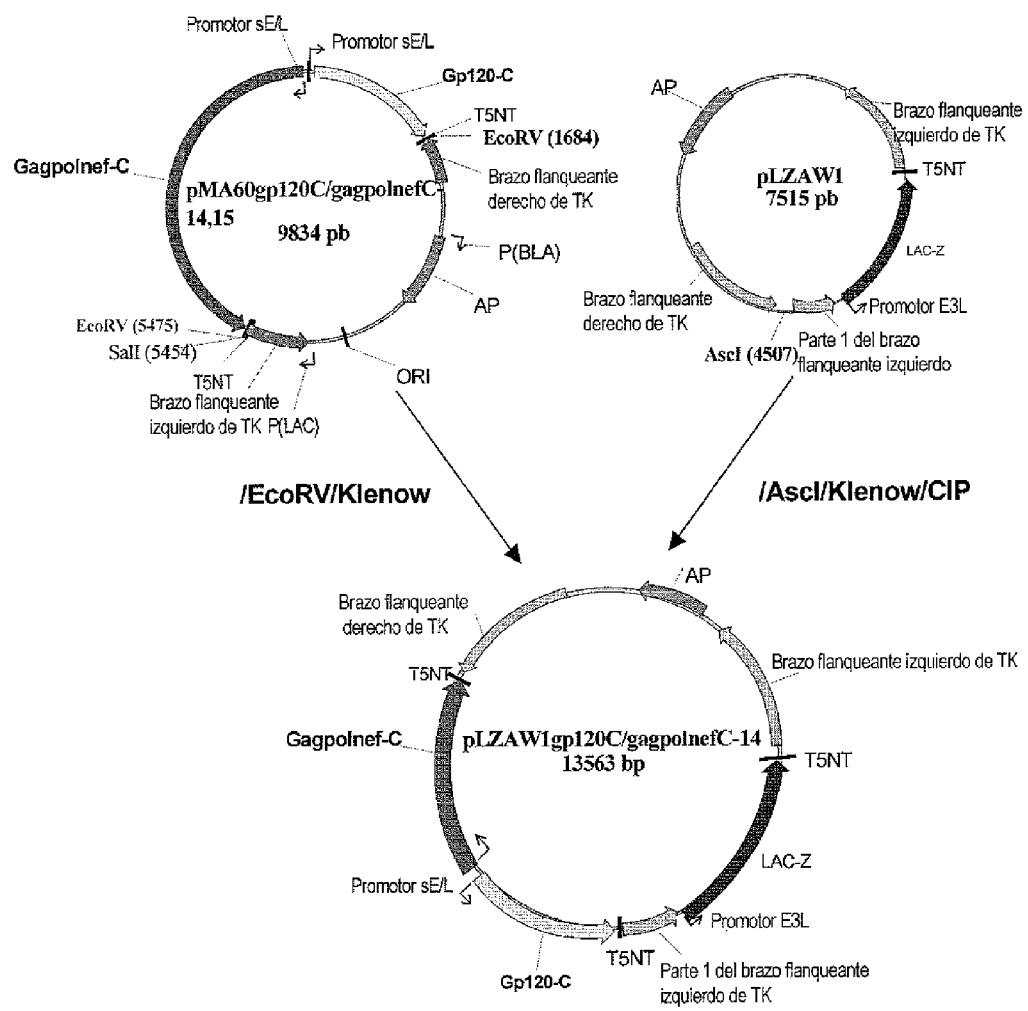

FIG. 22 shows an outline of the construction of the 120B/gagpolnef-C-14 plasmidic transfer vector and of the plasmids from which is generated.

Figure 23:
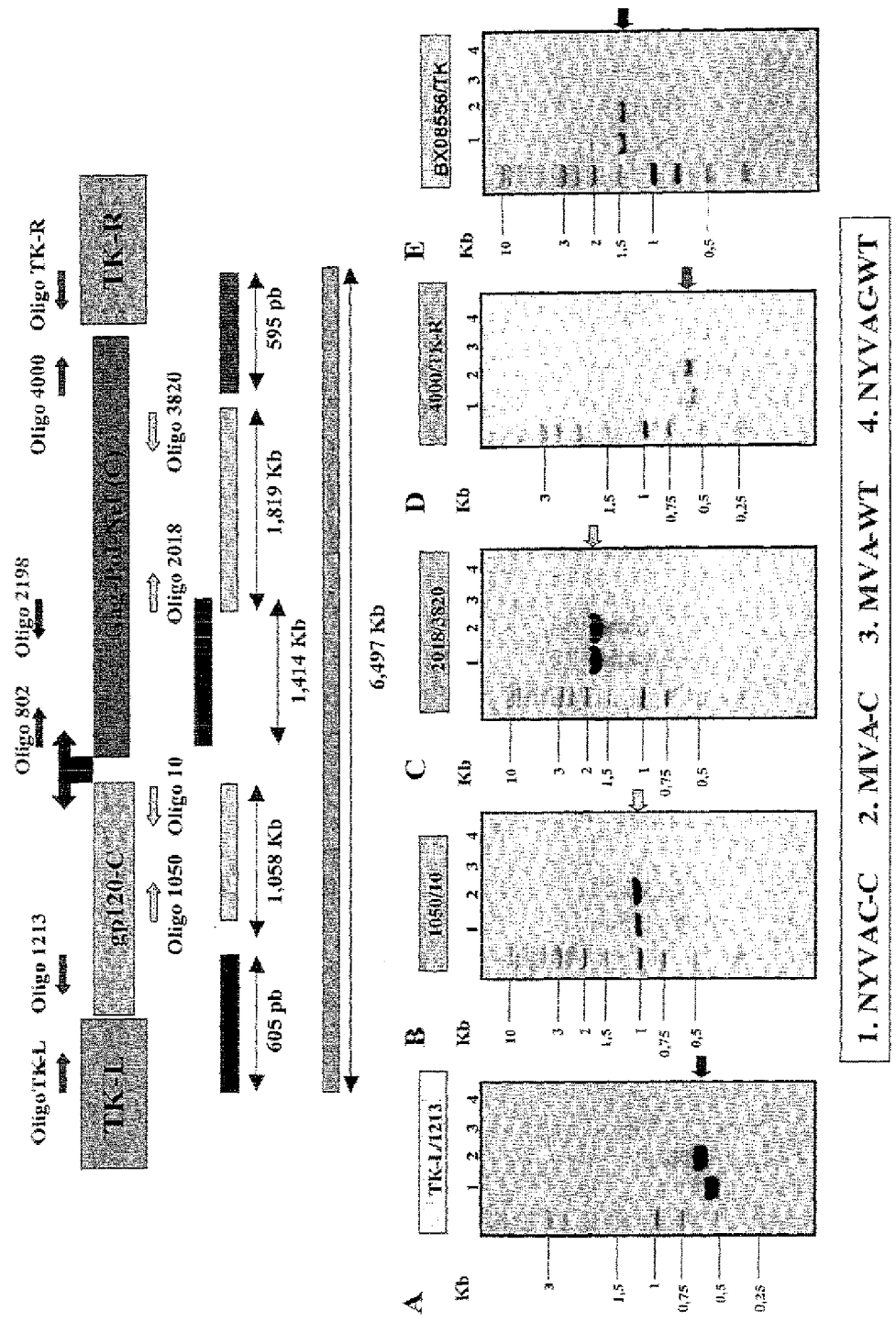

FIG. 23 shows the fragments generated during PCR analysis of the TK locus of the MVA-C virus. The sample on the upper part of the figure shows an outline of the size of the fragments that are generated with the different oligonucleotide combinations, as well as their location from the inserts and their flanking sequences. The sample on the lower part shows photographs of the gels obtained after subjecting to electrophoresis the products of the PCRs run with different primer pairs.
  A. PCR primed with the oligonucleotides TK-L and gp120-1213;
  B. PCR primed with the oligonucleotides gp120-1050 and gp120-;
  C. PCR primed with the oligonucleotides GPN-2018 and GPN-3820;
  D. PCR primed with the oligonucleotides GPN-4000 and TK-R;
  E. PCR primed with the oligonucleotides GPN-802 and GPN-2198.
The samples corresponding to each lane are:
  1: NYVAC-C;
  2: MVA-C(P2);
  3: MVA-WT;
  4: NYVAC-WT.

Figure 24:
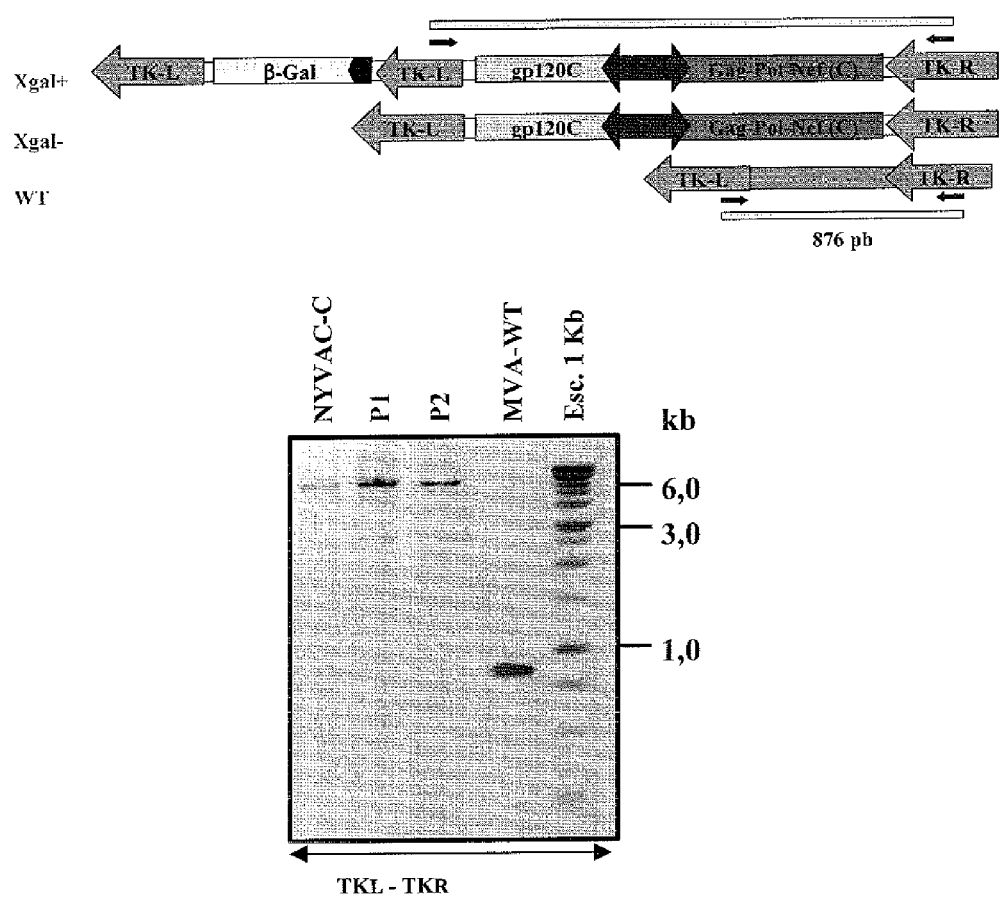

FIG. 24 shows, in the upper part, an outline of the fragments obtained enlarging by PCR the TK locus of the samples that contained or lacked inserts at said locus, while the sample on the lower part is a photograph of a gel obtained after subjecting to electrophoresis the products from a PCR run using the oligonucleotides that hybridize the TK gene flanking sequences as primers. The samples used were as follows: NYVAC-C (lane 1), MVA-C from the P1 stocks (lane 2) and the P2 stocks (lane 3), and MVA-WT (lane 4).

Figure 25:
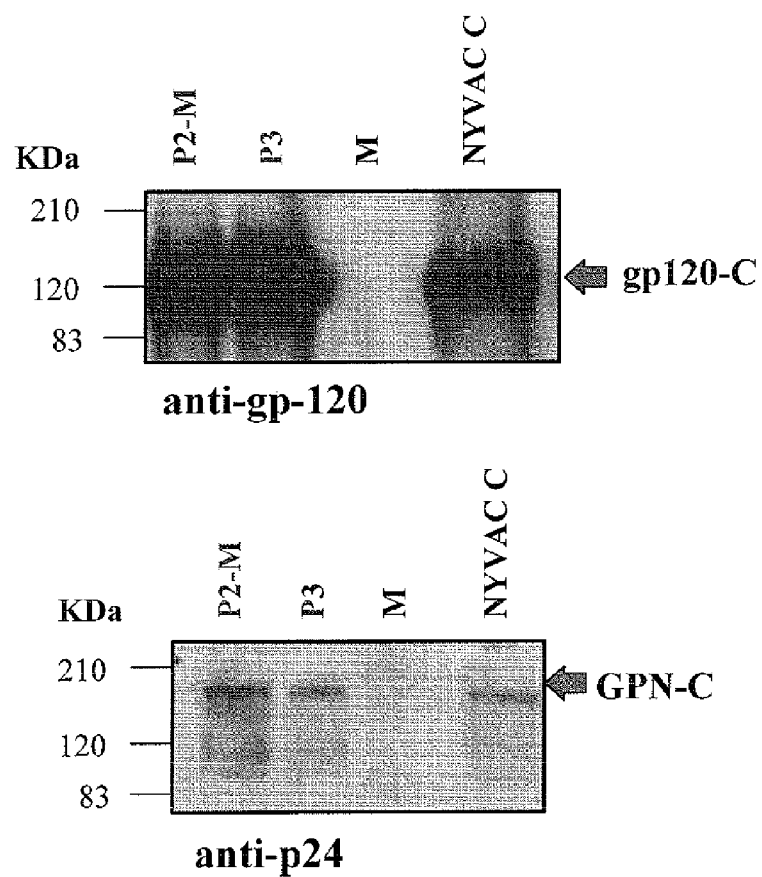

FIG. 25 shows the results of the Western blot transfer of the expression of the heterologous gp120-C genes (shown on the upper part) and gagpolnef-C genes (shown on the lower part, in which the gagpolnef-C protein appears abbreviated as GPN) from a NYVAC-C vector (last lane), from the P2 and P3 stocks (first and second lanes, marked P2-M and P3, respectively) and from cells in which the infection had been simulated (M).

FIG. 26 shows the results of the MVA-C vector stability tests. Part A shows the results of the immunostains of CEF cells infected with the MVA-C vector and treated with anti-WR (photo on the left), C clade specific anti-gp120 (central photos) and C clade specific anti-p24 (photo on the right) antibodies, as well as a graph that sample the percentages of the plates stained by each of the antibodies calculated from the total plates stained with the anti-WR antibody. Part B shows detection of gagpolnef-C (photo on the left) and gp120-C proteins expression (photo on the right side) by Western blot transfer and detection with antibodies directed against said proteins in cells infected with the recombinant NYVAC-C virus (lanes marked as "NYVAC-C"), cells in which the infection had been simulated (lanes marked as "CEF") and virus stocks corresponding to the passages 7¹ to 10 (lanes marked as P7, P8, P9 and P10).

As assumed by the context. Original text reads "... correspondiente a los pases y a 10)

FIG. 27 shows the kinetic expression of the gp120-C protein obtained by Western blot transfer using a C clade anti-gp120 antibody corresponding to samples taken after 6, 18, and 24 hours after infection with a recombinant virus. The sample on the upper part is that infected with the MVA-C virus and the lower is the sample infected with the NYVAC virus. The intensity of the signals obtained after incubating the samples with an anti-β-actin (β-act.) antibody appears immediately below each of the samples. P: precipitate; S: supernatant; M: infection simulation. P: precipitate; S: supernatant; M: infection simulation (sic).

Figure 28:
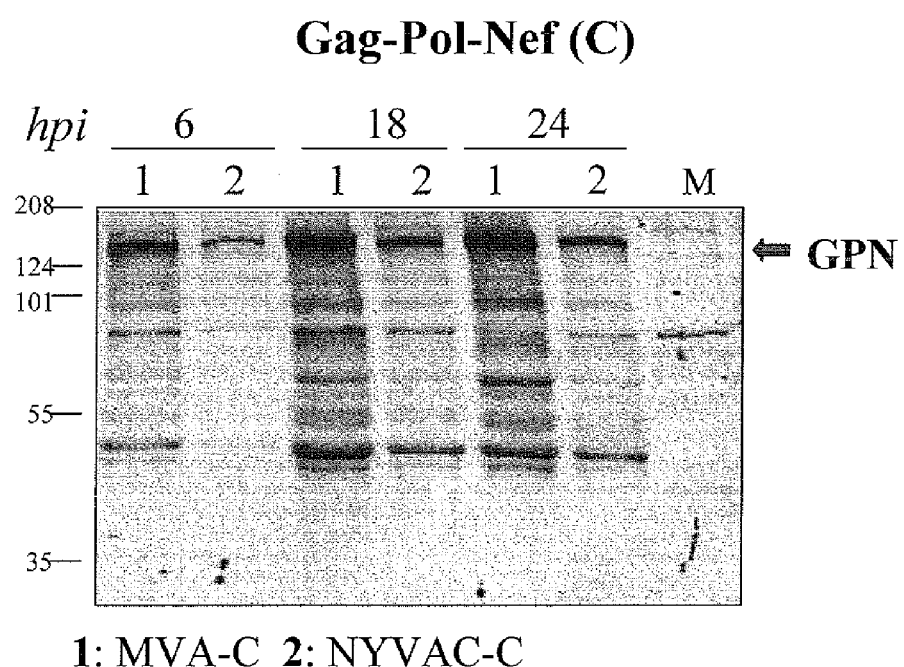

FIG. 28 shows the kinetic expression of the gagpolnef-C protein obtained by Western blot transfer using a C clade anti-p24 antibody corresponding to cellular precipitates of samples taken 6, 18 and 24 hours after infection with a recombinant virus. The lanes marked as "1" correspond to samples infected with the MVA-C virus, the lanes marked as "2" to samples infected with the NYVAC-C virus and the lanes marked as "M" to samples in which the infection was simulated. The arrow indicates the position of the gagpolnef-C protein (abbreviated as GPN).

FIG. 29 shows a graph corresponding to the detection by ELISPOT of IFN-γ secreting T cells generated by immunizing HHDII humanized mice with recombinant viruses from which the gp120c and the gagpolnef-C proteins can be expressed. Part A correspond to the IFN-γ secreting T cells, detected by each of the 10⁶ splenocytes, specific to each of the peptide groups of the C clade shown on the X axis. Part B correspond to the IFN-γ secreting T cells generated against the Vaccinia derived part of the recombinant viruses. Both in the case of the peptides (part A) as in the case of the anti-Vaccinia response, the first bar correspond to the value detected in animals immunized with MVA-C and the second to animals immunized with NYVAC-C.

Figure 30:
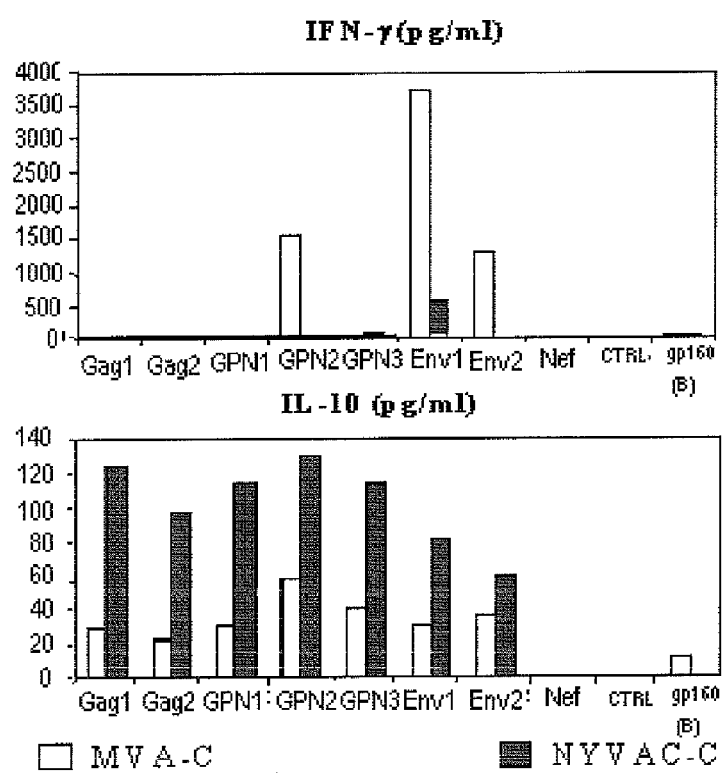

FIG. 30 shows the cytokine production detected in HHDII mice immunized with recombinant viruses from which the gp120-C and the galpolnef-C proteins can be expressed. The sample on the upper part correspond to the IFN-γ levels and the lower part to the levels of IL-10, both expressed in pg/ml, detected in the supernatants of the splenocytes of animals inoculated with MVA-C (first bar of each peptide group) or NYVAC-C (second bar of each of the peptide groups) versus specific peptide groups representative of the C clade.

Figure 31:
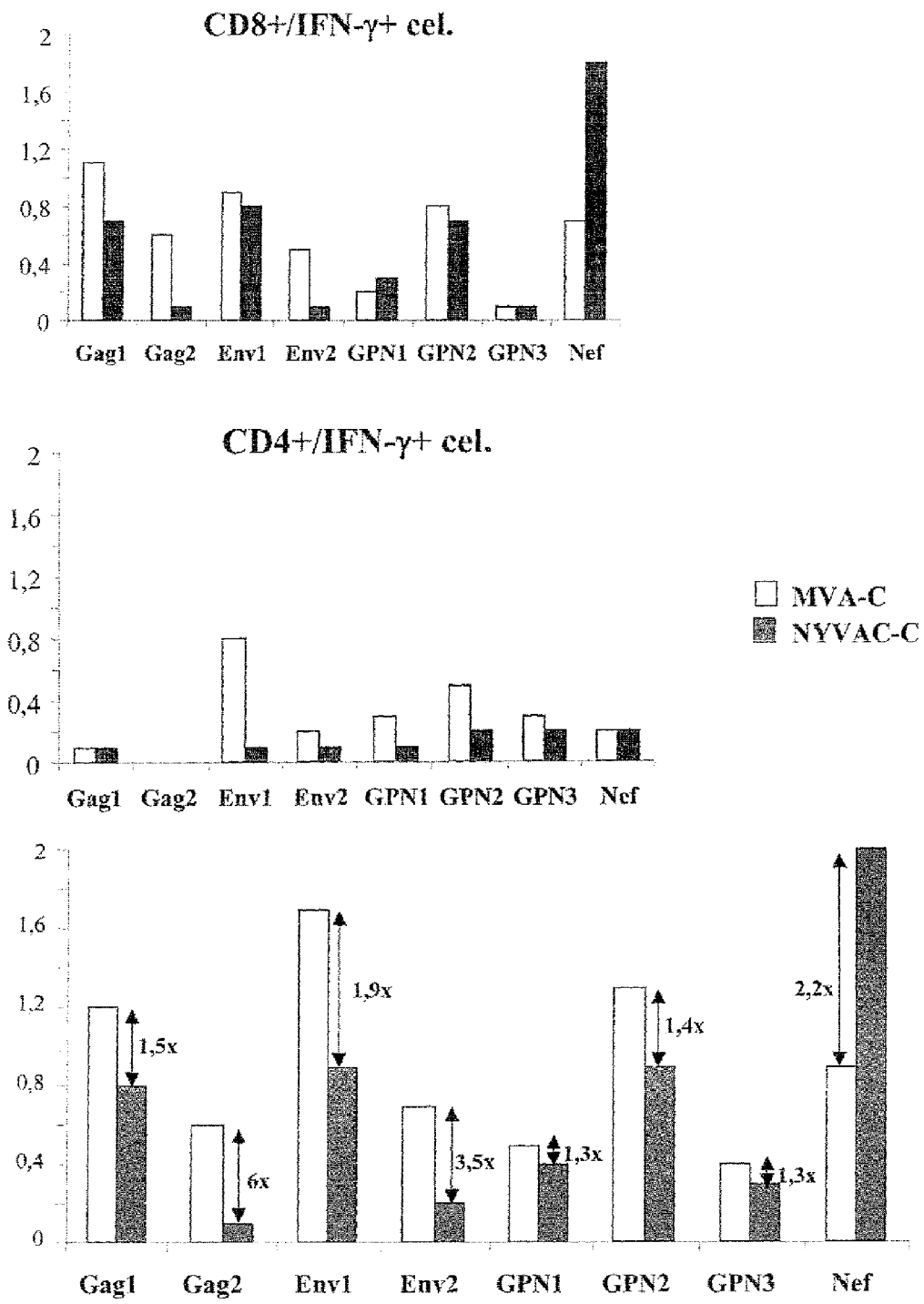

FIG. 31 shows graphs corresponding to the percentages of the different types of IFN-γ producing T cells generated versus specific peptide groups representative of the C clade after inoculating HDDII mice with the MVA-C virus (first bar of each peptide group) or NYVAC-C (second bar of each peptide group). the upper graph represents the percentage of CD8+⁺ cells from the total IFN-γ secreting cells, the intermediate graph represents the percentage of CD4⁺ cells, and the lower graph the percentage of the sums of CD8⁺ and CD4⁺ cells over the total IFN-γ secreting cells.

Figure 32:
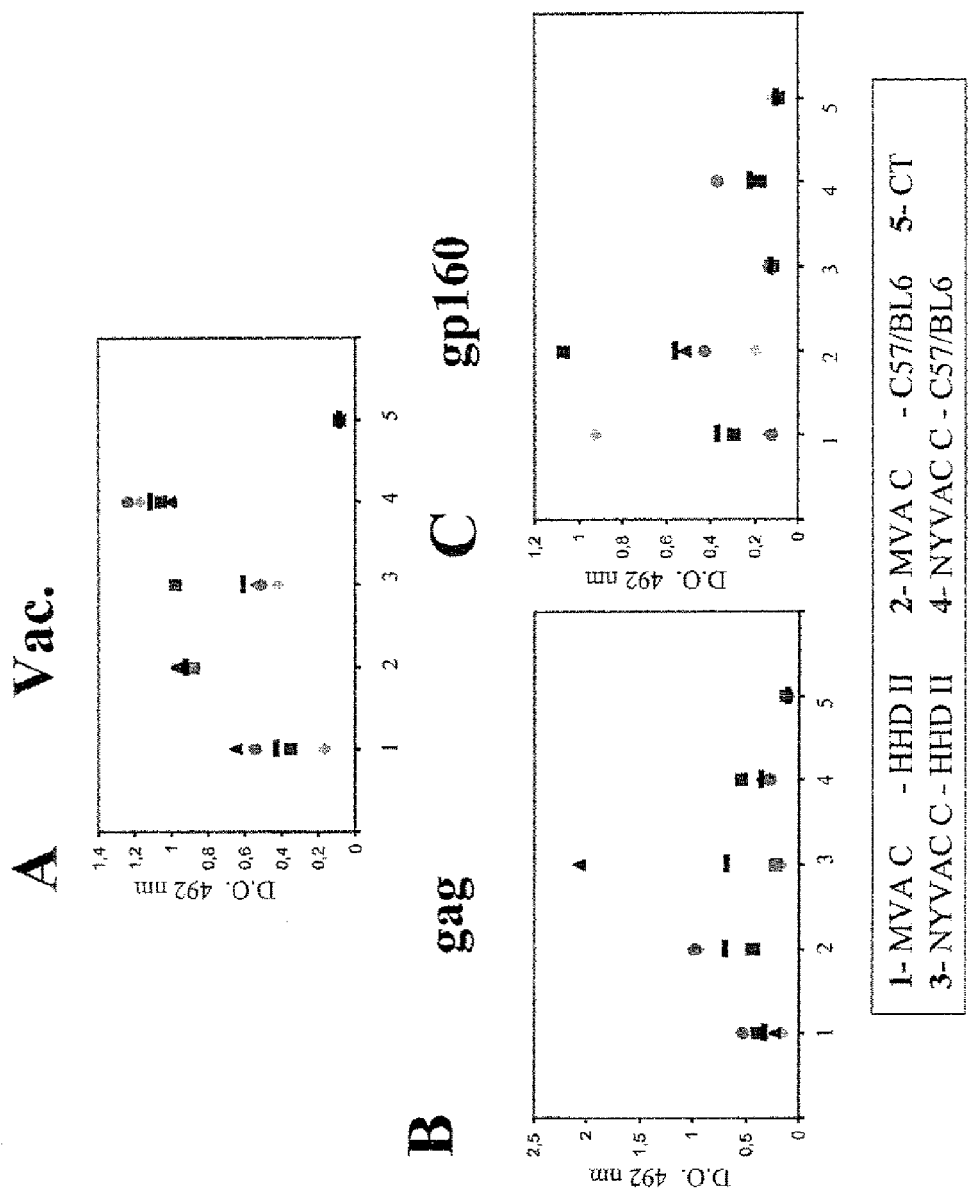

FIG. 32 shows the humoral response generated by inoculating HHDII or C57/BL6 mice with the MVA-C or the NYVAC-C viruses measured in optic density values at 492 nm obtained when detecting by ELISA IgG antibodies against: (A) cellular extracts of an infection with Vaccinia; (B) the Gag protein or (C) the gp160 protein. The immunization groups were: 1: MVA-C in HHDII; 2: MVA-C in C57/BL6; 3: NYVAC-C in HHDII; 4: NYVAC-C in C57/BL6; 5: control. In each group, the location of the symbols marks the value obtained for each of the mice of the group: ♦: mouse 1; ■: mouse 2; ▲: mouse 3; ●: mouse 4; the position of the horizontal bar indicates the average value for the four mice in each group.

Figure 33:
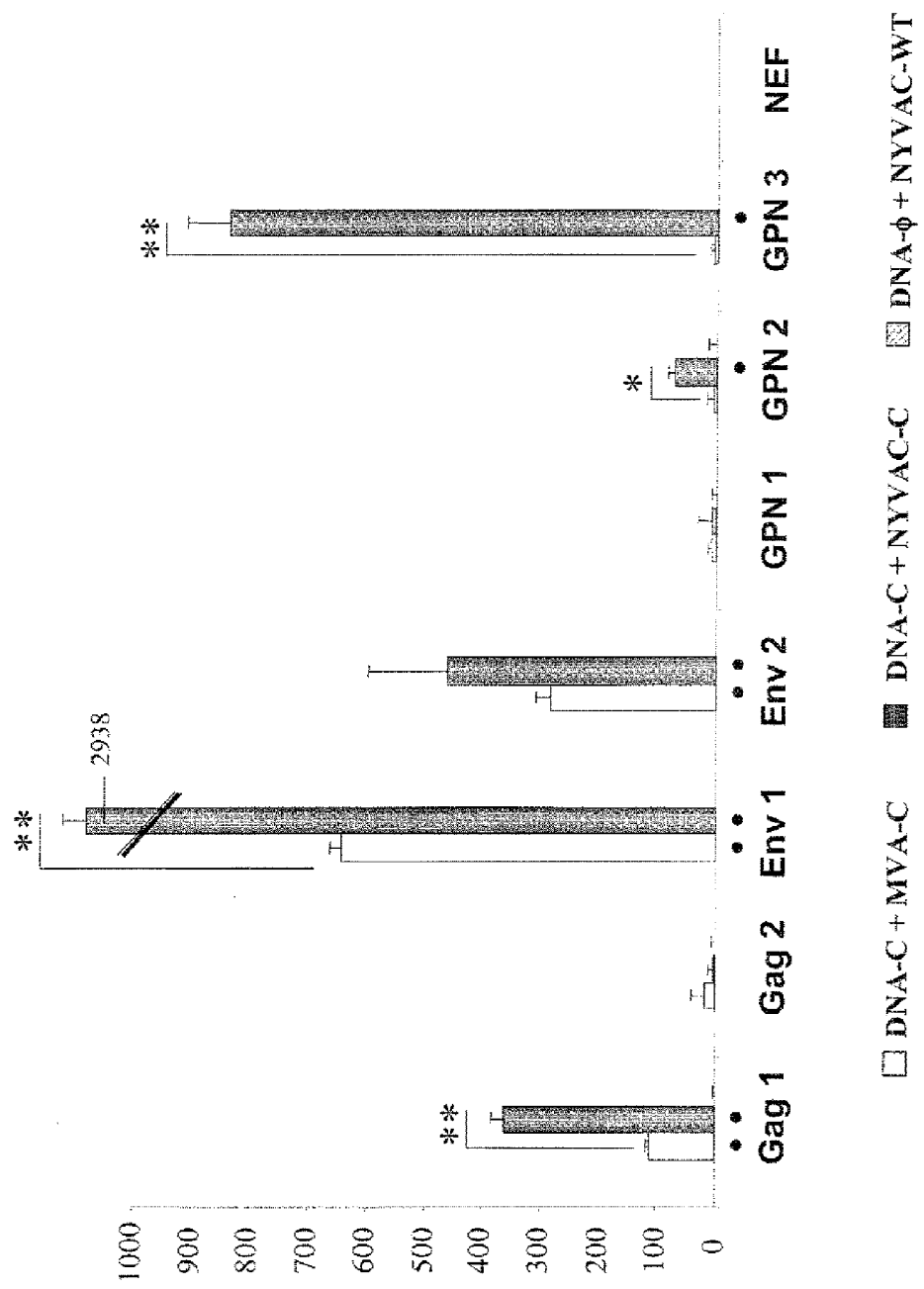

FIG. 33 shows a graph corresponding to the detection, by ELISPOT of IFN-γ secreting T cells specific to each peptide group of the C clade indicated on the X axis, present for each of the $10^6$ splenocytes of HHDII immunized mice using prime/boost protocols in which DNA-C is included in the first priming dose, and MVA-C is included in the second booster dose (first bar of each group) or NYVAC-C (second bar). The third bar corresponds to the inoculation control comprising an insertless DNA (DNA Ø) in the first dose and NYVAC-WT in the second. The circles (•) under the bars indicate the significant differences ($p<0.005$) found between each peptide group versus the negative control; asterisks indicate significant differences between the different groups: *: $p<0.05$; **: $p<0.005$.

Figure 34:
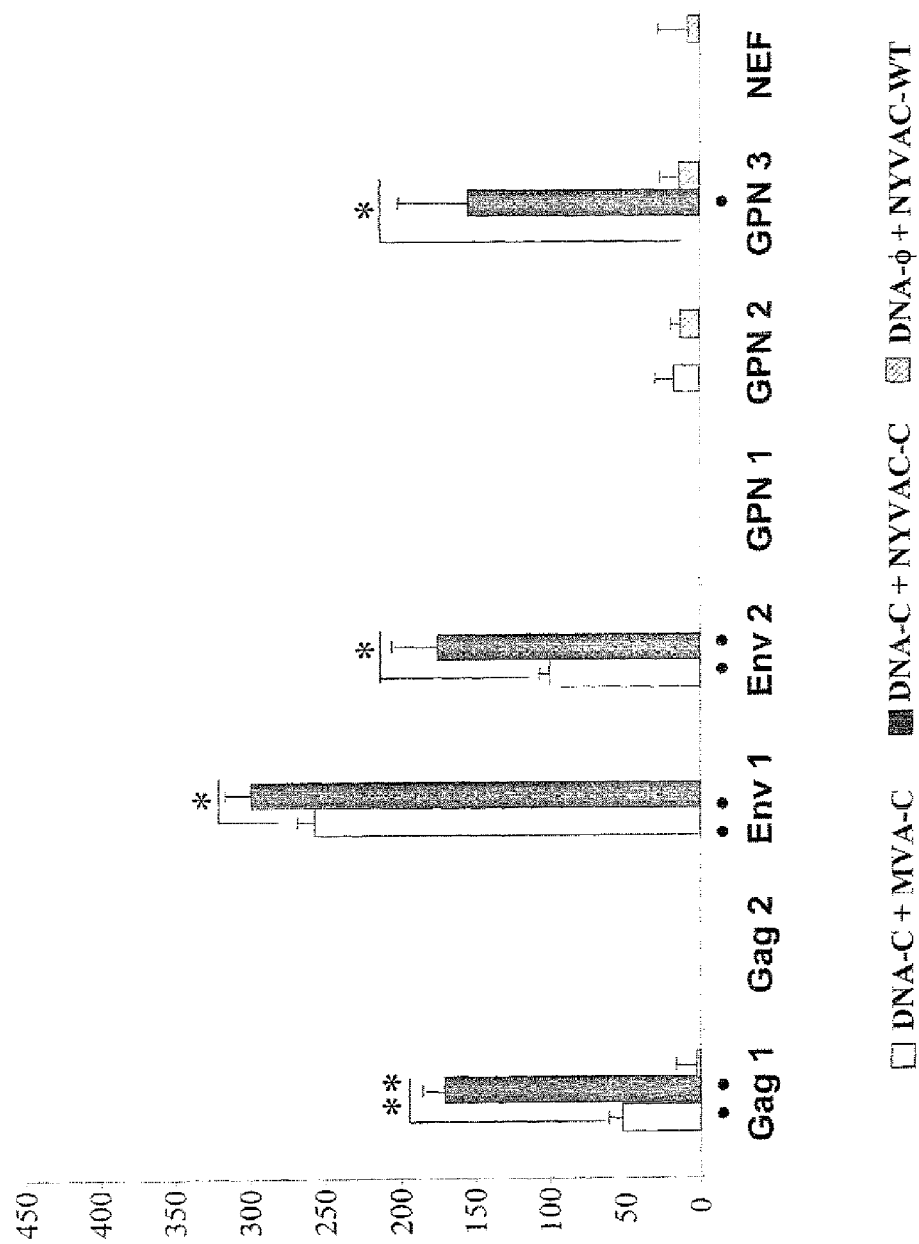

FIG. 34 shows a graph corresponding to the detection by ELISPOT of the IL-2 secreting T cells specific to each peptide group of the C clade indicated on the X axis, present for each of the $10^6$ splenocytes of HHDII immunized mice using prime/boost protocols in which DNA-C is included in the first response inducing dose, and MVA-c is inoculated in the second booster dose (first bar of each group) or NYVAC-C (second bar). The third bar corresponds to the inoculation control comprising an insertless DNA (DNA Ø) in the first dose and NYVAC-WT in the second. The circles (•) under the bars indicate the significant differences ($p<0.005$) found between each peptide group versus the negative control; asterisks indicate significant differences between the different groups: *: $p<0.05$; **: $p<0.005$.

Figure 35:
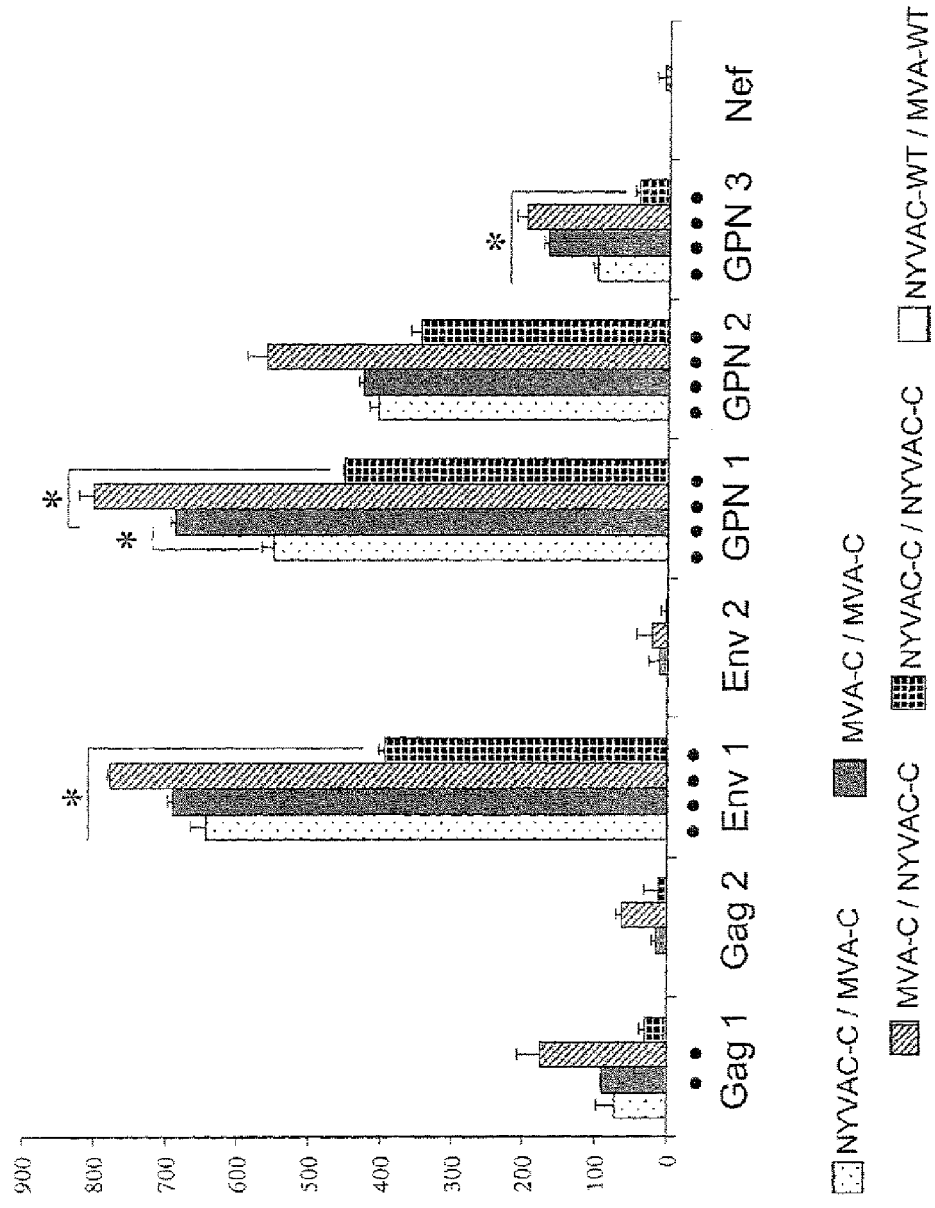

FIG. 35 shows a graph corresponding to the detection by ELISPOT of the IFN-γ secreting T cells specific to each peptide group of the C clade, indicated on the X axis, present for each of the $10^6$ splenocytes of immunized BALB/c mice using prime/boost protocols that combine MVA-derived Vaccinia vectors from which the gp120c and the gagpolnef-C proteins can be expressed. For each of those peptide groups, the first bar correspond to the value detected in animals immunized with NYVAC-C+MVA-C, the second to animals immunized with MVA-C+MVA-C, the third to animals immunized with MVA-C+NYVAC-C, the fourth to animals immunized with NYVAC-C+NYVAC-C and the fifth to animals immunized with NYVAC-WT+MVA-WT. The circles (•) under the bars indicate the significant differences ($p<0.005$) found between each peptide group versus the negative control; asterisks indicate significant differences between the different groups: *: $p<0.05$; **: $p<0.005$.

Figure 36:
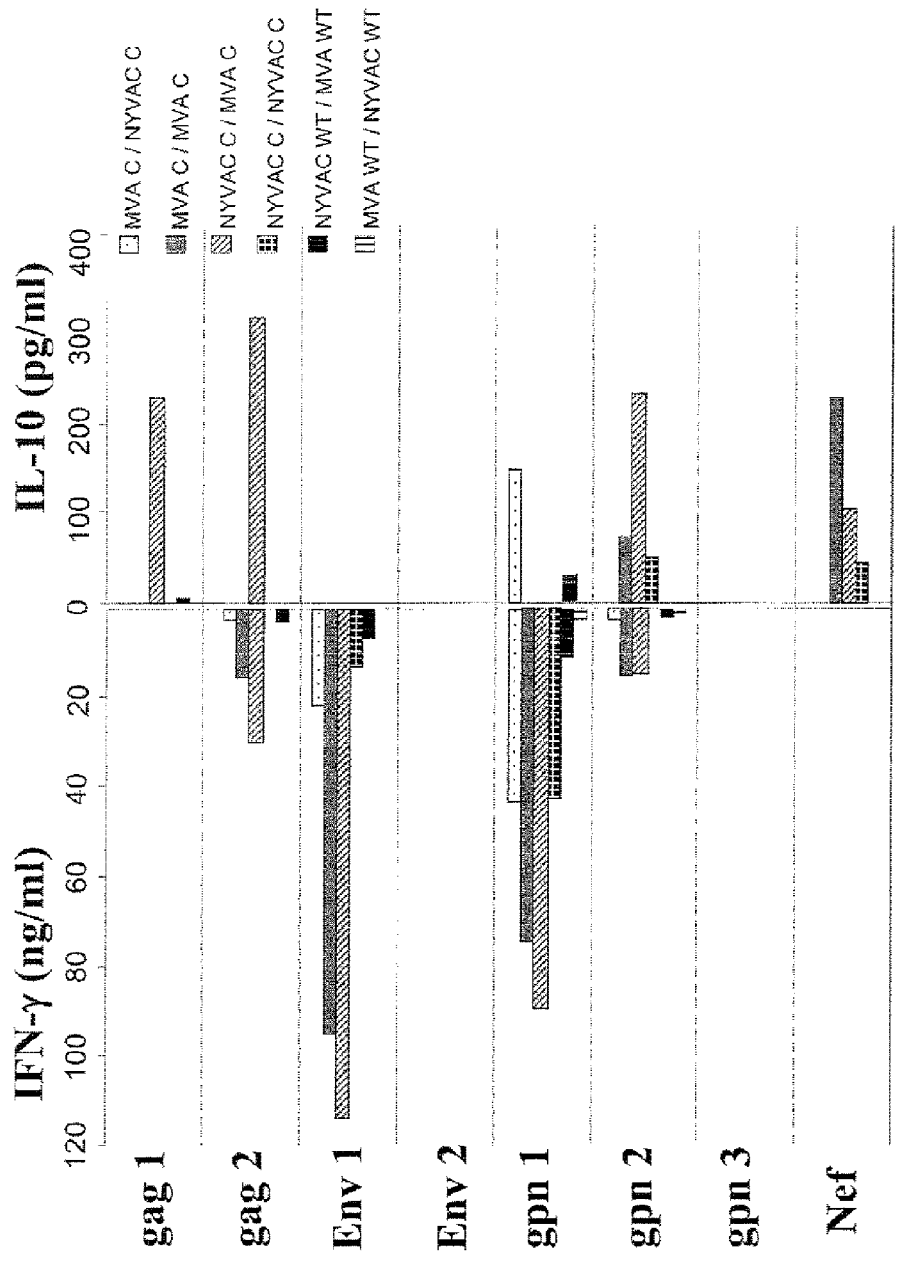

FIG. 36 shows cytokine production detected after immunizing BALB/c mice using prime/boost protocols that combine MVA-derived Vaccinia vectors from which the gp120-C and the gagpolnef-C proteins can be expressed. The left part shows the IFN-γ levels (expressed in pg/ml) and the right part shows the levels of IL-10 (expressed in pg/ml), detected in the supernatants of splenocytes, reestimulated with each of the peptide groups of the C clade indicated next to each group of bars, that have been extracted from animals inoculated with: MVA-C+NYVAC-C (first bar of each group), MVA-C+MVA-C (second bar), NYVAC-C+MVA-C (third bar), NYVAC-C+NYVAC-C (fourth bar), NYVAC-WT+MVA-WT (fifth bar) or MVA-WT+NYVAC-WT (sixth bar).

Figure 37:
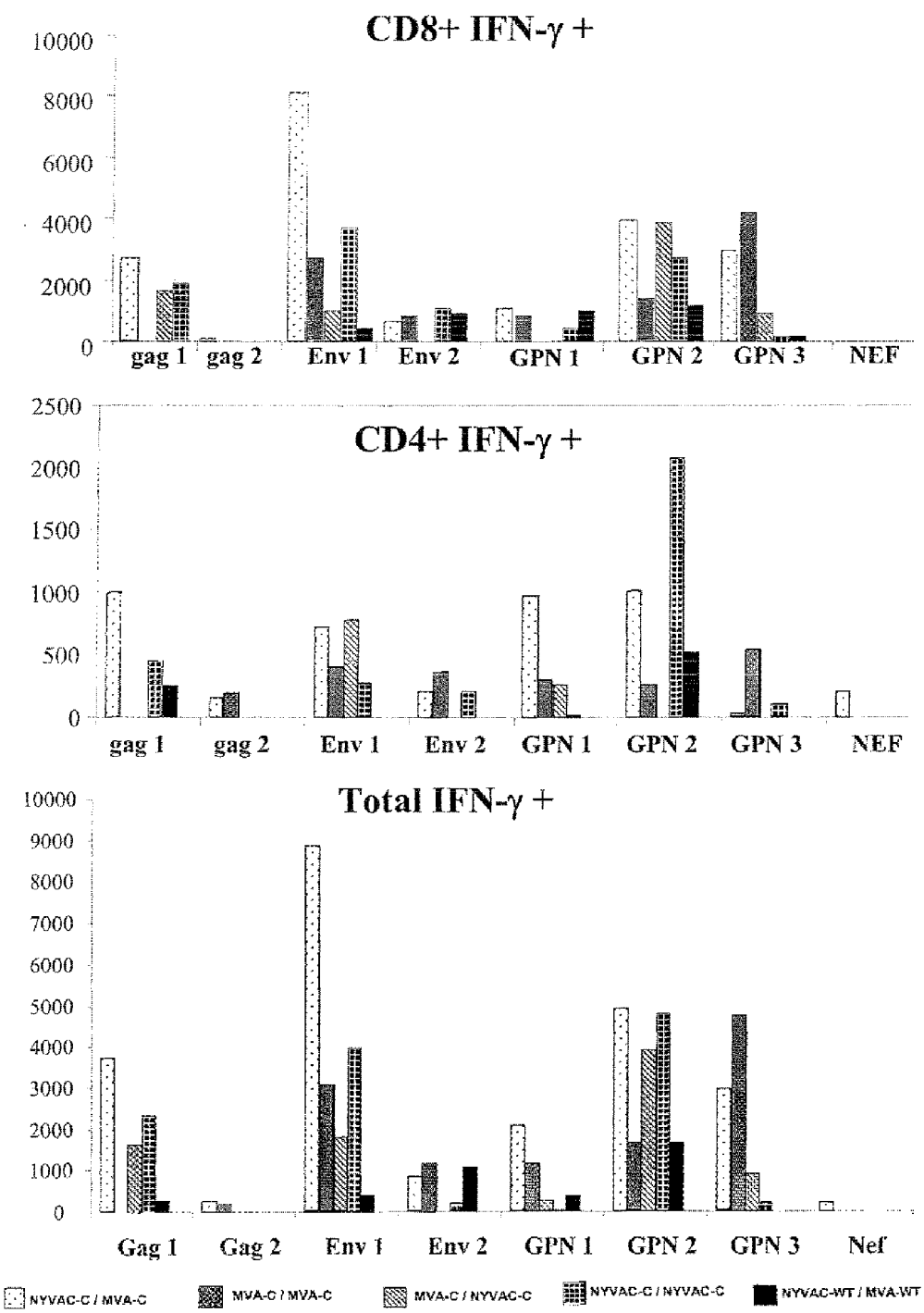

FIG. 37 shows graphs corresponding to the levels of the different types of IFN-γ secreting T cells and present in the splenocytes of BALB/c mice that have been immunized using prime/boost protocols that combine MVA-derived Vaccinia vectors from which the gp120-C and gagpolnef-C proteins can be expressed, after reestimulation by the peptide groups representative of the C clade indicated on the X axis. The upper graph correspond to the IFN-γ producing CD8+ cells present per each of the $3\times10^5$ CD8+ cells, the middle graph sample the IFN-γ producing CD4+ cells present per each of the $3\times10^5$ CD4+ cells and the lower graph represents the whole set of IFN-γ producing CD8+ and CD4+ cells present per each of the $3\times10^5$ CD8+ cells plus CD4+ cells. The bars that appear in each of the peptide groups correspond to animals inoculated with: NYVAC-C+MVA-C (first bar of each group), MVA-C+MVA-C (second bar), MVA-C+NYVAC-C (third bar), NYVAC-C+NYVAC-C (fourth bar), NYVAC-WT+MVA-WT (fifth bar).

Figure 38A:
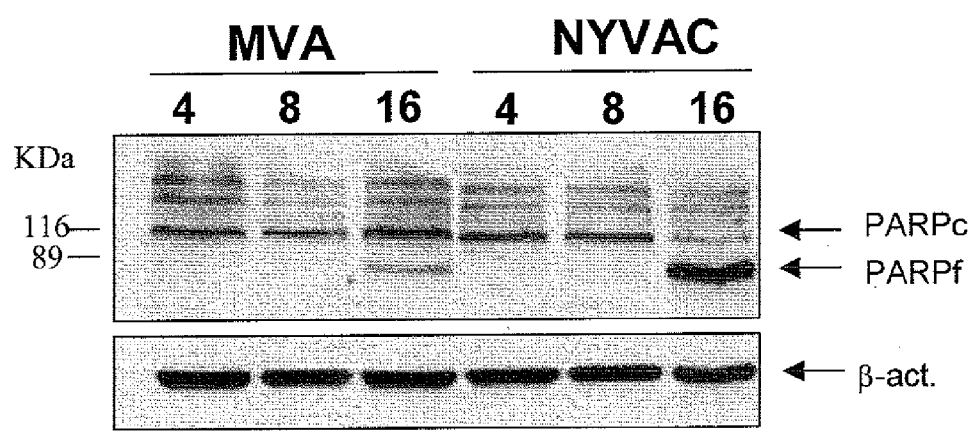

FIG. 38a shows the results obtained when HeLa cell lysates collected after several hourly times intervals—as indicated on the lanes—after infection with MVA-WT (lanes titled "MVA") or with NYVAC (lanes titled "NYVAC") are treated with antibodies directed to PARP proteins. The PARPc indicates the position of the complete PARP protein; PARf indicates the position of the PARP protein that has suffered a specific rupture. The sample on the lower part shows the intensity of the signals obtained after incubating the samples with an anti-β-actin (β-act.) antibody.

FIG. 38b shows the immunofluorescence signals detected from cells infected with MVA-WT (upper photo) or NYVAC-WT (lower photo) which nuclei had been stained with DAPI.

Figure 38C:
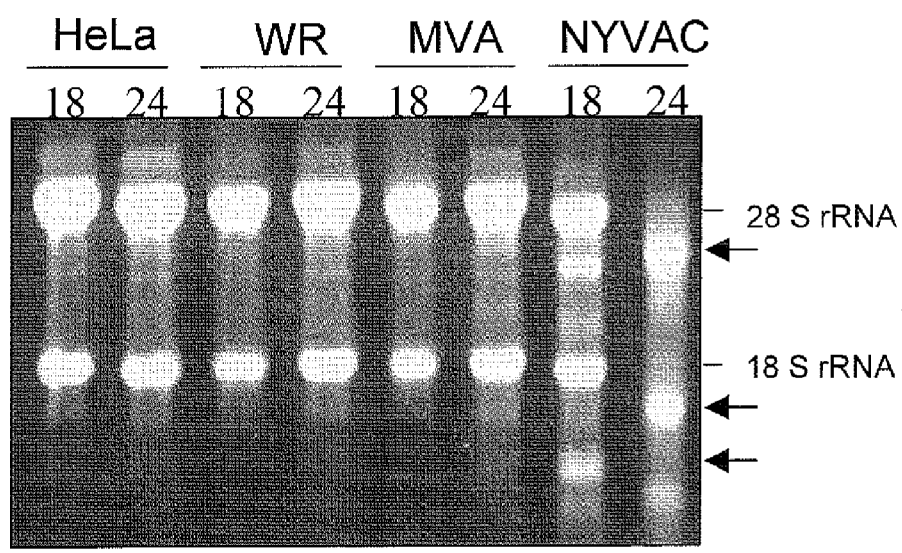

FIG. 38c shows a photograph of a gel obtained when subjecting to electrophoresis samples of ribosomal RNA cells obtained from HeLa cells after time intervals of 8 and 24 hours—as indicated on the lanes—after infecting said cells with: samples lacking the virus (gel wells labeled "HeLa"), Wild Vaccinia virus (gel wells labeled "WR"), MVA-WT (gel wells labeled "MVA"), or NYVAC-WT (gel wells labeled "NYVAC"). The position where 28S and 18S ribosomal RNAs (28S rRNA and 18S rRNA) were detected are indicated as well as the position of the bands resulting from their degradation.

Figure 38D:
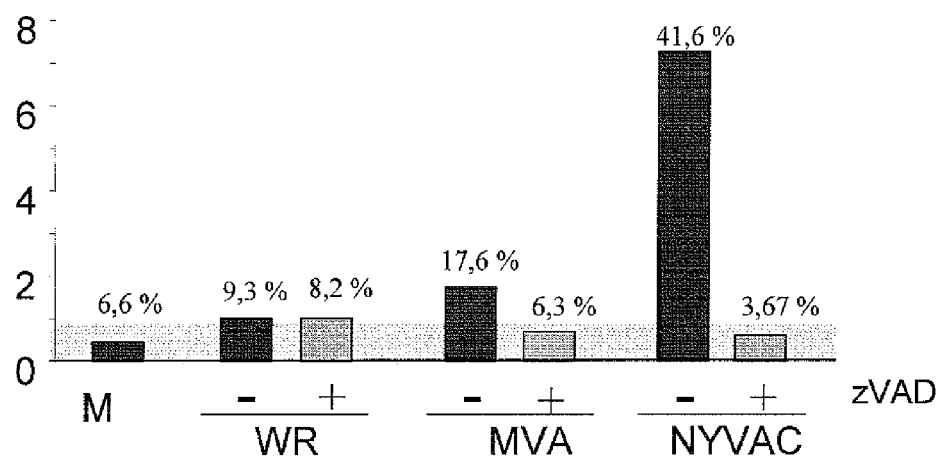

FIG. 38d shows a graph in which the increment factor of the number of apoptotic cells detected by flow cytometry in the HeLa cells infected are shown on the X axis as follows: M: infection simulation; WR: infection with wild Vaccinia virus from the Western Reserve strain; MVA: infection with MVA-WR; NYVAC: infection with NYVAC-WT. The "−" and "+" signs indicate, respectively, the absence or the presence of the zVAD caspase inhibitor in the samples used to provoke the infection.

Figure 39:
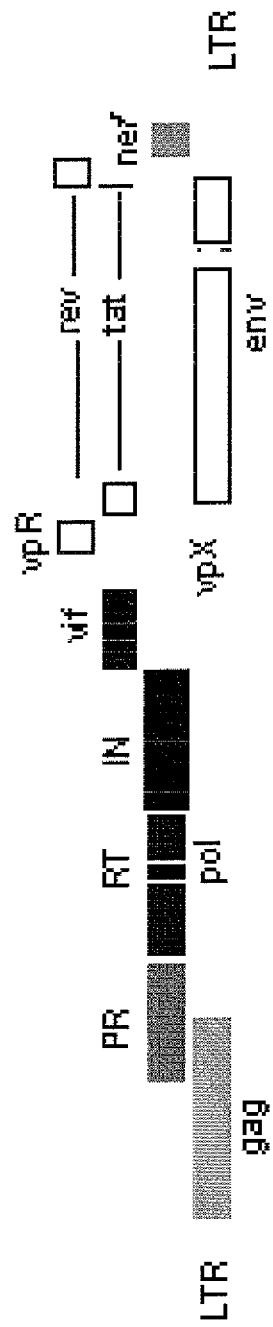

FIG. 39 shows an outline of the organization of the genome of the chimeric simian and human immunodeficiency SHIV virus 89.6P. The sequences represented by filled rectangles come from the genome of the simian virus SIVmac239, while the sequences represented by unfilled rectangles come from the genome of the HIV-1 isolate 89.6.

FIG. 40 shows the structure of the codifying sequences of retrovirus antigens present in the vectors object of the present invention. The sample on the upper part, labeled with the abbreviation "Env" correspond to different forms of the sequence that correspond to the envelope protein, the last of which labeled "C-env-120", represents the one present the vectors object of the invention, which lacks the part that correspond to the gp41 protein entirely. The sample on the lower part sample the outline of the Gag-Pol-Nef fusion protein synthesized from vectors which construction is described in Examples section. The modifications effected on the sequences deducted from the proteins of the SHIV89.P, which were generated by deducting the sequence of triplets corresponding to the proteins aminoacid sequence—for which the codons most often found in mammals were used—sequences over which the main modifications effected were as follows: the sequence corresponding to the antigen Gag that include the matrix proteins (MA), the capsid protein (CA), p2 and p7 were bound respecting the reading frame (at the point marked FS-1) with the sequence corresponding to the Pol antigen lacking the integrase; in addition, the active site of the reverse transcriptase (RT) was replaced by nef gene in which the order of the aminoacids had been altered (sc-nef), so the area that in its natural form contains the carboxyl end (RT-C) was the initial part, while the area that in its natural form contains the amine end (RT-A) was made to be the end area; the RT sequence that overlaps the active site (active site, RT) was translocated respecting the reading frame at the 3' end of the fusion protein codifying sequence; additionally, the glycine of the amine end was substituted by alanine (ΔMyr (G→A)) to prevent myristilation, while the enzymatic activity of protease (XPR) was cancelled by introducing a point mutation at its active site (ΔPRr (D→N)).

FIG. 41 shows an outline of the construction of the pLZAW-1-89.6P-SIVgpn-18 plasmidic transfer vector and of the plasmids from which it is generated.

FIG. 41*a* shows the steps necessary to obtain the pLZAWI-89.6P-9 vector;

FIG. 41*b* shows the steps necessary to obtain the pLZAW-1-89.6P-SIVgpn-18 vector from the pLZAW-1-89.6P-9 vector. In both cases the part corresponding to the Gag-Pol-Nef fusion protein, later called "SIVgpn" is indicated in the figures as "SIVsyngagpolnef", while the part that correspond to the envelope protein, later called 89.6gp120, is called "89.6Psynenv120".

FIG. 42 shows the fragments generated during PCR analysis of the thymidine kinase (TK) locus of the MVA virus-89.6P-SIVgpn. The sample on the upper part of the figure, labeled "A" shows an outline representing the pairing positions of the oligonucleotides used as primers from the left (TK-L) and the right (TK-D) arms of the TK locus, as well as the estimated sizes of the fragments generated during the course of the PCR in which the MVA virus-89.6P-SIVgpn (first line of the graph) or the insertless MVA virus (lower line of the graph, located in the area labeled "WT") were used as molds. The sample on the lower part, labeled "B", shows the photo of the gel obtained after subjecting to electrophoresis the products of the PCR done with the TK-L and TK-R2 primers on DNA extracted from cells infected with MVA-WT (lane 3), with P2 stock from the MVA-89.6P-SIVgpn (lane 4), P3 stock of the MVA-89.6P—SIVgpn (lane 5) or transfected with the pLZAWI-89.6P-SIVgpn-18 plasmid (positive control, C+) (lane 2). Lane 1 corresponds to a size marker.

FIG. 43 shows the results of the Western blot of the expression of the 89.6p-gp120 heterologous genes (shown on the upper part of the figure, labeled "anti-gp120", in which the position of the protein is indicated by the arrow labeled "89.6P") and SIVgpn (shown on the lower part of the figure and labeled "anti-SIVp27", in which the position of the SIVgpn protein is indicated by the arrow labeled "GPN") detected in extracts of cells transfected in a transitory manner with the pLZAWI-89.6P-SIVgpn-18 plasmid (second lane, labeled "C+") or in extracts from cells infected with PI (third lane, labeled "P1"), P2 (fourth lane, labeled "P2") and P3 (fifth lane, labeled "P3") stocks of the 89.6P.SIV-gpn MVA virus, or from cells treated under the same conditions but not having entered into contact with the pLZAW 1-89.6P-SIVgpn-18 plasmid or with any other virus stock (cell cultures in which the infection was simulated, analyzed in the first lane and labeled "M").

FIG. 44 shows, in the sample located on the upper part, the results of the immunostains of CEF cells infected with the MVA-89.6P-SIVgpn vector and treated with anti-WR antibodies (as recognized by the part of the vector derived from MVA) (photograph on the left), anti-gp120 (central photos) and anti-SIVp27 (recognized by the part of the SIVgpn protein corresponding to protein p27) (photo on the right)), while in the sample on the lower part there is a graph representing the percentages of the plates stained with each of the antibodies calculated from the total of plates stained with the anti-WR antibody.

FIG. 45 shows the fragments generated during PCR analysis of the TK locus of the NYVAC-89.6P-SIVgpn virus. The sample on the upper part of the figure, labeled "A", shows an outline that represents the pairing positions of the oligonucleotides used as primers from the left (TK-L) and right (TK-R) arms of the TK locus, as well as the estimated sizes of the fragments generated by the PCR in which the following viruses have been used as molds: the NYVAC-89.6P-SIVgpn virus (first line of the graph) or the insertless NYVAC virus, (lower line of the graph labeled "NYVAC-WT"). The sample on the lower part, labeled "B", shows the photo of the gel obtained after subjecting to electrophoresis the PCR products done with the TK-L and TK-R2 primers on DNA extracted from cells infected with NYVAC-WT (lane 2), P3 stock from the NYVAC-89.6P-SIVgpn virus (lane 3), P3 stock from the MVA-89.6P-SIVgpn virus (lane 4) or the MVA-WT virus, that lacks an insert (lane 5). Lane I correspond to a size marker.

FIG. 46 shows the results of the Western blot of the expression of the following heterologous genes: 89.6p-gp120 (shown on the upper part of the figure, labeled "anti-gp120", and in which the position of the protein is indicated by the arrow labeled "89.6P"), and SIVgpn (shown on the lower part of the figure, labeled "anti-SIVp27", in which the position of the SIVgpn protein is indicated by the arrow labeled "GPN") detected in extracts from cells infected with the P1 (lane 3), P2 (lane 4), and P3 (lane 5) stocks from the NYVAC-89.6P-SIVgpn vector, with P3 stock of the MVA-89.6P-SIVgpn vector (lane 2) or in extracts from cells treated under the same conditions but not having entered into contact with any virus stock (cell cultures in which the infection was simulated, as analyzed in lane 1).

FIG. 47 shows, in the sample on the upper part, the results of the immunostains of CEF cells infected with the NYVAC vector-89.6P-SIVgpn and treated with the anti-WR antibodies (photo on the left), anti-gp120 (central photos) and anti-SIVp27 (photo on the right), while in the sample on the lower part there is a graph showing the percentages of the plates stained with each of the antibodies calculated from the total of plates stained with the anti-WR antibody.

FIG. 48 shows photographs of Western blot transfer of polyacrylamide gels in which extracts from cells infected with different P3 stocks from the NYVAC-89.6P-SIVgpn virus (lanes 1 and 2, corresponding, respectively to P3.1 (29 Jan. 2004) and P3.2 stocks (25 Feb. 2004)), and MVA-89.6P-SIVgpn (P3 stocks from 20 Jun. 2003 (lane 3), P3 from 20 Sep. 2004 (lane 4), P3.1 from 20 Sep. 2004 (lane 5) and P3.2 from 1 Oct. 2004 (lane 6) had been subject to electrophoresis. Lane 7 corresponds to a cell extract in which the infection had been simulated. The photo on the left correspond to the incubation with a rabbit polyclonal anti-gp120 antibody; the position of the 89.6P-gp120 protein is indicated by an arrow labeled "89.6P". The photo on the right corresponds to the incubation with an anti-SIV-gag-p27 monoclonal antibody that recognizes the SIVgpn protein, which position in the gene is indicated an arrow labeled "SIVgpn".

Figure 49:
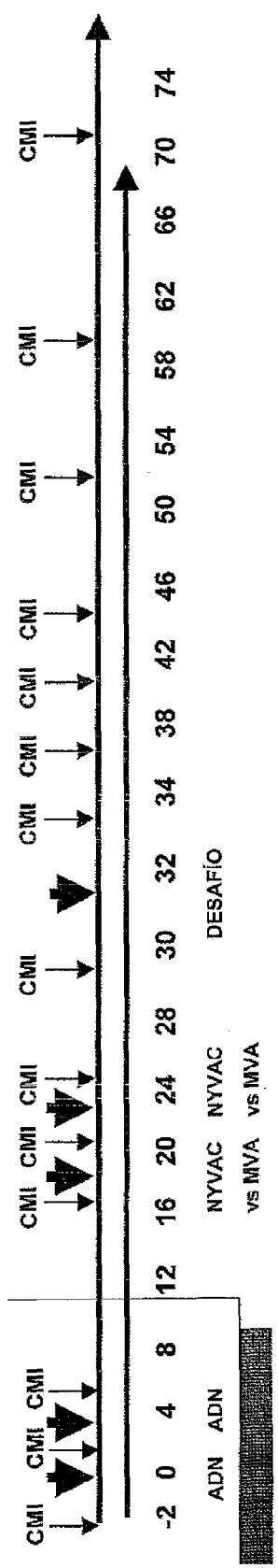

FIG. 49 shows an outline of the study done in Macacus monkeys to evaluate the immunogenecity and efficacy of the MVA-derived poxvirus vectors object of the invention as vaccines against the SHIV virus. The numbers in the outline mark the different events. The numbers located under the second horizontal line indicate the time passed, in weeks, from the beginning of the study. Point 0 corresponds to the time the first vaccination vector was inoculated. The thick arrows indicate the times at which the Macacus monkeys were inoculated with either a vaccination virus or a virus capable to produce infection as indicated by the lower line: DNA: inoculation of SHIV DNA, that is, two naked plasmids with inserts corresponding to the codifying sequences of proteins from SHIV89.6P, Env (pcDNA-gp120 89.6p) and SIVgpn (pcDNA-gag-pol-nef) (groups 1 and 2), or from the naked plasmid lacking the emp-DNA insert (group 3), NYVAC vs MVA: inoculation of the MVA-derived NYVAC-89.6P-SIVgpn poxvirus vector (group 2), MVA-89.6P-SIVgpn (group 1) or from the Wild NYVAC type vector, lacking an insert with codifying sequences of SHIV89.6P proteins (group 3); CHALLENGE: inoculation of the SHIV89.6P pathogenic chimeric virus. The thin arrows, labeled "CMI", indicate the times at which the peripheral blood samples were extracted from the Macacus monkeys.

Figure 50:
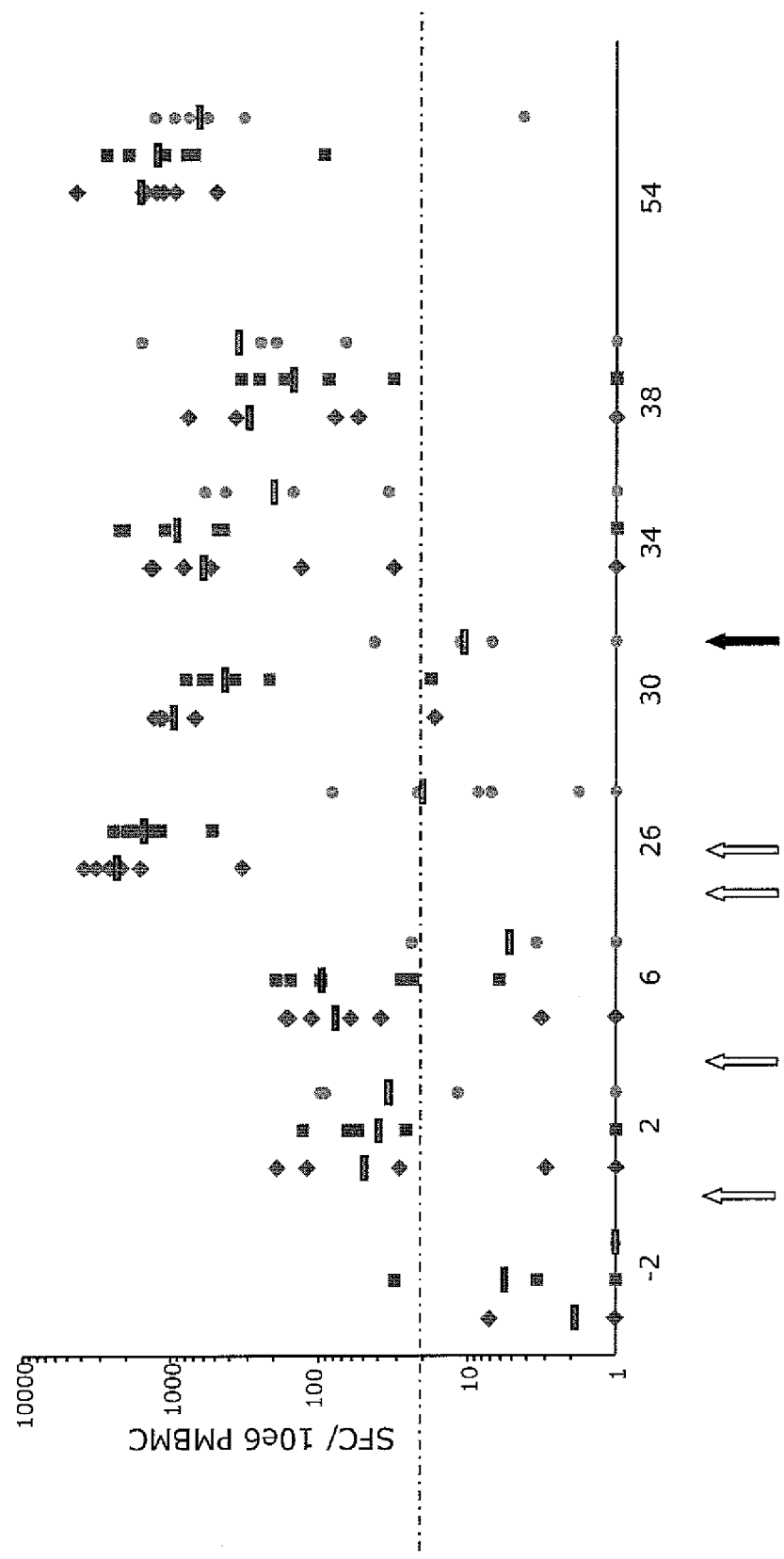

FIG. 50 show in logarithmic scale, the number of IFN-γ expressing SFC cells (spot forming cells) per $10^6$ peripheral blood mononuclear cells (PBMC) in samples taken from each Macacus monkey included in the vaccine efficacy study. The numbers on the X axis indicate, in weeks, the time at which each sample was taken, and where time 0 is the baseline at which the first vaccine dose was administered. There are three groups of values for each value of time. These values represent the behavior of each of the 7 animals used in the study and subjected to a specific immunization process: the first vertical point line sample points marked by squares positioned with one of their vertices pointing upwards (♦). this line correspond to samples taken from each of the Macacus monkeys of group 1 (immunized with plasmids with inserts corresponding to the gp120 protein from SHIV89.6P and the SIVgpn fusion protein from SHIV89.6P+MVA-89.6P-SIVgpn); the second vertical line of points marked by squares which vertices determine two parallel lines (■), correspond to samples taken from each of the Macacus monkeys from group 2 (immunized with plasmids with inserts from the SHIV89.6P gp120 protein and the SIVgpn fusion protein of the SHIV89.6P+NYVAC-89.6P-SIVgpn); the third vertical line of points is marked with circles (●), corresponds to samples taken from each of the Macacus monkeys from group 3 (immunized with a plasmid that did not express any antigen from SHIV89.6P+NYVAC-WT). Each point represents the value obtained for a particular Macacus monkey, while the rectangles located in each of the vertical lines indicate the average value for all the Macacus monkeys in said group calculated from samples taken at the same moment in time. When the number of points is less than 7 in some vertical lines, it indicates that the point located over the X axis represents more than one Macacus monkey. In each of said points, the value of the SFC detected by each of the $10^6$ PBMC analyzed did not exceed the value of 1. The broken line indicates values below which the values are not considered significant (20 SFC). The white arrows indicate inoculation of a vaccine vector; the black arrow indicates the time at which the challenge was caused by inoculating the SHIV89.6P virus.

Figure 51:
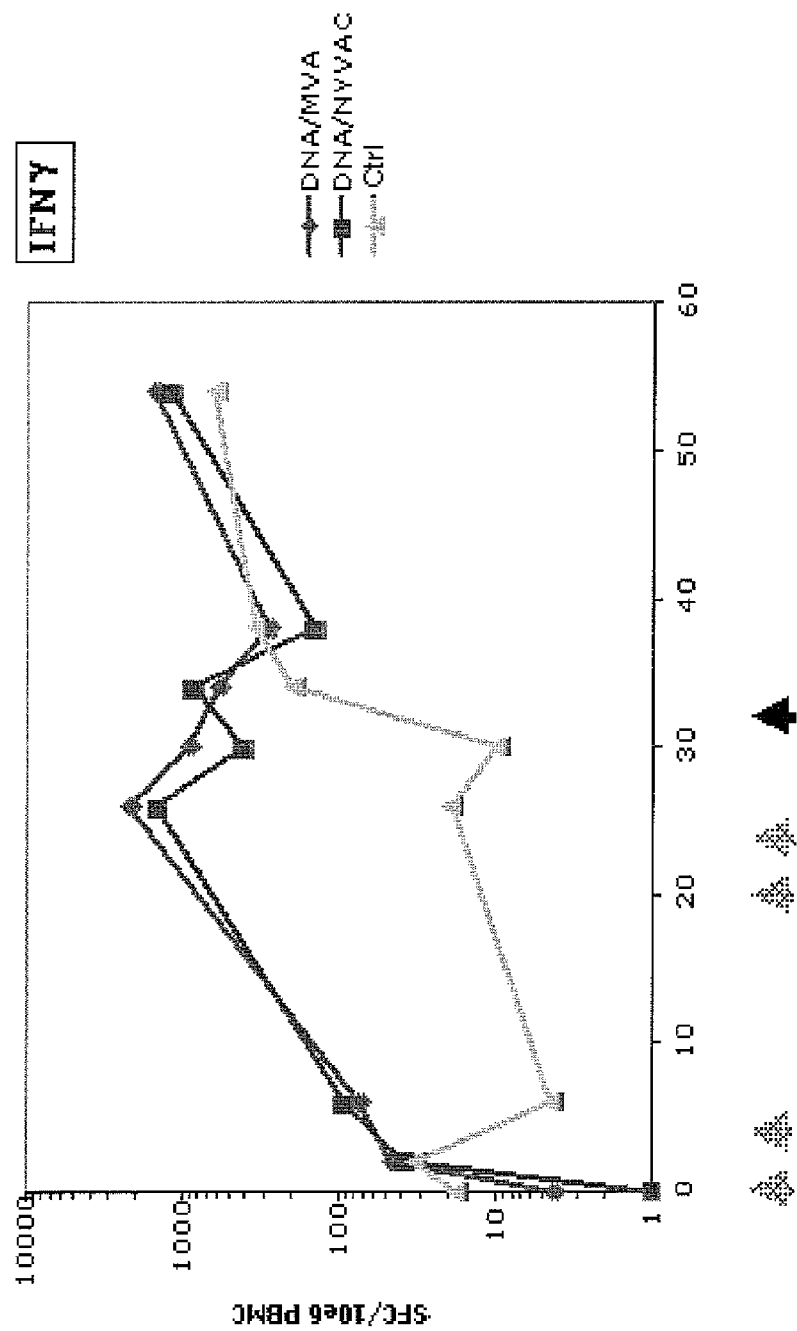

FIG. 51 shows, in logarithmic scale, the average values obtained for IFN-γ expressing SPF per each $10^6$ PBMC analyzed for each group of Macacus monkeys throughout the length of the study. this time is expressed weeks on the X axis. Time 0 corresponds to the time the first vaccine dose was administered. The arrows with dotted fill indicate the times at which the vaccine doses were administered. The arrow with solid dark fill indicates the time of the challenge by inoculation of the SHIV89.6P virus. The data indicated by squares positioned with one of their vertices pointing upwards (♦) are those of group 1 (the animals in this group were immunized plasmids with inserts from the gp120 protein of the SHIV89.6P virus and the SIVgpn fusion protein from SHIV89.6P+MVA-89.6P-SIVgpn); the data indicated by squares which vertices determine two parallel lines (■) is that of group 2 (immunized with plasmids with inserts from the SHIV 89.6P gp120 protein and the SIVgpn fusion protein from SHIV89.6P+NYVAC-89.6P-SIVgpn). The data indicated by triangles (▲) corresponds to group 3 (immunized with a plasmid from which SHIV89.6P+NYVAC-WT antigens are not expressed).

Figure 52:
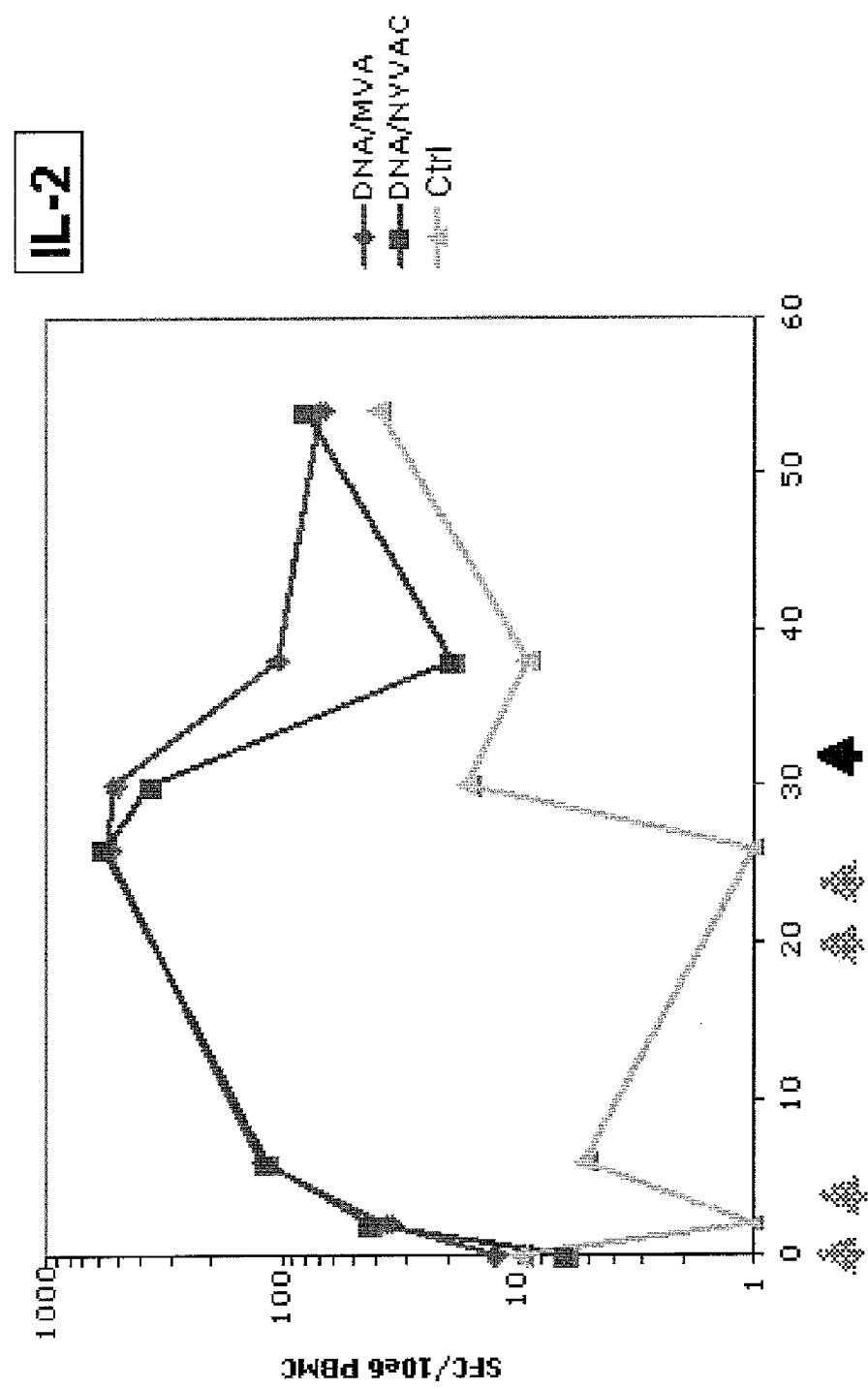

FIG. 52 shows in logarithmic scale, the average values of IL-2 expressing SPF obtained per each of the $10^6$ PBMC analyzed, for each group of Macacus monkeys throughout the time of the study. Time is expressed in weeks on the X axis, where Time 0 is the time the first vaccine dose was administered. The arrows with dotted fill indicate the times at which vaccines doses were administered. The arrow with solid black fill indicates the time at which the challenge was introduced by inoculating the SHIV89.6P virusSHIV89.6P virus. The data indicated by squares positioned with one of their vertices pointing upwards (♦) is that of group 1 (immunized with plasmids with inserts from the SHIV89.6P gp120 protein and the SHIV89.6P+MVA-89.6P-SIVgpn SIVgpn fusion protein); the data indicated by squares which vertices determine two parallel lines (■) is that of group 2 (immunized with plasmids with inserts from SHIV89.6P gp120 protein and the SIVgpn fusion protein from SHIV89.6P+NYVAC-89.6P-SIVgpn). The data indicated by triangles (♦) is that of group 3 (immunized with a plasmid from which SHIV89.6P+NYVAC-WT antigens are not expressed).

Figure 53:
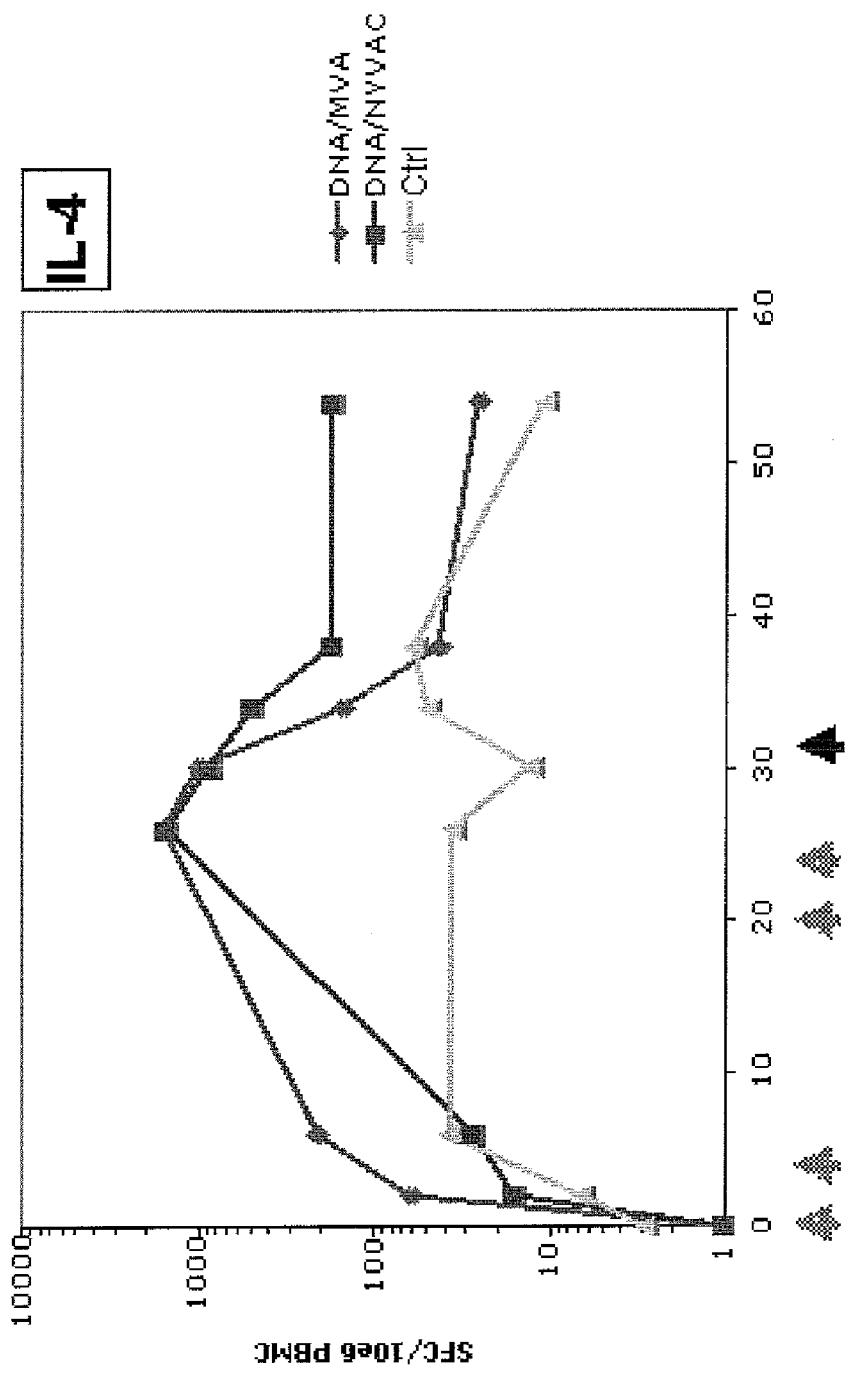

FIG. 53 shows in logarithmic scale, the average values of IL-4 expressing SPF obtained, by each of the $10^6$ PBMC analyzed, for each group of Macacus monkeys throughout the time of the study. Time is expressed in weeks on the X axis, where Time 0 corresponds to the first time the first vaccine dose was administered. The arrows with dotted fill indicate the times at which the vaccine doses were administered. The arrow with solid black fill indicates the time of the challenge by inoculating the SHIV89.6P virus. The data indicated by squares positioned with one of their vertices pointing upwards (♦) are those of group 1 (immunized with plasmids with inserts from the SHIV89.6 Pgp120 protein and the SIVgpn fusion protein from SHIV89.6P+MVA-89.6P-SIVgpn); the data indicated by squares which vertices determine two parallel lines (■) is that of group 2 (immunized with plasmids with inserts from SHIV89.6P gp120 protein and the SIVgpn fusion protein from SHIV89.6P+NYVAC-89.6P-SIVgpn). The data indicated by triangles (♦) is that of group 3 (immunized with a plasmid from which SHIV89.6P+NYVAC-WT antigens are not expressed).

Figure 54:
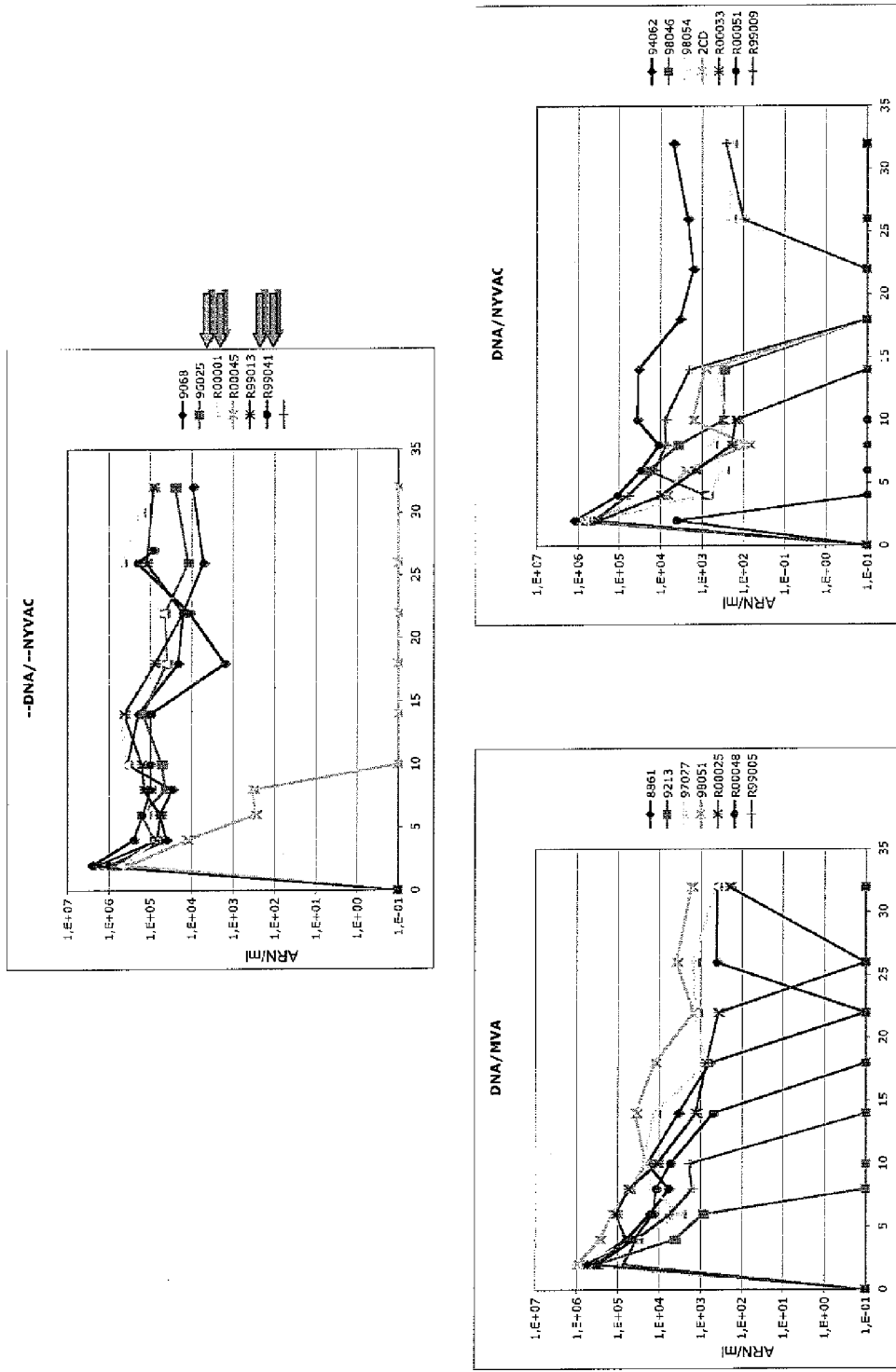

FIG. 54 corresponds to the assessment of the viremia in the three groups of the study. The upper graph corresponds to group 3, immunized with a plasmid from which SHIV89.6P+NYVAC-WT antigens are not expressed. The lower graphs represent the groups that received vectors derived from the poxvirus: the graph of the sample on the lower left part corresponds to group 1, that was immunized with plasmids with inserts from the SHIV89.6P gp120 protein and the SIVgpn fusion protein from SHIV89.6P+MVA-89.6P-SIVgpn; the graph of the sample on the lower right corresponds to group 2, that was immunized with plasmids with inserts from the SHIV89.6 Pgp120 protein and the SIVgpn fusion protein from SHIV89.6P+NYVAC-89.6P-SIVgpn. Each point connecting line represents one Macacus monkey. Each point marked with a symbol represents the RNA copies of SHIV89.6P, detected by QC RNA-PCR, in the plasma sample of that Macacus monkey taken in the week indicated on the X axis. Time 0 corresponds to the moment of inoculation with the SHIV89.6P virus.

Figure 55:
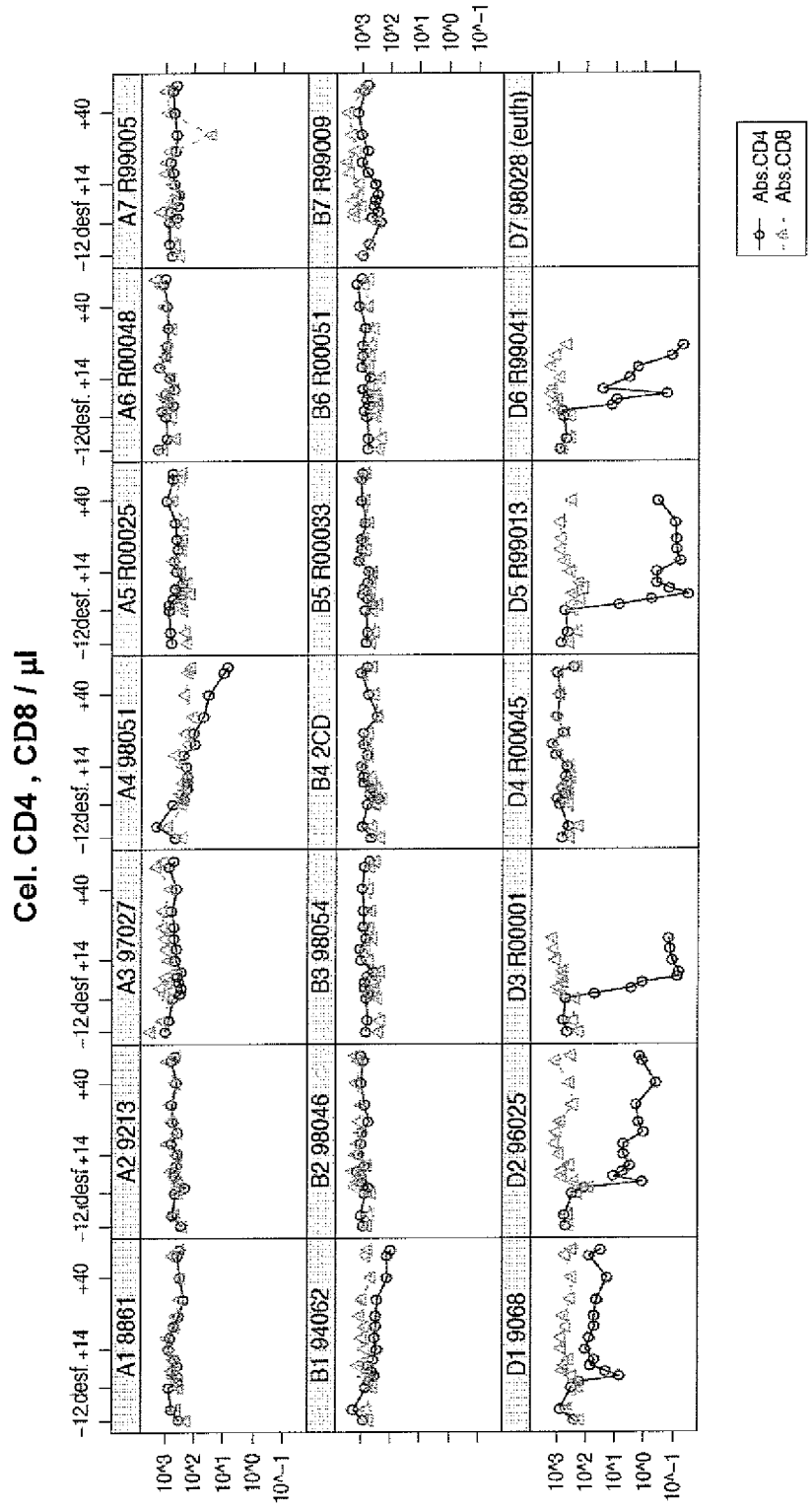

FIG. 55 shows the concentration, per microliter of blood, of CD4⁺ cells (points marked by unfilled circles (Ø) and of CD8⁺ cells (points marked by unfilled triangles, (Δ), detected by FACS analysis using specific antibodies directed against each of these cell types. Each group of points corresponds to the values obtained in the samples extracted at the times indicated from a different Macacus monkey. The time is expressed in weeks in the sample that appears on the upper part of the graphs. Time 0 corresponds to the time the SHIV89.6P virus was inoculated, as indicated by the abbreviation "desf.". The upper graphs correspond to Macacus monkeys from group 1 that were immunized with plasmids with inserts from the SHIV89.6 Pgp120 protein and the SIVgpn fusion protein from SHIV89.6P+MVA-89.6P-SIVgpn. The intermediate graphs correspond to Macacus monkeys from group 2, that were immunized with plasmids with inserts corresponding to the gp120 protein from SHIV89.6P and the SIVgpn fusion protein from SHIV89.6P+NYVAC-89.6P-SIVgpn. The lower graphs correspond to Macacus monkeys from group 3, that were immunized with a plasmid that did no express any SHIV89.6P+NYVAC-WT antigen. The last graph, lacking value indicating points and marked "D7 98028 (euth)", is that of a Macacus monkey that had to be sacrificed due to the advance stage of the disease triggered by having had the SHIV89.6P virus inoculated.

Figure 56:
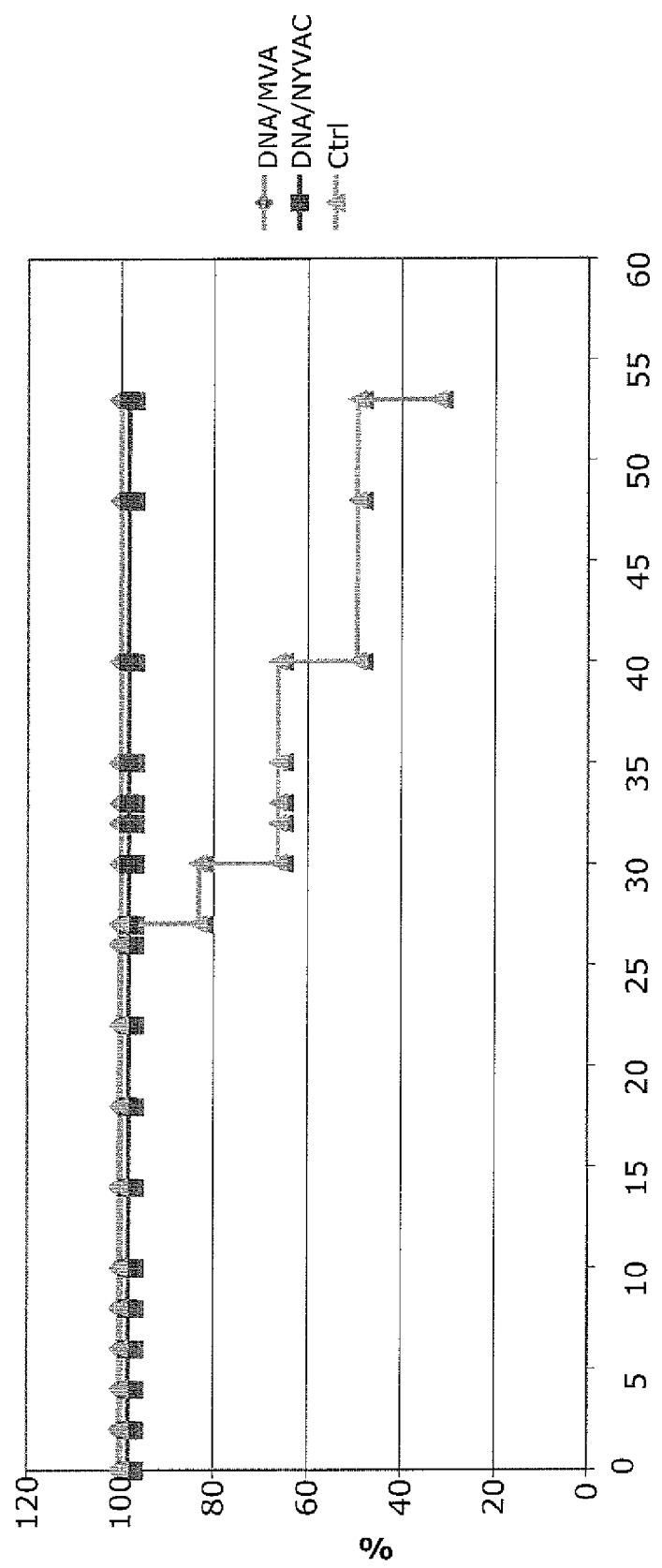

FIG. 56 shows, on the Y axis, the survival percentage of the Macacus monkeys that made up each group according to the number of weeks from the time of infection with the SHIV89.6P virus, shown on the X axis, and where Time 0 is the time said virus was first inoculated. The data indicated by squares positioned with one of their vertices pointing upwards (♦) are those of group 1 (immunized with plasmids with inserts from the SHIV89.6P gp120 protein and the SIVgpn fusion protein from SHIV89.6P+MVA-89.6P-SIVgpn); the data indicated by squares which vertices determine two parallel lines (■) is that of group 2 (immunized with plasmids with inserts from SHIV89.6P gp120 protein and the SIVgpn fusion protein from SHIV89.6P+NYVAC-89.6P-SIVgpn). The data indicated by triangles (▲) is that of group 3 (immunized with a plasmid from which SHIV89.6P+NYVAC-WT antigens are not expressed).

EXAMPLES

Construction and Immunogenecity Assays of Vectors Designed for Purposes of Human Vaccination Example 1

Generation of the MVA-B Vector

Construction of the pLZAWgp120B/gagpolnef-B-1 Plasmidic Vector
The pLZAWgp120B/gagpolnef-B-1 plasmidic vector was constructed by the inventors in order to generate the recombinant MVA virus that express the HIV-1 Env genes (BX08 isolation) and the Gag, Pot and Nef chimera (IIIB isolation), both belonging to the B clade. The DNA of the Gag-Pol-Nef chimera was generated by GeneArt (Regensburg, Germany) and the DNA of gp120 was generated by the Aventis Group; the plasmids that contain them and were used to construct the pLZAW1gp120B/gagpolnef-B-1 vector, and the MVA-B vector from the later, were provided to the group of inventors within the framework of the EuroVacI cooperation program.

The pLZAWIgp120B/gagpolnef-B-1 plasmid is a pUC derivative designed for blue/white plate screening. The plasmid contains the right (TK-R) and left (TK-L) flanking sequences of the thymidine kinase (TK) viral gene, the E3L promoter, directing the expression of the P-galactosidase screening marker and the ampicillin resistance gene (AP). The sequences whose expression is sought: gp120-BX08 (SEQ ID NO: 15) and gagpolnef-IIIB (SEQ ID NO: 16) are found between the two flanking sequences. The desired sequences have been modified to optimize the use of mammal codons. To direct the expression of each sequence there are corresponding early/late synthetic promoters (pE/L), located in opposite directions in the insert area furthest from the flanking sequences. Table 1 below sample the position of each component included in the plasmid:

TABLE 1

Position of the components of the pLZAW1gp12OB/gagpolnefB-1 plasmid

| | | |
|---|---|---|
| TK left flanking sequence | 90-410 | Complementary |
| T5NT for β-gal | 929-935 | Complementary |
| β-gal | ATG-TAA (936-4079) | Complementary |
| E3L promoter for β-gal | 4080-4140 | Complementary |
| Part 1 of the TK left flanking sequence | 4151-4498 | Complementary |
| gagpolnef-IIIB | ATG-TAA (4533-8513) | Complementary |
| E/L promoter for gagpolnef-IIIB | 8523-8561 | Complementary |
| E/L promoter for gp120-BXO8 | 8576-8614 | |
| BX08gp120 | ATG-TAA (8624-10105) | |
| T5NT for BX08gp120 | 10144-10150 | |
| TK right flanking sequence | 10212-10903 | Complementary |
| AP | ATG-TAA (12074-12934) | Complementary |

Two other plasmids were used in the construction of this plasmid:
pMA60gp120B/gagpolnefB-12,17
(provided by the Aventis Group, Canada). The plasmid is a pUC derivative that contains the right (TK-R) and left (TK-L) flanking sequences of the thymidine kinase (TK) viral gene, the E3L promoter that directs the expression of the screening marker β-galactosidase, and the ampicillin resistance gene (AP). The sequences whose expression is sought: gp120-BX08 and gagpolnef-IIIB are found between the two flanking sequences. The desired sequences have been modified to optimize the use of mammal codons. To direct the expression of each sequence there are corresponding early/late synthetic promoters (pE/L), located in opposite directions in the insert area furthest from the flanking sequences.

pLZAW 1: The plasmid was provided by Linong Zhang, from the Aventis Group, Canada. This is a pUC-based plasmid that contains a left arm of the TK gene, cloning sites to insert exogenous genes, a short repetition of the TK gene left arm, an E3L promoter that directs the expression of a β-gal containing cassette and a right arm of the TK gene.

Figure 2:
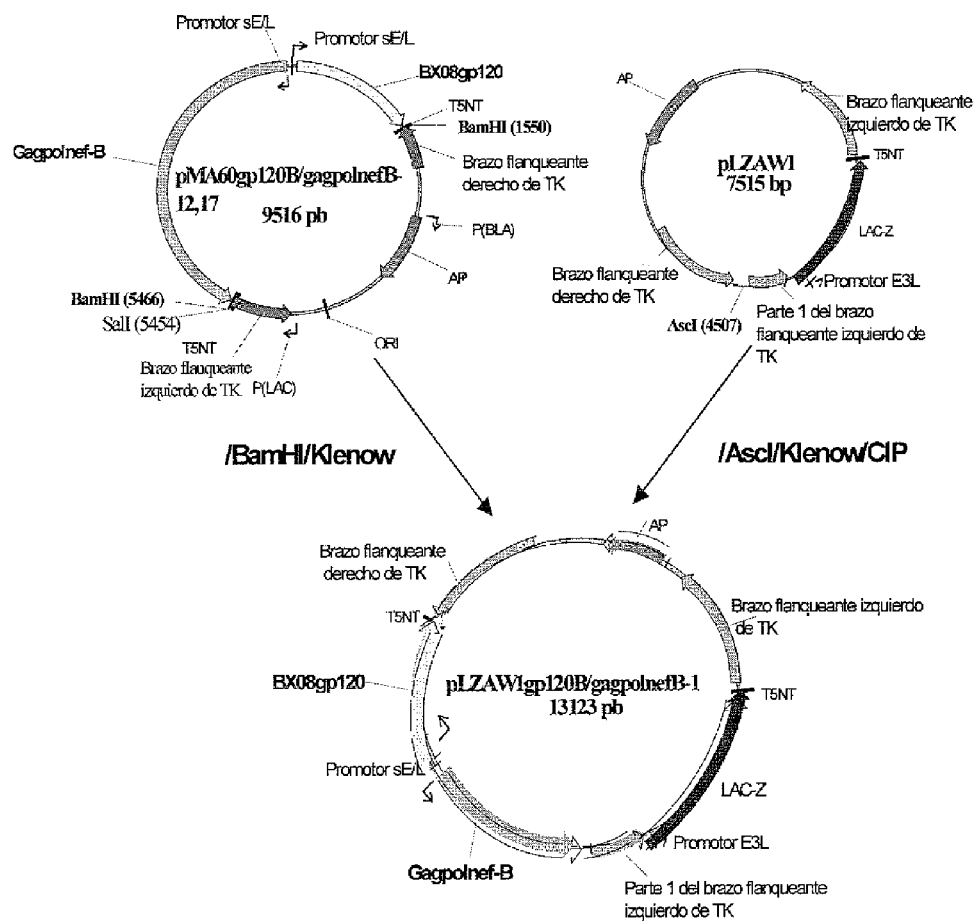
FIG. 2 shows an outline of the construction process of the pLZAW1gp12OB/gagpolnef-B-1 plasmidic transfer vector and the plasmids from which it has been generated.

FIG. 2 shows how the pLZAW1 gp12OB/gagpolnefB-I plasmid has been constructed from these other two plasmids. Briefly, a 5.6 Kb DNA fragment containing the genes of interest was obtained by digesting the pMA60gp120/gagpolnefB-12,17 plasmid with BamHI, then modified by incubating it with Klenow DNA polymerase to generate blunt ends and cloned in the pLZAWI vector that had been previously digested with the AscI restriction endonuclease, modified by incubating it with Klenow, and dephosphorylated by incubating it with the alkaline phosphatase enzyme, and thus generating the pLZAW1gp12OB/gagpolnef-B-1 plasmid transfer vector. The generated plasmid directs the insertion of the genes of interest in the TK locus of the genome of the attenuated MVA virus.

Construction of the MVA-B Recombinant Virus

Primary cultures of chicken embryo fibroblasts (CEF) were infected with attenuated MVA virus during passage 586 (pass 585 was MVA-F6 provided by Gerd Sutter) to a multiplicity of infection of 0.05 ufp/cell, and later transfected with 10 μg of the pLZAWIgp120B/gagpolnefB-1 plasmid transfer vector, using in the process commercial lipofectin supplied by Invitrogin according to the manufacturer's instructions. After 72 hours post-infection, the cells were collected, sonicated and used to select recombinant viruses. The recombinant MVA viruses that contained the gp120B/gagpolnef-B genes and coexpressed—in a transitory manner—the β-gal (MVA-B (X-Gal+)) gene marker, were selected by consecutive plate purification passages in CEF cells stained with -bromo-4-chloro-3-indolyl-β-galactoside (XGal) (300 μg/ml). The recombinant MVA that contained the gp120B/gagpolnef-B genes and had lost the gene marker (MVA-B (X-Gal")) was selected as non-stained viral foci in CEF cells in the presence of XGal. In each purification step the isolated plates were expanded in CEF during 3 days, and the raw viral extract obtained was used in the subsequent plate purification step of plates.

After 4 consecutive purification passages, 12 recombinant plates were isolated. These plates expressed both antigens efficiently and had lost the gene marker. The recombinant named MVA-B-4.1.5.2 (P1) was made to grow to generate a raw stock (P2) that was sent to production in GMP conditions for clinical trials. The sequence of the insert located at the thymidine kinase locus of this recombinant is represented as SEQ ID NO: 19. Table 2 below shows the localization in said sequence of each of the elements that composed the insert.

TABLE 2

| Position of the main components of the insert of the MVA-B vector | | |
|---|---|---|
| Part 1 of the left flanking sequence of TK | 1-502 | Complementary |
| gagpolnef-IIIB | ATG-TAA (537-4517) | Complementary |

TABLE 2-continued

| Position of the main components of the insert of the MVA-B vector | | |
|---|---|---|
| E/L promoter for gagpolnef-IIIB | 4527-4565 | Complementary |
| E/L promoter for gp 120-BX08 | 4580-4618 | |
| gp120-BX08 | ATG-TAA (4628-6109) | |
| TK right flanking sequence | 6216-6907 | Complementary |

A P3 stock of purified virus from CEF cells was prepared from P2 stock. Said CEF cells were infected to a multiplicity of infection of 0.05 ufp/cell through two 45% saccharose matrices. This P3 stock, having a titer of 2.4×109 ufp/ml, was the stock used in the immunization protocols.

MVA-B Characterization

To confirm the genetic homogeneity of the MVA-B virus generated and the integrity of the inserted genes, the viral DNA extracted from the CEF cells infected to a multiplicity of infection of 5 ufp/cell was subjected to a PCR analysis in which oligonucleotides that hybridize either with the flanking TK regions of the insert of interest or with internal regions of the genes inserted were used. Table 3 shows the sequence of the oligonucleotides used as primers and the position in which they appear on the pLZAW1 gp120B/gagpolnefB-1 plasmid transfer vector. The positions in which said oligonucleotides hybridize, as well as the estimated sizes of the fragments generated in the different PCRs and their locations in relation to the inserts and the flanking sequences, are shown in the sample on the upper part of FIG. 3.

TABLE 3

Oligonucleotides used as PCR primers for the characterization of the MVA-B vector

| Oligonucleotide | SEQUENCE | | Position |
|---|---|---|---|
| TK-L | 5' TGATTAGTTTGATGCGATTC 3' | (SEQ ID NO: 1) | 4338-4357 |
| TK-R | 5' TGTCCTTGATACGGCAG 3' | (SEQ ID NO: 2) | 10379-10395 |
| BX08556 | 5' TGCCCATCGACAACG 3' | (SEQ ID NO: 3) | 9129-9143 |
| GPN7649 | 5' AGCCCCATCGAGACCG 3' | (SEQ ID NO: 4) | 6698-6713 |
| GPN8170 | 5' ATTAGCCTGCCTCTCGG 3' | (SEQ ID NO: 5) | 7218-7234 |
| E/L | 5' TATTTTTTTTTTTGGAATATAAATAG 3' | (SEQ ID NO: 6) | 8522-8548 |

The lower part of FIG. 3 shows photographs of the gels obtained when subjecting to electrophoresis the products of the PCRs run with the different primer pairs to analyze the HIV-1 fragments included in the MVA-B virus. To do this, 100 ng of viral DNA extracted from chicken embryo cells (CEF) infected to a multiplicity of infection 5 ufp/cell with the MVA-B virus from the P3 stock (lane 2), MVA-WT (lane 3), and NYVAC-WT (lane 4) or with 10 ng of the pLZAWIgp120B/gagpolnef-B-1 plasmid (lane 1), were used to amplify by PCR the different HIV-1 fragments included in MVA-B. The conditions of each PCR are individually standardized for each pair of oligonucleotide primers used. As it can be seen in the photographs shown in the sample on the lower part of FIG. 3, the samples corresponding to the positive control, the pLZAW1gp120B/gagpolnef-B-1 plasmid, give rise in all cases to bands having the same size as those from the corresponding MVA-B samples, while lanes 3 and 4, corresponding to samples lacking inserts (MVA-WT and NYVACWT, respectively), no bands are observed.

The wild NYVAC virus type used in this example, as well as the recombinant NYVAC-B and NYVAC-C forms used later and were generated by inserting on the wild NYVAC type the same sequences used to generate, respectively, the MVA-B and MVA-C vectors object of the invention, were donated by the Aventis Group, within the framework of the EuroVacI cooperation project, in vials containing approximately $7 \times 10^7$ infectious units per vial. Before use, the NYVAC-B vector was grown in CEF cells and purified in saccharose matrix in the same conditions as the MVA-B vector.

Figure 1:
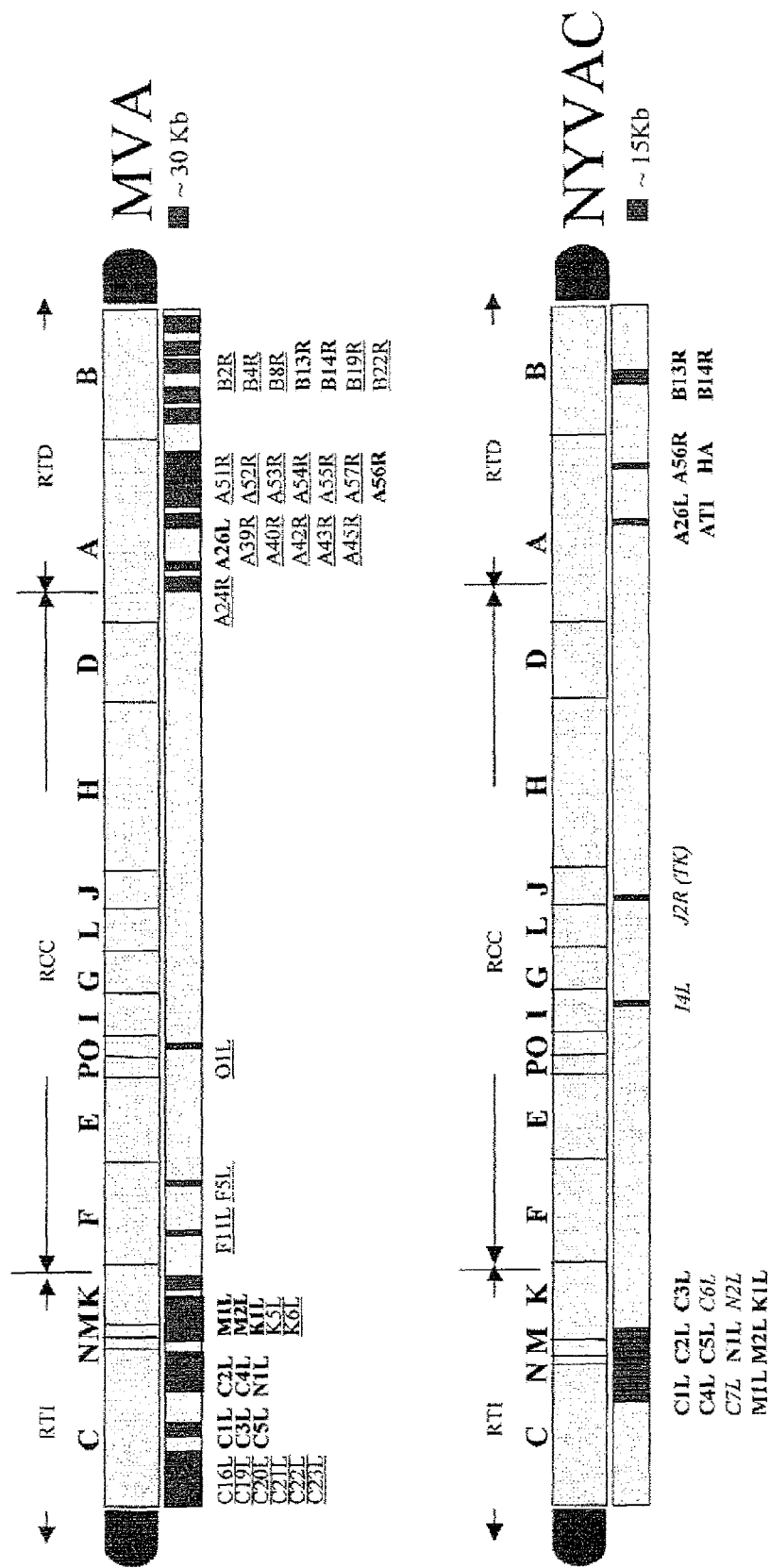
FIG. 1 shows an outline of the genome maps of the MVA viruses (shown on the upper part) and of the NYVAC viruses (shown on the lower part), in which the localization of the fragmented genes is indicated by a dark shadowing effect and their names are shown immediately below. Underlined names indicate the genes deleted in the MVA virus but intact in the NYVAC virus; names in bold type indicate the names of the genes deleted both in the MVA and the NYVAC viruses; and the names in italics indicate genes left intact in the MVA virus but with deletions in the NYVA virus. The letters A to Q located over each of the representations of the genomes refer to the names assigned to the different restriction fragments generated by digesting the genomic DNA of the MVA and NYVAC viruses with the HindIII enzyme. RTI: terminal left region; RCC: conserved central region; RTD: terminal right region.
Figure 4:
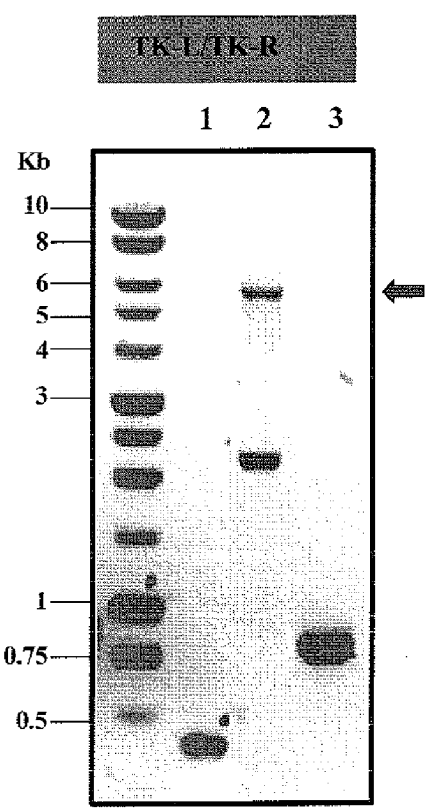
FIG. 4 shows a photograph of a gel obtained when subjecting to electrophoresis the products of a PCR in which oligonucleotides that hybridize with the flanking sequences of the TK gene were used as primers. The samples corresponding to each lane are: 1: NYVAC-WT; 2: MVA-B; 3: MVA-WT.

FIG. 4, shows a photograph of a gel resulting from the PRC products obtained from the TK locus. To obtain them, 100 ng of the viral DNA extracted from CEF cells infected to a multiplicity of infection of 5 ufp/cell with the NYVAC-WT (lane 1), MVA-B (lane 2) or MVA-WT (lane 3) viruses, were used as molds to run a PCR analysis of the TK locus, using as primers 100 ng of the oligonucleotides that hybridize with the flanking sequences of the TK, TK-L (SEQ ID NO:1) and TK-R (SEQ ID NO:2) gene in a reaction mix containing 0.3 mM of dNTPs, 2.5 mM of MgC12, and 2.5 U of the Platinum Taq polymerase enzyme. The program includes a denaturation cycle run at 94° C. during 5 minutes, 25 denaturation cycles run at 94° C. during 1 minute, hybridization at 60° C. during 1 minute and extension at 68° C. during 2 minutes, followed by a final extension cycle run at 68° C. during 10 minutes. The PCR products were analyzed in a 0.7% agarose gel obtaining the result shown in FIG. 4. In lane 2, corresponding to the MVA-B vector, a band of approximately 6 Kb compatible with the presence of the complete insert can be observed, while in the lanes corresponding to the wild MVA-WT(3) and NYVAC-WT (1) type viruses the bands that appear and would correspond to the insertless TK locus are much smaller. The differences observed in the band size of the insertless MVA-WT and NYVAC-WT viruses are caused because the TK gene is one of the genes that has suffered a selective inactivation in the NYVAC virus (see FIG. 1), which makes the TK gene have a smaller size in this attenuated from of Vaccinia.

Example 2

Analysis of the Expression of HIV Proteins from MVA-B

The expression of the gp120-BX08 and gagpolnef-B proteins by the MVA-B virus was analyzed by Western blot type transfer. Monolayers of CEF cells grown in 12 well gel plates were infected at a rate of 5 ufp/cell from the various MVA-B recombinant virus stocks: P1, P2 and P3. The cellular extracts were collected 24 hours post-infection, fractioned in polycrylamide denaturating gels (SDS-PAGE), transferred to nitrocellulose membranes, and subjected to the reaction versus a anti-gp120 polyclonal rabbit antibody (generated in the laboratory) that recognizes the gp120 protein from the BX08 isolation; and versus a anti-p24 polyclonal rabbit antibody (provided by the EVA program, ARP432) that recognizes the gagpolnef-B chimera from the IIIB isolation. Extracts from cells infected with the NYVAC vector-B were used as positive controls.

Figure 5:
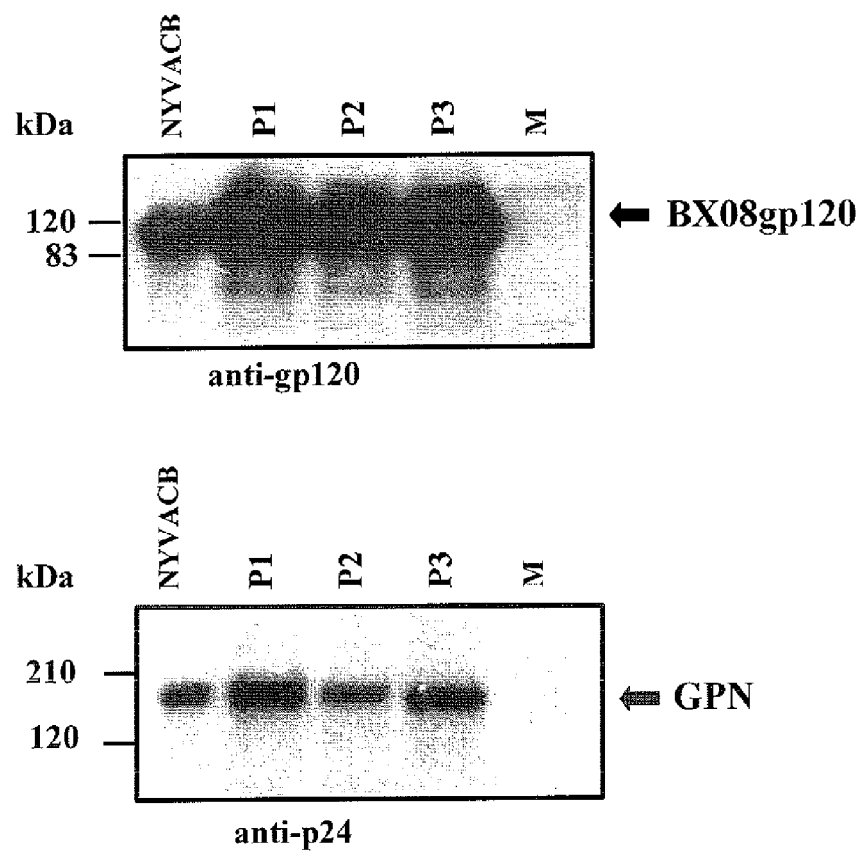
FIG. 5 shows the results of the Western blot transfer analysis of the expression of the heterologous gp120-BX08 genes (shown on the upper part of the figure) and gagpolnef-IIIB genes (shown on the lower part of the figure, in which the gagpolnef-IIIB protein appears abbreviated as GPN) from a NYVAC-B vector (first lane), from the P1, P2 and P3 stocks (lanes 2-4: P1, P2 and P3) and from cells in which the infection had been simulated (lane 5).

As can be observed in FIG. 5, both antigens are efficiently expressed by the different stocks of the MVA-B recombinant vector generated.

Example 3

Verification of the Stability of the MVA-B Vector

To verify the fact that the MVA-B recombinant vector could be passed successively without losing the expression of the genes inserted, a stability assay was carried out that entailed doing several successive passages of the MVA-B recombinant virus in CEF cells. Monolayers of CEF cells grown in P100 plates were successively infected to a multiplicity of infection of 0.05 ufp/cell, starting with the MVA-B P2 stock (pass 6) until pass 10 was generated (P10). The next step was to infect monolayers of CEF cells grown in 6 wells gel plates with a $10^{-5}$ dilution of the viral extract obtained during the last pass (P10). 48 hours post-infection, the lysis plates thus generated were immunostained, using anti-WR polyclonal antibodies (capable of recognizing proteins from the MVA virus); anti-gp120 polyclonal antibodies (capable of recognizing gp120 of the BX08 isolation); and anti-p24 polyclonal antibodies (capable of recognizing gagpolnef-B chimeras of the IIIB isolation). These last two antibodies were the same used in Example 2. The results of these immunostains are shown in part A of FIG. 6. Plate counts showed that 100% of the plates had been stained with the anti-WR, anti-p24 and anti-gp120 antibodies. Based on these results, it may be considered that after successive passages of the virus in CEF cells, both antigens are efficiently expressed (100% of the plates were recognized by the three antibodies), thus corroborating the stability of the product generated.

The extracts of CEF cells infected with passages 7, 8, 9 and 10 were also analyzed by Western blot type immunotransfer, as shown in stains that appear in part B of FIG. 6. For these tests, monolayers of CEF cells grown in 12 well gel plates were infected at a rate of 5 ufp/cell of the viral extracts obtained in passages 7 (P7), 8 (P8), 9 (P9) and 10 (P10) of the MVA-B recombinant virus. The cellular extracts were collected 24 hours post-infection, fractioned in polycrylamide denaturating gels (SDA-PAGE), transferred to nitrocellulose membranes and made to react with the same anti-gp120 (right part of Figure) or anti-p24 (left part of Figure) polyclonal antibodies used in the test which results are shown in part A of FIG. 6. Both antibodies were used at a 1/500 dilution rate. An extract of CEF cells infected with the NYVAC-B virus (provided by the Aventis Group) was used as positive control. The results confirm the correct expression of the gp120-BX08 and gagpolnef-B proteins in all the extracts obtained by infection with viruses obtained from the different passages Example 4

Release of gp120-BX08 and Kinetic Expression from the MVA-B Vector Through Time

Figure 7:
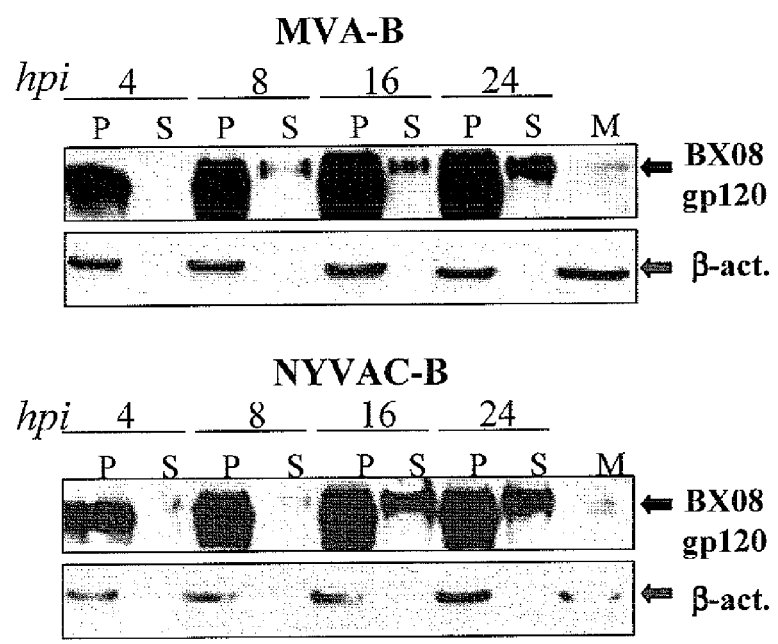
FIG. 7 shows the gp120-BX08 protein kinetic expression obtained by Western blot transfer with a B clade anti-gp120 antibody corresponding to samples taking after 4, 8, 16 and 24 hours from infection with a recombinant virus. The upper part corresponds to the MVA-B virus infection and the lower part to infection with the NYVAC-B virus. The intensity of the signals attained after incubating the samples with an anti-β-actin (β-act.) antibody appears immediately below each sample. P: precipitate; S: supernatant; M: infection simulation.

To define whether the gp120-BX08 protein was efficiently secreted, monolayers of CEF cells grown in 12 well gel plates were infected with MVA-B at a rate of 5 ufp/cell. After 4, 8, 16 and 24 hours post-infection had passed, the cells were collected separating the cellular precipitate (P) from the supernatant (S). The supernatants obtained from each time of collection were analyzed, concentrated and fractioned together with the cellular precipitates in polycrylamide denaturating gels (SDS-PAGE), transferred to nitrocellulose membranes and subjected to reaction versus the anti-gp120 polyclonal antibody (at a 1/500 dilution) previously used in Examples 2 and 3. The CEF cells infected with the NYVAC-B virus (provided by the Aventis Group) used as positive control in the assay were treated in the same manner. As internal control to verify that the same amount of protein had been applied to the gel, the membranes were also incubated versus an anti-6-actin monoclonal antibody. The results are shown in FIG. 7. It can be seen in the sample in the upper part of the figure that corresponds to the MVA-B sample, that the gp120-BX08 protein is efficiently expressed by the MVA-B vector after 4 hours post-infection, detected in the cellular supernatant after 8 hours post-infection, and with has a similar behavior to that observed in cells infected with the NYVAC-B, vector, the results of which are shown in the lower part of FIG. 7.

Figure 8:
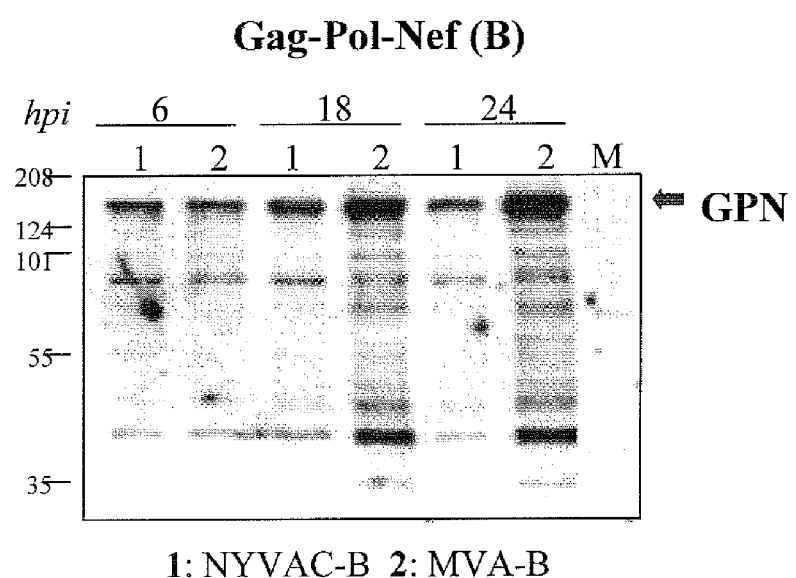
FIG. 8 shows the kinetic expression of the gagpolnef-IIIB protein obtained by Western blot transfers using a B clade anti-p24 antibody done with samples taken after 6, 18 and 24 hours of being infected with a recombinant virus. The lanes marked with the number "1" are those containing samples infected with the NYVAC-B virus, the lanes marked with the number "2" contain samples infected with the MVA-B virus, and the lane marked with the letter "M" show the sample in which the infection was simulated. The arrow indicates the position of the gagpolnef-IIIB protein (abbreviated as GPN).

The expression of the gagpolnef-B fusion protein was analyzed following a similar procedure: monolayers of CEF cells grown in 12 well gel plates were infected with MVA-B at a rate of 5 ufp/cell although, this case, the presence of the protein was tested in the cellular precipitate obtained after 6, 18 and 24 hours post-infection, and also by means of the Western blot transfer procedure and revealing the presence of the protein by reaction with the anti-p24 polyclonal antibody used in Examples 2 and 3. The results are shown in FIG. 8, where the correct expression of this fusion protein can be observed through the time of infection both from MVA-B (lane 2 of each time of infection) as from NYVAC-B (lane 1), although greater accumulation of the fusion protein occurs in cells infected with MVA-B.

Example 5

Immunogenecity of the MVA-B Vector: Specific Immune Response of IFN-γ Producing T Cells Once the MVA-B recombinant vector has been generated and characterized, the next objective was to analyze its capacity to induce a specific immune response in the murine model versus the antigens that it expresses. To do this, 6-8 weeks old BALB/c mice (n=4) were inoculated intraperitoneally (i.p.) with a $2\times10^7$ ufp/mouse of MVA-B (P3 stock) or of NYVAC-B dose. Ten (10) days after immunizing them the mice were sacrificed by cervical dislocation, and their spleens were removed to detect antigen specific T cells by ELISPOT according to their capability to produce IFN-γ, which is a positive indicator that an immunogen is capable of selectively activate a $CD4^+$ Th1 type cellular response, a characteristic that is considered as indicative of the efficacy of a vaccination process. To do this, 96 wells gel plates with nitrocellulose bottoms were covered with a 75μ/well of a 6 μg/ml concentration of a rat anti-murine IFN-γ monoclonal antibody (R4-6A2, Pharmingen, San Diego, Calif.) resuspended in PBS and then left to incubate all night at ambient temperature. Later the gel wells were washed three times with RPMI media. The last step was to incubate it with a media complemented by 10% FCS, for at least one hour at 37° C. in a 5% $CO_2$ atmosphere. On the other hand, the spleens of the immunized mice, that one extracted were kept in RPMI+10% FCS, were arranged on a sterile grids over a 60 mm plate, and were homogenized, disgregating the extract by passing it through different caliber needles (21G->25G). The disgregated cells were spun during 5 minutes at 1,500 rpm and at 4° C., and were washed twice with RPMI+% FCS. To lyse the erythrocytes obtained from the samples, 0.1 M of sterile $NH_4Cl$ 0.1 (2 ml/spleen) was added and the result and kept at 4° C. during 3-5 minutes, RPMI+% FCS was added and the solution was spun. The cells were washed twice, and were finally resuspended in 1-2 ml of RPMI+% FCS. The splenocyte viability count was done using Trypan blue stain (4% in water, Sigma).

To evaluate the specific immune response, different groups of 40-50 peptides having 15 aminoacids each, of which 11 of them were overlapped, were used, covering all the antigenic regions included in the inventive MVA-B recombinant vector. Each peptide group was diluted at a concentration of 10 μg/ml in RPM+% FCS, to which 30 U/ml of IL-2 were added. Once prepared, 100 μl of peptide group mix was added to each well, over which 100 gl/well of splenocytes of the animals immunized were added at a concentration of $10^7$ splenocytes/ml and 1/4 and 1/16 dilutions. The plates were incubated during 48 hours at 37° C. in a $CO_2$ atmosphere, were washed 5 times with PBS containing Tween 0.05% (PBST), and were incubated with 2 μg/ml of biotynalated rat anti-IFN-γ XMG1.2 monoclonal antibody (Pharmingen) diluted in PBST during 2 hours at ambient temperature. Then the plates were washed 5 times with PBST and a 1/800 dilution of avidine peroxidase (0, mg/ml) was added (Sigma). After 1 hour at ambient temperature it was washed 3 times with PBST and 2 with PBS, adding as final step the developing mix with 1 μg/ml of DAB substrate (Sigma), resuspended in 50 mM Tris-HCl pH 7.5 containing 0.015% of $H_2O_2$. The reaction was stopped by washing plate with abundant water and once dried the stains generated were counted with the aid of a Leica MZ122 APO stereomicroscope and the Imaging System QW1 N software (Leica, Cambridge, United Kingdom). The number of IFN-γ producing cells obtained versus a non-related antigenic peptides mix (negative control) was subtracted in all cases.

The results, shown in FIG. 9, demonstrate that the MVA-B vector is capable of boosting a specific immune response versus almost all the peptide groups tested, in a different proportion from its homologous, the NYVAC-B vector.

Example 6

Immunogenecity of the MVA-B Vector: Cytokine Production by Reestimulated Splenocytes The next step was to evaluate the cytokine production stimulated in the splenocytes of the immunized mice after mixing them with the different overlapping peptide groups. To do this, the splenocytes isolated in Example 5 were cultured ($5\times10^6$ cells/well) in a 24 well gel plate and stimulated with 1 μg/ml of each peptide group. The plate was incubated during 5 days at 37° C. in 5% $CO_2$ atmosphere, after this period the supernatants of the cultures were collected and spun at 1.500 rpm, 5 minutes, at 4° C., and then stored at −70° C. until further use. As mentioned previously, the levels of the inteferon gamma cytokine (IFN-γ) are a positive indicator of the activation of a $CD4^+$ Th1 type cellular response, while the IL-10 cytokine is an indicator of a $CD4^+$ Th2 type cellular response. The relation between the IFN-γ levels and IL-10 indicates whether the vaccination is more or less efficacious. The procedure followed to find out the existing levels of each cytokine (IL-10 e IFN-γ) present in the supernatants of reestimulated splenocytes cultures "in vitro" was to determine these levels by commercial ELISA kits manufactured by Pharmingen. Following the manufacturer's directions, 96-wells flat bottomed gel plates were covered with the anti-cytokine antibody, diluted in the corresponding buffer, and then incubated all night at 4° C. Afterwards, the gel wells were washed with PBST, and were blocked during 1 hour at ambient temperature with PBST+10% FCS (PBSTB). Later, serial dilutions in PBSTB of the samples and standard cytokines were added and the plate incubated at ambient temperature for 2 hours to be later washed with PBST and incubated at ambient temperature, during 1 hour, with the biotynalated anti-cytokine specific antibody, together with peroxidase-conjugated streptavidin, all of it diluted in PBSTB. Finally, the reaction was detected with TMB (3.3', 5.5'-tetramethylbenzydine, Sigma), at ambient temperature and in the dark, was stopped, after 30 minutes of incubation, with $H_2SO_2$ 2 N.

The absorbance was read at 450 nm and the values obtained were extrapolated in the standard curve (μg/ml). The results, shown in FIG. 10, indicate the polarization of the specific cellular response towards a Th1 subtype, characterized by the secretion of high levels of IFN-γ, both for MVA-B and for NYVAC-B, versus the different peptide groups tested. There are clear differences between The responses generated by each of the recombinant vectors.

Example 7

Immunogenecity of the MVA-B Vector:
Identification of the Different Types of Specific IFN-γ Secreting T Cells As the antigen presenting cells used up to this point to characterize the cellular response were spleen cells that express Class I Major Histocompatibility Complex (MHC-I) as of class II (MHC-II), the next step was to find out whether the cellular response obtained up to this point with the ELISPOT assay was due to the secretion of IFN-γ by TCD8$^+$ or TCD4+ cells. To do this the splenocytes obtained in Example 5 were reestimulated in vitro during 1 hour at 37° C. with 5 µg/ml of each overlapping peptide group from the B clade, followed by an addition of Brefeldin at a 10 µg/ml concentration that was incubated all night at 37° C. Seven days later the surface was stained using specific anti-CD4 or anti-CD8 FITC-conjugated antibodies, followed by intracellular staining with a PE-conjugated anti-IFN-and. Once the cells were fixed they were analyzed in the flow cytometer.

The results, shown in FIG. 11, make possible to appreciate that for both the group of animals immunized with the MVA-B vector, as for the group immunized with the NYVAC-B vector, the IFN-γ producing response is mostly due to the activated specific TCD8+ cell population against the different peptide group. When determining the total IFN-γ levels secreted by both types of cells, the result obtained with the ELISPOT test described in Example 5, where a specific response against the majority of the peptide groups was observed in the groups of animals immunized with both recombinant vectors was confirmed. Again, there are clear differences between the responses generated by each of the recombinant vectors.

Example 8

Use of MVA-B Virus in Prime/Boost Protocols:
Specific Immune Response of IFN-γ Producing T Cells Once it was established that administering a first MVA-B containing immunization dose containing was capable of inducing a specific immune response in the murine model, the next step was to evaluate whether using this inventive vector as part of prime/boost protocols increased the magnitude and amplitude of the immune response. To do this, groups of 4, 6-8 weeks old, BALB/c mice were inoculated intramuscularly (i.m.) with 100 µg of the DNA-B DNA vector (provided by GeneArt, Germany), containing the same HIV-1 proteins codifying sequences as those inserted in the MVA-B vector, but under the control of cytomegalovirus promoters and inserted in plasmidic vectors (one for gp120 and another for the Gag-Pol-Nef fusion protein). The control groups were inoculated (i.m.) with 100 µg of insertless DNA (DNA Ø). Fifteen (15) days later they were immunized intraperitoneally (i.p.) with 2×10$^7$ ufp/mouse of MVA-B (P3 stock) or of NYVAC-B (Aventis Group, France), that express the same HIV antigens as MVA-B. A third group received a second dose of DNA-B (100 µg, i.m.). The control groups received a 2× of 10$^7$ ufp/mouse dose of MVA-WT or NYVAC-WT. Ten (10) days after the last immunization the mice were sacrificed by cervical dislocation and their spleen was extracted to analyze it with an ELISPOT test. To detect the specific immune response, mixes of splenocytes from the animals immunized in each group were exposed to contact during 48 hours to different overlapping peptide mixes (pools) belonging to the B clade (5 µg/ml) comprising all the antigenic regions included in the MVA-B and NYVAC-B recombinant viruses. The number of IFN-γ producing cells obtained against non-related antigenic peptide mix (negative control) was subtracted in all cases. The results obtained are shown in FIG. 12 that shows the number of specific IFN-γ secreting cells detected by each of the 10$^6$ splenocytes in the immunized mice with the different vector combinations. It was observed that for nearly all the peptide groups analyzed the inclusion of poxvirus derived HIV-1 codifying antigens vectors in the second immune response booster dose causes, in almost all cases, a significant increase of the immune response compared to the cases in which only DNA vectors are used, and The response generated is different depending on whether the MVA-B or the NYVAC-B vectors are used.

Example 9

Use of the MVA-B Vector in Prime/Boost Protocols:
Cytokine Production by Reestimulated Splenocytes Five groups of BALB/c mice (n=4) were inoculated using a combined immune in using combined immune response priming regime by administering a first vector dose and a boosting dose administered by inoculation of another vector in a second dose similarly to the procedure described in Example 8 and using the same vector combinations. The extracted splenocytes were then stimulated in vitro with the different mixes of B clade overlapping peptides (1 µg/mL) and incubated during 5 days at 37° C. After this time, the supernatants were collected and stored at −70° C. The IFN-γ levels were determined by ELISA using a commercial kit (Pharmigen). The results are shown in FIG. 13, where it can be observed that the IFN-γ production differs depending on whether MVA-B or NYVAC-B are used as second immunization vector.

Example 10

Use of the MVA-B Vector in Prime/Boost Protocols:
β-Chemiokines Production by Reestimulated Splenocytes Five groups of BALB/c mice (n=4) were inoculated with a combination immune response priming regime by administering a first dose of vector and booster by inoculating another vector in a second dose, in a manner similar to that described in Example 8 and using the same vector combinations. The extracted splenocytes were stimulated in vitro with the different mixes of overlapping peptides from the B clade (1 µg/ml) and incubated during 5 days at 37° C. After this time, the supernatants were collected and stored at −70° C. The levels of MIP-1 β and RANTES were determined by the ELISA test using commercial kits (Pharmigen).

The results are shown in FIG. 14, where it can be observed that the production of chemiokines MIP-1 B and RANTES differ depending on whether MVA-B or NYVAC-B are used as second immunization vector.—

Example 11

Use of the MVA-B Vector in Prime/Boost Protocols:
Identification of the Types of Specific IFN-γ and TNF-α Producing T Cells Five groups of BALB/c mice (n=4) were inoculated in using combined immune response priming regime by administering a first dose of vector and a booster dose by inoculating another vector in a second dose, in a manner similar to that described in Example 8 and using the same vector combinations. The extracted splenocytes were stimulated in vitro with the peptide from the envelope of the Bx08 isolate (5 µg/ml) and incubated during 1 hour at 37° C. After this time Brefeldin A was added (10 µg/mL) and was left incubating at 37° C. Seven days after, the surface was stained using specific anti-CD4 or anti-CD8 FITC conjugated antibodies (1/100 dilution), followed by intracellular staining using PE-conjugated anti-IFN-γ or anti-TNF-α (1/100 dilution). Once fixed, the cells were analyzed in the flow cytometer.

The results are shown in FIG. 15, where the differences in the levels of CD8+ cells displayed by the different groups can be observed. There is a greater increase of TNF-α secreting cells in the group that received DNA-B+MVA-B.

Example 12

Use of the MVA-B Vector in Prime/Boost Protocols that Combine Several MVA-Derived Vaccinia Vectors: Specific Immune Response of IFN-γ Producing T Cells Groups of 4, 6-8 weeks old, BALB/c mice were inoculated intraperitoneally (i.p.) with a 2×107 ufp/mouse dose of MVA-B (P3 stock), NYVAC B (Aventis Group) or MVA-WT. Fifteen (15) days after the mice received a second intraperitoneal dose (i.p.) of 2×10$^7$ ufp/mouse of vector, inoculating with NYVAC-B the mice that had received MVA-B in the first dose, with MVA-B those mice that had received NYVAC-B in the first dose and with NYVAC-WT (Aventis Group) the mice that had received MVA-WT in the first dose. In this manner groups of mice were generated that had been inoculated with the following vector combinations: NYVAC-B+MVA-B, MVA-B+NYVAC-B and MVA-WT+NYVAC-WT. Ten (10) days after the last immunization the mice were sacrificed by cervical dislocation and their spleens extracted to carry out an ELISPOT test. To detect the specific immune response, groups containing a mix of the splenocytes from the animals that had received the different immunization combinations were exposed to contact during 48 hours to different mixes of overlapping peptides from the B clade (5 µg/ml) comprising all the antigenic regions included in the recombinant viruses MVA10 B and NYVAC-B. The number of IFN-γ producing cells obtained against a mix of non-related antigenic peptides (negative control) was subtracted in all cases.

The results obtained are shown in FIG. 16. It can be observed how the two vector combinations that contained HIV-1 derived sequences increase both the magnitude and the amplitude of the specific immune response generated, as can be observed in each of the different peptide groups. The combination in which NYVAC-B is inoculated in the first dose and MVA-B in the second was the combination that originated the highest number of IFN-γ secreting cells versus the different peptide groups.

Example 13

Use of the MVA-B Vector in Prime/Boost Protocols Combining Different MVA-Derived Vaccinia Vectors: IFN-γ Production of Stimulated Splenocytes Three groups of 6-8 weeks old BALB/c mice (n=4) were inoculated using a combined immune response priming regime by administering to them a first dose of vector followed by a booster dose containing a different vector, in a similar manner to that described in Example 12 and using the same vector combinations. The splenocytes thus extracted were stimulated in vitro with the different mixes of overlapping peptides from the B clade (1 µg/ml) used in the previous Examples and incubated during 5 days at 37° C. After this time, the supernatants were collected and stored at −70° C. The IFN-γ levels were determined by the ELISA test using a commercial kit (Pharmigen).

The results are shown in FIG. 17, where it can be observed that the largest IFN-γ production is obtained with the NYVAC-B+MVA-B combination, as was the case for Example 12.

Example 14

Use of the MVA-B Vector in Prime/Boost Protocols in which DNA Vectors and Vaccinia Derived Viral Vectors are Combined: Specific Immune Response of IFN-γ Producing T Cells in HHDII Humanized Mice Experiments were also done with HHDII humanized mice. These mice, generated by F. Lemonier in France whom provided them to be used in the experiments described in this report, only allow antigen presentation within the context of class I human MHC because their original murine class I MHC genes and their species P-microglobulin have both been replaced by the corresponding human genes. Groups of 4, 6-10 weeks old, HHDII mice were inoculated intramuscularly (i.m.) with 100 µg of the DNA vector DNA-B (provided by GeneArt, Germany) also used in Example 8. The control groups were inoculated (i.m.) with 100 µg of insertless DNA (DNA Ø). Fifteen (15) days they were immunized intraperitoneally (i.p.) with 2×10$^7$ ufp/mouse of MVA-B (P3 stock) or of NYVAC-B (Aventis Group, France), that expresses the same HIV antigens as MVA-B. A third group of mice received a second dose of DNA-B (100 µg, i.m.). The control group received a dose of 2× of 10$^7$ ufp/mouse of MVA-WT. Ten (10) days after the last immunization the mice were sacrificed by cervical dislocation and their spleens extracted to be analyzed with the ELISPOT assay. To detect the specific immune response, mixes of splenocytes of the animals immunized in each group were exposed to contact during 48 hours with different mixes of overlapping peptides from the B clade (5 µg/ml) comprising all the antigenic regions included in the MVA-B and NYVAC-B recombinant viruses. The number of IFN-γ producing cells obtained against a non-related antigenic peptide mix (negative control) was subtracted in all cases. The notation ● indicates the presence of significant differences (p<0.005) in each group versus the negative control. The notation * indicates significant differences (p<0.05) between the different groups.

FIG. 18 sample the results obtained. It can be observed that the combinations DNA-B+MVA-B and DNA-B+NYVAC-B induce a broad response against the peptide groups, with immunodominance versus Env.

Example 15

Use of the MVA-B Vector in Prime/Boost Protocols in which DNA Vectors and Vaccinia Derived Viral Vectors are Combined: Specific Immune Response of IL-2 Producing T Cells in HHDII Humanized Mice Groups of 4, 6-10 weeks old, HHDII mice were inoculated intramuscularly (i.m.) with 100 µg of the DNA vector DNA-B (provided by GenArt, Germany). The control group was inoculated (i.m.) with 100 μg of insertless DNA (DNA Ø). Fifteen (15) days later they were immunized intraperitoneally (i.p.) with $2\times10^7$ ufp/mouse of MVA-B (P3 stock) or of NYVAC-B (Aventis Group, France), that expresses the same HIV antigens as MVA-B. A third group received a second dose of DNA-B (100 μg, i.m.). The control group received a 2× of 107 ufp/mouse dose of MVA-WT. Ten (10) days after the last immunization the mice were sacrificed by cervical dislocation and their spleens extracted to be analyzed with the ELISPOT assay. To detect the specific immune response, mixes of splenocytes from animals assigned to the different immunization groups were exposed to contact during 48 hours with different mixes of overlapping peptides belonging to the B clade (5 μg/ml) comprising all the antigenic regions included in the recombinant viruses MVA-B and NYVAC-B. The number of IL-2 producing cells obtained against a non-related antigenic peptide mix (negative control) was subtracted in all cases. FIG. 19 shows the results obtained, in which the notation: ● indicates the presence of significant differences ($p<0.005$) in each pool versus the negative control. The notation: * indicates significant differences ($p<0.05$) between the different groups. Immunodominance of Env antigens is observed, showing a broad response against the different peptide groups and significant differences between the DNA-B+MVA-B and DNA-B+NYVAC-B groups.

Example 16

Use of the MVA-B Vector in Prime/Boost Protocols in which DNA Vectors and Vaccinia Derived Viral Vectors are Combined: Specific Immune Response of IFN-γ Producing T Cells in HHDII Humanized Mice Five groups of 4, 6-10 weeks old, HHDII mice were inoculated intraperitoneally (i.p.) with a $2\times10^7$ ufp/mouse dose of MVA-B (P3 stock) (2 groups), NYVAC B (Aventis Group) (2 groups) or NYVAC WT (control group). Fifteen (15) days later the mice were administered a second intraperitoneal dose (i.p.) of $2\times10^7$ ufp/mouse of vector, in a manner in which one of the groups that received MVA-B in the first dose was inoculated with NYVAC-B, and another group received MVA-B again, one of the groups that had received NYVAC-B in the first dose was inoculated with NYVAC-B again, and another group received MVA-B and, finally, the control group received MVA-WT in the second dose (Aventis-Pasterur). In this manner groups of mice that had received the following combinations of vectors were generated: MVA-B+NYVAC-B, NYVAC-B+MVA-B, MVA-B+MVA-B, NYVAC-B+NYVAC-B and NYVAC-WT+MVA-WT.

Ten (10) days after the last immunization shot the mice were sacrificed by cervical dislocation and their spleens were removed to analyze them with the ELISPOT test. To detect the specific immune response, groups containing a mix of the splenocytes from the animals that had received the different immunization combinations were exposed to contact during 48 hours with different mixes of overlapping peptides from the B clade (5 μg/ml) comprising all the antigenic regions included in the recombinant viruses MVA-B and NYVAC-B. The number of IFN-γ producing cells obtained against non-related antigenic peptide mix (negative control) was subtracted in all cases. FIG. 20 shows the results obtained, in which the notation ● indicates there are significant differences ($p<0.005$) in each peptide group versus the negative control. It can be observed that immunization with the combined viral vectors MVA-B and NYVAC-B induces an ample immune response against different HIV antigens.

Example 17

Use of the MVA-B Vector in Prime/Boost Protocols in which DNA Vectors and Vaccinia Derived Viral Vectors are Combined: Specific Immune Response of IL-2 Producing T Cells in HHDII Humanized Mice Five groups of 4, 6-10 weeks old, HHDII mice were inoculated intraperitoneally (i.p.) with a $2\times10^7$ ufp/mouse dose of MVA-B (P3 stock) (2 groups), NYVAC B (Aventis Group) (2 groups) or NYVAC WT (control group). Fifteen (15) days after the mice received a second intraperitoneal dose (i.p.) of $2\times10^7$ ufp/mouse of vector, in a manner in which one of the groups that received MVA-B in the first dose was inoculated with NYVAC-B and another group received MVA-B again, one of the groups that had received NYVAC-B in the first dose was inoculated NYVAC-B again and another group received MVA-B and, finally, the control group received MVA-WT in the second dose (Aventis Group). In this manner groups of mice that had received the following combinations of vectors were generated: MVA-B+NYVAC-B, NYVAC-B+MVA-B, MVA-B+MVA-B, NYVAC-B+NYVAC-B and NYVAC-WT+MVA-WT.

Ten (10) days after the last immunization the mice were sacrificed by cervical dislocation and their spleens extracted to be analyzed by ELISPOT. To detect the specific immune response, groups containing a mix of the splenocytes from the animals that had received the different immunization combinations were exposed to contact during 48 hours with different mixes of overlapping peptides from the B clade (5 μg/ml) comprising all the antigenic regions included in the recombinant viruses MVA-B and NYVAC-B. The number of IL-2 producing cells obtained against non-related antigenic peptide mix (negative control) was subtracted in all cases. FIG. 21 shows the results obtained, in which the notation: ● indicates the existence of significant differences ($p<0.005$) of each peptide group versus the negative control. Similarly to Example 16, it can be observed that the combination of vectors induces an ample immune response (production of IL-2) against different HIV antigens.

Example 18

Generation of the MVA-C Vector Construction of the pLZAW 1gp120C/gagpolnef-C-14 Plasmidic Vector The plasmidic vector pLZAWIgp120C/gagpolnef-C-14 was constructed by the inventors to generate the MVA recombinant virus that expresses genic sequences from the gp120 protein (gp120-C) and the Gag, Pol and Nef chimera (gagpolnef-C) of the CN54 isolate, from the C clade. The pMA60gp120C/gagpolnefC-14 vector, used in the construction process, contains the codifying sequences of both proteins; it was constructed using the codifying sequence of the gagpolnef-C fusion protein generated by GeneArt (Regensburg, Germany) and was ceded to the inventors to construct the MVA-C vector within the framework of the EuroVacI cooperation program.

The pLZAWIgp120C/gagpolnef-C-14 plasmid is a pUC derivative designed for blue/white plate screening. It contains the right (TK-R) and left (TK-L) flanking sequences of the thymidine kinase (TK) viral gene, the E3L promoter directing the expression of the screening marker β-galactosidase, and the ampicillin resistance gene (AP). Between the two flanking sequences are the two sequences which expression is sought, gp120-C (SEQ ID NO: 17) and gagpolnef-C (SEQ ID NO:18), that have been modified to optimize the use of mammal codons. The corresponding early/late (pE/L), synthetic promoters are used to direct the expression of each sequence and are located in opposite directions at the furthest area of the flanking sequences. Table 4 below describes the position of each of the components included in the plasmid.

TABLE 4

Components of the pLZAW1gp120C/gagpolnef-C-14 plasmid

| | | |
|---|---|---|
| TK left flanking sequence | 410-908 | Complementary |
| T5NT for β-gal | 929-935 | Complementary |
| β-gal | ATG-TAA (936-4079) | Complementary |
| E3L promoter for β-gal | 4080-4140 | Complementary |
| Part 1 of the TK left flanking sequence | 4151-4498 | Complementary |
| T5NT for gp120 | 4607-4614 | Complementary |
| gp120 | ATG-TAA (4643-6139) | Complementary |
| E/L promoter for gp 120 | 6149-6187 | Complementary |
| E/L promoter for gagpolnef | 6202-6240 | |
| gagpolnef | ATG-TAA (6250-10503) | |
| T5NT for gagpolnef | 10584-10590 | |
| TK right flanking sequence | 10652-11343 | Complementary |
| AP | ATG-TAA (12514-13374) | Complementary |

Two other different plasmids were used in the construct this plasmid:

pMA60gp120C/gagpolnef-C-14,15 (provided by the Aventis Group, Canada). This plasmid is a pUC derivative containing the right (TK-R) and left (TK-L) flanking sequences of the thymidine kinase (TK) viral gene in pUC cloning sites. Between the two flanking sequences are the two sequences which expression is sought: gp120-C and gagpolnef-C, which have been modified to optimize the use of mammal codons. The corresponding early/late (pE/L), synthetic promoters are used to direct the expression of each sequence and are located in opposite directions in the furthest area of the flanking sequences.

pLZAW 1: This plasmid was provided by Linong Zhang, from the Aventis Group, Canada. This is a pUC based plasmid containing a left arm of the TK gene, cloning sites to insert exogenous genes, a short repetition of the left arm of the TK gene, an E3L promoter that directs the expression of a cassette with n-gal and a right arm of the TK gene.

FIG. 22 shows a representation of the construction of the pLZAW1gp120C/gagpolnefC-14 plasmid from these two other plasmids. Briefly, a 6047 kpb DNA fragment containing the genes of interest was extracted by digesting the pMA60gp120C/gagpolnefC-14 plasmid with EcoRV, then modified by incubation with the DNA polymerase from Klenow to generate blunt ends, and cloned in the pLZAW1 vector that had been previously digested with the AscI restriction endonuclease, modified by incubation with Klenow, and dephosphorylated by incubation with alkaline phosphatase extracted from calf intestines, thus generating by the process the pLZAW1gp12OC/gagpolnef-C-14 plasmid transfer vector. The plasmid thus generated directs the insertion of the genes of interest in the locus of the TK of the genome of the attenuated MVA virus. After isolating the desired recombinant virus by analyzing the expression activity of β-galactosidase, the subsequent propagation of the recombinant virus leads to the self-deletion of β-gal by homologous recombination between the left arm of TK and the short repeat of the left arm of TK that flank the marker.

Construction of the MVA-C Recombinant Virus

Primary cultures of chicken embryo fibroblast (CEF) were infected with attenuated MVA virus in pass 586 (MVA-F6, pass 586, provided by Gerd Sutter) to a multiplicity of infection 0.05 ufp/cell, and later transfected with μg 10 of DNA from the pLZAW1gp120C/gagpolnefC-14 transfer plasmid, using to this effect commercial lipofectin supplied by Invitrogen and following the manufacturer's directions. Seventy-two (72) hours post-infection the cells were collected, sonicated and used for the selection of the recombinant viruses. The recombinant MVA viruses that contained the gp120C/gagpolnef-C genes and coexpressed transitorily the P-Gal (MVA-B (X-Gal$^+$)) gene marker, were selected by consecutive plate purification passages in CEF cells stained with 5-bromo-4-chloro-3-indolyl-β-galactoside (XGal) (300 μg/mL). Subsequently, the recombinant MVA that contained the gp120C/gagpolnef-C genes and had lost the gene marker (MVA-B (X-Gal$^+$)), were selected as non-stained viral foci in CEF cells in the presence of XGal. In each step of the purification process the isolated plates were expanded in CEF during 3 days, and the raw viral extract obtained was used in the consecutive plate purification step.

After 4 consecutive purification passages 24 recombinant plates that efficiently expressed both antigens and had lost the gene marker were isolated. The recombinant named MVA-C-1.7.1.2 (P1) (SEQ ID NO:16) was made to grow to generate a raw stock (P2) that was sent to production in under good manufacturing practices conditions for clinical trials. The insert sequence this recombinant has at the thymidine kinase site is represented as SEQ ID NO: 20. Table 5 below shows the localization in said sequence of each of the elements that composed the insert

TABLE 5

Position of the main components of the MVA-C insert

| | | |
|---|---|---|
| Part 1 of the left TK flanking sequence | 1-502 | Complementary |
| gp120-C | ATG-TAA (647-2143) | Complementary |
| E/L promoter for gp120-C | 2153-2191 | Complementary |
| E/L promoter for gagpolnef | 2206-2244 | |
| gagpolnef-C | ATG-TAA (2254-6507) | |
| TK right flanking sequence | 6656-7347 | Complementary |

From the P2 stock a P3 virus stock was prepared by purifying it from the infected CEF cells to a multiplicity of infection of 0.05 per pass through two 36% saccharose matrices. This P3 stock, having a titer of 4.25×10$^8$ ufp/ml, was the stock used in the immunization protocols in the murine model.

Characterization of the MVA-C Recombinant Virus

To confirm the genetic homogeneity of the MVA-C virus generated and the integrity of the genes inserted, a PCR analysis was run with the viral DNA extracted from CEF cells infected to a multiplicity of infection of 5 ufp/cell, using oligonucleotides that hybridize either with the TK regions flanking the insert or with internal regions of the genes inserted. Table 6 below shows the sequence of the oligonucleotides used as primers and the position in which they appear on the pLZAW1gp120C/gagpolnef C-14 plasmid transfer vector. FIG. 23 shows (in the upper part) the positions in which said oligonucleotides hybridize, as well as the estimated sizes of the fragments generated in the different PCRs run and in relation to the inserts and the flanking sequences.

TABLE 6

Oligonucleotides used as primers during the characterization
PCRs run for the MVA-C vector

| Oligonucleotide | SEQUENCE | | Position |
|---|---|---|---|
| TK-L | 5' TGATTAGTTTGATGCGATTC 3' | (SEQ ID NO: 1) | 4338-4357 |
| TK-R | 5' TGTCCTTGATACGGCAG 3' | (SEQ ID NO: 2) | 10819-10835 |
| gp120-10 | 5' TCGAGCATGGACAGGGCC 3' | (SEQ ID NO: 7) | 6128-6145 |
| gp120-1050 | 5' GTCTTGTTCTGGAAGTGC 3' | (SEQ ID NO: 8) | 5088-5105 |
| gp120-1213 | 5' ATCATCACCATCCCCTGC 3' | (SEQ ID NO: 9) | 4925-4942 |
| GPN-802 | 5' TGGGTTTAAACAAGATCG 3' | (SEQ ID NO: 10) | 7043-7060 |
| GPN-2018 | 5' CAAGGTGAAGCAGTGGCC 3' | (SEQ ID NO. 11) | 8260-8276 |
| GPN-2198 | 5' TGGGTCCTCTTGTTCAGC 3' | (SEQ ID NO: 12) | 8439-8456 |
| GPN-3820 | 5' CGGCCTTGCCGATCTTGG 3' | (SEQ ID NO: 13) | 10061-10078 |
| GPN-4000 | 5' CCGACAAGAGCGAGAGCG 3' | (SEQ ID NO: 14) | 10241-10258 |

The photographs on the lower part of FIG. 23 show the gels obtained when subjecting to electrophoresis the products of the PCRs run with the different primer pairs to analyze the HIV-1 fragments included in the MVA-C virus. To do this, 100 ng of the viral DNA extracted from CEF cells infected to a multiplicity of infection of 5 ufp/cell with the NYVAC-C (lane 1), MVA-C (lane 2), MVA-WT (lane 3) or NYVAC-WT (lane 4) viruses, were used as molds to amplify by PCR the different fragments of HIV-1 included in the MVA-C virus. The conditions of each PCR are individually standardized for each pair of oligonucleotide primers used. As can be observed in the photographs shown in the sample on the lower part of FIG. 23, in lanes 3 and 4, corresponding to samples lacking the insert, no bands are observed in any case, while the NYVAC-C positive control expresses the same genes included in the MVA-C vector.

FIG. 24 sample a photograph of a gel obtained after subjecting the products from a PCR to electrophoresis in which TK-L and TK-R were used as oligonucleotide primers that hybridize with the flanking sequences of the TK gene. In lanes 2 and 3, corresponding to stocks P1 and P2 from the MVA-C vector, a band slightly over 6 Kb and compatible with the presence of the complete insert can be observed, while in lane 4, that corresponds to the DNA extracted from CEF cells infected with the wild MVA-WT strain of the MVA virus the band that appears, that would be the one corresponding to the insertless TK locus, is much smaller.

Example 19

Analysis of the Expression of HIV Proteins from the MVA-C Vector

The expression of gp120-C and gagpolnef-C proteins by the MVA-C virus was analyzed by means of the Western blot type transfer. Monolayers of CEF cells grown in 12 well gel plates were infected with 5 ufp/cell from different stocks of the MVA-B recombinant vector. The cellular extracts were collected 24 hours post-infection, fractioned in denaturating polycrylamide genes (SDS-PAGE), transferred to nitrocellulose membranes, and subjected to reaction versus a polyclonal rabbit anti-gp120 antibody (generated in the laboratory) that recognizes the gp120 protein from the CN54 isolate; and against a polyclonal rabbit anti-p24 antibody (provided by the EVA program, ARP432) that recognizes the gagpolnef-C chimera obtained from the same isolation. Extracts from cells infected with the NYVAC-C vector were used as positive control.

As can be observed in FIG. 25, both antigens are expressed efficiently by different stocks (P2, P3) of the recombinant MVA-C generated.

Example 20

Verification of the Stability of the MVA-C Vector

To verify that the recombinant MVA-C could be passed successively without losing the expression of the inserted genes, a stability assay similar to that described in Example 3 was run, carrying out several successive passages of the recombinant MVA-C virus in CEF cells. Monolayers of CEF cells grown in P100 plates were infected successively, to a multiplicity of infection of 0.05 ufp/cell, from the P2 stock of the MVA-C virus (passage 6) until passage 10 was generated (P10). The next step was to infect monolayers of CEF cells grown in 6 wells gel plates with a $10^{-5}$ dilution of the viral extract obtained during the last pass (P10). Forty-eight (48) hours post-infection, the lysis plates generated were immunostained, using polyclonal anti-WR antibodies (able to recognize MVA virus proteins); anti-gp120 antibodies (able to recognize the gp120 protein from the CN54 isolate); and anti-p24 antibodies (able to recognize the gagpolnef-C chimera obtained from the same isolation); these last two antibodies were the same used in Example 19. The results of these immunostains are shown in part A of FIG. 26. The plate count show that after successive passages of the virus in CEF cells, both antigens are efficiently expressed (100% of the plates recognized by the anti-WR antibody were recognized by the anti-gp120 and anti-p24 antibodies), verifying the stability of the product generated. The extracts of CEF cells infected during passages 7, 8, 9 and 10 were also analyzed by Western blot type immunotransfer tests, shown in part B of FIG. 26. To carry out these assays, monolayers of CEF cells grown in 12 well gel plates were infected at a rate of 5 ufp/cell with the viral extract obtained in passages 7 (P7), 8 (P8), 9 (P9) and 10 (P10) of the recombinant MVA-C virus. The cellular extracts were collected 24 hours post-infection, fractioned in polycrylamide denaturating gels (SDA-PAGE), transferred to nitrocellulose membranes and made to react with the same polyclonal anti-gp120 antibodies (right part of the same figure) or anti-p24 antibodies (left part of the figure) and then used in the test which results are shown in part A of FIG. 26. Both antibodies were used at a 1/500 dilution rate. An extract of CEF cells infected with the NYVAC virus (provided by the Aventis Group) was used as positive control. The results confirm the correct expression of the gp120-C and gagpolnef-C proteins in all the extracts obtained by infection with viruses from different passages.

Example 21 gp120-C Release and Kinetic Expression from the MVA-C Vector Through Time

To define whether the gp120-C protein was efficiently secreted, monolayers of CEF cells grown in 12 wells gel plates were infected with the recombinant MVA-C virus at a rate of 5 ufp/cell, and 6, 18 and 24 hours post-infection the cells were collected and the precipitate (P) separated from the cellular supernatant (S). The supernatants obtained from each of the collection times were concentrated and fractioned together with the cellular precipitates in polycrylamide denaturating gels (SDS-PAGE), transferred to nitrocellulose membranes, and made to react against a polyclonal anti-gp120 antibody specific to the CN54 isolate previously used in Examples 19 and 20. The CEF cells infected with NYVAC-C (provided by the Aventis Group) were treated in the same manner and used as positive control in the assay. To use as internal control to verify that the same amount of protein had been applied to the gel, the membranes were also incubated against a monoclonal anti-β-actin antibody. The results are shown in FIG. 27 where it can be seen in the MVA-C sample shown in the upper part that the gp120-C protein is efficiently expressed by the MVA-C after 6 hours post-infection, and is detected in the cellular supernatant 18 hours post-infection, and has a similar behavior to that observed in cells infected with the NYVAC-C virus, which results are shown in the sample on the lower part of FIG. 27.

The expression of the gagpolnef-C fusion protein was analyzed in the cellular precipitate also at 6, 18 and 24 hours post-infection following a similar procedure to that used for the gp120-C protein, although in this case the anti-p24 antibody specific to the CN54 isolate was used instead. The results are shown in FIG. 28. It can be observed that this fusion protein is expressed efficiently throughout the time of infection both from MVA-C (lane 1 of each time of infection) as from NYVAC (lane 2).

Example 22

Immunogenecity of the MVA-C Virus: Specific Immune Response of IFN-γ Producing T Cells Once the recombinant MVA-C virus was generated and characterized the next objective was to analyze its capacity to induce a specific immune response in the murine model against the antigens that expresses. To do this, 10 weeks old transgenic HHDII mice (n=4) were inoculated intraperitoneally (i.p.) with a dose of $2 \times 10^7$ ufp/mouse of MVA-C or of NYVAC-C. Eight (8) days after receiving the immunization the mice were sacrificed by cervical dislocation, and their spleens were removed to be analyzed by an ELISPOT test analogous to that described in Example 5, and following the same methodology described in said Example except that in this case, different groups containing 40 to 50 C clade overlapping peptides of 15 aminoacids each covering all the antigenic regions included in the MVA-C recombinant object of the invention were used to evaluate the specific immune response.

The results, shown in FIG. 29, demonstrate that the recombinant MVA-C virus is capable of boosting a specific immune response against almost all the peptide groups tested, showing a better response the peptide groups representative of the envelope genes (Env1 and Env2).

Additionally, The response generated against the proteins expressed from parts of the vector derived from the attenuated forms of Vaccinia used to construct the recombinant MVA and NYVAC viruses was also evaluated. To do this, the splenocytes of the animals immunized were exposed by contact during 48 hours to RMAS-HDD cells previously infected during 5 hours with 5 ufp/cell of MVA-WT and NYVAC-WT wild strains of MVA and NYVAC viruses. The number of IFN-γ producing cells obtained against the non-infected RMAS-HHDII cells (negative control) was subtracted in all cases. The results, shown in part B of FIG. 29, demonstrate the anti-Vaccinia response was higher in the group of mice immunized with NYVAC-C.

Example 23

Immunogenecity of the MVA-C Virus: Cytokine Production by Reestimulated Splenocytes The splenocyte isolates of the animals immunized with MVA-C and NYVAC-C isolates in Example 22 were cultured ($5 \times 10^6$ cells/well) in a 24 well gel plate and stimulated with 1 μg/ml of each peptide group from clade C. The plate was incubated 5 days at 37° C. in a 5% $CO_2$ atmosphere. After this period, the supernatants were collected off the cultures and spun at 1500 rpm, for 5 minutes at 4° C., and stored at −70° C. until needed. To find out the levels of IL-10 e IFN-γ present in the supernatants from cultures of reestimulated splenocytes in vitro, commercial kits of ELISA tests manufactured by Pharmigen were used following the manufacturer's directions in the same manner described in Example 6. The results, shown in FIG. 30, indicate that MVA-C induces the secretion of IL-10 and IFN-γ cytokines in the supernatant from reestimulated splenocytes cultures. The IFN-γ levels were significantly higher against the GPN2, Env-1 and Env-2 peptide groups, showing a clear polarization of the antigen-specific cellular response towards the Th1 subtype.

Example 24

Immunogenecity of the MVA-C Virus: Identifying the Types of Specific IFN-γ Producing T Cells To dilucidate whether the cellular response obtained with the ELISPOT test was due to the secretion of IFN-γ by the $TCD8^+$ or TCD4+ cells, the splenocytes obtained in Example 22 were reestimulated during 1 hour with 5 μg/ml of each peptide group, followed by an addition of Brefeldin at a 10 μg/ml concentration and left to incubate all night. Later it was surface stained with specific FITC-conjugated anti-Cd4 or anti-CD8 antibodies, followed by intracellular staining using PE-conjugated anti-IFN-γ. Once fixed, the cells were analyzed in the flow cytometer.

The results, shown in FIG. 31, show that both for the group of animals immunized with the MVA-C as for the group immunized with NYVAC-C, the IFN-γ producing response is mainly due to the specific TCD8+ cells activated against the different peptide groups. When determining the total levels of IFN-γ secreted by both types of cells, it was verified that the result obtained in the ELISPOT test, where a specific response was observed against the majority of the of the peptide groups in the animals immunized with both recombinant virus. Again, there are clear differences between the responses generated by each of the recombinant viruses.

Example 25

Immunogenecity of the MVA-C virus: Humoral Response Generated

To evaluate the humoral response generated after inoculating MVA-C and NYVAC-C viruses, groups of 4, 6 to 10 weeks old, HHDII or C57BL/6 mice were inoculated intraperitoneally (i.p.) with a $2 \times 10^7$ ufp/mouse dose of MVA-C (P3 stock) or of NYVAC-C (Aventis Group, France). Fourteen (14) days after, blood was extracted from the suborbital plexus of the immunized mice. The blood was spun after having been left all night at 4° C. to obtain the serum. The total amount of IgG antibodies present in the serum samples against the Gag protein (2 μg/ml), the gp-160 envelop protein (2 μg/mL) or against cellular extracts infected with vaccinia was determined by an ELISA test. To this effect, the serum samples were diluted to 1/500 to detect the antibodies against Vaccinia and 1/50 to detect the antibodies against the Gag protein and the. The results, shown in FIG. 32, shows an increase of the humoral response generated against the envelope protein mice immunized with the MVA-C derived recombinant vector compared to the controls and the mice immunized with NYVAC-C, the mice immunized with MVA-C showing lower humoral response against the Vaccinia vector than the mice of the same type immunized with NYVAC-C.

Example 26

Use of the MVA-C Virus in Priming/Boosting Protocols that Combine Vaccinia Derived Viral DNA Vectors: Specific Immune Response of IFN-γ Producing T Cells Generated in HHDII Humanized Mice Groups of 4, 6-10 weeks old, HHDII mice were inoculated intramuscularly (i.m.) with 100 μg of the DNA-C vector (provided by GeneArt, Germany), formed by two pcDNA derived recombinant plasmids, each containing the sequences that codify for HIV-1 proteins (gp120-C and gagpolnef-C) inserted in the MVA-C virus, under the control of the corresponding cytomegalovirus promoters. The control group was inoculated (i.m.) with 100 μg of insertless DNA (DNA Ø). Fifteen (15) days after they were immunized intraperitoneally (i.p.) with a $2 \times 10^7$ ufp/mouse dose of MVA-C(P3 stock) or of NYVAC-C (Aventis Group, France), that expresses the same HIV antigens than MVA-C. The control group received a $2 \times 10^7$ ufp/mouse dose of NYVAC-WT. Ten (10) days after receiving the last immunization dose the mice were sacrificed by cervical dislocation and their spleens extracted to be analyzed with the ELISPOT test. To detect the specific immune response, mixes of splenocytes of the animals immunized in each group were exposed during 48 hours to different mixes of C clade overlapping peptides (5 μg/ml) comprising all the antigenic regions included in the recombinant viruses MVA-C and NYVAC-C. The number of IFN-γ producing cells obtained against a non-related antigenic peptide mix (negative control) was subtracted in all cases.

The results are shown in FIG. 33. It can be observed that immunizing with a combination of vectors generates a broad immune response, with production of IFN-γ against different HIV antigens, with significant differences between the vectors. The DNA-C+NYVAC-C combination produced immunodominance against Env.

Example 27

Use of the MVA-C Virus in Priming/Boosting Protocols that Combine Vaccinia Derived Viral DNA Vectors: Specific Immune Response of IL-2 Producing T Cells Generated in HHDII Humanized Mice Groups of 4, 6-10 weeks old, HHDII mice were inoculated intramuscularly (i.m.) with 100 μg of the DNA-C DNA vector (provided by GeneArt, Germany) used in Example 26. The control group was inoculated (i.m.) with 100 μg of insertless DNA (DNA Ø). Fifteen (15) days later they were immunized intraperitoneally (i.p.) with a $2 \times 10^7$ ufp/mouse dose of MVA-C(P3 stock) or of NYVAC-C (Aventis Group, France), that expresses the same HIV antigens than MVA-C. The control group received a $2 \times 10^7$ ufp/mouse dose of NYVAC-WT. Ten (10) days after the last immunization the mice were sacrificed by cervical dislocation and their spleens extracted to be analyzed with an ELISPOT test. To detect the specific immune response, mixes of splenocytes of the animals immunized in each group were exposed during 48 hours to mixes of C clade overlapping peptides (5 μg/ml), comprising all the antigenic regions included in the recombinant viruses MVA-C and NYVAC-C, used in previous examples regarding the MVA-C virus. The number of IL-2 producing cells obtained against non-related antigenic peptide mix (negative control) was subtracted in all cases.

The results obtained are shown in FIG. 34. It can be observed that immunization doses that combine vectors generate a broad immune response, with IL-2 production against the different HIV antigens, with significant differences between the vectors. The DNA-C+NYCVAC-C combination resulted in immunodominance against Env.

Example 28

Use of the MVA-C Virus in Priming/Boosting Protocols that Combine Vaccinia Derived Viral DNA Vectors: Specific Immune Response of IFN-γ Producing T Cells Generated in BALB/c Humanized Mice Having established that administration of a first dose of immunization containing the MVA-C virus was capable to induce a specific immune response in the murine model, the next step was to evaluate whether using this inventive vector as part of a prime/boost protocol, containing different combinations of MVA-C and NYVAC-C, caused an increase in the magnitude and amplitude of the immune response. Based on the results, a first immunization dose was administered intraperitoneally to 4 groups of 6 to 8 weeks old BALB/c mice (n=4) containing $2 \times 10^7$ ufp/mouse of MVA-C(P3), NYVAC-C (Aventis Group), MVA-WT or NYVAC-WT. Fifteen (15) days after the mice received a second intraperitoneal (i.p.) of $2 \times 10^7$ ufp/mouse dose, so one of the groups that received MVA-B in the first dose was inoculated with NYVAC-C and another group received MVA-C again; one of the groups that had received NYVAC-C in the first dose was inoculated NYVAC-C again, and another group received MVA-B and, finally, the control group that had received MVA-WT received NYVAC-C in the second dose (Aventis Group). In this manner groups of mice that had received the following combinations of vectors were generated: MVA-C+NYVAC-C, NYVAC-C+MVA-C, MVA-C+MVA-C, NYVAC-C+NYVAC-C and NYVAC-WT+MVA-WT.

Ten (10) days after receiving the last immunization dose, the mice were sacrificed by cervical dislocation and their spleens were removed to be analyzed with the ELISPOT test. To detect the specific immune response, groups containing a mix of the splenocytes from the animals that had received the different immunization combinations were exposed to contact during 48 hours with different mixes of overlapping C clade peptides (5 µg/ml) comprising all the antigenic regions included in the recombinant MVA-C and NYVAC-C viruses. The number of IFN-γ producing cells obtained against a mix of non-related antigenic peptides (negative control) was subtracted in all cases.

It can be deduced from the results obtained, shown in FIG. 35, that the different combinations of MVA-derived poxvirus vectors (MVA-C+NYVAC-C, MVA-C+MVA-C, NYVAC-C+MVA-C, NYVAC-C+NYVAC-C, NYVAC-WT+MVA-WT, MVA-WT+NYVAC-WT) increase both the magnitude and the amplitude of the specific immune response generated, as can be observed in each of the different peptide groups. The best recognized peptide groups were those corresponding to Env I, GPN1 and GPN2, followed by GPN3 and Gag1.

Combinations of MVA-C and NYVAC-C caused greater responses than the administration of two doses of homologous viruses, MVA-C+MVA-C or NYVAC-C+NYVAC-C. The mice group that was administered NYVAC-C in the first dose and MVA-C in the booster dose was the group that exhibited the highest number of IFN-γ secreting cells against the different peptide group.

Example 29

Use of the MVA-C Virus in Priming/Boosting Protocols that Combine Vaccinia Derived Viral DNA Vectors: Cytokine Production by Reestimulated Splenocytes from BALB/c Mice Six groups of BALB/c mice (n=4) were inoculated with a combined immune response priming regime by administering them a first dose of vector and then a booster dose administered by inoculating a second vector in a second dose, in a similar manner to that described in Example 28 and using the same vector combinations. The extracted splenocytes were stimulated in vitro with the different mixes of C clade overlapping peptides (1 µg/ml) and incubated during 5 days at 37° C. After this time, the supernatants were collected and stored at −70° C. The levels of IFN-γe IL-10 were determined by commercial ELISA kits (Pharmigen).

The results are shown in FIG. 36. It can be observed that the combination of viral vectors induced a Th2 type cellular response, with polarization towards the Env and gpn1 antigens.

Example 30

Use of the MVA-C Virus in Priming/Boosting Protocols that Combine Vaccinia Derived Vectors: Identifying Specific IFN-γ Producing T Cells Generated in BALB/c Mice Five groups of BALB/c mice (n=4) were inoculated using a combined immune response priming regime in which a first dose of vector was administered followed by a booster dose in which a second vector was administered in a similar manner to that described in Example 28 and using the same vector combinations except in the case of the controls, where the MVA-WT+NYVAC-WT combination was not inoculated in this order.

The extracted splenocytes were reestimulated in vitro during 1 hour at 37° C. with 5 µg/ml of each group of C clade overlapping peptides, followed by Brefeldin added at a 10 µg/ml concentration, incubated all night at 37° C. Seven days later it was surface stained with specific FITC-conjugated anti-Cd4 or anti-CD8 antibodies, followed by intracellular staining using PE-conjugated anti-IFN-γ. Once fixed, the cells were analyzed in the flow cytometer.

The results obtained are shown in FIG. 37. It can be observed that the increase of IFN-γ producing $CD8^+$ cells caused by the viral vectors was lower than the production of $CD4^+$ cells and the NYVAC-C+MVA-C combination was the combination that induced greater increase against the Gag I, Env I, Gpn1 and Gpn2 peptides.

Example 31

Differential Profile of Changes in the Levels of Expression of Human Genes Induced During Infection with the MVA and NYVAC Vectors To evaluate whether the differences in the immune responses induced by inoculating recombinant viruses derived from MVA and NYVAC were also accompanied by different variation inducing profiles of the gene expression levels infected cells, an experiment was carried out in which HeLa cells were infected with MVA and NYVAC viruses and the changes in the levels of expression of 15,000 human genes were evaluated using microarrays with human cDNA. To do this, cDNA microarrays were generated as previously described (20), using the human cDNA 40K gene bank from Research Genetics www.resgen.com/products/SVHcDNA.php3, that contained 15,360 cDNA sequences, (of which 13,295 corresponded to known genes and 2,257 correspond to control genes), using CMT-GAPS II slides (Coring) on which the cDNA sequences were fixed using the Microgrid 11 (BioRobotics) at 22° C. and at a relative humidity of 40-45%. Meantime, the HeLa cells (from the American Type Culture Collection) were cultured in 10 cm (diameter) plates in Dulbecco' media to which 10% new born calf serum and antibiotics had been previously added and then infected with the MVA-WT and NYVAC-WT viruses to a multiplicity of infection of 5 ufp/cell. The total RNA was isolated from the infected cells using Ultraespect-II RNA (Biotecx), following the manufacturer's directions, from duplicate samples of cells infected with each of the virus after 2, 6 and 16 hours from the time of infection. Each RNA sample was used in two different hybridizations: in one hybridization the sample infected with MVA-WT was stained with dUTP-Cy3 and the sample infected with NYVAC-WT was stained with dUTP-Cy5, while the other sample infected with MVA-WT was stained with dUTP-Cy5 and the sample infected with NYVAC-WT was stained with dUTP-Cy3. Double staining was used to suppress differences in the staining and the hybridization due to specific characteristics of Cy-dUTP. A mix containing 40 µg of RNA, 150 pmols of 0.5 mM oligo$(dT)_{20}$dATP, 0.5 mM dGTP, 0.5 mM dCTP, 0.1 mM dTTP 0.05 mM Cy3/Cy5-dUTP (Amersham), 1× reaction buffer for the first strand (Invitrogen) and 10 mM dithiothreitol in a 38 µl volume was heated (65° C., 5 minutes) and was preincubated (42° C., 5 minutes), after which 400 U of SuperScript II (Invitrogen)

and 40 U of RNase inhibitor (Roche) were added and the resulting mix incubated a 42° C. during 2.5 hours. The reaction was finished by adding EDTA and the starter RNA mold was removed adding 2 µl of 10 N NaOH, followed by incubation (20 minutes, 65° C.). The reaction was neutralized by adding 4 µl of 5M acetic acid. Probes Cy5 and Cy3 were mixed and the colorants that had not been incorporated were removed by isopropanol precipitation. The probes were resuspended in deionized water; the blocking agents added to increment specificity were poly (A) (20 µg, Sigma), ARNt (20 µg, Sigma) and human Cot-1 DNA (20 µg, Invitrogen). While the probes were drying in a Speed-Vac, the microarrays were pre-hybridized with a mix containing SSC 6× (SSC 1× is composed by 0.15 M NaCl and M 0.015 sodium citrate), 0.5% sodium dodecylsulfate (SDS) and 1% bovine serum albumin (42° C., 1 hour), then washed five times with water, and spin-dried (563×g, 1 minutes). The probes were resuspended in 40 µl of hybridizing buffer (50% formamid, SSC 6×, SDS 0.5%, Denhardt's solution) and were incubated with the slides that contained the microarrays (42° C., 16 hours) in hybridization chambers (Array-It) in a water bath in the dark. After incubation, the slides were washed twice in 0.1% SSC 0.1×-SDS during 5 minutes each time and three times in 0.1×SSC during 5 minutes each time z. Finally, the slides were spin-dried as previously described and were scanned in a ScanArray 4000 (Packard Biosciences) using the ScanArray 3.1 software. Preliminary data was obtained from after-images of Cy5 and Cy3 using the QuantArray 3.0 software (Packard Biosciences), and processed with the SOLAR software (BioALMA, Madrid, Spain. The background signal is subtracted from the signal. It is represented as $\log_{10}$(signal) versus $\log_2$(relationship) and then a minimum standardization is done. This value is calculated for the four replicas obtaining a table listing the average signal, the exchange factor, log (relationship), the standard deviation of the relationship logarithm and the z value (a measure of the proximity of a particular value [log relationship] to other values having similar signals) (21). Once this data was obtained, the data set was reduced eliminating the genes with a>1 standard deviation between the replicas and those showing values of z≤2, then the data was reprocessed, and the genes were grouped using the classic Kohonen's Self-Organizing map (22,23,24) and the resulting map was analyzed with the Engene software, available at www.engene.cnb.uam.es The more representative differences detected in the cells infected with one or the other virus are summarized in Table 7 below, listing the observed increase factor in the expression of several representative genes after different time intervals (hours post-infection: h.p.i.) after the time of infection. The table shows that the variation induction profile of the levels of gene expression in the infected cells is different according to which was the virus used for the infection. For instance, the increase of immune response co-stimulating genes such as IL-7, protein B7, NFATC3 and MAP2K5 caused by MVA and not by NYVAC, may condition that the immune response triggered by one vector to be lower than that triggered by the other vector.

TABLE 7

Expression profiles of representative genes modified by infecting human HeLa cells with MVA and NYVAC virus strains

| NAME AND FUNCTION OF GENE<br>Genes increased with MVA and NYVAC | GENE SYMBOL | MVA exchange factor | | | NYVAC exchange factor | | |
|---|---|---|---|---|---|---|---|
| | | 2 hpi | 6 hpi | 16 hpi | 2 hpi | 6 hpi | 16 hpi |
| Early growth response1 | EGR1 | 4.17 | 4.60 | 1.94 | 4.74 | 10.38 | 6.83 |
| Nuclear factor similar to factor 2 derived from erythroidal cells 3 | NFE2L3 | 2.36 | 2.36 | 2.52 | 1.19 | 2.13 | 1.32 |
| Nuclear factor of the kappa 2 light polypeptide | NFKB2 | 2.03 | 2.22 | 2.34 | 1.53 | 2.02 | 1.79 |
| Interleukin 6 | IL6 | 2.65 | 2.14 | 1.56 | 2.02 | .85 | 2.68 |
| Protein stimulated by interferon, 15 kDa | ISG15 | 2.57 | 2.25 | 1.61 | 1.21 | 1.14 | 3.39 |
| CD80 antigen | CD80 | | | | | | |
| Dual specifity phosphatase 5 | DUSP5 | 3.01 | 2.91 | 1.87 | 1.98 | 4.16 | 2.18 |
| JUN B proto-oncogene | JUNB | .93 | 3.92 | 1.06 | 2.16 | 2.14 | 1.32 |
| V-jun avian sarcoma virus 17 oncogen homolog | JUN | 2.17 | 2.02 | 1.31 | 2.14 | 13.75 | 8.01 |
| V-MYC avian myelocytomatosis viral oncogene homolog | MYC | 2.22 | 1.53 | 1.05 | 1.05 | 2.93 | 1.65 |
| Kinesin 5A family member | KIF5A | 2.05 | 1.88 | 1.73 | 1.89 | 5.45 | 4.64 |
| Genes increased with MVA | | | | | | | |
| Interleukin 7 | IL7 | 6.10 | 5.3 | 3.2 | 0.80 | 0.55 | 0.88 |
| Protein B7 | B7 | 1.97 | 1.75 | 3.53 | 1.58 | 1.58 | 1.78 |
| CD47 antigen | CD47 | 5.35 | 4.08 | 3.16 | 1.02 | 0.76 | 1.03 |
| Mitogen-activated protein kinase | MAP2K5 | 2.37 | 2.74 | 1.69 | 1.02 | 0.76 | 1.03 |
| Nuclear factor of kappa epsilon light polypeptide | NFKBIE | 2.41 | 1.61 | 1.12 | 1.18 | 1.27 | 1.42 |
| Nuclear factor of activated T cells, cytoplasmic | NFATC3 | 3.46 | 2.97 | 1.30 | 1.01 | 1.34 | 1.34 |
| Genes increased with NYVAC | | | | | | | |
| Transcription activation factor 3 | ATF3 | 1.78 | 1.98 | 0.99 | 2.42 | 8.36 | 6.10 |
| Caspase 9, apoptosis-related cysteine protease | CASP9 | 1.1 | 0.82 | 0.32 | 2.59 | 2.37 | 1.98 |
| Dual specifity phosphatase 2 | DUSP2 | 3.93 | 3.59 | 1.85 | 2.43 | 5.25 | 1.56 |

TABLE 7-continued

Expression profiles of representative genes modified by infecting human HeLa cells with MVA and NYVAC virus strains

| NAME AND FUNCTION OF GENE Genes increased with MVA and NYVAC | GENE SYMBOL | MVA exchange factor | | | NYVAC exchange factor | | |
|---|---|---|---|---|---|---|---|
| | | 2 hpi | 6 hpi | 16 hpi | 2 hpi | 6 hpi | 16 hpi |
| 88 kD nucleoporin | NUP88 | 0.87 | 0.93 | 0.92 | 3.52 | 6.49 | 4.23 |
| Connective tissue growth factor | CTGF | 5.77 | 4.51 | 1.12 | 4.24 | 11.45 | 5.14 |
| Domain similar to Pleckstrine homology domains, Family A, member 1 | PHLDAI | 1.01 | 0.95 | 0.99 | 4.19 | 8.24 | 5.28 |

Example 32

Differential Change Profile in the Levels of Apoptosis Induction During Infection of Cultured Cells by the MVA and NYVAC Vectors To evaluate whether the differences observed in the immune response induced by inoculating MVA and NYVAC-derived vectors are accompanied by variations in the levels of cellular death induction by apoptosis, several experiments were carried out to evaluate the degree of apoptosis, evaluating several parameters that describe it. One of the characteristics of apoptosis is the specific rupture by proteases of the PARP protein. To evaluate this particular characteristic, HeLa cells were infected with 5 ufp/cell of MVA or NYVAC and were collected 4, 8 and 16 hours post-infection in a lysis buffer (50 mM Tris-HCl (pH 8.0), 0.5 M NaCl, 10% NP-40, 1% SDS). Equal quantities of protein lysates were separated (10 μg) by electrophoresis in SDS-polycrylamide gels (SDS-PAGE), then transferred to nitrocellulose membranes and incubated with a human anti-PARP antibody (1:500 dilution) from Cell Signaling, obtaining the results shown in the sample that appears on the upper part of FIG. 38a, in which the position of the band corresponding to the complete PARP protein (PARPc) and the position of a fragment spliced from the complete PARP protein (PARPf) are shown. As internal control to verify that the same amount of protein had been applied to the gel, the membranes were also incubated against a monoclonal anti-β-actin antibody (SIGMA), obtaining the signal shown in the sample on the lower part of said Figure. The results show that infection of HeLa cells with NYVAC induce with the time of infection the degradation of the PARP protein. This degradation is much lower in cells infected with MVA. The induction of apoptosis by NYVAC was also confirmed by subjecting to immunofluorescence tests the HeLa cells infected with 5 ufp/cell and staining their nuclei 24 hours post-infection with DAPI during 30 minutes at ambient temperature and then photographing the cells. The results are shown in FIG. 38b. In the lower part of the figure, that corresponding to the HeLa cells infected with NYVAC, it can be observed that NYVAC favors condensation of chromatin and formation of apoptotic bodies, an effect that is not observed when the cells have infected with MVA (shown on the upper part of the figure). Another indicator of apoptosis is the activation of the RNasa L enzyme, which favors the rupture of the Ribosomal DNA. To evaluate this activation, the total of RNA was isolated using the Ultraspec-II RNA resin purification (Bioteck), from the samples of HeLa cells infected with 5 ufp/cell obtained after 18 or 24 [] after infection with the Western Reserve (WR) strain of Vaccinia, with MVA or with NYVAC, and adding a control in which the infection was simulated. The RNAs (2 micrograms) were subjected to electrophoresis in 1% agarose-formaldehyde gel that contained ethidium bromide and then the pattern of bands obtained was photographed under ultraviolet light. The results, shown in FIG. 38c show that infection of HeLa cells with NYVAC induces after 18 hours degradation of ribosomal DNA in fragments characteristic of activation of the RNasa L enzyme, an effect not observed infection with MVA.

Finally, other indicator of apoptosis is the quantification of the number of apoptotic cells by flow cytometry. This assay was done again HeLa cells infected (5 ufp/cell) with WR, MVA and NYVAC Vaccinia viruses, as well as in controls in which the infection was simulated. The different stages of the cellular cycle and the percentage of cells in the subGo phase were analyzed with propidium iodide (PI) stain. Each stage was assayed in samples incubated in the absence or in the presence of zVAD, a general caspase inhibitor (4 micromolar, Calbiochem). After 24 hours the cells were collected, washed with PBS and permeabilized with 70% ethanol in PBS at 4° C. during 30 minutes. After three rinses with PBS, the cells were incubated during 45 minutes at 37° C. with A RNase and stained with IP (10 micrograms/ml). The percentage of cells displaying hypodiploid DNA was determined by flow cytometry. The data were acquired in 15,000 cells by sample and the results are represented as number of times of increase in apoptotic cells versus non-infected cells. The graph shown in FIG. 38d shows the apoptotic cell increase factor observed in each case. The graph shows that infection with NYVAC provokes apoptosis in a large part of the cellular population (more than 40%) and this phenomenon is prevented by adding general caspase inhibitor zVAD. The induction of apoptosis by MVA was much lower.

The results of these assays demonstrate that NYVAC induces apoptosis during infection, while MVA does not seem to activate apoptosis or exhibits lower rates of activation. These biochemical differences, together with the genetic differences defined in Example 31, indicate that it is expected that the recombinant vectors generated from the MVA and NYVAC viruses, despite containing the same HIV-1 codifying sequences under the control of identical promoters, give rise different behavior when inoculated in human beings with the intention to provoke an immune response against HIV. The recombinant vectors derived from MVA, therefore, represent an interesting alternative to substitute or complement advantageously the recombinant vectors derived from NYVAC in immunization protocols to combat HIV-1.

Constructions and Assays Carried Out with Vectors that Had been Designed for Macacus Monkeys

Example 33

Generation of the MVA-89.6P-SIVgpn Virus Construction of the pLZAW 1-89.6p-SIVgpn-18 Plasmidic Vector The pLZAW1-89.6p-SIVgpn-18 plasmid transfer vector was built by the inventors to generate vectors derived from MVA and from NYVAC capable of expressing the part the gp120 protein of the Env gene from the SHIV 89.6P virus (known as 89.6Psynenv120 and from now on abbreviated in the text as 89.6P-gp120) and the chimera of the Gal, Pol and Nef genes from the same virus (SIVmac239-gagpolnef, and from now on abbreviated in the text as SIVgpn), the latter coming from a nucleotide sequence obtained after sequences of the Gal, Pol and Nef genes of the SHIV89.6P virus in which the same modifications as those effected to obtain the chimeras of the Gal, Pol and Nef genes present in the MVA-B and MVA-C vectors had been done. The pLZAW1-89.6p-SIVgpn-18 plasmid is a pUC derivative designed to screen blue/white plates and the generation, as a safety measure, of a viral vector that lacks the β-Gal marker, as it was done for the MVA-B and MVA-C vectors, also as a safety measure. It contains the flanking sequences right (TK-R) and left (TK-L) of the thymidine kinase gene (TK) of the MVA, a short repetition of the left flanking sequence ("left arm") of the TK gene, the E3L promoter that directs the expression of the screening marker β-galactosidase, and the ampicillin resistance gene (AP). Between the two flanking sequences are the two sequences which expression is sought, 89.6P-gp120 (SEQ ID NO: 22) and SIVgpn (SEQ ID NO: 23), that have been modified to optimize the use of mammal codons. To direct the expression of each of the sequences there are the corresponding early/late synthetic promoters (pE/L), located in opposite direction to the insertion area furthest from the flanking sequences. Table 8 below describes the position of each of the components included in the plasmid.

TABLE 8

Position of the components of the pLZAW1gp120B/gagpolnefB-1 plasmid

| | | |
|---|---|---|
| TK left flanking sequence | 410-908 | Complementary |
| T5NT for β-gal | 929-935 | Complementary |
| β-gal | ATG-TAA (936-4079) | Complementary |
| E3L promoter for β-gal | 4080-4140 | Complementary |
| Part 1 of the TK left flanking sequence | 4151-4498 | Complementary |
| 89.6p-gp120 | ATG-TAA (4518-6032) | Complementary |
| E/L promoter for 89.6P-gp120 | 6080-6118 | Complementary |
| E/L promoter for SIVgpn | 6143-6181 | |
| SIVgpn | ATG-TAG (6226-10443) | |
| T5NT for SIVgpn | 10499-10505 | |
| TK right flanking sequence | 10488-11179 | Complementary |
| AP | ATG-TAA (12350-13210) | Complementary |

Two other plasmids were used to construct this plasmid:
pcDNA89.6P-syn-CD5-GPI20REKR: (provided by Ralf Wagner, Regensburg, Germany).
pCR-ScriptSIV-syn-gagpoinef: (provided by Ralf Wagner, Regensburg, Germany).
pLZAW1: The plasmid was provided by Linong Zhang, from the Aventis Group, Canada. This is a pUC based plasmid containing a left arm of the TK gene, cloning sites to insert exogenous genes, a short repeat of the TK gene left arm, an E3L promoter that directs the expression of a cassette with P-gal and a right arm of the TK gene.
pJR101: This plasmid was generated by the inventors. It was derived from pUC and contains the right and left flanking sequences of the locus HA of the MVA virus, cloning sites to insert exogenous genes under the transcription control of the early/late synthetic promoter (E/L), and the promoter 7.5 of the MVA virus (P7.5) that directs the expression of the β-gus gene.

Figure 41A:
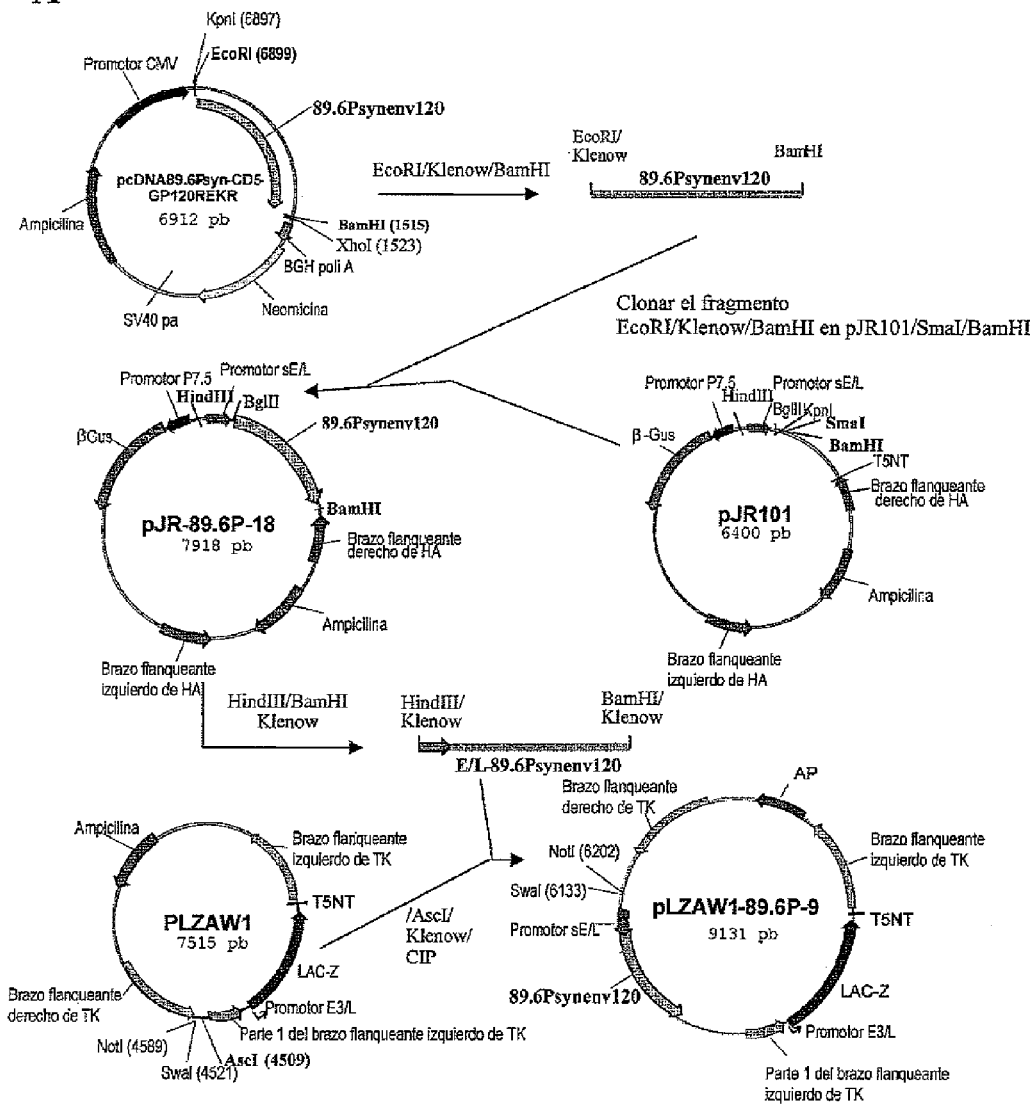
Figure 41B:
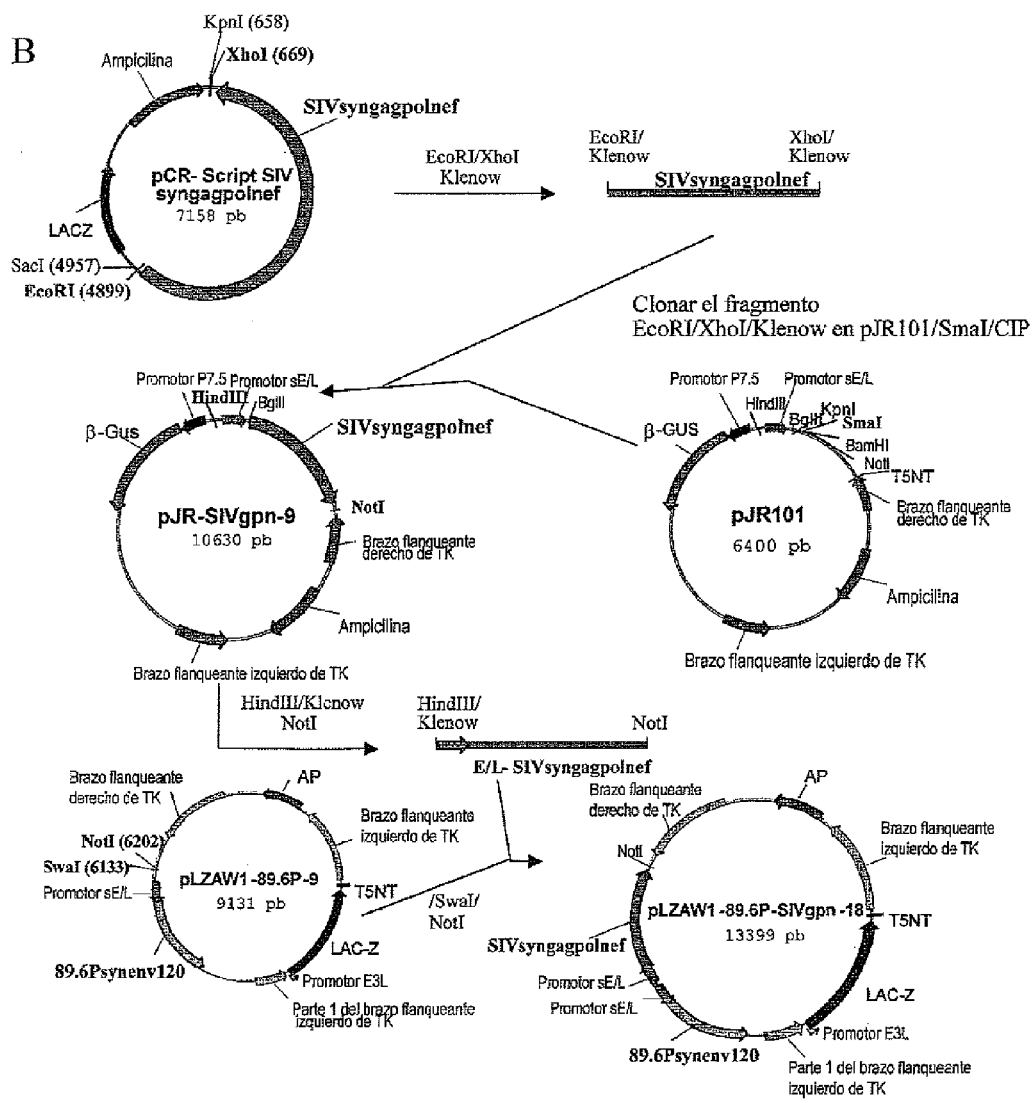

The construction process of the pLZAW1-89.6p-SIVgpn-18 plasmid from these two other plasmids is represented in FIGS. 41a and 41b. Briefly, a 1,518 Kb DNA fragment containing the 89.6P-gp120 gene (which in the figure is called 89.6synenvI20) was spliced from the pcDNA89.6P-syn-CD5-GP120REKR plasmid by digesting it with EcoRI, treating it with Klenow's fragment of the DNA polymerase to generate blunt ends, and digestion with BamHI. The fragment of DNA was then subcloned in the pJR101 vector (that had been previously digested with SmaI restriction endonuclease and BamHI), thus generating the pJR-89.6P-18 plasmid (7918 pb). A 1.612 kb DNA fragment containing the early/late synthetic promoter (E/L) that directs the 89.6-gp120 gene was spliced from the pJR-89.6P-18 plasmid digesting it with HindIII and BamHI, followed by modification with Klenow's fragment of the DNA polymerase, and cloned in the pLZAW1 vector (that had been previously digested with the AscI restriction endonuclease, modified by incubating it with Klenow's fragment, and dephosphorylated by incubation with the calf's intestinal alkaline phosphatase (CIP)), generating in this manner the pLZAW I-89.6P-9 plasmidic vector (9131 pb) (FIG. 41 a).

Meantime, a 4.230 kb DNA fragment of 4,230 kb containing the SIVgpn gene (that in the figures appears named as SIVsyngagpolnef) was spliced from the pCR-Script SIV-syn-gagpolnef plasmid by digesting it with EcoRI and XhoI and then modified with Klenow's fragment of the DNA polymerase, and was then subcloned in the pJR101 vector (that had been previously digested with SmaI restriction endonuclease and dephosphorylated by incubation with calf's intestinal alkaline phosphatase (CIP)), thus generating the pJR-SIVgpn-9 plasmid (10630 pb). A 4.3 kb DNA fragment containing the early/late synthetic promoter(E/L) that directs al gene SIVgpn was spliced from the pJR-SIVgpn-9 plasmid digesting it with HindIII, treating it with Klenow's fragment of the DNA polymerase, digesting it with NotI, and cloned in the pLZAW 1-89.6P-9 vector (that had been previously digested with SwaI and NotI restriction endonucleases, thus generating the pLZAW 1-89.6P-SIVgpn-18 plasmid transfer vector (13399 pb) (FIG. 41 b).

The pLZAWI-89.6P-SIVgpn-18 thus plasmid generated directs the insertion of the genes of interest in the TK locus of the genome of the MVA and NYVAC viruses. After the intended recombinant viruses were isolated by evaluating the expression of the β-galactosidase activity, the subsequent propagation of the recombinant viruses leads to the self-deletion of the β-gal gene by means of homologous recombination between the left arm of TK and the short repeat of the left arm of TK that flank the marker.

Construction of the MVA-89.6P-SIVgpnn Recombinant Virus

Primary cultures of chicken embryo fibroblast (CEF) from Specific Pathogen Free eggs (SPF) were infected with an attenuated MVA virus in pass 586 (where MVA-F6 was the previous pass, pas, 585, provided by Gerd Sutter) to a multiplicity of infection of 0.05 ufp/cell, and later transfected with 10 μg of the pLZAWI-89.6P-SIVgpn-18 plasmid transfer, using the lipofectamin transfection reactive (Lipofectamin™ 2000, Cat. 18324-012, batch 1198865, supplied by Invitrogen S.A., EL Prat of Llobregat, Barcelona, Spain) and as per the manufacturer's directions. After 72 hours post-infection the cells were collected, sonicated and used in the selection of the recombinant viruses.

The recombinant MVA viruses that contained the 89.6P-gp120/SIVgpn genes and coexpressed transitorily the β-Gal gene marker (MVA-SHIV (X-Gal$^+$)), were selected by consecutive plate purification passages in CEF cells stained with -bromo-4-chloro-3-indolyl-β-galactoside (XGal) (300 μg/ml). The recombinant MVA viruses that contained the 89.6P-gp120/SIVgpn genes and had lost the gene marker (MVA-SHIV (X-Gal$^-$)) were selected as non-stained viral foci in CEF cells in the presence of XGal. In each purification step the isolated plates were expanded in CEF cells during 3 days, and the raw viral extract obtained was used for the next step of plate purification.

In the first step of the screening process, 3 X-Gal$^+$ plates were isolated and named MVA-89.6P-SIVgpn-(1 to 3). The plate named MVA-89.6P-SIVgpn-1—that expressed efficiently the 89.6P-gp120 and SIVgpn antigens—was amplified and used in the next purification step. In the second pass, 22 X-Gal$^+$ plates were isolated, and all expressed both proteins efficiently. Three plates were amplified and named MVA-89.6P-SIVgpn-1.4, MVA-89.6P-SIVgpn-1.6 and MVA-89.6P-SIVgpn-1.18, and used in the next purification step. In the third pass, 20 X-Gal$^+$ plates and 4 X-Gal$^-$ plates were isolated all of which expressed both antigens efficiently. One of the X-Gal$^-$ plates (MVA-89.6P-SIVgpn-1.6.8) and one of the X-Gal$^+$ plates (MVA-89.6P-SIVgpn-1.18.2) were amplified and used in the next purification step; the first one, the MVA-89.6P-SIVgpn-1.6.8 plate, was used to prepare the P1 stock by infection from the p150 plate in CEF cells). In the fourth pass 6 X-Gal$^-$ plates and 6 plates X-Gal$^+$ were isolated. The recombinant named WA-89.6P-SIVgpn-1.6.8.5 (X-Gal$^-$) was used to prepare the P2 stocks by infecting five p150 plates to a multiplicity of infection of 0.01 ufp/cell. The P3 stocks (generated infected CEF cells in 40-100 p150 plates to a multiplicity of infection of 0.05 ufp/cell, collected after 3-4 days after infection and purified through two 45% saccharose matrices) were only prepared from MVA-89.6P-SIVgpn-1.6.8. (X-Gal$^-$) for the immunization assays in monkeys; Example 38 describes the characteristics of the different P3 stocks obtained.

Characterization of MVA-89.6P-SIVgpn

To confirm the genetic homogeneity of the MVA-89.6P-SIVgpn-1.6.8.5 virus (X-Gal$^-$) generated and the integrity of the genes inserted, the P2 and P3 stocks were amplified (WA-89.6P-SIVgpn-1.6.8.) by infecting CEF cells to a multiplicity of infection of 5 ufp/cell and recovering the cellular extracts 24 hours post-infection. The DNA virus was purified and analyzed by PCR with oligonucleotide primers that hybridize with the TK left (oligonucleotide TK-L) or right (oligonucleotide TK-R2) flanking regions of the insert of interest with the following sequences:

```
TK-L:  5' TGATTAGTTTGATGCGATTC 3' (SEQ ID NO: 1)

TK-R2: 5' CTGCCGTATCAAGGACA 3'    (SEQ ID NO: 21)
```

The positions in which said oligonucleotides hybridize in relation to the insert present in MVA-89.6P-SIVgpn, as well as the estimated sizes of the fragments generated in the PCR analysis in which the molds used were the DNA of said virus and the DNA corresponding to the wild type MVA virus (WT), which lacks an insert, are shown in the sample on the upper part of FIG. 42.

A photograph of a gel that resulted from the PCR analysis of the products located between the left (TK-L) and right (TK-R) arms of the TK locus in the MVA-SHIV virus of the P2 (MVA-89.6P-SIVgpn (P2)) and P3 (MVA-89.6P-SIVgpn (P3) stocks), the Wild type MVA virus(MVA-WT) and the pLZAWI-89.6P-SIVgpn-18 transfer plasmid is shown n the lower part of FIG. 42. The procedure to obtain said gel was as follows: 100 ng of the viral DNA extracted from CEF cells infected to a multiplicity of infection of 5 ufp/cell with the MVA-WT virus (lane 3), MVA-89.6P-SIVgpn (P2) (lane 4) or MVA-89.6P-SIVgpn (P3) (lane 5) or 10 ng of the pLZAWI-89.6P-SIVgpn-18 plasmid were used as molds to run a PCR analysis of the sequence located between both arms of the TK locus using as primers 100 ng of the oligonucleotides that hybridize with the flanking sequences of the TK gene, TK-L (SEQ ID NO:1) and TK-R2 (SEQ ID NO:21) in a reaction mix containing 0.3 mM of dNTPs, 2.5 mM of MgCl2 and 2.5 U of the Platinum Taq polymerase enzyme. The program includes a denaturation cycle a 94° C. during 5 minutes, 25 denaturation cycles at 94° C. during 5 minutes, hybridization at 60° C. during 1 minutes and extension at 68° C. during 2 minutes, and finally an extension cycle at 68° C. during 10 minutes. The PCR products were analyzed in 0.7% agarose gel, obtaining the results shown in the sample that appears on the lower part of FIG. 3. Lanes 4 and 5, which correspond to the two stocks of the MVA-SHIV vector, show a band located slightly above the 6 Kb band of the marker (lane 1), compatible with the presence of the complete insert complete. This band also appears in the lane containing the pLZAWI-89.6P-SIVgpn-18 plasmid that acted as positive control, while the lane containing the wild MVA-WT type virus (3) shows a much smaller band that would be the one corresponding to the insertless TK locus.

Additionally, the DNA from the MVA-89.6P-SIVgpn virus from the P2 stock, was sequenced using the TK-L (SEQ ID NO: 1), TK-R2 (SEQ ID NO:21) and E/L (SEQ ID NO:25) oligonucleotides as primers and thus obtaining the sequence represented as SEQ ID NO:24.

Table 9 below lists the elements that are part of the insert present in the genome of the MVA-89.6-SIVgpn virus.

TABLE 9

Position of the main insert components of the MVA-89.6P-SIVgpn vector

| | | |
|---|---|---|
| Part 1 of the TK left flanking sequence | 1-499 | Complementary |
| 89.6P-gp 120 | ATG-TAA (519-2033) | Complementary |
| E/L promoter for 89.6P-gp120 | 2081-2119 | Complementary |
| E/L promoter for SIVgpn | 2144-2183 | |
| SIVgpn | ATG-TAG (2227-6444) | |
| TK right flanking sequence | 6488-7179 | Complementary |

Example 34

Analysis of the Expression of SHIV Proteins from MVA-89.6P-SIVzpn

34.1

Western Blot Transfer

The expression of the 89.6P-gp120 and SIVgpn proteins by the P2 and P3 stocks from the MVA-89.6P-SIVgpn virus was analyzed using the Western blot type transfer. Monolayers of CEF cells grown in 12 well gel plates were infected with 5 ufp/cell of P2 or P3 stock. The cellular extracts were collected hours post-infection, fractioned by electrophoresis in denaturating polycrylamide gels with SDS (SDS-PAGE), transferred to nitrocellulose membranes, and made to react against a polyclonal rabbit anti-gp120 antibody (generated by the inventors in their laboratory) that recognizes the SHIV89.6P gp120 protein of the; and against a monoclonal anti-SIV-gag-p27 antibody (provided by the EVA program, ARP392) capable to recognize the part corresponding to protein p27 of the Gag antigen from SIV and, therefore, the SIVgpn fusion protein. Extracts from cells transfected transitorily with the pLZAWI-89.6P-SIVgpn-18 plasmidic transfer vector were used as positive controls.

As shown in FIG. 43, both the 89.6-gp120 protein (upper photo, labeled "anti-gp120") as the SIVgpn fusion protein (lower photo, labeled "anti-SIVp27") were detected in the extracts of cells infected with viruses from the P1, P2 and P3 stocks of MVA-89.6P-SIVgpn, as well as in the extract of cells transfected transitorily with the plasmid used as positive control (lanes marked "C+"), indicating that the MVA-derived recombinant vectors expressed both antigens correctly.

34.2

Plate Immunostaining

The expression of the 89.6P-gp120 and SIVgpn proteins by the recombinant MVA-89.6P-SIVgpn was also analyzed in CEF cells infected with a $10^{-5}$ dilution of the P3 stock, by immunostaining using either a polyclonal antibody directed against the wild type MVA vector (anti-WR), or a B clade polyclonal anti-gp120 antibody (anti-gp120), or the monoclonal anti-SIVgag-p27 antibody provided by the EVA program (ARP392).

The results, shown in FIG. 44, show that more than 97% of the viral plates that had been stained with the anti-WR antibody were also positive for the anti-gp120 (photographs and bars marked as "antigp120") and anti-SIVgag-p27 antibodies (photographs and bars marked as "anti-SIVp27").

Example 35

Construction and Characterization of the NYVAC -89.6P-SIV gagpolnef Recombinant Virus BSC40 cells (a cellular line derived from monkeys' kidneys that lacks myogenic potential) were infected with a wild type strain of NYVAC (donated by the Aventis Group, as part of the cooperation framework of the project financed by the V Framework Programme of the European Union (European Vaccine Effort Against HIV, also known by its acronym Euro-VacI), to a multiplicity of infection of 0.025 ufp/cell, that were later transfected with 10 µg of DNA from the pLZAW1-89.6P-SIVgpn-18 plasmid transfer vector (which characteristics were described in Example 33), using lipofectamin as reactive (Invitrogen, Cat. 18324-012, batch 1198865) following the manufacturer's directions. Seventy-two (72) hours post-infection the cells were collected, sonicated and used to screen for recombinant viruses. The NYVAC recombinant vector that contained the 89.6P-gp 1/SIVgpn genes and coexpressed transitorily the n-Gal gene marker (NYVAC-89.6P-SIVgpn (X-Gal+)), were selected by consecutive plate purification passages in BSC40 cells stained with 5-bromo-4-chloro-3-indolyl-β-galactoside (XGal) (300 µg/ml). The NYVAC recombinant viruses that contained the 89.6P-gp120/SIVgpn genes and had lost the n-Gal indicator gene (NYVAC-89.6P-SIVgpn (X-Gal−)) were selected as nonstained viral foci in BSC40 cells in the presence of XGal. In each purification step the isolated plates were expanded in BSC40 cells during 2 days, and the raw viral extract obtained was used for the following plate purification step:

In the first screening step 3 X-Gal− plates were isolated and named NYVAC-89.6P-SIVgpn-(1 to 3). The three plates, that expressed efficiently the 89.6P-gp120 and SIVgpn antigens, were amplified and used in the next plate purification step. In the second pass 18 plates X-Gal+ were isolated; 8/18 expressed both proteins. The plate named NYVAC-89.6P-SIVgpn-2.1 was amplified and used in the next purification step. In the third pass 12 X-Gal+ plates were isolated, all of them expressed the 89.6P-gp120 protein efficiently and 11/12 expressed the SIVgpn protein. The plates named NYVAC-89.6P-SIVgpn-2.1.1 and NYVAC-89.6P-SIVgpn-2.1.2 were amplified and used in the next purification step. In the fourth pass 12 X-Gal− and 12 X-Gal+ plates were isolated; all of them expressed the 89.6P-gp120 protein efficiently and 22 out of 24 expressed the SIVgpn protein. The recombinants named NYVAC-89.6P-SIVgpn-2.1.1.1 (X-Gal+) and NYVAC-89.6P-SIVgpn-2.1.2.3 (X-Gal−) were amplified and used in the next purification step. In the fifth pass 12 X-Gal+ plates were isolated and all of them expressed both antigens efficiently. The recombinant named NYVAC-89.6P-SIVgpn-2.1.1.1.4 (X-Gal+) was amplified in CEF cells (a plate of p150 to generate the P1 stock) and then used to prepare the P2 stocks (infecting five p150 plates with 0.01 ufp/cell). The P3 stocks (grown in 40 to 100 p150 plated of CEF cells infected to a multiplicity of infection of 0.05 ufp/cell, collected after 3-4 days post-infection and purified through two 45% saccharose matrices) were prepared for immunization assays in apes; the characteristics of each of the P3 stocks generated are mentioned in Example 37.

Characterization of NYVAC-89.6P-SIVgpn

To confirm the genetic homogeneity and purity of the NYVAC-89.6P-SIVgpn virus generated and the integrity of the genes inserted, the P3 stock was amplified by infecting CEF cells to a multiplicity of infection of 5 ufp/cell, recovering the cellular extract 24 hours post-infection. The DNA from the virus was purified and analyzed by PCR with oligonucleotide primers that hybridize with the left (TK-L) (SEQ ID NO: 1) and right (TK-R2) (SEQ ID NO:21) TK regions flanking the insert of interest, in a manner similar to that described in Example 33.

The positions in which said oligonucleotides hybridize in relation to the insert present in NYVAC-SHIV, as well as the estimated sizes of the fragments generated by the PCR in which the mold used was the DNA of the Wild type NYVAC virus (WT) lacking an insert are shown on the upper part of FIG. 45. The sample on the lower part of said FIG. 45 shows a photograph of the genes obtained after subjecting to electrophoresis the products of the PCR run with a pair of TK-L/ TK-R2 primers to analyze the insert included in the NYVAC-SHIV virus present in the P3 stock (NYVAC-89.6P-SIVgpn (P3)) (lane3), that was compared to the PCR products generated from the positive control MVA-SHIV (MVA-89.6P-SIVgpn (P3)) (lane 4) and to the insertless wild type vectors as positive controls, that is, NYVAC-WT (lane 2) and MVA-WT (lane 5). To do this, 100 µg of viral DNA extracted from chicken embryo cells (CEF) infected to a multiplicity of infection of 5 ufp/cell with the NYVAC-WT, NYVAC-89.6P-SIVgpn (P3) (MVA-SHIV), MVA-89.6P-SIVgpn (P3) (MVA-SHIV) and MVA-WT viruses, were used as molds to amplify by PCR the fragment of the sequence located between the TK-L and TK-R arms in each one. As it can be seen in the photo shown in the sample on the lower part of FIG. 45, the sample corresponding to the positive control, the recombinant MVA-89.6P-SIVgpn virus (P3) (lane 4), results in a band having the same size as those of the recombinant virus samples described in this example NYVAC-SHIV (NY-VAC-89.6P-SIVgpn (P3), lane 3), while lane 2, corresponding to the insertless wild type NYVAC virus (NYVAC-WT), shows a band of approximately 400 pb compatible with the absence of insert in the NYVAC TK locus, shorter than that of MVA-WT that produces a band of nearly 900 pb, which is to be expected according to the characteristics of the TK locus of this latter virus.

Example 36

Analysis of the Expression of SHIV Proteins from NYVAC-89.6P-SIVgpn 36.1

Western Blot Transfer

The expression of the 89.6P-gp120 and SIVgpn proteins by the recombinant NYVAC-89.6P-SIVgpn virus was analyzed by means of the Western blot type transfer. Monolayers of CEF cells grown in 12 well gel plates were infected with 5 ufp/cell from the P1, P2 or P3 stocks. The cellular extracts were collected 24 hours post-infection, fractioned by electrophoresis in denaturating polycrylamide gels with SDS (SDS-PAGE), transferred to nitrocellulose membranes, and made to react against a polyclonal rabbit anti-gp120 antibody (generated by the inventors in their laboratory immunizing rabbits with the gp120 protein from the IIIB isolate), capable of recognizing the gp120 protein from SHIV89.6P; and against a monoclonal anti-SIV-gag-p27 antibody (provided by the EVA program, ARP392) that recognizes the gag protein from SIV and, therefore, the fusion SIVgpn protein. As positive controls were used extracts from cells infected with the MVA-SHIV virus (MVA.89.6P-SIVgpn (P3)).

As shown in FIG. 46, both the 89.6-gp120 protein (upper photo, labeled "anti-gp120") as the SIVgpn fusion protein (lower photo, labeled "anti-SIVp27") were detected in the extracts of cells infected with viruses from NYVAC-89.6P-SIVgpn (NYVAC-SHIV) P1, P2 and P3 stocks, as well as in the extract of cells infected with the positive control MVA30 SHIV, indicated the correct expression of both antigens by the recombinant viruses derived from NYVAC thus generated.

36.2

Plate Immunostaining

The expression of 89.6P-gpl20 and SIVgpn proteins by the recombinant NYVAC-89.6P-SIVgpn virus was also analyzed in DF-1 cells infected with a $10^{-5}$ dilution of NYVAC-SHIV P3 stock (NYVAC-89.6P-SIVgpn (P3)), by immunostaining it with either a polyclonal antibody directed against the proteins characteristic of the wild type MVA vector (anti-WR), a B clade polyclonal anti-gp120 antibody (anti-gp120) or the monoclonal anti-SIVgag-p27 antibody provided by the EVA program (ARP392). The results, shown in FIG. 47, show that more than 98% of the viral plates that had been stained with the anti-WR antibody were also positive for the anti-gp120 antibodies (photographs and bars marked as "antigp120") and anti-SIVgag-p27 (photographs and bars marked as "anti-SIVp27").

Example 37

Control of the Viral Stocks Sent to be Used in Macacus Monkeys Immunization Studies Table 10 shows the recombinant viruses selected from the MVA-SHIV and NYVAC-SHIV recombinant viruses obtained for use in immunization studies with Macacus monkeys:

TABLE 10

Stocks of recombinant viruses selected for experimental immunization studies in Macacus monkeys

| Stock | Titer (UFP/ml) | Total UFP sent | Shipment date |
|---|---|---|---|
| MVA-89.6P-SIVgpn | | | |
| P3 (20/06/03) | $1.6 \times 10^9$ | $7.5 \times 10^9$ | 10/03/04 |
| P3 (20/09/04) | $8.75 \times 10^8$ | $5 \times 10^9$ | 6/10/04 |
| P3.1 (20/09/04) | $1.1 \times 10^9$ | $2.2 \times 10^9$ | 6/10/04 |
| P3.2 (01/10/04) | $2 \times 10^9$ | $0.5 \times 10^9$ | 13/10/04 |
| NYVAC-89.6P-SIVgpn | | | |
| P3.1 (29/01/04) | $1.2 \times 10^9$ | $7.2 \times 10^9$ | 10/03/04 |
| P3.2 (25/02/04) | $5 \times 10^8$ | $1.2 \times 10^9$ | 6/10/04 |

Figure 48:
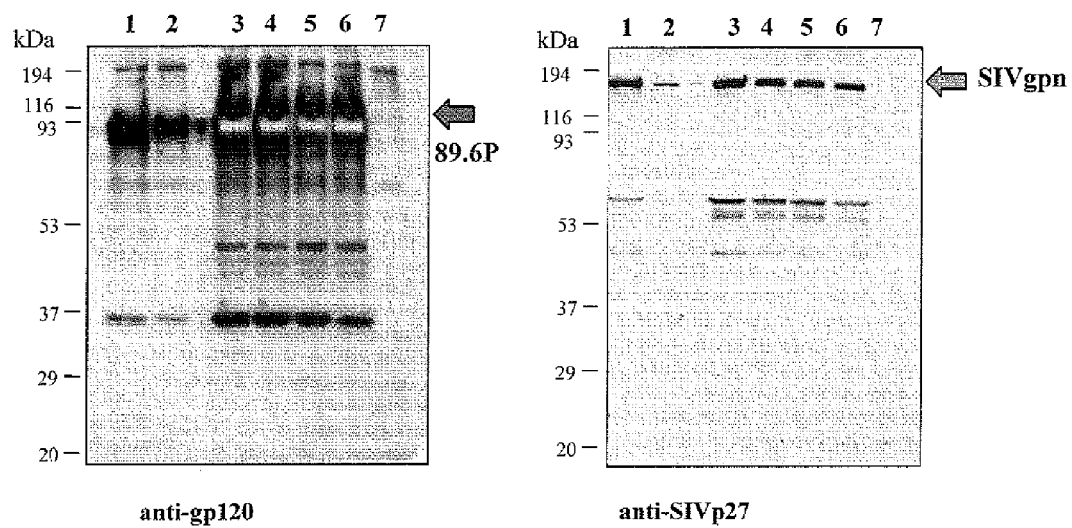

The expression of the 89.6P-gp120 and SIVgpn proteins by the different stocks of MVA-89.6P-SIVgpn and NYVAC-89.6P-SIVgpn recombinant viruses was analyzed by means of the Western blot type transfer. Monolayers of CEF cells grown in 12 well gel plates were infected with 5 ufp/cell from one of the stocks listed in Table 10. The cellular extracts were collected 24 hours post-infection, fractioned by electrophoresis in polycrylamide denaturating gels with SDS (SDS-PAGE), transferred to nitrocellulose membranes, and made to react against an anti-gp120 polyclonal rabbit antibody (generated by the inventors in their laboratory immunizing rabbits with the gp120 protein of the IIIB isolate), capable of recognizing the gp120 protein from SHIV89.6P; and against a monoclonal anti-SIV-gag-p27 antibody (provided by the programs EVA, ARP392) that recognizes the gag protein of the SIV and, and therefore, the SIVgpn fusion protein. An extract of cells in which the infection had been simulated—that is, cells subjected to the same steps as the infected cells but without having received the virus in the infective solution (M extract)—was used as negative control. FIG. 48 shows the results of the immunostains for each of the antibodies. The left part shows the anti-gp120-C antibody stain and the right the antibody antiSIV-gag-p27 stain.

Once the efficient expression of both proteins in the extracts from each of the stocks was verified, extract aliquots were sent to Drs. Jonathan Heeney and Petra Mooij, of the Biomedical Primate Research Center of Rijswijk, Holland, where the Macacus monkeys were subjected to the experiments described in the followings examples.

Preclinical Study of the Efficacy of the Vectors as Vaccine
Immunization Protocol and Subsequent Challenge The assays described below in Examples 38 and 39 were carried out to evaluate the immunogenecity and the efficacy of the vectors which construction process is described in Examples 33 and 35 to protect the apes immunized with these vector against the development of the acquired immunodeficiency syndrome disease in order to assess from the results obtained the expected degree of efficacy of the vectors described in the main patent after using them to immunize human beings. Said assays were carried out in the Biomedical Primate Research Center of Rijswisjk (Netherlands). Young adult Macacus rhesus (*Macaca mulatta*) monkeys were used in the experiment after verifying they were negative for SIV, the simian retrovirus and the simian leukemia virus. The animals stabling and handling conditions followed the ethical standards established by said experimentation center.

The aim of the study was not limited to establish correlations with immunogenecity and efficacy that would be expected when using the vectors of the main patent as vaccines in human beings, but the scope included also an attempt to obtain data that could be compared to the results obtained when using a vector, also derived from the poxvirus, that contains the same SHIV89.6P antigen codifying sequences insert than the MVA-derived vector which construction and characterization has been described in Examples 33 and 34, the MVA-89.6P-SIVgpn vector that will be also referred to in the next examples under the general abbreviation of MVA-SHIV. The alternative vector used which construction process has also bee described in the present report is the NYVAC-89.6P-SIVgpn vector derived from NYVAC, that is also mentioned in the next examples under the general abbreviation of NYVAC-SHIV. Both the MVA-SHIV as the NYVAC-SHIV vectors, both containing the same insert, were administered in immune response booster doses after the initial priming dose—intended to trigger the immune response—was administered. The animals included in the experiment received naked DNA containing an insert identical to that in the DNA of vectors MVA-SHIV and NYVAC-SHIV, the DNA-SHIV vector, configured by two expression plasmids, pcDNA-gp120.89.6p, that express the gp120 protein from SHIV89.6P, and pcDNA-SIVgag-pol-nef, that expresses the SIVgpn protein generated from sequences from the SHIV89.6P virus. These plasmids were generated by Dr. Ralf Wagner, Regensburg, Germany, and the ceded them for the study. Examples 38 and 39 below describe the studies and the results obtained in depth.

Example 38

Immunization of the Macacus Monkeys and Assessment of the Immunity Generated The 21 Macacus monkeys used in the study were in three groups (groups 1, 2, and 3), each group containing 7 subjects. Each of the groups was subjected to a different immunization protocol as shown in Table 11 below:

TABLE 11

| | | | | | | |
|---|---|---|---|---|---|---|
| | | Immunization groups and treatment received | | | | |
| Group | N° of Macacus monkeys | IMMUNIZATIONS | | | | Challenge |
| | | Week 0 | Week 4 | Week 20 | Week 24 | Week 32 |
| 1 | 7 | DNA-SHIV | DNA-SHIV | MVA-SHIV | MVA-SHIV | SHIV89.6P |
| 2 | 7 | DNA-SHIV | DNA-SHIV | NYVAC-SHIV | NYVAC-SHIV | SHIV89.6P |
| 3 | 7 | DNA-emp | DNA-emp | NYVAC-WT | NYVAC-WT | SHIV89.6P |

Group 3 was the control group. Group 3 received insertless naked DNA with the characteristic SHIV89.6P sequences (DNA-emp) in the first two doses and in the last two doses received the NYVAC-WT vector, which also lacks the insert. To carry out the study, the NYVAC-WT vector was grown in CEF cells and purified in two saccharose matrixes in the same manner as with the MVA-SHIV and NYVAC-SHIV recombinants. A total of $8\times10^9$ ufp, having a titer of $1\times10^9$ ufp/ml of the stock thus generated were sent to the Primate Center in Holland, the $20^{th}$ of April of 2004.

The naked DNA immunizations contained a total of 4 mg of plasmid, using in the case of the DNA-SHIV vector 2 mg of each of the plasmids that configure it, pcDNA-gp12089.6p and pcDNA-SIV-gag-pol-nef, and using 4 mg of the DNA-emp vector for the controls. In each of the two inoculations of naked DNA that were received by each Macacus monkey, 2 mg of plasmid in 1.5 ml of PBS were administered intramuscularly in the upper part of each limb.

Immunizations shots containing the NYVAC-SHIV, MVA-SHIV and NYVAC-WT vectors were administered inoculating intramuscularly in the upper part of the right arm 0.5 ml containing $5\times10^8$ ufp, inoculating thus $5\times10^8$ ufp/Macacus monkey. The following stocks were used:

for MVA-SHIV, P3 (20 Jun. 2003), having a titer of $1.6\times10^9$ ufp/ml;

for NYVAC-SHIV, P3.1 (29 Jan. 2004), having a titer of $1.2\times10^9$ ufp/ml;

for NYVAC-WT, the previously mentioned stock having a titer of $1\times10^9$ ufp/ml.

In all cases, 32 weeks after receiving the first immunization dose the Macacus monkeys were subjected to a viral challenge, that is, the animals were inoculated intravenously a dose of 50-100 MID50 of SHIV89.6P in a 1:1000 dilution of Letvin's stock (understanding as MID50 or "Monkey Infectious Dose" the amount of virus capable to produce infection in 50% of the animals thus treated) and the evolution of each individual animal was observed.

Two (2) weeks before starting the immunization protocol, at different times throughout the protocol, and after administering the challenge dose, peripheral blood samples were extracted from each animal by intravenous punction. PBMC cells (peripheral blood mononuclear cells) were obtained from the heparinized blood and then used in cellular response assays. FIG. 49 shows an outline of the timeline of the study, showing the times at which the blood samples were taken (CMI, cell mediated immunity), the times at which the different immunization doses were administered (DNA and MVA-derived poxvirus vectors: NYVAC or MVA) and the time at which the SHIV89.6P challenge was administered.

In order to evaluate the immunity generated, ELISPOT assays were carried out to detect the IFN-γ, IL-2 and IL-4 response in the animals of each group and their evolution in time as described immediately below.

The cytokine response was evaluated in PBMC cells fractions extracted from each of the Macacus monkeys. To do this, samples of said cells of each of the Macacus monkeys in the trial were incubated during 48 hours with peptide groups. For the gp120 ELISPOT test, a group of 48 peptides, specifically 4702 to 4749 from Cat. No 4827 of the NIH AIDS Research and Reference Reagents Program, were used. Each peptide having 20 aminoacids 10 of overlapping the next peptide, and which represent the sequence of protein 89.6P-gp120. For the SIVgpn ELISPOT the peptides were synthesized by SynPep Dublin (California, United States) and are groups of 15 aminoacids with 11 overlapping aminoacids that can be grouped in pools: Gag-pool 11, 1-54; Gag-pool 12, 55-108; Pol-pool 11, 109-168; Pol pool 12, 169-173+236-290; Pol-pool 13, 291-349; Nef-pool 11, 174-235. The response of the 7 peptide groups was analyzed using 2 micrograms/ml of each peptide included in the assay. After incubation, Spot Forming Cells (SPF) were measured in each of the samples. SPFs are PBMC cells that express a particular cytokine, after stimulation with specific peptides included in proteins 89.6P-gp120 and SIVgpn proteins. It is a measure of the cells that have been specifically stimulated by the inoculated vector that express said proteins. ELISPOT assays were carried out to detect SPFs that expressed IFN-γ, IL-2 or IL-4 (29). In the case of IFN-γ expressing SPF, the results obtained with each of the animals of the study, expressed as total SPF (those stimulated by 89.6P-gp120 and by SIVgpn) detected by each $10^6$ PBMC analyzed, are represented graphically in FIG. 50, with a logarithmic scale in the Y axis. The numbers on the X axis indicate the time at which each of the samples was taken. There are three groups of values for each value of time that represent the behavior of each of the 7 animals subjected to a specific immunization procedure: the first vertical line of points corresponds to samples taken from Macacus monkeys assigned to group 1 (DNA-SHIV/MVA-SHIV); the second vertical line of points corresponds to samples taken from Macacus monkeys from group 2 (DNA-SHIV/NYVAC-SHIV); the third vertical line of points corresponds to samples taken from mice (sic) assigned to group 3 (DNA-emp/NYVAC-WT). Each point represents the value obtained for a specific Macacus monkey, while the rectangles located in each of the vertical lines indicate the average value for all the Macacus monkeys of that particular group calculated from samples taken at the same moment in time. If the number of points is less than 7 in some vertical lines it means that the point located on the X axis represents more than 1 Macacus monkey, in each of which the SFC value detected per each of the $10^6$ PBMC analyzed did not exceed the value of 1. The broken line indicates the value below which values are considered insignificant (20 SFC). The white arrows indicate inoculation of a vaccination vector; the black arrow represents the time at which the SHIV89.6P was inoculated. It can be observed how before the challenge the points corresponding to the two first groups, and particularly, their average value are above those obtained in the control group, immunized with insertless DNA/NYVAC. Once the pathogen SHIV89.6P caused the infection the values were equalized in all the groups when SHIV immunity occurs.

To simplify the interpretation of the data FIG. 51 shows the average values for the total number of cells that express IFN-γ obtained for each of the groups, again logarithmic scale, based on the time at which the samples were taken, which in this case is the first time the Macacus monkeys were administered a naked DNA dose. FIGS. 52 and 53, represent the average values obtained for each of the groups, also expressed in logarithmic scale and based on time, on IL-4 expressing SFCs (FIG. 53) or IL-2 expressing SFC (FIG. 52).

It can observed that both in group 1 (the group that received the MVA-SHIV vector, the MVA-89.6P-SIVgpn in the booster dose) (data indicated by squares with a vertice pointing upwards ◆) as in the group 2 (that received the NYVAC-SHIV vector, the NYVAC-89.6P-SIVgpn, in the booster dose) (data indicated by squares whose vertices configure two parallel lines ■), the magnitude of the immune response is similar and clearly higher than that detected in group 3, in which the Macacus monkeys received vectors that did not expressed SHIV antigens (data indicated by triangles ▲). In this last group it can be observed how the immune response clearly increases after administration of the SHIV89.6P virus as challenge, due to virus replication, which causes that from that moment on, the values are similar in the three groups.

This data indicates that the total immune response average (IFN-γ production) is clearly boosted when the vectors MVA-89.6P-SIVgpn and NYVAC-89.6P-SIVgpn vectors are administered to the Macacus monkeys. The immune response induced by these two vectors is similar. Both induce a good cellular response versus the 89.6P-gp120 and SIVgpn antigens Example 39

Efficacy of the Immune Response Generated as Protection Against the Development of the SHIV Virus To assess the efficacy of the protection generated against an infection caused by the SHIV 89.6 virus in relation to the immune responses evaluated in the studies described in Example 38, data was extracted about two significant magnitudes: the number of viral particles that could be detected in the plasma of the blood samples extracted from the Macacus monkeys at the time in which the pathogenic SHIV89.6P virus had already been inoculated, and the percentage of $CD4^+$ and $CD8^+$ cells from the total of peripheral blood mononuclear cells (PBMC).

39.1

Viral RNA Detectable in Plasma

The values that refer to the number of detectable viral particles in plasma is a good indicative value of the capacity of the immune response generated to control the possible infection caused by the inoculated SHIV89.6P virus. It is considered that values above 100,000 copies/ml will lead to the Macacus monkey thus inoculated to develop AIDS followed by the death of the animal, while values close to 10,000 copies/ml or lower keep the animal free from apparent pathogenic effects. Detecting a concentration of viral copies lower than the last value may be considered as an indication that the immune response generated is capable of conferring protection in the animal models used.

Consequently, the next step was to detect the RNA of the SHIV89.6P virus present in the plasma of the blood samples extracted from the Macacus monkeys just before (time 0) and after said virus was inoculated. The technique used was the real time quantitative QC RNA-PCR, that measures the number of viral copies by milliliter of plasma and is capable of detecting 50 copies per ml. The values obtained for each of the Macacus monkeys in the study are shown in the three graphic representations of FIG. 54. The upper graphic represents group 3 (in which the Macacus monkeys used as control had been immunized with insertless DNA and NYVAC and therefore could not express SHIV antigens). The graph in the lower left part of the figure represents group 1, (the group immunized with DNA-SHIV/MVA-SHIV) and, while the graph of the sample in the lower right represents group 2 (immunized with DNA-SHIV/NYVAC-SHIV).

The Figure shows how 32 weeks after receiving the challenge, of the 7 Macacus monkeys 6 present continuous viremia values that oscillate between 10,000-100,000 copies/ml, while one sole animal in the group did not respond to the infection.

Of the animals vaccinated, all the animals in the group inoculated with DNA-SHIV/MVA-SHIV showed a reduction of the viremia levels compared to the control group. Three (3) eliminated completely the virus before the 20 week milestone, more specifically after 7, 14 or 18 weeks. As for the remaining animals, after 32 weeks, three Macacus monkeys showed viremia reduced below 1,000 copies/ml and one monkey maintained a viremia value of around 2,000 copies/ml. Of the animals in the group vaccinated with DNA-SHIV/NYVAC-SHIV, 4 animals eliminated the virus completely before the 20 week mark, specifically after 4, 14 or 17 weeks. After 32 weeks or the remaining animals in the group, two Macacus monkeys maintained viremia levels below 1,000 copies/ml and one of them below 10,000 copies/ml.

These results demonstrate clearly that the two poxvirus derived vectors, MVA-SHIV (MVA-89.6P-SIVgpn) and NYVAC-SHIV (MVA-89.6P-SIVgpn), induce a high degree of protection in Macacus monkeys against the pathogenic SHIV89.6P virus when used in prime/boost type protocols when used in the booster dose.

39.2

Percentage of $CD4^+$ and $CD8^+$ Cells

The values that refer to the percentages of detectable peripheral blood $TCD4^+$ and $TCD8^+$ are also significant data, since $CD4^+$ cells are used both by the HIV as by the SIV as target cells for infection. When the number of these cells decreases to below 200 cells by ml is considered as a symptom of the AIDS disease. The proportion of $TCD4^+$ and $TCD8^+$ is therefore a good indicator of the status of the infection.

To detect said infection indicator cells in the PBMC fraction of the blood samples extracted from the Macacus monkeys 12 weeks before challenge with the SHIV89.6P virus, just before (time 0) and after inoculation with said virus. To carry out the tests, antibodies specific to each population were used and the proportion of $CD4^+$ and $CD8^+$ cells present was detected by FACS. The results are shown in FIG. 55.

In the sample on the upper part of said Figure, corresponding to the group immunized with DNA-SHIV/MVA-SHIV, it can be observed that 6 of the Macacus monkeys maintained normal levels of $CD^+$cells, similar to the levels of $CD8^+$cells, and only in one of the monkeys did said levels go below 100. The middle part of the figure, corresponding to the group immunized with DNA-SHIV/NYVAC-SHIV, shows the results obtained for this group, similar to the first group: 6 animals maintained normal levels of $CD4^+$ cells and only one animal experienced a reduction below 100. In the control group, however, as can be observed in the sample on the lower part of FIG. 55, in 5 of the Macacus monkeys the levels of $CD4^+$ cells decreased below 100. It was necessary to sacrifice one of the other two Macacus monkeys (D7 98928, which name is followed by the abbreviation "euth") due to the advance stage of the disease. One of the Macacus monkeys in the control group, however, maintained protection.

39.3

Survival Rate of the Infected Macacus Monkeys (%)

Additionally, the percentage of survival of the Macacus monkeys in each of the three groups was calculated by computing the number of Macacus monkeys that were still alive after being inoculated the SHIV89.6P virus. FIG. 56 shows the data obtained after the established time intervals after infection, in weeks, on the X axis. It can be observed in said Figure that after more than 50 weeks from infection with the SHIV89.6P virus, both the Macacus monkeys from the group immunized with DNA-SHIV/MVA-SHIV (data indicated by squares with a vertice pointing upwards ♦) as the those from group immunized with DNA-SHIV/NYVAC-SHIV (data indicated by squares whose vertices configure two parallel lines ■), the Macacus monkeys had a 100% survival rate, while in the control group (data indicated by triangles ▲) after 27 weeks of inoculation of the SHIV89.6P virus not all the Macacus monkeys were alive. After more than 50 weeks from inoculation this group had a survival rate lower than 40%.

Taking this data as a whole, it can be concluded that both MVA-89.6P-SIVgpn, the recombinant generated from the MVA virus, as NYVAC-89.6P-SIVgpn the recombinant generated from the NYVAC virus, that have the same genic organization in their inserts and are able to simultaneously express the 89.6P-gp120 and SIVgpn antigens, have shown in the Macacus rhesus non-human primate models to be excellent vector to be used as vaccination against simian AIDS. These results reinforce the results obtained in the studies described in the Examples of the main patent document and are meant as support for the possible use of these vectors in vaccines against human AIDS.

BIBLIOGRAPHY

1. Antonie, G., F., Scheiflinger, F. Dorner, y F. G. Falkner. 1998. The complete genomic sequence of the modified vaccinia Ankara strain: comparison with other orthopoxviruses. Virology 244:365-396.
2. Meyer, H., G. Sutter, and A. Mayr. 1991. Mapping of deletions in the genome of highly attenuated vaccinia virus MVA and their influence on virulence. J. Gen. Virol. 72:1031-1038.
3. Blanchard, T. J., Alcamí, P. Andrea, and G. L. Smith. 1998. Modified vaccinia virus Ankara undergoes limited replication in human cells and lacks several immunomodulatory proteins: implication for use as a human vaccine. J. Gen. Virol. 79:1159-1167.
4. Altenburger, W., C-P. Sutter, and J. Altenburger. 1989. Partial deletion of the human host range in the attenuated vaccinia virus MV A. Arch. Viro 1. 105: 15-27.
5. Wyatt, L. S., M. W. Carroll, C-P. Czerny, M. Merchlinsky, J. R. Sisler, and B. Moss. 1998. Marker rescue of the host range restrictions defects of modified vaccinia virus Ankara. Virology 251:334-342.
6. Carroll, M. W. and B. Moss. 1997. Host range and cytopathogenicity of the highly attenuated MV A strain of vaccinia virus: propagation and generation of recombinant viruses in a non human mammalian cell line. Virology 238: 198-211.
7. Drexler, 1., K. Heller, B. Wahren, V. Erfle and G. Sütter. 1998. Highly attenuated modified vaccinia virus Ankara replicates in baby hamster kidney cells, a potential host for virus propagation, but not in various human transformed and primary. J. Gen. Virol. 79:347-52.
8. Sancho, M. C., S. Schleich, G. Griffiths, and J. Krijnse-Locker. 2002. The block in assembly of modified vaccinia virus Ankara in HeLa cells reveals new insights into vaccinia virus morphogenesis. J. Virol. 76: 8318-8334.
9. Sütter, G., and B. Moss. 1992. Nonreplicating vaccinia vector efficiently expresses recombinant genes. Proc. Natl. Acad. Sci. USA. 89:10847-10851.

10. Carroll, M. W., W. W. Overwijk, R. S. Chamberlain, S. A. Rosenberg, B. Moss, and N. P. Restifo. 1997. Highly attenuated modified vaccinia virus Ankara (MV A) as an effective recombinant vector: a murine tumor model. Vaccine 15:387-394.
11. Ramirez, J. C., M. M. Gherardi, and M. Esteban. 2000. Biology of attenuated modified vaccinia virus Ankara recombinant vector in mice: virus fate and activation of B- and T-cell immune responses in comparison with the Western Reserve strain and advantages as a vaccine. J. Virol. 74:923-933.
12. Hirsch, V. M., T. R. Fuerst, G. Sutter, M. W. Carrol, L. C. Yang, S. Goldstein, M. Piatak, Jr., W. R. Elkins, W. G. Alvord, D. C. Montefiori, B. Moss, and J. D. Lifston. 1996. Patterns of viral replication correlate with outcome in simian immunodeficiency virus (SIV)-infected macaques: effect of prior immunization with a trivalent SW vaccine in modified vaccinia virus Ankara. J. Virol. 70:3741-3552.
13. Mahnel, H. and A. Mayr. 2002. Experiences with immunization against orthopox viruses of humans and animals using vaccine strain MV A. Berl. Muench. Tierazetl. Wochnschr. 107:253-256.
14. Mayr, A., H. Stickl, H. K. Muller, K. Danner, and H. Singer. 1978. The smallpox vaccination strain MV A: marker, genetic structure, experience gained with parenteral vaccination and behaviour in organism with a debilitated defense mechanism. Zentbl. Bakteriol. B. 167: 375-390.
15. Schneider, J., S. C. Gilbert, T. J. Blanchard, T. Hanke, K. J. Robson, C. M. Hannan, M. Becker, R. Sinden, g. L. Smith and A. V. S. Hill. 1998. Enhanced immunogenicity for CD8+ T cell induction and complete protective efficacy of malaria DNA vaccination by boosting with modified vaccinia virus Ankara. Nat. Med. 4:397-402.
16. Sutter, G., L. S. Wyatt, P. L. Foley, J. R. Benninnk, and B. Moss. 1994. A recombinant vector derived from the host range-restricted and highly attenuated MVA strain of vaccinia virus stimulates protective immunity in mice to influenza virus. Vaccine 12:1032-1040.
17. Sutter, G. 2003. Vaccinia vectors as candidate vaccines: The development of Modified Vaccinia Virus Ankara for antigen delivery. Current Targets-Infectious Disorders 3, 263-271.
18. Didierlaurent A., Ramírez J C, Gherardi Mi, Zimmerli S C, Graf M, Orbea H A, Pantaleo G, Wagner R, Esteban M, Kraehenbuhl J P, Sirard J C. 2004. Attenuated poxviruses expressing a synthetic HIV protein stimulate HLA-A2-restricted cytotoxic T-cell responses. Vaccine 22:3395-3403.
19. Chakrabarti, S, Sisler, R. J., Moss, B. Compact, synthetic, vaccinia virus early/late promoter for protein expression. 1997. BioTechniques 23, 1094-1097.
20. Guerra, S., L. A. López-Fernanández, A. Pascual-Montano, M. Muñoz, K. Harshman y M. Esteban. Cellular gene expression survey of vaccinia virus infection of human HeLa cells. 2003. J. Virol. 77:6493-6506.
21. Quackenbush, J. Microarray data normalization and transformation. 2002. Nat. Genet. 32:496-501.
22. Kohonen, T. Self-organization maps, $2^a$ edición. 1997. Springer-Verlag, Heidelberg, Alemania.
23. Jones, J. O. y A. M. Arvin. Microarray analysis of host cell gene transcription in response to Varicella-Zoster virus infection of human T cells and fibroblasts in vitro and SCIDhu skin xenografts in vivo. 2003. J. Virol. 77:1268-1280.
24. Eisen, M. B., P. T. Spellman, P. O. Brown, y D. Botstein. Cluster analysis and display of genome-wide expression patterns. 1998. Proc. Natl. Acad. Sci. USA 95:14863-14868.
25. Li, J., Lord, C. I., Haseltine, W., Letvin, N. L., Sodroski, J. Infection of cynomolgus monkeys with a chimeric HIV-1/SIVmac virus that expresses the HIV-1 envelope glycoproteins. 1992. J. Acuir. Immune Defic. Syndr 5:639-646.
26. Reimann, K. A., J. T. Li, G. Voss, C. Lekutis, K. Tenner-Racz, P. Racz, W. Lin, D. C. Montefiori, D. E. Lee-Parritz, Y. Lu, et al. An env gene derived from a primary human immunodeficiency virus type 1 isolate confers high in vivo replicative capacity to a chimeric simian/human immunodeficiency virus in rhesus monkeys. 1996. J. Virol. 70:3198.
27. Reimann, K. A., J. T. Li, R. Veazey, M. Halloran, I. W. Park, G. B. Karlsson, J. Sodroski, N. L. Letvin. A chimeric simian/human immunodeficiency virus expressing a primary patient human immunodeficiency virus type 1 isolate env causes an AIDS-like disease after in vivo passage in rhesus monkeys. 1996. J. Virol. 70:6922.
28. Guerra, S., López-Fernández, L. A., Pascual-Montano, A., Nájera, J. L., Zavallos, A., Esteban, M. Host response to the attenuated poxvirus vector NYVAC: upregulation of apoptotic genes and NF-kB responsive genes in infected HeLa cells. 2006. J. Virol 80:985-998.
29. Mooij, P., Nieuwenhuis I. G., Knoop C. J., Doms R. W., Bogers W. M. J. M., ten Haaft P. J. F., Niphuis H., Koornstra W., Bieler K., Köstler J., Morein B., Cafaro A., Ensoli B., Wagner R., Heeney J. L. Qualitative T-Helper Responses to Multiple Viral Antigens Correlate with Vaccine-Induced Immunity to Simian/Human Immunodeficiency Virus Infection. 2004. J. Virol. 78:3333-3342.

The invention claimed is:

1. A recombinant modified Vaccinia Ankara (MVA) vector comprising nucleotide sequences encoding a modified human immunodeficiency type 1 virus (HIV-1) Env protein and a HIV-1 Gag-Pol-Nef fusion protein, wherein the nucleotide sequence encoding the modified HIV-1 Env protein is SEQ ID NO:15 or SEQ ID NO:17, wherein the nucleotide sequence encoding the Env protein and the nucleotide sequence encoding the Gag-Pol-Nef fusion protein are under the control of identical promoters and are both inserted at the thymidine kinase locus of the vector so that the recombinant vector lacks the thymidine kinase gene.

2. The recombinant vector according to claim 1, wherein the nucleotide sequences are generated from natural isolates.

3. The recombinant vector according to claim 2, wherein the nucleotide sequence encoding the modified HIV-1 Env protein is generated by eliminating the entire sequence of the gp41 gene that naturally appears after the last nucleotide of the gp120 gene.

4. The recombinant vector according to claim 2, wherein the nucleotide sequence encodes a Gag-Pol-Nef fusion protein that is not proteolyzed by HIV protease.

5. The recombinant vector according to claim 2, wherein the identical promoters allow the expression of the proteins during both early and late stages of the MVA infection cycle.

6. The recombinant vector according to claim 5, wherein the identical promoters are synthetic pE/L promoters.

7. The recombinant vector according to claim 1, wherein the nucleotide sequence encoding the Env protein is modified to eliminate the natural sequence that appears after the last nucleotide of the gp120 gene, the nucleotide sequence encodes a Gag-Pol-Nef fusion protein that is not proteolyzed by HIV protease, and the promoters that control the expression of the Env protein and the Gag-Pol-Nef fusion protein are synthetic pE/L promoters.

8. The recombinant vector according to claim 7, wherein both the nucleotide sequence encoding the Env protein and the nucleotide sequence encoding the Gag-Pol-Nef fusion protein have been generated from natural B clade isolates.

9. The recombinant vector according to claim 8, wherein SEQ ID NO:15 encodes the Env protein, gp120, from isolate BX08.

10. The recombinant vector according to claim 8, wherein the nucleotide sequence encoding said fusion protein is SEQ ID NO:16 and is generated from isolate IIIB.

11. The recombinant vector according to claim 7, wherein both the nucleotide sequence encoding the Env protein and the nucleotide sequence encoding the Gag-Pol-Nef fusion protein are generated from natural C clade isolates.

12. The recombinant vector according to claim 11, wherein the nucleotide sequence encoding the Env protein is SEQ ID NO:17 and is generated from isolate CN54.

13. The recombinant vector according to claim 11, wherein the nucleotide sequence encoding the fusion protein is SEQ ID NO:18 and is generated from isolate CN54.

14. The recombinant vector according to claim 12, wherein the nucleotide sequence encoding the Env protein is SEQ ID NO:17 from isolate CN54 and the nucleotide sequence encoding the fusion protein is SEQ ID NO:18 from isolate CN54.

15. A composition comprising a recombinant vector according to claim 1.

16. The composition according to claim 15 for administration to a subject to provoke or reinforce an immune response against HIV.

17. The composition according to claim 15 for administration to a subject as part of an immunization protocol in which a first dose is administered to trigger the immune response and one or more doses are administered subsequently to boost the initial immune response.

18. The composition according to claim 17, containing: (1) a first recombinant vector comprising SEQ ID NO:15 encoding the Env protein, gp120, from isolate BX08, and SEQ ID NO:16 encoding the Gag-Pol-Nef fusion protein from isolate IIIB, and (2) a second recombinant vector comprising SEQ ID NO:17 encoding the Env protein, gp120, from isolate CN54, and SEQ ID NO:18 encoding the Gag-Pol-Nef fusion protein from isolate CN54.

19. A method comprising administering to a subject the vector according to claim 1 to trigger and/or boost an immune response against HIV.

20. The method according to claim 19, comprising administering to the subject a single dose of the vector to trigger an immune response against HIV.

21. The method according to claim 19, comprising administering to the subject more than one dose of the vector to trigger and boost an immune response against HIV.

22. A method comprising administering to a subject the vector according to claim 8 to trigger and/or boost an immune response against HIV.

23. A method comprising administering to a subject the vector according to claim 11 to trigger and/or boost an immune response against HIV.

24. A method comprising administering to a subject the vector according to claim 13 to trigger and/or boost an immune response against HIV.

25. A method comprising administering to a subject the vector according to claim 10 to trigger and/or boost an immune response against HIV.

26. A method comprising administering to a subject the vector according to claim 12 to trigger and/or boost an immune response against HIV.

27. A method comprising administering to a subject the vector according to claim 14 to trigger and/or boost an immune response against HIV.

28. The method according to claim 21, comprising administering to the subject one or more booster doses of the vector.

29. The method according to claim 28, comprising administering to the subject a third dose comprising the vector.

30. The method according to claim 28, comprising administering to the subject a fourth dose comprising the vector.

31. A composition comprising the recombinant vector of claim 8 for administration to a subject to provoke or reinforce an immune response against an HIV clade B virus.

32. The composition according to claim 31 for administration to a subject to provoke or reinforce an immune response against an HIV BX08 isolate.

33. A composition comprising the recombinant vector of claim 11 for administration to a subject to provoke or reinforce an immune response against an HIV clade B virus.

34. The composition according to claim 33 for administration to a subject to provoke or reinforce an immune response against an HIV CN54 isolate.

35. The composition according to claim 18 for administration to a subject to provoke or reinforce an immune response against an HIV clade B virus and/or an HIV clade C virus.

* * * * *

UNITED STATES PATENT AND TRADEMARK OFFICE
CERTIFICATE OF CORRECTION

| | | |
|---|---|---|
| PATENT NO. | : 8,871,219 B2 | |
| APPLICATION NO. | : 11/989425 | |
| DATED | : October 28, 2014 | |
| INVENTOR(S) | : Gomez Rodriguez et al. | |

It is certified that error appears in the above-identified patent and that said Letters Patent is hereby corrected as shown below:

On the title page, change item (12) to Gomez Rodriguez, et al.

On the title page, in item (75) Inventors, please replace, "Jonathan Heeney, Rijswijk, (NL); Petra Mooij, Rijswijk, (NL); Carmen Elena Gomez Rodriguez, Madrid, (ES); Jose Luis Najera Garcia, Madrid, (ES); Victoria Jimenez Tentor, Madrid, (ES); Mariano Esteban Rodriguez, Madrid, (ES)" with -- Carmen Elena Gomez Rodriguez, Madrid, (ES); Jose Luis Najera Garcia, Madrid, (ES); Victoria Jimenez Tentor, Madrid, (ES); Mariano Esteban Rodriguez, Madrid, (ES) --.

Signed and Sealed this
Twenty-fourth Day of February, 2015

Michelle K. Lee
*Deputy Director of the United States Patent and Trademark Office*

SEQUENCE LISTING

```
<160> NUMBER OF SEQ ID NOS: 25

<210> SEQ ID NO 1
<211> LENGTH: 20
<212> TYPE: DNA
<213> ORGANISM: Artificial sequence
<220> FEATURE:
<223> OTHER INFORMATION: synthetic construct; primer
<220> FEATURE:
<221> NAME/KEY: MISC_FEATURE
<223> OTHER INFORMATION: TK-L

<400> SEQUENCE: 1
tgattagttt gatgcgattc                                                 20
```

<210> SEQ ID NO 2
<211> LENGTH: 17
<212> TYPE: DNA
<213> ORGANISM: Artificial sequence
<220> FEATURE:
<223> OTHER INFORMATION: synthetic construct; primer
<220> FEATURE:
<221> NAME/KEY: misc_feature
<223> OTHER INFORMATION: TK-R

<400> SEQUENCE: 2
tgtccttgat acggcag                    17

<210> SEQ ID NO 3
<211> LENGTH: 15
<212> TYPE: DNA
<213> ORGANISM: Artificial sequence
<220> FEATURE:
<223> OTHER INFORMATION: synthetic construct; primer
<220> FEATURE:
<221> NAME/KEY: misc_feature
<223> OTHER INFORMATION: BX08556

<400> SEQUENCE: 3
tgcccatcga caacg                      15

<210> SEQ ID NO 4
<211> LENGTH: 16
<212> TYPE: DNA
<213> ORGANISM: Artificial sequence
<220> FEATURE:
<223> OTHER INFORMATION: synthetic construct; primer
<220> FEATURE:
<221> NAME/KEY: misc_feature
<223> OTHER INFORMATION: GPN7649

<400> SEQUENCE: 4
agccccatcg agaccg                     16

<210> SEQ ID NO 5
<211> LENGTH: 17
<212> TYPE: DNA
<213> ORGANISM: Artificial sequence
<220> FEATURE:
<223> OTHER INFORMATION: synthetic construct; primer
<220> FEATURE:
<221> NAME/KEY: misc_feature
<223> OTHER INFORMATION: GPN8170

<400> SEQUENCE: 5
attagcctgc ctctcgg                    17

<210> SEQ ID NO 6
<211> LENGTH: 27
<212> TYPE: DNA
<213> ORGANISM: Artificial sequence
<220> FEATURE:
<223> OTHER INFORMATION: synthetic construct; primer
<220> FEATURE:
<221> NAME/KEY: misc_feature
<223> OTHER INFORMATION: E/L

<400> SEQUENCE: 6 tattttttttt ttttggaata taaatag        27

<210> SEQ ID NO 7
<211> LENGTH: 18

```
<212> TYPE: DNA
<213> ORGANISM: Artificial sequence
<220> FEATURE:
<223> OTHER INFORMATION: synthetic construct; primer
<220> FEATURE:
<221> NAME/KEY: misc_feature
<223> OTHER INFORMATION: gp120-10

<400> SEQUENCE: 7
tcgagcatgg acagggcc                                              18

<210> SEQ ID NO 8
<211> LENGTH: 18
<212> TYPE: DNA
<213> ORGANISM: Artificial sequence
<220> FEATURE:
<223> OTHER INFORMATION: synthetic construct; primer
<220> FEATURE:
<221> NAME/KEY: misc_feature
<223> OTHER INFORMATION: gp120-1050

<400> SEQUENCE: 8
gtcttgttct ggaagtgc                                              18

<210> SEQ ID NO 9
<211> LENGTH: 18
<212> TYPE: DNA
<213> ORGANISM: Artificial sequence
<220> FEATURE:
<223> OTHER INFORMATION: synthetic construct; primer
<220> FEATURE:
<221> NAME/KEY: misc_feature
<223> OTHER INFORMATION: gp120-1213

<400> SEQUENCE: 9
atcatcacca tccctgc                                               18

<210> SEQ ID NO 10
<211> LENGTH: 18
<212> TYPE: DNA
<213> ORGANISM: Artificial sequence
<220> FEATURE:
<223> OTHER INFORMATION: synthetic construct; primer
<220> FEATURE:
<221> NAME/KEY: misc_feature
<223> OTHER INFORMATION: GPN-802

<400> SEQUENCE: 10
tgggtttaaa caagatcg                                              18

<210> SEQ ID NO 11
<211> LENGTH: 18
<212> TYPE: DNA
<213> ORGANISM: Artificial sequence
<220> FEATURE:
<223> OTHER INFORMATION: synthetic construct; primer
<220> FEATURE:
<221> NAME/KEY: misc_feature
<223> OTHER INFORMATION: GPN-2018

<400> SEQUENCE: 11
caaggtgaag cagtggcc                                              18

<210> SEQ ID NO 12
<211> LENGTH: 18
<212> TYPE: DNA
<213> ORGANISM: Artificial sequence
<220> FEATURE:
<223> OTHER INFORMATION: synthetic construct; primer
```

```
<220> FEATURE:
<221> NAME/KEY: misc_feature
<223> OTHER INFORMATION: GPN-2198

<400> SEQUENCE: 12
tgggtcctct tgttcagc                                                       18

<210> SEQ ID NO 13
<211> LENGTH: 18
<212> TYPE: DNA
<213> ORGANISM: Artificial sequence
<220> FEATURE:
<223> OTHER INFORMATION: synthetic construct; primer
<220> FEATURE:
<221> NAME/KEY: misc_feature
<223> OTHER INFORMATION: GPN-3820

<400> SEQUENCE: 13
cggccttgcc gatcttgg                                                       18

<210> SEQ ID NO 14
<211> LENGTH: 18
<212> TYPE: DNA
<213> ORGANISM: Artificial sequence
<220> FEATURE:
<223> OTHER INFORMATION: synthetic construct; primer
<220> FEATURE:
<221> NAME/KEY: misc_feature
<223> OTHER INFORMATION: GPN-4000

<400> SEQUENCE: 14
ccgacaagag cgagagcg                                                       18

<210> SEQ ID NO 15
<211> LENGTH: 1482
<212> TYPE: DNA
<213> ORGANISM: Artificial sequence
<220> FEATURE:
<223> OTHER INFORMATION: synthetic construct
<220> FEATURE:
<221> NAME/KEY: misc_feature
<223> OTHER INFORMATION: gp120-bX08; from isolate BX08 of HIV-1; Coding
      Sequence

<400> SEQUENCE: 15
atggaccgcg ccaagctgct gctgctgctg ctgctgctgc tgctgcccca ggcccaggcc         60
gctagcgacc gcctgtgggt gacagtgtac tacggcgtgc ccgtgtggaa ggacgccacc        120
accaccctgt tctgcgcctc cgacgccaag gcctacgaca ccgaggtgca caacgtgtgg        180
gccacccacg cctgcgtgcc caccgacccc aaccccagg aggtggtgct gggcaacgtg         240
accgagaact tcaacatggg caagaacaac atggtggagc agatgcacga ggacatcatc        300
agcctgtggg accagtccct gaagccctgc gtgaagctga ccccctgtg cgtgaccctg         360 aactgcacca gctgaagaa cagcaccgac accaacaaca cccgctgggg cacccaggag         420
atgaagaact gctccttcaa catcagcacc tccgtgcgga caagatgaa gagagagtac        480 gccctgttct actccctgga catcgtgccc atcgacaacg acaacaccag ctaccgcctg        540
aggtcctgca cacctccat catcacccag gcctgcccca agtgagctt cgagcccatc         600 cccatccact tctgcgcccc cgccggcttc gccatcctga agtgcaacaa caagaccttc        660
aacggcaccg cccctgcac caacgtgagc accgtgcagt gcacccacgg catccgcccc        720
gtggtgtcca cccagctgct gctgaacggc agcctggccg aggaggaggt ggtgatccgg        780
tccgagaact tcaccaacaa cgccaagacc atcatcgtgc agctgaacga gagcgtggag        840
```

| | | | | |
|---|---|---|---|---|
| atcaactgca | ccagacccaa | caacaacacc | aggaagtcca | tccacatcgg | ccccggccgc | 900 |
| gccttctaca | ccaccggcga | catcatcggc | gacatccggc | aggcccactg | caacatctcc | 960 |
| agaaccaact | ggaccaacac | cctgaagagg | gtggccgaga | gctgcgcga | gaagttcaac | 1020 |
| aacaccacca | tcgtgttcaa | ccagagcagc | ggcggcgacc | ccgagatcgt | gatgcactcc | 1080 |
| ttcaactgcg | gcggcgagtt | cttctactgc | aacaccaccc | agctgttcaa | ctccacctgg | 1140 |
| aacgagacca | cagcgagggg | caacatcacc | tccggcacca | tcaccctgcc | ctgccggatc | 1200 |
| aagcagatca | tcaacatgtg | gcaggaggtg | ggcaaggcca | tgtacgcccc | cccatcggc | 1260 |
| ggccagatca | agtgcctgtc | caacatcacc | ggcctgctgc | tgaccagaga | cggcggctcc | 1320 |
| gacaacagca | gcagcggcaa | ggagatcttc | cgccccggcg | gcggcgacat | gagggacaac | 1380 |
| tggcgctccg | agctgtacaa | gtacaaggtg | gtgaagatcg | agcccctggg | catcgccccc | 1440 |
| accaaggcca | agaggagggt | ggtgcagcgc | gagaagcgct | ga | | 1482 |

<210> SEQ ID NO 16
<211> LENGTH: 3981
<212> TYPE: DNA
<213> ORGANISM: Artificial sequence
<220> FEATURE:
<223> OTHER INFORMATION: synthetic construct;
<220> FEATURE:
<221> NAME/KEY: misc_feature
<223> OTHER INFORMATION: gagpolnef-IIIB; derived from isolate IIIB of
   HIV; Coding Sequence

<400> SEQUENCE: 16

| | | | | |
|---|---|---|---|---|
| atggccgcca | gggccagcgt | gctgagcggc | ggcgagctgg | acaggtggga | gaagatcagg | 60 |
| ctgaggcccg | gcggcaagaa | gaagtataag | ctgaagcaca | tcgtgtgggc | cagcagggag | 120 |
| ctggagaggt | tcgccgtgaa | ccccggcctg | ctggagacca | gcgagggctg | caggcagatc | 180 |
| ctgggccagc | tgcagcccag | cctgcagacc | ggcagcgagg | agctgaggag | cctgtacaac | 240 |
| accgtggcca | ccctgtactg | cgtgcaccag | aggatcgaga | tcaaggacac | caaggaggcc | 300 |
| ctggacaaga | tcgaggagga | gcagaacaag | tccaagaaga | aggcccagca | ggccgccgcc | 360 |
| gacaccggcc | acagcagcca | ggtgagccag | aactacccca | tcgtgcagaa | catccagggc | 420 |
| cagatggtgc | accaggccat | cagccccagg | accctgaacg | cctgggtgaa | ggtggtggag | 480 |
| gagaaggcct | tcagccccga | ggtgatcccc | atgttcagcg | ccctgagcga | gggagccacc | 540 |
| ccccaggacc | tgaacaccat | gctgaacacc | gtgggcggcc | accaggccgc | catgcagatg | 600 |
| ctgaaggaga | ccatcaacga | ggaggccgcc | gagtgggaca | gggtgcaccc | cgtgcacgcc | 660 |
| ggccccatcg | ccccggcca | gatgagggag | cccgcggca | gcgacatcgc | cggcaccacc | 720 |
| agcaccctgc | aggagcagat | cggctggatg | accaacaacc | cccccatccc | cgtgggcgaa | 780 |
| atctacaaga | ggtggatcat | cctgggcctg | aacaagatcg | tgaggatgta | cagccccacc | 840 |
| agcatcctgg | atatcaggca | gggccccaaa | gagcccttca | gggactacgt | ggacaggttc | 900 |
| tacaagaccc | tgcgcgccga | gcaggccagc | caggaggtga | agaactggat | gaccgagacc | 960 |
| ctgctggtgc | agaacgccaa | ccccgactgc | aagaccatcc | tgaaggccct | ggacccgcc | 1020 |
| gccacctgg | aggagatgat | gaccgcctgc | cagggcgtgg | gcggccccgg | ccacaaggcc | 1080 |
| agggtgctgg | ccgaggccat | gagccaggtg | accaacaccg | ccaccatcat | gatgcagagg | 1140 |
| ggcaacttca | ggaaccagag | gaagatggtg | aagtgcttca | actgcggcaa | ggagggccac | 1200 |
| accgccagga | actgccgcgc | ccccaggaag | aagggctgct | ggaagtgcgg | caaggagggc | 1260 |

```
caccagatga aggactgcac cgagaggcag gctaatttta gggaagatct ggccttccta      1320
caagggaagg ccaggaatt ttcttcagag cagaccagag ccaacagccc caccatttct       1380
tcagagcaga ccagagccaa cagccccacc agaagagagc ttcaggtctg ggtagagac       1440 aacaactccc cctcagaagc aggagccgat agacaaggaa ctgtatcctt aacttccct       1500 cagatcactc tttggcaacg acccctcgtc acaataaaga tcggtggcca gctgaaggag      1560
gccctgctgg ccaccggcgc cgacgacacc gtgctggagg agatgagcct gcccggcagg      1620
tggaagccca agatgatcgg cggcatcggc ggcttcatca aggtgaggca gtacgaccag      1680
atcctgatcg agatctgcgg ccacaaggcc atcggcaccg tgctggtggg acctacacct      1740
gtgaacatca tcggcaggaa cctgctgacc cagatcggct gcaccctgaa cttccccatc      1800
agccccatcg agaccgtgcc cgtgaagctg aagcccggca tggacggccc taaggtgaag      1860
cagtggcccc tgaccgagga aagatcaag gccctggtgg agatctgcac cgagatggag       1920
aaggagggca agatcagcaa gatcggcccc gagaacccct acaacacccc cgtgttcgcc      1980
atcaagaaga aggacagcac caagtggagg aagctggtgg acttcaggga gctgaacaag      2040
aggacccagg acttctggga ggtgcagctg gcatccccc acccgccgg cctgaagaag        2100 aagaagagcg tgaccgtgct ggacgtgggc gacgcctact cagcgtgcc cctggacgag       2160 gacttcagga agtatacccc tttaagacca atgacttaca aggcagctgt agatcttagc      2220 cacttttaa aagaaaaggg gggactggaa gggctaattc actcccaacg aagacaagat       2280
atccttgatc tgtggatcta ccacacacaa ggctacttcc ctgatccaag gatgggtggc      2340
aagtggtcaa aaagtagtgt ggttggatgg cctgctgtaa gggaaagaat gagacgagct      2400
gagccagcag cagatggggt gggagcagca tctcgagacc tagaaaaaca tggagcaatc      2460
acaagtagca acacagcagc taacaatgct gattgtgcct ggctagaagc acaagaggag      2520
gaggaggtgg gttttccagt cacacctcaa gtaccattcc tgtggatggg ctacgagctg      2580 cacccccgaca agtggaccgt gcagcccatc gtgctgcccg agaaggacag ctggaccgtg      2640
aacgacattc agaagctggt gggcaagctg aactgggcca ccagatcta ccccggcatc      2700 aaggtgagc agctgtgcaa gctgctgagg ggcacaaagg ctctgaccga ggtgatcccc       2760
ctgaccgagg aggccgagct ggagctggcc gagaacaggg agatcctgaa ggagcccgtg      2820 cacgcgtgt actacgaccc cagcaaggac ctgatcgccg agatccagaa gcagggccag       2880
ggccagtgga cctaccagat ctaccaggag cccttcaaga acctgaagac cggcaagtac      2940
gcccgcatgc gcggcgccca ccacaacgac gtgaagcagc tgaccgaggc cgtgcagaag      3000
atcaccaccg agagcatcgt gatctggggc aagactccta agttcaagct gcccatccag      3060
aaggagacct gggagacctg gtggaccgag tactggcagg ccacctggat tcccgagtgg      3120
gagttcgtga acaccccctcc cctggtgaag ctgtggtatc agctggagaa ggagcccatc      3180
gtgggcgccg agaccttcta cgtggacggc gccgccaaca gggagaccaa gctgggcaag      3240
gccggctacg tgaccaacaa gggccgccag aaggtggtgc ccctgaccaa caccaccaac      3300
cagaagaccg agctgcaggc tatctacctg gccctgcagg actcaggcct ggaggtgaac      3360
atcgtgaccg acagccagta cgccctgggc atcatccagg cccagccga caagagcgag       3420 agcgagctgg tgaaccagat catcgagcag ctgatcaaga aggagaaggt gtacctggcc      3480
tgggtgcccg cccacaaggg catcggcggc aacgagcagg tggacaagct ggtgagcgcc      3540
ggcatcagga gatcctgtt cctggacggc atcgacaagg cccaggacga gcacgagaag       3600
taccacagca actggagggc tatggctagc gacttcaacc tgcctcccgt ggtggctaag      3660
```

```
gagatcgtgg ccagcgcctt caccatcccc agcatcaaca acgagacccc cggcatccgc    3720
taccagtaca acgtgctgcc ccagggctgg aagggcagcc ccgccatctt ccagagcagc    3780
atgacaaaga tcctggagcc cttcaagaag cagaaccccg acatcgtgat ctatcagtac    3840
atggacgacc tgtacgtggg cagcgacctg gagatcggcc agcacaggac caagatcgag    3900
gagctgaggc agcacctgct gaggtggggc ctgaccaccc ccgacaagaa gcaccagaag    3960
gagcccccat tcctgtggta a                                              3981

<210> SEQ ID NO 17
<211> LENGTH: 1497
<212> TYPE: DNA
<213> ORGANISM: Artificial sequence
<220> FEATURE:
<223> OTHER INFORMATION: synthetic construct
<220> FEATURE:
<221> NAME/KEY: misc_feature
<223> OTHER INFORMATION: gp120-C; derived from isolate CN54 of HIV-1;
      Coding Sequence

<400> SEQUENCE: 17
atggacaggg ccaagctgct gctgctgctg ctgctgctgc tgctgcccca ggcccaggcc      60
gtgggcaacc tgtgggtgac cgtgtactac ggcgtgcccg tgtggaaggg cgccaccacc     120
accctgttct cgccagcga cgccaaggcc tacgacaccg aggtgcacaa cgtgtgggcc     180
acccacgcct gcgtgcccgc cgaccccaac ccccaggaga tggtgctgga aacgtgacc     240 gagaacttca acatgtggaa gaacgagatg gtgaaccaga tgcaggagga cgtcatcagc     300
ctgtgggacc agagcctgaa gccctgcgtg aagctgaccc cctgtgcgt gaccctggag     360 tgcaggaacg tgagcagcaa cagcaacgac acctaccacg agacctacca cgagagcatg     420
aaggagatga agaactgcag cttcaacgcc accaccgtgg tgagggacag gaagcagacc     480
gtgtacgccc tgttctacag gctggacatc gtgcccctga ccaagaagaa ctacagcgag     540
aacagcagcg agtactacag gctgatcaac tgcaacacca cgccatcac ccaggcctgc     600 cccaaggtga ccttcgaccc catccccatc cactactgca cccccgccgg ctacgccatc     660
ctgaagtgca cgacaagat cttcaacggc accggcccct gccacaacgt gagcaccgtg     720
cagtgcaccc cacggcatca agcccgtggtg agcacccagc tgctgctgaa cggcagcctg     780
gccgagggcg agatcatcat caggagcgag aacctgacca caacgtgaa aaccatcatc     840 gtgcacctga ccagagcgt ggagatcgtg tgcaccaggc ccggcaacaa caccaggaag     900
agcatcagga tcggccccgg ccagaccttc tacgccaccg gcgacatcat cggcgacatc     960
aggcaggccc actgcaacat cagcgaggac aagtggaacg agaccctgca gagggtgagc    1020
aagaagcttg ccgagcactt ccagaacaag accatcaagt tcgccagcag cagcggcggc    1080
gacctggagg tgaccacccca cagcttcaac tgcagggcg agttcttcta ctgcaacacc    1140 agcgcctgt tcaacggcgc ctacacccccc aacggcacca gagcaacag cagcagcatc    1200 atcaccatcc cctgcaggat caagcagatc atcaacatgt ggcaggaggt gggcagggcc    1260
atgtacgccc tccccatcaa gggcaacatc acctgcaaga gcaacatcac cggcctgctg    1320
ctggtgaggg acggcggcac cgagcccaac gacaccgaga ccttcaggcc cggcggcggc    1380
gacatgagga caactggag gagcgagctg tacaagtaca aggtggtgga gatcaagccc    1440
ctgggcgtgg ccccccaccac caccaagagg agggtggtgg agagggagaa gaggtga      1497

<210> SEQ ID NO 18
```

<211> LENGTH: 4254
<212> TYPE: DNA
<213> ORGANISM: Artificial sequence
<220> FEATURE:
<223> OTHER INFORMATION: synthetic construct
<220> FEATURE:
<221> NAME/KEY: misc_feature
<223> OTHER INFORMATION: gagpolnef-C; derived from isolate CN54 of
      HIV-1; Coding Sequence

<400> SEQUENCE: 18

```
atggccgcca gggccagcat cctgaggggc ggcaagctgg acaagtggga agagatcagg     60
ctgaggcccg cggcaagaa gcactacatg ctgaagcacc tggtgtgggc cagcagggag    120
ctggagaggt tcgccctgaa ccccggcctg ctggagacca gcgagggctg caagcagatc    180
atgaagcagc tgcagagcgc cctgcagacc ggcaccgagg agctgaggag cctgttcaac    240
accgtggcca cccctactg cgtgcacacc gagatcgacg tgagggacac cagggaggcc    300
ctggacaaga tcgaggagga gcagaacaag atccagcaga gacccagca ggccaaggag    360
gccgacggca aggtgagcca gaactacccc atcgtgcaga acctgcaggg ccagatggtg    420
caccagccca tcagccccag gaccctgaat gcatgggtga aggtggtgga ggagaaggcc    480
ttcagccccg aggtgatccc catgttcagc gccctgagcg agggcgccac ccctcaggac    540
ctgaacacca tgctgaacac cgtgggcggc caccaggccg ccatgcagat cctgaaggac    600
accatcaacg aggaggccgc cgagtgggac aggctgcacc ccgtgcacgc cggccccatc    660
gcccccggcc agatgaggga gcccaggggc agcgacatcg ccggcaccac cagcaacctg    720
caggagcaga tcgcctggat gaccagcaac ccacccgtgc ccgtgggcga catctacaag    780
aggtggatca tcctgggttt aaacaagatc gtgaggatgt acagccccac cagcatcctg    840
gacatcaagc agggccccaa ggagcccttc agggactacg tggacaggtt cttcaagacc    900
ctgagggccg agcaggccac ccagggcgtg aagaactgga tgaccgacac cctgctggtg    960
cagaacgcca cccccgactg caagaccatc ctgagggccc tgggcccggg cgccagcatc   1020
gaggagatga tgaccgcctg ccagggcgtg ggcggcccca gccacaaggc caaggtgctg   1080
gccgaggcca tgagccagac caacagcgcc atcctgatgc agaggagcaa cttcaagggc   1140
agcaagagga tcgtgaagtg cttcaactgc ggcaaggagg ccacatcgc caggaactgc   1200
agggccccca ggaagaaggg ctgctggaag tgcggcaagg agggccacca gatgaaggac   1260
tgcaccgaga ggcaggccaa cttcctgggc aagatctggc ccagccacaa gggcggcccc   1320
ggcaacttcc tgcagaacag gcccgagccc accgcccccc ccgaggagag cttcaggttc   1380
gaggaggaga ccaccacccc cagccagaag caggagccca tcgacaagga gctgtacccc   1440
ctgaccagcc tgaagagcct gttcggcaac gaccccagca gccaggaatt cttcagggag   1500
aacctggccc tgcccaggg cagggccagg gagttcagca gcgagcagac cagggccaac   1560
agccccacca ggggcgagct gcaggtgtgg ggcaggacaa caacagcat cagcgaggcc   1620
ggcgccaaca ggcagggcac catcagcttc aacttccccc agatcaccct gtggcagagg   1680
cccctggtga ccatcaagat cggcggccag ctgaaggagg ccctgctgaa caccggcgcc   1740
ggcgacaccg tgctggagga cctgaacctg cccggcaagt ggaagcccaa gatgatcggc   1800
ggcatcggcg gcttcatcaa ggtgaggcag tacgagcaga tccccatcga gatctgcggc   1860
cacaaggcca tcggcaccgt gctggtgggc cccacccccg tgaacatcat cggcaggaac   1920
ctgctgaccc agctggcctg caccctgaac ttccccatca gccccatcga gaccgtgccc   1980
gtgaagctga gcccggcat ggacggcccc aaggtgaagc agtggcccct gaccgaggag   2040
```

-continued

```
aagatcaagg ccctgaccgc catctgcgac gagatggaga aggagggcaa gatcaccaag    2100
atcggccccg agaaccccta caacacccccc atcttcgcca tcaagaagaa ggacagcacc    2160
aagtggagga agctggtgga cttcaggag ctgaacaaga ggacccagga cttctgggag    2220
gtgcagctgg gcatccccca ccccgccggc ctgaagaaga gaagagcgt gaccgtgctg    2280
gacgtgggcg acgcctactt cagcatcccc ctgtacgagg acttcaggaa gtacaccgcc    2340
ttcaccatcc ccagcaggaa caacgagacc cccggcatca gctaccagta caacgtgctg    2400
ccccagggct ggaagggcag cctcgccatc ttccagcagca gcatgaccat cgaggagctg    2460
atctacagca agaagaggca ggagatcctg gacctgtggg tgtaccacac ccagggctac    2520
ttcccccgact ggcacaacta caccccccggc cccggcgtga ggttcccccct gaccttcggc    2580
tggtgcttca agctggtgcc cgtggacccc agggaggtgg aggaggccaa cgagggcgag    2640
gacaactgcc tgctgcaccc cgtgtgccag cacggcatgg aggacgacca cagggaggtg    2700
ctgaagtgga gttcgacag ccagctggcc cacaggcaca gggccaggga gctgcaccccc    2760
gagttctaca aggactgcat gggcggcaag tgagcaaga gcagcatcgt gggctggccc    2820
gccatcaggg agaggatgag gaggaccgag cccgccgccg acggcgtggg cgccgtgagc    2880
agggacctgg agaagcacgg cgccatcacc agcagcaaca ccgccgccac caacgaggac    2940
tgcgcctggc tggaggccca ggaggagggc gaggtgggct ccccgtgag gccccaggtg    3000
cccctgaggc ccatgaccta aagggcgcc gtggacctga gcttcttcct gaaggagaag    3060
ggcggcctgg agggcctgag gcagcacctg ctgaggtggg gcttcaccac ccccgacaag    3120
aagcaccaga aggagccccc cttcctgtgg atgggctacg agctgcaccc cgacaagtgg    3180
accgtgcagc ccacccagct gcccgagaag gatagctgga ccgtgaacga catccagaag    3240
ctggtgggca agctgaactg ggccagccag atctaccccg gcatcaaggt gaggcagctg    3300
tgcaagctgc tgagggggcgc caaggccctg accgacatcg tgcccctgac cgaggaggcc    3360
gagctggagc tggccgagaa cagggagatc ctgaaggagc ccgtgcacgg cgtgtactac    3420
gaccccagca aggacctgat cgccgagatc cagaagcagg gccaggagca gtggacctac    3480
cagatctacc aggagccctt caagaacctg aagaccggca gtacgccaa gatgaggacc    3540
gcccacacca cgacgtgaa gcagctgacc gaggccgtgc agaagatcgc catggagggc    3600
atcgtgatct ggggcaagac ccccaagttc aggctgccca tccagaagga gacctgggag    3660
acctggtgga ccgactactg gcaggccacc tggatccccg agtgggagtt cgtgaacacc    3720
cctcccctgt gaagctgtg gtatcagctg gagaaggacc ccatcgtggg cgtggagacc    3780
ttctacgtgg acggcgccgc caacagggag accaagatcg gcaaggccgg ctacgtgacc    3840
gacaggggca ggaagaagat cgtgagcctg accgagacca ccaaccagaa gaccgagctg    3900
caggccatct gcatcgccct gcaggacagc ggcagcgagg tgaacatcgt gaccgacagc    3960
cagtacgccc tgggcatcat ccaggccag cccgacaaga gcgagagcga gctggtgaac    4020
cagatcatcg agcagctgat gaagaaggag agggtgtacc tgagctgggt gcccgcccac    4080
aagggcatcg gcggcaacga gcaggtggac aagctggtga gcagcggcat caggaaggtg    4140
ctgaagaccc tggagccctt caggaagcag aaccccggca tcgtgatcta ccagtacatg    4200
gacgacctgt acgtgggcag cgacctggag atcggccagc acaggaccaa gtaa          4254
```

<210> SEQ ID NO 19
<211> LENGTH: 6907
<212> TYPE: DNA

```
<213> ORGANISM: Artificial sequence
<220> FEATURE:
<223> OTHER INFORMATION: synthetic construct; Insert of MVA-B
<220> FEATURE:
<221> NAME/KEY: MISC_FEATURE
<222> LOCATION: (1)..(502)
<223> OTHER INFORMATION: LEFT FLANKING SEQUENCE; TkL
<220> FEATURE:
<221> NAME/KEY: MISC_FEATURE
<222> LOCATION: (537)..(4517)
<223> OTHER INFORMATION: SEQUENCE COMPLEMENTARY TO CDS; gagpolnef-IIIB
<220> FEATURE:
<221> NAME/KEY: MISC_FEATURE
<222> LOCATION: (4527)..(4565)
<223> OTHER INFORMATION: SEQUENCE COMPLEMENTARY TO PROMOTOER; pE/L for
      gagpolnef-IIIB
<220> FEATURE:
<221> NAME/KEY: Promoter
<222> LOCATION: (4580)..(4618)
<223> OTHER INFORMATION: pE/L for gp120-BX08
<220> FEATURE:
<221> NAME/KEY: Misc_feature
<222> LOCATION: (4628)..(6109)
<223> OTHER INFORMATION: gp120-BX08
<220> FEATURE:
<221> NAME/KEY: MISC_FEATURE
<222> LOCATION: (6216)..(6907)
<223> OTHER INFORMATION: RIGHT FLANKING SEQUENCE; TkR

<400> SEQUENCE: 19
aagcttttgc gatcaataaa tggatcacaa ccagtatctc ttaacgatgt tcttcgcaga      60
tgatgattca tttttaagt atttggctag tcaagatgat gaatcttcat tatctgatat     120
attgcaaatc actcaatatc tagactttct gttattatta ttattgatcc aatcaaaaaa     180
taaattagaa gccgtgggtc attgttatga atctctttca gaggaataca gacaattgac     240
aaaattcaca gactctcaag attttaaaaa actgtttaac aaggtcccta ttgttacaga     300
tggaagggtc aaacttaata aaggatattt gttcgacttt gtgattagtt tgatgcgatt     360
caaaaaagaa tcctctctag ctaccaccgc aatagatcct attagataca tagatcctcg     420
tcgcgatatc gcattttcta acgtgatgga tatattaaag tcgaataaag tgaacaataa     480
ttaattcttt attgtcatca tgggtaccaa ggcgcggatc cccgggtacc gagctcttac     540
cacaggaatg ggggctcctt ctggtgcttc ttgtcggggg tggtcaggcc ccacctcagc     600
aggtgctgcc tcagctcctc gatcttggtc ctgtgctggc cgatctccag gtcgctgccc     660
acgtacaggt cgtccatgta ctgatagatc acgatgtcgg ggttctgctt cttgaagggc     720
tccaggatct ttgtcatgct gctctggaag atggcgggc tgcccttcca gccctggggc     780
agcacgttgt actggtagcg gatgccgggg gtctcgttgt tgatgctggg gatggtgaag     840
gcgctggcca cgatctcctt agccaccacg ggaggcaggt tgaagtcgct agccatagcc     900
ctccagttgc tgtggtactt ctcgtgctcg tcctgggcct tgtcgatgcc gtccaggaac     960
aggatcttcc tgatgccggc gctcaccagc ttgtccacct gctcgttgcc gccgatgccc    1020
ttgtgggcgg gcacccaggc caggtacacc ttctccttct tgatcagctg ctcgatgatc    1080
tggttcacca gctcgctctc gctcttgtcg ggctgggcct ggatgatgcc cagggcgtac    1140
tggctgtcgg tcacgatgtt cacctccagg cctgagtcct gcagggccag gtagatagcc    1200
tgcagctcgg tcttctggtt ggtggtgttg gtcaggggca ccaccttctg gcggcccttg    1260
ttggtcacgt agccggcctt gcccagcttg gtctccctgt tggcggcgcc gtccacgtag    1320
aaggtctcgg cgcccacgat gggctccttc tccagctgat accacagctt caccagggga    1380
ggggtgttca cgaactccca ctcgggaatc caggtggcct gccagtactc ggtccaccag    1440
```

```
gtctcccagg tctccttctg gatgggcagc ttgaacttag gagtcttgcc ccagatcacg    1500
atgctctcgg tggtgatctt ctgcacggcc tcggtcagct gcttcacgtc gttggtgtgg    1560
gcgccgcgca tgcgggcgta cttgccggtc ttcaggttct tgaagggctc ctggtagatc    1620
tggtaggtcc actggccctg gccctgcttc tggatctcgg cgatcaggtc cttgctgggg    1680
tcgtagtaca cgccgtgcac gggctccttc aggatctccc tgttctcggc cagctccagc    1740
tcggcctcct cggtcagggg gatcacctcg gtcagagcct tgtgcccct cagcagcttg     1800 cacagctgcc tcaccttgat gccggggtag atctggctgg cccagttcag cttgcccacc    1860
agcttctgaa tgtcgttcac ggtccagctg tccttctcgg gcagcacgat gggctgcacg    1920
gtccacttgt cggggtgcag ctcgtagccc atccacagga atggtacttg aggtgtgact    1980
ggaaaaccca cctcctcctc tcttgtgct tctagccagg cacaatcagc attgttagct     2040
gctgtgttgc tacttgtgat tgctccatgt ttttctaggt ctcgagatgc tgctcccacc    2100
ccatctgctg ctggctcagc tcgtctcatt ctttcccttta cagcaggcca tccaaccaca   2160
ctactttttg accacttgcc acccatcctt ggatcaggga agtagcctg tgtgtggtag     2220 atccacagat caaggatatc ttgtcttcgt tgggagtgaa ttagcccttc cagtccccc     2280 tttctcttta aaaagtggct aagatctaca gctgccttgt aagtcattgg tcttaaaggg    2340
gtatacttcc tgaagtcctc gtccaggggc acgctgaagt aggcgtcgcc cacgtccagc    2400
acggtcacgc tcttcttctt cttcaggccg gcggggtggg ggatgcccag ctgcacctcc    2460
cagaagtcct gggtcctctt gttcagctcc ctgaagtcca ccagcttcct ccacttggtg    2520
ctgtccttct tcttgatggc gaacacgggg gtgttgtagg ggttctcggg gccgatcttg    2580
ctgatcttgc cctccttctc catctcggtg cagatctcca ccagggcctt gatcttctcc    2640
tcggtcaggg gccactgctt caccttaggg ccgtccatgc cgggcttcag cttcacgggc    2700
acggtctcga tggggctgat ggggaagttc agggtgcagc cgatctgggt cagcaggttc    2760
ctgccgatga tgttcacagg tgtaggtccc accagcacgg tgccgatggc cttgtggccg    2820
cagatctcga tcaggatctg gtcgtactgc ctcaccttga tgaagccgcc gatgccgccg    2880
atcatcttgg gcttccacct gccgggcagg ctcatctcct ccagcacggt gtcgtcggcg    2940
ccggtggcca gcagggcctc cttcagctgg ccaccgatct ttattgtgac gagggggtcgt   3000 tgccaaagag tgatctgagg gaagttaaag gatacagttc cttgtctatc ggctcctgct    3060
tctgaggggg agttgttgtc tctaccccag acctgaagct ctcttctggt ggggctgttg    3120
gctctggtct gctctgaaga aatggtgggg ctgttggctc tggtctgctc tgaagaaaat    3180
tccctggcct tcccttgtag gaaggccaga tcttccctaa aattagcctg cctctcggtg    3240
cagtccttca tctggtggcc ctccttgccg cacttccagc agcccttctt cctggggcg     3300 cggcagttcc tggcggtgtg gccctccttg ccgcagttga agcacttcac catcttcctc    3360
tggttcctga agttgcccct ctgcatcatg atggtggcgg tgttggtcac ctggctcatg    3420
gcctcggcca gcaccctggc cttgtggccg gggccgccca cgccctggca ggcggtcatc    3480
atctcctcca gggtggcggc gggtcccagg gccttcagga tggtcttgca gtcggggttg    3540
gcgttctgca ccagcagggt ctcggtcatc cagttcttca cctcctggct ggcctgctcg    3600
gcgcgcaggg tcttgtagaa cctgtccacg tagtccctga agggctcttt ggggccctgc    3660
ctgatatcca ggatgctggt ggggctgtac atcctcacga tcttgttcag gcccaggatg    3720
atccacctct tgtagatttc gcccacgggg atggggggg tgttggtcat ccagccgatc     3780
tgctcctgca gggtgctggt ggtgccggcg atgtcgctgc cgcgggctc cctcatctgg     3840
```

```
ccggggcga tggggccggc gtgcacgggg tgcaccctgt cccactcggc ggcctcctcg    3900
ttgatggtct ccttcagcat ctgcatggcg gcctggtggc cgcccacggt gttcagcatg   3960
gtgttcaggt cctgggggt ggctccctcg ctcagggcgc tgaacatggg gatcacctcg    4020
gggctgaagg ccttctcctc caccaccttc acccaggcgt tcagggtcct ggggctgatg   4080
gcctggtgca ccatctggcc ctggatgttc tgcacgatgg ggtagttctg gctcacctgg   4140
ctgctgtggc cggtgtcggc ggcggcctgc tgggccttct tcttggactt gttctgctcc   4200
tcctcgatct tgtccagggc ctccttggtg tccttgatct cgatcctctg gtgcacgcag   4260
tacagggtgg ccacggtgtt gtacaggctc ctcagctcct cgctgccggt ctgcaggctg   4320
ggctgcagct ggcccaggat ctgcctgcag ccctcgctgg tctccagcag gccggggttc   4380
acggcgaacc tctccagctc cctgctggcc cacacgatgt gcttcagctt atacttcttc   4440
ttgccgccgg gcctcagcct gatcttctcc cacctgtcca gctcgccgcc gctcagcacg   4500
ctggccctgg cggccatgct cgagtctatt tatattccaa aaaaaaaaaa taaaatttca   4560
attttgtcg acaagcttaa aaattgaaat tttatttttt ttttttggaa tataaataag    4620
ctcgagcatg gaccgcgcca agctgctgct gctgctgctg ctgctgctgc tgccccaggc   4680
ccaggccgct agcgaccgcc tgtgggtgac agtgtactac ggcgtgcccg tgtggaagga   4740
cgccaccacc accctgttct gcgcctccga cgccaaggcc tacgacaccg aggtgcacaa   4800
cgtgtgggcc acccacgcct gcgtgcccac cgaccccaac ccccaggagg tggtgctggg   4860
caacgtgacc gagaacttca acatgggcaa gaacaacatg gtggagcaga tgcacgagga   4920
catcatcagc ctgtgggacc agtccctgaa gccctgcgtg aagctgaccc ccctgtgcgt   4980
gaccctgaac tgcaccaagc tgaagaacag caccgacacc aacaacaccc gctggggcac   5040
ccaggagatg aagaactgct ccttcaacat cagcacctcc gtgcggaaca gatgaagag    5100
agagtacgcc ctgttctact ccctggacat cgtgcccatc gacaacgaca caccagcta   5160
ccgcctgagg tcctgcaaca cctccatcat cacccaggcc tgccccaagg tgagcttcga   5220
gcccatcccc atccacttct gcgccccgc cggcttcgcc atcctgaagt gcaacaacaa   5280
gaccttcaac ggcaccggcc cctgcaccaa cgtgagcacc gtgcagtgca cccacggcat   5340
ccgccccgtg gtgtccaccc agctgctgct gaacggcagc ctggccgagg aggaggtggt   5400
gatccggtcc gagaacttca ccaacaacgc caagaccatc atcgtgcagc tgaacgagag   5460
cgtggagatc aactgcacca gacccaacaa caccaccagg aagtccatcc acatcggccc   5520
cggccgcgcc ttctacacca ccggcgacat catcggcgac atccggcagg cccactgcaa   5580
catctccaga accaactgga ccaacaccct gaagagggtg ccgagaagc tgcgcgagaa   5640
gttcaacaac accaccatcg tgttcaacca gagcagcggc ggcgaccccg agatcgtgat   5700
gcactccttc aactgcggcg gcgagttctt ctactgcaac accacccagc tgttcaactc   5760
cacctggaac gagaccaaca gcgagggcaa catcacctcc ggcaccatca ccctgccctg   5820
ccggatcaag cagatcatca acatgtggca ggaggtgggc aaggccatgt acgcccccc    5880
catcggcggc cagatcaagt gcctgtccaa catcaccggc ctgctgctga ccagagacgg   5940
cggctccgac aacagcagca gcggcaagga gatcttccgc cccggcggcg gcgacatgag   6000
ggacaactgg cgctccgagc tgtacaagta caaggtggtg aagatcgagc ccctgggcat   6060
cgcccccacc aaggccaaga ggagggtggt gcagcgcgag aagcgctgat aatagggatc   6120
cgcgccaaat ttaaatgatc ctgatccttt ttctgggtaa gtaatacgtc aaggagaaaa   6180
```

```
cgaaacgatc tgtagttagc ggccgcctaa ttaactaata ttatattttt tatctaaaaa    6240
actaaaaata aacattgatt aaattttaat ataatactta aaaatggatg ttgtgtcgtt    6300
agataaaccg tttatgtatt ttgaggaaat tgataatgag ttagattacg aaccagaaag    6360
tgcaaatgag gtcgcaaaaa aactgccgta tcaaggacag ttaaaactat tactaggaga    6420 attattttt cttagtaagt tacagcgaca cggtatatta gatggtgcca ccgtagtgta    6480
tataggatcg gctcctggta cacatatacg ttatttgaga gatcatttct ataatttagg    6540
aatgattatc aaatggatgc taattgacgg acgccatcat gatcctattc taaatggatt    6600
gcgtgatgtg actctagtga ctcggttcgt tgatgaggaa tatctacgat ccatcaaaaa    6660
acaactgcat ccttctaaga ttattttaat ttctgatgta agatccaaac gaggaggaaa    6720
tgaacctagt acggcggatt tactaagtaa ttacgctcta caaaatgtca tgattagtat    6780
tttaaacccc gtggcatcta gtcttaaatg gagatgcccg tttccagatc aatggatcaa    6840 ggactttat atcccacacg gtaataaaat gttacaacct tttgctcctt catattcagg    6900
ggaattc                                                              6907

<210> SEQ ID NO 20
<211> LENGTH: 7346
<212> TYPE: DNA
<213> ORGANISM: artificial sequence
<220> FEATURE:
<223> OTHER INFORMATION: synthetic construct; Insert of MVA-C
<220> FEATURE:
<221> NAME/KEY: MISC_FEATURE
<222> LOCATION: (1)..(502)
<223> OTHER INFORMATION: LEFT FLANKING SEQUENCE; TkL
<220> FEATURE:
<221> NAME/KEY: MISC_FEATURE
<222> LOCATION: (647)..(2143)
<223> OTHER INFORMATION: SEQUENCE COMPLEMENTARY TO CDS; gp120-C
<220> FEATURE:
<221> NAME/KEY: MISC_FEATURE
<222> LOCATION: (2153)..(2191)
<223> OTHER INFORMATION: SEQUENCE COMPLEMENTARY TO PROMOTER; pE/L for
      gp120-C
<220> FEATURE:
<221> NAME/KEY: PROMOTER
<222> LOCATION: (2206)..(2244)
<223> OTHER INFORMATION: pE/L for gp120-C
<220> FEATURE:
<221> NAME/KEY: CDS
<222> LOCATION: (2254)..(6507)
<223> OTHER INFORMATION: gagpolnef-C
<220> FEATURE:
<221> NAME/KEY: MISC_FEATURE
<222> LOCATION: (6656)..(7347)
<223> OTHER INFORMATION: RIGHT FLANKING SEQUENCE; TkR

<400> SEQUENCE: 20
agcttttgcg atcaataaat ggatcacaac cagtatctct taacgatgtt cttcgcagat      60
gatgattcat tttttaagta tttggctagt caagatgatg aatcttcatt atctgatata     120
ttgcaaatca ctcaatatct agactttctg ttattattat tattgatcca atcaaaaaat     180
aaattagaag ccgtgggtca ttgttatgaa tctctttcag aggaatacag acaattgaca     240
aaattcacag actctcaaga ttttaaaaaa ctgtttaaca aggtccctat tgttacagat     300
ggaagggtca aacttaataa aggatatttg ttcgactttg tgattagttt gatgcgattc     360
aaaaaagaat cctctctagc taccaccgca atagatccta ttagatacat agatcctcgt     420
cgcgatatcg cattttctaa cgtgatggat atattaaagt cgaataaagt gaacaataat     480
taattcttta ttgtcatcat gggtaccaag gcgcgatcgc attttctaac gtgatggata     540
```

```
tattaaagtc gaataaagtg aacaataatt aattctttat tgtcatcatg taattaacta    600
gctacccgga ataaaaattc cgggagatct ctcgagagat ctttatcacc tcttctccct    660
ctccaccacc ctcctcttgg tggtggtggg ggccacgccc aggggcttga tctccaccac    720
cttgtacttg tacagctcgc tcctccagtt gttcctcatg tcgccgccgc cgggcctgaa    780
ggtctcggtg tcgttgggct cggtgccgcc gtccctcacc agcagcaggc cggtgatgtt    840
gctcttgcag gtgatgttgc ccttgatggg aggggcgtac atgggccctgc ccacctcctg    900 ccacatgttg atgatctgct tgatcctgca ggggatggtg atgatgctgc tgctgttgct    960
cttggtgccg ttggggggtgt aggcgccgtt gaacaggccg ctggtgttgc agtagaagaa   1020
ctcgcccctg cagttgaagc tgtgggtggt cacctccagg tcgccgccgc tgctgctggc   1080
gaacttgatg gtcttgttct ggaagtgctc ggcaagcttc ttgctcaccc tctgcagggt   1140
ctcgttccac ttgtcctcgc tgatgttgca gtgggcctgc ctgatgtcgc cgatgatgtc   1200
gccggtggcg tagaaggtct ggccggggcc gatcctgatg ctcttcctgg tgttgttgcc   1260
gggcctggtg cacacgatct ccacgctctg gttcaggtgc acgatgatgg ttttcacgtt   1320
gttggtcagg ttctcgctcc tgatgatgat ctcgccctcg ccaggctgc cgttcagcag    1380 cagctgggtg ctcaccacgg gcttgatgcc gtgggtgcac tgcacggtgc tcacgttgtg   1440
gcaggggccg gtgccgttga agatcttgtc gttgcacttc aggatggcgt agccggcggg   1500
ggtgcagtag tggatgggga tggggtcgaa ggtcaccttg gggcaggcct gggtgatggc   1560
gctggtgttg cagttgatca gcctgtagta ctcgctgctg ttctcgctgt agttcttctt   1620
ggtcaggggc acgatgtcca gcctgtagaa cagggcgtac acggtctgct tcctgtccct   1680
caccacggtg gtggcgttga agctgcagtt cttcatctcc ttcatgctct cgtggtaggt   1740
ctcgtggtag gtgtcgttgc tgttgctgct cacgttcctg cactccaggg tcacgcacag   1800
gggggtcagc ttcacgcagg gcttcaggct ctggtccac aggctgatga cgtcctcctg     1860
catctggttc accatctcgt tcttccacat gttgaagttc tcggtcacgt tctccagcac   1920
catctcctgg gggttggggt cggcgggcac gcaggcgtgg gtggcccaca cgttgtgcac   1980
ctcggtgtcg taggccttgg cgtcgctggc gcagaacagg gtggtggtgg cgcccttcca   2040
cacgggcacg ccgtagtaca cggtcaccca caggttgccc acggcctggg cctggggcag   2100
cagcagcagc agcagcagca gcagcagctt ggccctgtcc atgctcgagc ttatttatat   2160
tccaaaaaaa aaaaataaaa tttcaatttt taagcttgtc gacaaaaatt gaaatttat    2220 tttttttttt tggaatataa atagactcga gcatggccgc cagggccagc atcctgaggg   2280
gcggcaagct ggacaagtgg gagaagatca ggctgaggcc cggcggcaag aagcactaca   2340
tgctgaagca cctggtgtgg gccagcaggg agctggagag gttcgccctg aaccccggcc   2400
tgctggagac cagcgagggc tgcaagcaga tcatgaagca gctgcagagc gccctgcaga   2460
ccggcaccga ggagctgagg agcctgttca cacccgtggc caccccctac tgcgtgcaca   2520
ccgagatcga cgtgagggac accagggagg ccctggacaa gatcgaggag gagcagaaca   2580
agatccagca gaagacccag caggccaagg aggccgacgg caaggtgagc cagaactacc   2640
ccatcgtgca gaacctgcag ggccagatgg tgcaccagcc catcagcccc aggaccctga   2700
atgcatgggt gaaggtggtg gaggagaagg ccttcagccc cgaggtgatc cccatgttca   2760
gcgccctgag cgagggcgcc acccctcagg acctgaacac catgctgaac accgtgggcg   2820
gccaccaggc cgccatgcag atcctgaagg acaccatcaa cgaggaggcc gccgagtggg   2880
acaggctgca ccccgtgcac gccggcccca tcgcccccgg ccagatgagg gagcccaggg   2940
```

```
gcagcgacat cgccggcacc accagcaacc tgcaggagca gatcgcctgg atgaccagca    3000
acccacccgt gcccgtgggc gacatctaca agaggtggat catcctgggt ttaaacaaga    3060
tcgtgaggat gtacagcccc accagcatcc tggacatcaa gcagggcccc aaggagccct    3120
tcagggacta cgtggacagg ttcttcaaga ccctgagggc cgagcaggcc acccagggcg    3180
tgaagaactg gatgaccgac accctgctgg tgcagaacgc caaccccgac tgcaagacca    3240
tcctgagggc cctgggcccc ggcgccagca tcgaggagat gatgaccgcc tgccagggcg    3300
tgggcggccc cagccacaag gccaaggtgc tggccgaggc catgagccag accaacagcg    3360
ccatcctgat gcagaggagc aacttcaagg gcagcaagag gatcgtgaag tgcttcaact    3420
gcggcaagga gggccacatc gccaggaact gcagggcccc caggaagaag gctgctgga     3480 agtgcggcaa gagggccac cagatgaagg actgcaccga gaggcaggcc aacttcctgg     3540
gcaagatctg gcccagccac aagggcggcc ccggcaactt cctgcagaac aggcccgagc    3600
ccaccgcccc ccccgaggag agcttcaggt tcgaggagga gaccaccacc cccagccaga    3660
agcaggagcc catcgacaag gagctgtacc ccctgaccag cctgaagagc ctgttcggca    3720
acgaccccag cagccaggaa ttcttcaggg agaacctggc cctgccccag ggcagggcca    3780
gggagttcag cagcgagcag accagggcca acagccccac caggggcgag ctgcaggtgt    3840
ggggcaggga caacaacagc atcagcgagg ccggcgccaa caggcagggc accatcagct    3900
tcaacttccc ccagatcacc ctgtggcaga ggcccctggt gaccatcaag atcggcggcc    3960
agctgaagga ggccctgctg aacaccggcg ccggcgacac cgtgctggag gacctgaacc    4020
tgcccggcaa gtggaagccc aagatgatcg gcggcatcgg cggcttcatc aaggtgaggc    4080
agtacgagca gatccccatc gagatctgcg gccacaaggc catcggcacc gtgctggtgg    4140
gccccacccc cgtgaacatc atcggcagga acctgctgac ccagctgggc tgcacccgtga   4200 acttccccat cagcccccatc gagaccgtgc ccgtgaagct gaagcccggc atggacggcc    4260
ccaaggtgaa gcagtggccc ctgaccgagg agaagatcaa ggccctgacc gccatctgcg    4320
acgagatgga gaaggagggc aagatcacca agatcggccc cgagaacccc tacaacaccc    4380
ccatcttcgc catcaagaag aaggacagca ccaagtggag gaagctggtg gacttcaggg    4440
agctgaacaa gaggacccag gacttctggg aggtgcagct gggcatcccc caccccgccg    4500
gcctgaagaa gaagaagagc gtgaccgtgc tggacgtggg cgacgcctac ttcagcatcc    4560
ccctgtacga ggacttcagg aagtacaccg ccttcaccat ccccagcagg aacaacgaga    4620
cccccggcat cagctaccag tacaacgtgc tgccccaggg ctggaagggc agcctcgcca    4680
tcttccagag cagcatgacc atcgaggagc tgatctacag caagaagagg caggagatcc    4740
tggacctgtg ggtgtaccac acccagggct acttccccga ctggcacaac tacacccccg    4800
gccccggcgt gaggttcccc ctgaccttcg gctggtgctt caagctggtg cccgtggacc    4860
ccagggaggt ggaggaggcc aacgagggcg aggacaactg cctgctgcac ccgtgtgcc    4920 agcacggcat ggaggacgac cacagggagg tgctgaagtg gaagttcgac agccagctgg    4980
cccacaggca cagggccagg gagctgcacc ccgagttcta caaggactgc atgggcggca    5040
agtggagcaa gagcagcatc gtgggctggc ccgccatcag ggagaggatg aggaggaccg    5100
agcccgccgc cgacggcgtg ggcgccgtga gcagggacct ggagaagcac ggcgccatca    5160
ccagcagcaa caccgccgcc accaacgagg actgcgcctg gctggaggcc caggaggagg    5220
gcgaggtggg cttccccgtg aggccccagg tgcccctgag gcccatgacc tacaagggcg    5280
```

```
ccgtggacct gagcttcttc ctgaaggaga agggcggcct ggagggcctg aggcagcacc      5340
tgctgaggtg gggcttcacc accccgaca agaagcacca aaggagccc cccttcctgt        5400
ggatgggcta cgagctgcac cccgacaagt ggaccgtgca gcccacccag ctgcccgaga      5460
aggatagctg gaccgtgaac gacatccaga agctggtggg caagctgaac tgggccagcc     5520
agatctaccc cggcatcaag gtgaggcagc tgtgcaagct gctgaggggc gccaaggccc     5580
tgaccgacat cgtgcccctg accgaggagg ccgagctgga gctggccgag aacagggaga     5640
tcctgaagga gcccgtgcac ggcgtgtact acgaccccag caaggacctg atcgccgaga     5700
tccagaagca gggccaggag cagtggacct accagatcta ccaggagccc ttcaagaacc     5760
tgaagaccgg caagtacgcc aagatgagga ccgcccacac caacgacgtg aagcagctga     5820
ccgaggccgt gcagaagatc gccatggagg gcatcgtgat ctggggcaag accccccaagt    5880
tcaggctgcc catccagaag gagacctggg agacctggtg gaccgactac tggcaggcca    5940
cctggatccc cgagtgggag ttcgtgaaca cccctcccct ggtgaagctg tggtatcagc    6000
tggagaagga cccatcgtg ggcgtggaga ccttctacgt ggacgcgcc gccaacaggg      6060
agaccaagat cggcaaggcc ggctacgtga ccgacagggg caggaagaag atcgtgagcc    6120
tgaccgagac caccaaccag aagaccgagc tgcaggccat ctgcatcgcc ctgcaggaca    6180
gcggcagcga ggtgaacatc gtgaccgaca gccagtacgc cctgggcatc atccaggccc    6240
agcccgacaa gagcgagagc gagctggtga accagatcat cgagcagctg atgaagaagg    6300
agagggtgta cctgagctgg gtgcccgccc acaagggcat cggcggcaac gagcaggtgg    6360
acaagctggt gagcagcggc atcaggaagg tgctgaagac cctggagccc ttcaggaagc    6420
agaaccccgg catcgtgatc taccagtaca tggacgacct gtacgtgggc agcgacctgg    6480
agatcggcca gcacaggacc aagtaaagat ctctcgagga gctcaagcgg gcggatcccc    6540
cgggctgcag gaattcgatc gcgccaaatt taaatgatcc tgatccttt tctgggtaag     6600
taatacgtca aggagaaaac gaaacgatct gtagttagcg gccgcctaat taactaatat    6660
tatatttttt atctaaaaaa ctaaaaataa acattgatta aattttaata taatacttaa    6720
aaatggatgt tgtgtcgtta gataaaccgt ttatgtattt tgaggaaatt gataatgagt    6780
tagattacga accagaaagt gcaaatgagg tcgcaaaaaa actgccgtat caaggacagt    6840
taaaactatt actaggagaa ttattttttc ttagtaagtt acagcgacac ggtatattag    6900
atggtgccac cgtagtgtat ataggatcgg ctcctggtac acatatacgt tatttgagag    6960
atcatttcta taatttaggaa atgattatca aatggatgct aattgacgga cgccatcatg    7020
atcctattct aaatggattg cgtgatgtga ctctagtgac tcggttcgtt gatgaggaat    7080
atctacgatc catcaaaaaa caactgcatc cttctaagat tatttaatt tctgatgtaa     7140
gatccaaacg aggaggaaat gaacctagta cggcggattt actaagtaat tacgctctac    7200
aaaatgtcat gattagtatt ttaaaccccg tggcatctag tcttaaatgg agatgcccgt    7260
ttccagatca atggatcaag gacttttata tcccacacgg taataaaatg ttacaacctt    7320
ttgctccttc atattcaggg gaattc                                         7346
```

<210> SEQ ID NO 21
<211> LENGTH: 17
<212> TYPE: DNA
<213> ORGANISM: Artificial sequence
<220> FEATURE:
<223> OTHER INFORMATION: Synthetic construct; Primer
<220> FEATURE:
<221> NAME/KEY: misc_feature

<223> OTHER INFORMATION: TK-R2

<400> SEQUENCE: 21
ctgccgtatc aaggaca                                                  17

<210> SEQ ID NO 22
<211> LENGTH: 1515
<212> TYPE: DNA
<213> ORGANISM: Artificial sequence
<220> FEATURE:
<223> OTHER INFORMATION: Synthetic construct; from SHIV89.6P Env gene,
      lacking gp41 nucleotides; Coding Sequence
<220> FEATURE:
<221> NAME/KEY: misc_feature
<223> OTHER INFORMATION: 89.6P-gp120
<220> FEATURE:
<221> NAME/KEY: CDS
<222> LOCATION: (1)..(1509)
<223> OTHER INFORMATION: 89.6P-gp120

<400> SEQUENCE: 22

```
atg ccc atg ggg tct ctg caa ccg ctg gcc acc ttg tac ctg ctg ggg    48
Met Pro Met Gly Ser Leu Gln Pro Leu Ala Thr Leu Tyr Leu Leu Gly
1               5                   10                  15 atg ctg gtc gct tcc gtg cta gcg acc gag aag ctg tgg gtg acc gtg    96
Met Leu Val Ala Ser Val Leu Ala Thr Glu Lys Leu Trp Val Thr Val
                20                  25                  30 tac tac ggc gtg ccc gtg tgg agg gag gcc acc acc acc ctg ttc tgc   144
Tyr Tyr Gly Val Pro Val Trp Arg Glu Ala Thr Thr Thr Leu Phe Cys
            35                  40                  45 gcc agc gac gcc aaa gcc tac gac acc gag gtg cac aac gtg tgg gcc   192
Ala Ser Asp Ala Lys Ala Tyr Asp Thr Glu Val His Asn Val Trp Ala
        50                  55                  60 acc cac gcc tgc gtg ccc acc gac ccc aac ccc cag gag gtg gtg ctg   240
Thr His Ala Cys Val Pro Thr Asp Pro Asn Pro Gln Glu Val Val Leu
65                  70                  75                  80 ggc aac gtg acc gag aac ttc aat atg tgg aag aac aac atg gtg gac   288
Gly Asn Val Thr Glu Asn Phe Asn Met Trp Lys Asn Asn Met Val Asp
                85                  90                  95 cag atg cac gag gac atc atc agc ctg tgg gac gag agc ctg aag ccc   336
Gln Met His Glu Asp Ile Ile Ser Leu Trp Asp Glu Ser Leu Lys Pro
            100                 105                 110 tgc gtg aag ctg acc ccc ctg tgc gtg acc ctg aac tgc acc aac ctg   384
Cys Val Lys Leu Thr Pro Leu Cys Val Thr Leu Asn Cys Thr Asn Leu
        115                 120                 125 aac atc acc aag aac acc acc aac ctg acc agc agc agc tgg ggc atg   432
Asn Ile Thr Lys Asn Thr Thr Asn Leu Thr Ser Ser Ser Trp Gly Met
    130                 135                 140 atg gag gag ggc gag atc aag aac tgc agc ttc tac atc acc acc tcc   480
Met Glu Glu Gly Glu Ile Lys Asn Cys Ser Phe Tyr Ile Thr Thr Ser
145                 150                 155                 160 atc agg aac aag gtg aag aag gag tac gcc ctg ttc aac agg ctg gac   528
Ile Arg Asn Lys Val Lys Lys Glu Tyr Ala Leu Phe Asn Arg Leu Asp
                165                 170                 175 gtg gtg ccc gtg aag aac acc agc aac acc aag tac agg ctg att agc   576
Val Val Pro Val Lys Asn Thr Ser Asn Thr Lys Tyr Arg Leu Ile Ser
            180                 185                 190 tgc aac acc agc gtg att acc cag gcc tgc cct aaa gtg agc ttc cag   624
Cys Asn Thr Ser Val Ile Thr Gln Ala Cys Pro Lys Val Ser Phe Gln
        195                 200                 205 ccc atc ccc atc cac tac tgc gtg ccc gcc ggc ttc gcc atc ctg aag   672
Pro Ile Pro Ile His Tyr Cys Val Pro Ala Gly Phe Ala Ile Leu Lys
    210                 215                 220
```

```
tgc aac aac aag acc ttc aac ggc agc ggc ccc tgc acc aac gtg agc        720
Cys Asn Asn Lys Thr Phe Asn Gly Ser Gly Pro Cys Thr Asn Val Ser
225                 230                 235                 240 acc gtg cag tgc acc cac ggc atc agg ccc gtg gtg tct acc cag ctg        768
Thr Val Gln Cys Thr His Gly Ile Arg Pro Val Val Ser Thr Gln Leu
            245                 250                 255 ctg ctg aac ggc agc ctg gcc gaa gag gac atc gtg atc agg agc gag        816
Leu Leu Asn Gly Ser Leu Ala Glu Glu Asp Ile Val Ile Arg Ser Glu
        260                 265                 270 gac ttc acc gac aac gtg aag acc atc atc gtg cag ctg aac gag agc        864
Asp Phe Thr Asp Asn Val Lys Thr Ile Ile Val Gln Leu Asn Glu Ser
    275                 280                 285 gtg gtg att aac tgc acc agg ccc aac aac aac acc agg gag agg ctg        912
Val Val Ile Asn Cys Thr Arg Pro Asn Asn Asn Thr Arg Glu Arg Leu
290                 295                 300 agc atc ggc ccc ggc agg gcc ttc tac gcc agg agg aac atc atc ggc        960
Ser Ile Gly Pro Gly Arg Ala Phe Tyr Ala Arg Arg Asn Ile Ile Gly
305                 310                 315                 320 gac atc agg cag gcc cac tgc aac atc agc agg gcc aag tgg aac aac       1008
Asp Ile Arg Gln Ala His Cys Asn Ile Ser Arg Ala Lys Trp Asn Asn
            325                 330                 335 acc ctg cag cag atc gtc atc aag ctg agg gag aag ttc agg aac aag       1056
Thr Leu Gln Gln Ile Val Ile Lys Leu Arg Glu Lys Phe Arg Asn Lys
        340                 345                 350 acc atc gcc ttc aac cag agc agc ggc ggc gac ccc gag atc gtg atg       1104
Thr Ile Ala Phe Asn Gln Ser Ser Gly Gly Asp Pro Glu Ile Val Met
    355                 360                 365 cac agc ttc aac tgc ggc ggc gag ttc ttc tac tgc aac acc gcc cag       1152
His Ser Phe Asn Cys Gly Gly Glu Phe Phe Tyr Cys Asn Thr Ala Gln
370                 375                 380 ctg ttc aac agc acc tgg aac gtg gcc ggc ggc acc aac ggc acc gag       1200
Leu Phe Asn Ser Thr Trp Asn Val Ala Gly Gly Thr Asn Gly Thr Glu
385                 390                 395                 400 ggc aac gac atc atc acc ctg cag tgc agg atc aag cag atc atc aac       1248
Gly Asn Asp Ile Ile Thr Leu Gln Cys Arg Ile Lys Gln Ile Ile Asn
            405                 410                 415 atg tgg cag aag gtg ggc aag gcc atg tac gcc cct ccc atc acc ggc       1296
Met Trp Gln Lys Val Gly Lys Ala Met Tyr Ala Pro Pro Ile Thr Gly
        420                 425                 430 cag atc agg tgc agc agc aac atc acc ggc ctg ctg ctg act cgc gac       1344
Gln Ile Arg Cys Ser Ser Asn Ile Thr Gly Leu Leu Leu Thr Arg Asp
    435                 440                 445 ggc ggc aac agc acc gag acc gag acc gag atc ttc agg ccc ggc ggc       1392
Gly Gly Asn Ser Thr Glu Thr Glu Thr Glu Ile Phe Arg Pro Gly Gly
450                 455                 460 ggc gac atg agg gac aac tgg agg agc gag ctg tac aag tac aag gtg       1440
Gly Asp Met Arg Asp Asn Trp Arg Ser Glu Leu Tyr Lys Tyr Lys Val
465                 470                 475                 480 gtg agg atc gag ccc atc ggc gtg gcc ccc acc agg gcc aag agg agg       1488
Val Arg Ile Glu Pro Ile Gly Val Ala Pro Thr Arg Ala Lys Arg Arg
            485                 490                 495 acc gtg cag agg gag aag agg tagtaa                                    1515
Thr Val Gln Arg Glu Lys Arg
                500

<210> SEQ ID NO 23
<211> LENGTH: 4218
<212> TYPE: DNA
<213> ORGANISM: Artificial sequence
<220> FEATURE:
```

```
<223> OTHER INFORMATION: synthetic construct; Coding Sequence; derived
      from virus SHIV89.6P by modifications at corresponding Gag, Pol
      and Nef antigen loci
<220> FEATURE:
<221> NAME/KEY: misc_feature
<223> OTHER INFORMATION: SIVgpn
<220> FEATURE:
<221> NAME/KEY: CDS
<222> LOCATION: (1)..(4215)
<223> OTHER INFORMATION: SIVgpn

<400> SEQUENCE: 23 atg cgc gtg agg aac agc gtg ctg agc ggc aag aag gcc gac gag ctg       48
Met Arg Val Arg Asn Ser Val Leu Ser Gly Lys Lys Ala Asp Glu Leu
1               5                   10                  15 gag aag atc agg ctg agg ccc aac ggc aag aag aag tat atg ctg aag       96
Glu Lys Ile Arg Leu Arg Pro Asn Gly Lys Lys Lys Tyr Met Leu Lys
            20                  25                  30 cac gtg gtg tgg gcc gcc aac gag ctg gac agg ttc ggc ctg gcc gag      144
His Val Val Trp Ala Ala Asn Glu Leu Asp Arg Phe Gly Leu Ala Glu
        35                  40                  45 agc ctg ctg gag aac aag gag ggc tgc cag aag atc ctg agc gtg ctg      192
Ser Leu Leu Glu Asn Lys Glu Gly Cys Gln Lys Ile Leu Ser Val Leu
    50                  55                  60 gcc ccc ctg gtg ccc acc ggc agc gag aac ctg aag agc ctg tac aac      240
Ala Pro Leu Val Pro Thr Gly Ser Glu Asn Leu Lys Ser Leu Tyr Asn
65                  70                  75                  80 acc gtg tgc gtg atc tgg tgc atc cac gcc gag gag aag gtg aag cac      288
Thr Val Cys Val Ile Trp Cys Ile His Ala Glu Glu Lys Val Lys His
                85                  90                  95 acc gag gag gcc aag cag atc gtg cag agg cac ctg gtg gtg gag acc      336
Thr Glu Glu Ala Lys Gln Ile Val Gln Arg His Leu Val Val Glu Thr
            100                 105                 110 ggc acc acc gag acc atg ccc aag acc agc agg ccc acc gcc ccc agc      384
Gly Thr Thr Glu Thr Met Pro Lys Thr Ser Arg Pro Thr Ala Pro Ser
        115                 120                 125 tcc ggc cgc ggc ggc aac tac ccc gtg cag cag atc ggc ggc aac tac      432
Ser Gly Arg Gly Gly Asn Tyr Pro Val Gln Gln Ile Gly Gly Asn Tyr
    130                 135                 140 gtg cac ctg ccc ctg agc ccc agg acc ctg aac gcc tgg gtg aag ctg      480
Val His Leu Pro Leu Ser Pro Arg Thr Leu Asn Ala Trp Val Lys Leu
145                 150                 155                 160 atc gag gag aag aag ttc ggc gcc gag gtg gtg ccc ggc ttc cag gcc      528
Ile Glu Glu Lys Lys Phe Gly Ala Glu Val Val Pro Gly Phe Gln Ala
                165                 170                 175 ctg agc gag ggc tgc acc cct tac gac atc aac cag atg ctg aac tgc      576
Leu Ser Glu Gly Cys Thr Pro Tyr Asp Ile Asn Gln Met Leu Asn Cys
            180                 185                 190 gtg ggc gac cac cag gcc gcc atg cag atc atc agg gac atc atc aac      624
Val Gly Asp His Gln Ala Ala Met Gln Ile Ile Arg Asp Ile Ile Asn
        195                 200                 205 gag gag gcc gcc gac tgg gac ctg cag cac cct cag ccc gcc cct cag      672
Glu Glu Ala Ala Asp Trp Asp Leu Gln His Pro Gln Pro Ala Pro Gln
    210                 215                 220 cag ggc cag ctg agg gag ccc agc ggc agc gac atc gcc ggc acc aca      720
Gln Gly Gln Leu Arg Glu Pro Ser Gly Ser Asp Ile Ala Gly Thr Thr
225                 230                 235                 240 agc agc gtg gac gag cag atc cag tgg atg tac agg cag cag aac cct      768
Ser Ser Val Asp Glu Gln Ile Gln Trp Met Tyr Arg Gln Gln Asn Pro
                245                 250                 255 atc ccc gtg ggc aac atc tac agg agg tgg atc cag ctg ggc ctc cag      816
Ile Pro Val Gly Asn Ile Tyr Arg Arg Trp Ile Gln Leu Gly Leu Gln
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     |     | 260 |     |     |     |     | 265 |     |     |     |     | 270 |     |      |
| aag | tgc | gtg | agg | atg | tac | aac | ccc | aca | aac | atc | ctg | gac | gtg | aag | cag | 864  |
| Lys | Cys | Val | Arg | Met | Tyr | Asn | Pro | Thr | Asn | Ile | Leu | Asp | Val | Lys | Gln |      |
|     |     |     |     | 275 |     |     |     |     | 280 |     |     |     |     | 285 |     |      |
| gga | cca | aag | gag | ccc | ttc | cag | tca | tat | gtg | gac | agg | ttc | tac | aag | agc | 912  |
| Gly | Pro | Lys | Glu | Pro | Phe | Gln | Ser | Tyr | Val | Asp | Arg | Phe | Tyr | Lys | Ser |      |
|     |     |     | 290 |     |     |     |     | 295 |     |     |     |     | 300 |     |     |      |
| ctg | agg | gcc | gag | cag | acc | gac | gcc | gcc | gtg | aag | aac | tgg | atg | acc | cag | 960  |
| Leu | Arg | Ala | Glu | Gln | Thr | Asp | Ala | Ala | Val | Lys | Asn | Trp | Met | Thr | Gln |      |
| 305 |     |     |     |     | 310 |     |     |     |     | 315 |     |     |     |     | 320 |      |
| acc | ctg | ctg | atc | cag | aac | gcc | aac | ccc | gac | tgc | aag | ctg | gtg | ctg | aag | 1008 |
| Thr | Leu | Leu | Ile | Gln | Asn | Ala | Asn | Pro | Asp | Cys | Lys | Leu | Val | Leu | Lys |      |
|     |     |     |     | 325 |     |     |     |     | 330 |     |     |     |     | 335 |     |      |
| ggc | ctg | ggc | gtg | aac | ccc | acc | ctg | gag | gag | atg | ctg | acc | gcc | tgc | cag | 1056 |
| Gly | Leu | Gly | Val | Asn | Pro | Thr | Leu | Glu | Glu | Met | Leu | Thr | Ala | Cys | Gln |      |
|     |     |     | 340 |     |     |     |     | 345 |     |     |     |     | 350 |     |     |      |
| ggc | gtg | ggc | ggc | ccc | ggc | cag | aag | gct | agg | ctg | atg | gcc | gag | gct | ctg | 1104 |
| Gly | Val | Gly | Gly | Pro | Gly | Gln | Lys | Ala | Arg | Leu | Met | Ala | Glu | Ala | Leu |      |
|     |     | 355 |     |     |     |     | 360 |     |     |     |     | 365 |     |     |     |      |
| aag | gag | gcc | ctg | gcc | ccc | gtg | ccc | atc | ccc | ttc | gcc | gcc | gcc | cag | cag | 1152 |
| Lys | Glu | Ala | Leu | Ala | Pro | Val | Pro | Ile | Pro | Phe | Ala | Ala | Ala | Gln | Gln |      |
| 370 |     |     |     |     | 375 |     |     |     |     | 380 |     |     |     |     |     |      |
| agg | gga | ccc | agg | aag | ccc | atc | aag | tgc | tgg | aac | tgc | ggc | aag | gag | ggc | 1200 |
| Arg | Gly | Pro | Arg | Lys | Pro | Ile | Lys | Cys | Trp | Asn | Cys | Gly | Lys | Glu | Gly |      |
| 385 |     |     |     |     | 390 |     |     |     |     | 395 |     |     |     |     | 400 |      |
| cac | agc | gcc | agg | cag | tgc | agg | gcc | ccc | agg | agg | cag | ggc | tgc | tgg | aag | 1248 |
| His | Ser | Ala | Arg | Gln | Cys | Arg | Ala | Pro | Arg | Arg | Gln | Gly | Cys | Trp | Lys |      |
|     |     |     |     | 405 |     |     |     |     | 410 |     |     |     |     | 415 |     |      |
| tgc | ggc | aag | atg | gac | cac | gtg | atg | gcc | aag | tgc | ccc | gac | agg | cag | gcc | 1296 |
| Cys | Gly | Lys | Met | Asp | His | Val | Met | Ala | Lys | Cys | Pro | Asp | Arg | Gln | Ala |      |
|     |     |     | 420 |     |     |     |     | 425 |     |     |     |     | 430 |     |     |      |
| ggt | ttt | agg | cct | tgg | tcc | atg | ggg | aaa | gaa | gcc | ccg | caa | ttt | ccc | cat | 1344 |
| Gly | Phe | Arg | Pro | Trp | Ser | Met | Gly | Lys | Glu | Ala | Pro | Gln | Phe | Pro | His |      |
|     |     | 435 |     |     |     |     | 440 |     |     |     |     | 445 |     |     |     |      |
| ggc | tca | agt | gca | tca | ggg | gct | gat | gcc | aac | tgc | tcc | ccc | aga | gga | ccc | 1392 |
| Gly | Ser | Ser | Ala | Ser | Gly | Ala | Asp | Ala | Asn | Cys | Ser | Pro | Arg | Gly | Pro |      |
| 450 |     |     |     |     | 455 |     |     |     |     | 460 |     |     |     |     |     |      |
| agc | tgt | gga | tct | gct | aaa | gaa | cta | cat | gca | gtt | ggg | caa | gca | gca | gag | 1440 |
| Ser | Cys | Gly | Ser | Ala | Lys | Glu | Leu | His | Ala | Val | Gly | Gln | Ala | Ala | Glu |      |
| 465 |     |     |     |     | 470 |     |     |     |     | 475 |     |     |     |     | 480 |      |
| aga | aaa | gca | gag | aga | aag | cag | aga | gaa | gcc | tta | caa | gga | ggt | gac | aga | 1488 |
| Arg | Lys | Ala | Glu | Arg | Lys | Gln | Arg | Glu | Ala | Leu | Gln | Gly | Gly | Asp | Arg |      |
|     |     |     |     | 485 |     |     |     |     | 490 |     |     |     |     | 495 |     |      |
| gga | ttt | gct | gca | cct | caa | ttc | tct | ctt | tgg | agg | aga | cca | gta | gtg | acc | 1536 |
| Gly | Phe | Ala | Ala | Pro | Gln | Phe | Ser | Leu | Trp | Arg | Arg | Pro | Val | Val | Thr |      |
|     |     |     | 500 |     |     |     |     | 505 |     |     |     |     | 510 |     |     |      |
| gcc | cac | atc | gag | ggc | cag | ccc | gtg | gag | gtg | ctg | ctg | aac | acc | ggc | gcc | 1584 |
| Ala | His | Ile | Glu | Gly | Gln | Pro | Val | Glu | Val | Leu | Leu | Asn | Thr | Gly | Ala |      |
|     |     | 515 |     |     |     |     | 520 |     |     |     |     | 525 |     |     |     |      |
| gac | gac | agc | atc | gtg | acc | ggc | atc | gag | ctg | gga | ccc | cac | tac | acc | ccc | 1632 |
| Asp | Asp | Ser | Ile | Val | Thr | Gly | Ile | Glu | Leu | Gly | Pro | His | Tyr | Thr | Pro |      |
|     |     |     | 530 |     |     |     |     | 535 |     |     |     |     | 540 |     |     |      |
| aag | atc | gtg | ggc | ggc | atc | ggc | ggc | ttc | atc | aac | aca | aag | gag | tac | aag | 1680 |
| Lys | Ile | Val | Gly | Gly | Ile | Gly | Gly | Phe | Ile | Asn | Thr | Lys | Glu | Tyr | Lys |      |
| 545 |     |     |     |     | 550 |     |     |     |     | 555 |     |     |     |     | 560 |      |
| aac | gtg | gag | atc | gag | gtg | ctg | ggc | aag | agg | atc | aag | ggc | acc | atc | atg | 1728 |
| Asn | Val | Glu | Ile | Glu | Val | Leu | Gly | Lys | Arg | Ile | Lys | Gly | Thr | Ile | Met |      |
|     |     |     |     | 565 |     |     |     |     | 570 |     |     |     |     | 575 |     |      |
| acc | ggc | gac | acc | ccc | atc | aac | atc | ttc | ggc | agg | aac | ctg | ctg | acc | gcc | 1776 |

```
                Thr Gly Asp Thr Pro Ile Asn Ile Phe Gly Arg Asn Leu Leu Thr Ala
                            580             585                 590 ctg ggc atg agc ctg aac ttc ccc atc gcc aag gtg gag ccc gtg aag         1824
Leu Gly Met Ser Leu Asn Phe Pro Ile Ala Lys Val Glu Pro Val Lys
        595                 600                 605 gtg gcc ctg aag ccc ggc aag gac ggc ccc aag ctg aag cag tgg cct         1872
Val Ala Leu Lys Pro Gly Lys Asp Gly Pro Lys Leu Lys Gln Trp Pro
610                 615                 620 ctg agc aag gag aag atc gtg gcc ctg agg gaa atc tgc gag aag atg         1920
Leu Ser Lys Glu Lys Ile Val Ala Leu Arg Glu Ile Cys Glu Lys Met
625                 630                 635                 640 gag aag gac ggc cag ctg gag gag gcc cct ccc acc aac ccc tac aac         1968
Glu Lys Asp Gly Gln Leu Glu Glu Ala Pro Pro Thr Asn Pro Tyr Asn
                645                 650                 655 acc ccc acc ttc gcc atc aag aag aag gac aag aac aag tgg agg atg         2016
Thr Pro Thr Phe Ala Ile Lys Lys Lys Asp Lys Asn Lys Trp Arg Met
            660                 665                 670 ctg atc gac ttc agg gag ctg aac agg gtg aca cag gac ttc acc gag         2064
Leu Ile Asp Phe Arg Glu Leu Asn Arg Val Thr Gln Asp Phe Thr Glu
        675                 680                 685 gtg cag ctg ggc atc cct cac ccc gcc ggc ctg gcc aag aag gag aag         2112
Val Gln Leu Gly Ile Pro His Pro Ala Gly Leu Ala Lys Lys Glu Lys
690                 695                 700 ggc ggc ctg gag ggc atc tac tac agc gcc agg agg cac agg atc ctg         2160
Gly Gly Leu Glu Gly Ile Tyr Tyr Ser Ala Arg Arg His Arg Ile Leu
705                 710                 715                 720 gac atg tac ctg gag aag gag gag ggc atc atc ccc gac tgg cag gac         2208
Asp Met Tyr Leu Glu Lys Glu Glu Gly Ile Ile Pro Asp Trp Gln Asp
                725                 730                 735 tac acc agc ggc ccc ggc atc aga tac ccc aag acc ttc ggc tgg ctg         2256
Tyr Thr Ser Gly Pro Gly Ile Arg Tyr Pro Lys Thr Phe Gly Trp Leu
            740                 745                 750 tgg aag ctg gtg ccc gtg aac gtg agc gac gag gcc cag gag gac gag         2304
Trp Lys Leu Val Pro Val Asn Val Ser Asp Glu Ala Gln Glu Asp Glu
        755                 760                 765 agg cac tac ctg atg cag ccc gcc cag acc agc aag tgg gac gac ccc         2352
Arg His Tyr Leu Met Gln Pro Ala Gln Thr Ser Lys Trp Asp Asp Pro
770                 775                 780 tgg ggc gag gtg ctg gcc tgg aag ttt gac ccc acc ctg gcc tac acc         2400
Trp Gly Glu Val Leu Ala Trp Lys Phe Asp Pro Thr Leu Ala Tyr Thr
785                 790                 795                 800 tac gag gcc tac gcc aga tac ccc gag gag ctg gag gcc agc cag gcc         2448
Tyr Glu Ala Tyr Ala Arg Tyr Pro Glu Glu Leu Glu Ala Ser Gln Ala
                805                 810                 815 tgc cag agg aag agg ctg gag gag ggc atg ggc ggc gcc atc agc atg         2496
Cys Gln Arg Lys Arg Leu Glu Glu Gly Met Gly Gly Ala Ile Ser Met
            820                 825                 830 agg agg agc aag ccc gcc ggc gac ctg agg cag aag ctg ctg agg gcc         2544
Arg Arg Ser Lys Pro Ala Gly Asp Leu Arg Gln Lys Leu Leu Arg Ala
        835                 840                 845 agg ggc gag acc tac ggc agg ctg ctg ggc gag gtg gag gac ggc agc         2592
Arg Gly Glu Thr Tyr Gly Arg Leu Leu Gly Glu Val Glu Asp Gly Ser
850                 855                 860 agc cag agc ctg ggc ggc ctg ggc aag ggc ctg agc agc agg agc tgc         2640
Ser Gln Ser Leu Gly Gly Leu Gly Lys Gly Leu Ser Ser Arg Ser Cys
865                 870                 875                 880 gag ggc cag aag tac aac cag ggc cag tac atg aac acc ccc tgg agg         2688
Glu Gly Gln Lys Tyr Asn Gln Gly Gln Tyr Met Asn Thr Pro Trp Arg
                885                 890                 895
```

| | | |
|---|---|---|
| aac ccc gcc gag gag aag gag aag ctg gcc tac agg aag cag aac atg<br>Asn Pro Ala Glu Glu Lys Glu Lys Leu Ala Tyr Arg Lys Gln Asn Met<br>900                      905                   910 | 2736 | |
| gac gac atc gac gag gag gac gac ctg gtg ggc gtg agc gtg agg<br>Asp Asp Ile Asp Glu Glu Asp Asp Leu Val Gly Val Ser Val Arg<br>    915                    920                 925 | 2784 | |
| ccc aag gtg ccc ctg agg gcc atg acc tac aag ctg gcg atc gac atg<br>Pro Lys Val Pro Leu Arg Ala Met Thr Tyr Lys Leu Ala Ile Asp Met<br>930                      935                   940 | 2832 | |
| agc cac ttc atc ctg aac agc atc ggc ttc agc acc ccc gag gag aag<br>Ser His Phe Ile Leu Asn Ser Ile Gly Phe Ser Thr Pro Glu Glu Lys<br>945                      950                   955                 960 | 2880 | |
| ttc cag aag gac cct ccc ttc cag tgg atg ggc tac gag ctg tgg ccc<br>Phe Gln Lys Asp Pro Pro Phe Gln Trp Met Gly Tyr Glu Leu Trp Pro<br>             965                   970                 975 | 2928 | |
| acc aag tgg aag ctc cag aag atc gag ctg ccc cag agg gag acc tgg<br>Thr Lys Trp Lys Leu Gln Lys Ile Glu Leu Pro Gln Arg Glu Thr Trp<br>980                      985                   990 | 2976 | |
| acc gtg aac gac atc cag aag ctg gtg ggc gtg ctg aac tgg gcc gcc<br>Thr Val Asn Asp Ile Gln Lys Leu Val Gly Val Leu Asn Trp Ala Ala<br>    995                    1000                 1005 | 3024 | |
| cag att tac ccc ggc atc aag acc aag cac ctg tgc agg ctg atc<br>Gln Ile Tyr Pro Gly Ile Lys Thr Lys His Leu Cys Arg Leu Ile<br>1010                    1015                 1020 | 3069 | |
| cgc ggc aag atg aca ctg acc gag gag gtg cag tgg acc gag atg<br>Arg Gly Lys Met Thr Leu Thr Glu Glu Val Gln Trp Thr Glu Met<br>     1025                 1030                 1035 | 3114 | |
| gcc gag gcc gag tac gag gag aac aag atc att ctg agc cag gag<br>Ala Glu Ala Glu Tyr Glu Glu Asn Lys Ile Ile Leu Ser Gln Glu<br>1040                    1045                 1050 | 3159 | |
| cag gag ggc tgc tac tac cag gag ggc aag ccc ctg gag gcc acc<br>Gln Glu Gly Cys Tyr Tyr Gln Glu Gly Lys Pro Leu Glu Ala Thr<br>     1055                 1060                 1065 | 3204 | |
| gtg atc aag agc cag gac aac cag tgg agc tac aag atc cac cag<br>Val Ile Lys Ser Gln Asp Asn Gln Trp Ser Tyr Lys Ile His Gln<br>1070                    1075                 1080 | 3249 | |
| gag gac aag atc ctg aag gtg ggc aag ttc gcc aag atc aag aac<br>Glu Asp Lys Ile Leu Lys Val Gly Lys Phe Ala Lys Ile Lys Asn<br>     1085                 1090                 1095 | 3294 | |
| acc cac acc aac ggc gtg agg ctg ctg gcc cac gtg atc cag aag<br>Thr His Thr Asn Gly Val Arg Leu Leu Ala His Val Ile Gln Lys<br>1100                    1105                 1110 | 3339 | |
| atc ggc aag gag gcc atc gtg atc tgg ggc cag gtg ccc aag ttc<br>Ile Gly Lys Glu Ala Ile Val Ile Trp Gly Gln Val Pro Lys Phe<br>     1115                 1120                 1125 | 3384 | |
| cac ctg ccc gtg gag aag gac gtg tgg gag cag tgg tgg acc gac<br>His Leu Pro Val Glu Lys Asp Val Trp Glu Gln Trp Trp Thr Asp<br>1130                    1135                 1140 | 3429 | |
| tac tgg cag gtg aca tgg atc ccc gag tgg gac ttc atc agc acc<br>Tyr Trp Gln Val Thr Trp Ile Pro Glu Trp Asp Phe Ile Ser Thr<br>     1145                 1150                 1155 | 3474 | |
| cct cct ctg gtg agg ctg gtg ttc aat ctg gtg aag gac ccc atc<br>Pro Pro Leu Val Arg Leu Val Phe Asn Leu Val Lys Asp Pro Ile<br>1160                    1165                 1170 | 3519 | |
| gag ggc gag gag acc tac tac acc gac ggc agc tgc aac aag cag<br>Glu Gly Glu Glu Thr Tyr Tyr Thr Asp Gly Ser Cys Asn Lys Gln<br>     1175                 1180                 1185 | 3564 | |
| agc aag gag ggc aag gcc ggc tac atc acc gac agg ggc aag gac<br>Ser Lys Glu Gly Lys Ala Gly Tyr Ile Thr Asp Arg Gly Lys Asp<br>1190                    1195                 1200 | 3609 | |

```
aag gtg  aag gtg ctg gag cag  acc acc aac cag cag  gcc gag ctg      3654
Lys Val  Lys Val Leu Glu Gln  Thr Thr Asn Gln Gln  Ala Glu Leu
    1205                 1210                 1215 gag gcc  ttc ctg atg gcc ctg  acc gac agc ggc ccc  aag gcc aac      3699
Glu Ala  Phe Leu Met Ala Leu  Thr Asp Ser Gly Pro  Lys Ala Asn
    1220                 1225                 1230 atc atc  gtg gac agc cag tat  gtg atg ggc atc atc  acc ggc tgc      3744
Ile Ile  Val Asp Ser Gln Tyr  Val Met Gly Ile Ile  Thr Gly Cys
    1235                 1240                 1245 ccc acc  gag agc gag agc agg  ctg gtg aac cag atc  atc gag gag      3789
Pro Thr  Glu Ser Glu Ser Arg  Leu Val Asn Gln Ile  Ile Glu Glu
    1250                 1255                 1260 atg att  aag aag agc gag att  tac gtg gcc tgg gtg  ccc gcc cac      3834
Met Ile  Lys Lys Ser Glu Ile  Tyr Val Ala Trp Val  Pro Ala His
    1265                 1270                 1275 aag ggc  atc ggc ggc aac cag  gag atc gac cac ctg  gtg agc cag      3879
Lys Gly  Ile Gly Gly Asn Gln  Glu Ile Asp His Leu  Val Ser Gln
    1280                 1285                 1290 ggc atc  agg cag gtg ctg agg  aag agg atc acc gtg  ctg gac atc      3924
Gly Ile  Arg Gln Val Leu Arg  Lys Arg Ile Thr Val  Leu Asp Ile
    1295                 1300                 1305 ggc gac  gcc tac ttc agc atc  cct ctg gac gag gag  ttc agg cag      3969
Gly Asp  Ala Tyr Phe Ser Ile  Pro Leu Asp Glu Glu  Phe Arg Gln
    1310                 1315                 1320 tac acc  gcc ttc acc ctg ccc  agc gtg aac aac gcc  gag ccc ggc      4014
Tyr Thr  Ala Phe Thr Leu Pro  Ser Val Asn Asn Ala  Glu Pro Gly
    1325                 1330                 1335 aag agg  tac atc tac aag gtg  ctg ccc cag ggc tgg  aag ggc agc      4059
Lys Arg  Tyr Ile Tyr Lys Val  Leu Pro Gln Gly Trp  Lys Gly Ser
    1340                 1345                 1350 ccc gcc  atc ttc cag tac acc  atg agg cac gtg ctg  gag ccc ttc      4104
Pro Ala  Ile Phe Gln Tyr Thr  Met Arg His Val Leu  Glu Pro Phe
    1355                 1360                 1365 agg aag  gcc aac ccc gac gtg  acc ctg gtg cag tac  atg gac gac      4149
Arg Lys  Ala Asn Pro Asp Val  Thr Leu Val Gln Tyr  Met Asp Asp
    1370                 1375                 1380 atc ctg  atc gcc tcc gac agg  acc gac ctg gag cac  gac agg gtg      4194
Ile Leu  Ile Ala Ser Asp Arg  Thr Asp Leu Glu His  Asp Arg Val
    1385                 1390                 1395 gtg ctc  cag agc aag gag ctg  tag                                   4218
Val Leu  Gln Ser Lys Glu Leu
    1400                 1405
```

<210> SEQ ID NO 24
<211> LENGTH: 7180
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<223> OTHER INFORMATION: Sequence present in the insert located in the genome of MVA-89.6P-SIVgpn and NYVAC-89.6P-SIVgpn vectors
<220> FEATURE:
<221> NAME/KEY: MISC_FEATURE
<222> LOCATION: (1)..(499)
<223> OTHER INFORMATION: Left-flanking Sequence; TK-L
<220> FEATURE:
<221> NAME/KEY: MISC_FEATURE
<222> LOCATION: (519)..(2033)
<223> OTHER INFORMATION: Sequence complementary to the Coding Sequence of protein 89.6P-gp120
<220> FEATURE:
<221> NAME/KEY: MISC_FEATURE

```
<222> LOCATION: (2081)..(2119)
<223> OTHER INFORMATION: Sequence complementary to pE/L promoter for
      89.6P-gp120
<220> FEATURE:
<221> NAME/KEY: Promoter
<222> LOCATION: (2144)..(2183)
<223> OTHER INFORMATION: pE/L promoter for SIVgpn
<220> FEATURE:
<221> NAME/KEY: CDS
<222> LOCATION: (2227)..(6444)
<223> OTHER INFORMATION: Coding Sequence of protein SIVgpn
<220> FEATURE:
<221> NAME/KEY: MISC_FEATURE
<222> LOCATION: (6488)..(7179)
<223> OTHER INFORMATION: Right-flanking Sequence;TK-R

<400> SEQUENCE: 24
aagcttttgc gatcaataaa tggatcacaa ccagtatctc ttaacgatgt tcttcgcaga      60
tgatgattca ttttttaagt atttggctag tcaagatgat gaatcttcat tatctgatat    120
attgcaaatc actcaatatc tagactttct gttattatta ttgatccaat caaaaaataa    180
attagaagcc gtgggtcatt gttatgaatc tctttcagag gaatacagac aattgacaaa    240
attcacagac tctcaagatt ttaaaaaact gtttaacaag gtccctattg ttacagatgg    300
aagggtcaaa cttaataaag gatatttgtt cgactttgtg attagtttga tgcgattcaa    360
aaaagaatcc tctctagcta ccaccgcaat agatcctatt agatacatag atcctcgtcg    420
cgatatcgca ttttctaacg tgatggtat attaaagtcg aataaagtga acaataatta    480
attctttatt gtcatcatgg gtaccaaggc gcggatcctt actacctctt ctccctctgc    540
acggtcctcc tcttggccct ggtggggccc acgccgatgg gctcgatcct caccaccttg    600
tacttgtaca gctcgctcct ccagttgtcc ctcatgtcgc cgccgccggg cctgaagatc    660
tcggtctcgg tctcggtgct gttgccgccg tcgcgagtca gcagcaggcc ggtgatgttg    720
ctgctgcacc tgatctggcc ggtgatggga ggggcgtaca tggccttgcc caccttctgc    780
cacatgttga tgatctgctt gatcctgcac tgcagggtga tgatgtcgtt gccctcggtg    840
ccgttggtgc cgccggccac gttccaggtg ctgttgaaca gctgggcggt gttgcagtag    900
aagaactcgc cgccgcagtt gaagctgtgc atcacgatct cggggtcgcc gccgctgctc    960
tggttgaagg cgatggtctt gttcctgaac ttctccctca gcttgatgac gatctgctgc   1020
agggtgttgt tccacttggc cctgctgatg ttgcagtggg cctgcctgat gtcgccgatg   1080
atgttcctcc tggcgtagaa ggccctgccg gggccgatgc tcagcctctc cctggtgttg   1140
ttgttgggcc tggtgcagtt aatcaccacg ctctcgttca gctgcacgat gatggtcttc   1200
acgttgtcgg tgaagtcctc gctcctgatc acgatgtcct cttcggccag gctgccgttc   1260
agcagcagct gggtagacac cacgggcctg atgccgtggg tgcactgcac ggtgctcacg   1320
ttggtgcagg ggccgctgcc gttgaaggtc ttgttgttgc acttcaggat ggcgaagccg   1380
gcgggcacgc agtagtggat ggggatgggc tggaagctca ctttagggca ggcctgggta   1440
atcacgctgg tgttgcagct aatcagcctg tacttggtgt tgctggtgtt cttcacgggc   1500
accacgtcca gcctgttgaa cagggcgtac tccttcttca ccttgttcct gatggaggtg   1560
gtgatgtaga agctgcagtt cttgatctcg ccctcctcca tcatgcccca gctgctgctg   1620
gtcaggttgg tggtgttctt ggtgatgttc aggttggtgc agttcagggt cacgcacagg   1680
ggggtcagct tcacgcaggg cttcaggctc tcgtcccaca ggctgatgat gtcctcgtgc   1740
atctggtcca ccatgttgtt cttccacata ttgaagttct cggtcacgtt gcccagcacc   1800
acctcctggg ggttggggtc ggtgggcacg caggcgtggg tggcccacac gttgtgcacc   1860
```

```
tcggtgtcgt aggctttggc gtcgctggcg cagaacaggg tggtggtggc ctccctccac    1920
acgggcacgc cgtagtacac ggtcacccac agcttctcgg tcgctagcac ggaagcgacc    1980
agcatcccca gcaggtacaa ggtggccagc ggttgcagag accccatggg catgctggcg    2040
gcgaattggg taccaggcct agatctgtcg acttcgagct tatttatatt ccaaaaaaaa    2100
aaaataaaat ttcaattttt aagctcgcgc caaatttagc ttaaaaattg aaattttatt    2160
ttttttttt ggaatataaa taagctcgaa gtcgacagat ctaggcctgg tacccaattc    2220
gccaggatgc gcgtgaggaa cagcgtgctg agcggcaaga aggccgacga gctggagaag    2280
atcaggctga ggcccaacgg caagaagaag tatatgctga agcacgtggt gtgggccgcc    2340
aacgagctgg acaggttcgg cctggccgag agcctgctgg agaacaagga gggctgccag    2400
aagatcctga gcgtgctggc ccccctggtg cccaccggca gcgagaacct gaagagcctg    2460
tacaacaccg tgtgcgtgat ctggtgcatc cacgccgagg agaaggtgaa gcacaccgag    2520
gaggccaagc agatcgtgca gaggcacctg gtggtggaga ccggcaccac cgagaccatg    2580
cccaagacca gcaggcccac cgcccccagc tccggccgcg gcggcaacta ccccgtgcag    2640
cagatcggcg gcaactacgt gcacctgccc ctgagcccca ggaccctgaa cgcctgggtg    2700
aagctgatcg aggagaagaa gttcggcgcc gaggtggtgc ccggcttcca ggccctgagc    2760
gagggctgca cccttacga catcaaccag atgctgaact gcgtgggcga ccaccaggcc    2820
gccatgcaga tcatcaggga catcatcaac gaggaggccg ccgactggga cctgcagcac    2880
cctcagcccg cccctcagca gggccagctg agggagccca cgcggcagcg catcgccggc    2940
accacaagca gcgtggacga gcagatccag tgatgtaca ggcagcagaa ccctatcccc    3000
gtgggcaaca tctacaggag gtggatccag ctgggcctcc agaagtgcgt gaggatgtac    3060
aaccccacaa acatcctgga cgtgaagcag ggaccaaagg agcccttcca gtcatatgtg    3120
gacaggttct acaagagcct gagggccgag cagaccgacg ccgccgtgaa gaactggatg    3180
acccagaccc tgctgatcca gaacgccaac cccgactgca agctggtgct gaagggcctg    3240
ggcgtgaacc ccaccctgga ggagatgctg accgcctgcc agggcgtggg cggcccggc    3300
cagaaggcta ggctgatggc cgaggctctg aaggaggccc tggccccgt gcccatcccc    3360
ttcgccgccg cccagcagag gggacccagg aagcccatca gtgctggaa ctgcggcaag    3420
gagggccaca gcgccaggca gtgcagggcc cccaggaggc agggctgctg gaagtgcggc    3480
aagatggacc acgtgatggc caagtgcccc gacaggcagg ccggttttag gccttggtcc    3540
atggggaaag aagcccgca atttccccat ggctcaagtg catcaggggc tgatgccaac    3600
tgctccccca gagacccag ctgtggatct gctaaagaac tacatgcagt tgggcaagca    3660
gcagagagaa aagcagagag aaagcagaga gaagccttac aaggaggtga cagaggattt    3720
gctgcacctc aattctctct ttggaggaga ccagtagtga ccgcccacat cgagggccag    3780
cccgtggagg tgctgctgaa caccggcgcc gacgacagca tcgtgaccgg catcgagctg    3840
ggaccccact acacccccaa gatcgtgggc ggcatcggcg gcttcatcaa cacaaaggag    3900
tacaagaacg tggagatcga ggtgctgggc aagaggatca agggcaccat catgaccggc    3960
gacaccccca tcaacatctt cggcaggaac ctgctgaccg ccctgggcat gagcctgaac    4020
ttccccatcg ccaaggtgga gcccgtgaag gtggccctga gcccggcaa ggacggcccc    4080
aagctgaagc agtggcctct gagcaaggag aagatcgtgg ccctgaggga aatctgcgag    4140
aagatggaga aggacggcca gctggaggag gcccctccca ccaaccccta caacaccccc    4200
```

-continued

```
accttcgcca tcaagaagaa ggacaagaac aagtggagga tgctgatcga cttcagggag    4260
ctgaacaggg tgacacagga cttcaccgag gtgcagctgg gcatccctca ccccgccggc    4320
ctggccaaga aggagaaggg cggcctggag ggcatctact acagcgccag gaggcacagg    4380
atcctggaca tgtacctgga gaaggaggag ggcatcatcc ccgactggca ggactacacc    4440
agcggccccg gcatcagata ccccaagacc ttcggctggc tgtggaagct ggtgcccgtg    4500
aacgtgagcg acgaggccca ggaggacgag aggcactacc tgatgcagcc cgcccagacc    4560
agcaagtggg acgacccctg gggcgaggtg ctggcctgga gtttgacccc accctggcc    4620
tacacctacg aggcctacgc cagataccc gaggagctgg aggccagcca ggcctgccag    4680
aggaagaggc tggaggaggg catgggcggc gccatcagca tgaggaggag caagcccgcc    4740
ggcgacctga ggcagaagct gctgagggcc aggggcgaga cctacggcag gctgctgggc    4800
gaggtggagg acggcagcag ccagagcctg ggcggcctgg gcaagggcct gagcagcagg    4860
agctgcgagg gccagaagta caaccagggc cagtacatga acacccctg gaggaacccc    4920
gccgaggaga aggagaagct ggcctacagg aagcagaaca tggacgacat cgacgaggag    4980
gacgacgacc tggtgggcgt gagcgtgagg cccaaggtgc ccctgagggc catgacctac    5040
aagctggcga tcgacatgag ccacttcatc ctgaacagca tcggcttcag caccccccgag   5100
gagaagttcc agaaggaccc tcccttccag tggatgggct acgagctgtg gccaccaag    5160
tggaagctcc agaagatcga gctgccccag agggagacct ggaccgtgaa cgacatccag    5220
aagctggtgg gcgtgctgaa ctgggccgcc cagatttacc ccggcatcaa gaccaagcac    5280
ctgtgcaggc tgatccgcgg caagatgaca ctgaccgagg aggtgcagtg gaccgagatg    5340
gccgaggccg agtacgagga gaacaagatc attctgagcc aggagcagga gggctgctac    5400
taccaggagg gcaagcccct ggaggccacc gtgatcaaga ccaggacaa ccagtgggagc    5460
tacaagatcc accaggagga caagatcctg aaggtgggca gttcgccaa gatcaagaac    5520
acccacacca acggcgtgag gctgctggcc cacgtgatcc agaagatcgg caaggaggcc    5580
atcgtgatct ggggccaggt gcccaagttc cacctgcccg tggagaagga cgtgtgggag    5640
cagtggtgga ccgactactg gcaggtgaca tggatccccg agtgggactt catcagcacc    5700
cctcctctgg tgaggctggt gttcaatctg gtgaaggacc ccatcgaggg cgaggagacc    5760
tactacaccg acggcagctg caacaagcag agcaaggagg gcaaggccgg ctacatcacc    5820
gacaggggca aggacaaggt gaaggtgctg gagcagacca ccaaccagca ggccgagctg    5880
gaggccttcc tgatggccct gaccgacagc ggccccaagg ccaacatcat cgtggacagc    5940
cagtatgtga tgggcatcat caccggctgc cccaccgaga gcgagagcag gctggtgaac    6000
cagatcatcg aggagatgat taagaagagc gagatttacg tggcctgggt gcccgcccac    6060
aagggcatcg gcggcaacca ggagatcgac cacctggtga gccagggcat caggcaggtg    6120
ctgaggaaga ggatcaccgt gctggacatc ggcgacgcct acttcagcat ccctctggac    6180
gaggagttca ggcagtacac cgccttcacc ctgcccagct gaacaacgc cgagcccggc    6240
aagaggtaca tctacaaggt gctgccccag ggctggaagg gcagccccgc catcttccag    6300
tacaccatga gcacgtgct ggagcccttc aggaaggcca ccccgacgt gaccctggtg    6360
cagtacatgg acgacatcct gatcgcctcc gacaggaccg acctggagca cgacagggtg    6420
gtgctccaga gcaaggagct gtagctcgag ggggatccac tagttctaga gcggccgccc    6480
taattaacta atattatat ttttatctaa aaaactaaaa ataaacattg attaaattttt    6540
aatataatac ttaaaaatgg atgttgtgtc gttagataaa ccgtttatgt attttgagga    6600
```

-continued

```
aattgataat gagttagatt acgaaccaga aagtgcaaat gaggtcgcaa aaaaactgcc   6660
gtatcaagga cagttaaaac tattactagg agaattattt tttcttagta agttacagcg   6720
acacggtata ttagatggtg ccaccgtagt gtatatagga tcggctcctg gtacacatat   6780
acgttatttg agagatcatt tctataattt aggaatgatt atcaaatgga tgctaattga   6840
cggacgccat catgatccta ttctaaatgg attgcgtgat gtgactctag tgactcggtt   6900
cgttgatgag gaatatctac gatccatcaa aaaacaactg catccttcta agattatttt   6960
aatttctgat gtaagatcca aacgaggagg aaatgaacct agtacggcgg atttactaag   7020
taattacgct ctacaaaatg tcatgattag tattttaaac cccgtggcat ctagtcttaa   7080
atggagatgc ccgtttccag atcaatggat caaggacttt tatatcccac acggtaataa   7140
aatgttacaa ccttttgctc cttcatattc aggggaattc                         7180

<210> SEQ ID NO 25
<211> LENGTH: 27
<212> TYPE: DNA
<213> ORGANISM: Artificial sequence
<220> FEATURE:
<223> OTHER INFORMATION: synthetic construct
<220> FEATURE:
<221> NAME/KEY: misc_feature
<223> OTHER INFORMATION: E/L

<400> SEQUENCE: 25
tatttttttt ttttggaata taaatag                                          27
```